(12) United States Patent
Xie et al.

(10) Patent No.: US 10,562,857 B2
(45) Date of Patent: Feb. 18, 2020

(54) ION CHANNEL INHIBITORY COMPOUNDS, PHARMACEUTICAL FORMULATIONS, AND USES

(71) Applicant: AFASCI, Inc., Redwood City, CA (US)

(72) Inventors: Xinmin Xie, Burlingame, CA (US); Frank Kayser, San Francisco, CA (US)

(73) Assignee: AFASCI, INC., Burlingame, CA (US)

( * ) Notice: Subject to any disclaimer, the term of this patent is extended or adjusted under 35 U.S.C. 154(b) by 0 days.

(21) Appl. No.: 15/772,365

(22) PCT Filed: Nov. 14, 2016

(86) PCT No.: PCT/US2016/061918
§ 371 (c)(1),
(2) Date: Apr. 30, 2018

(87) PCT Pub. No.: WO2017/083867
PCT Pub. Date: May 18, 2017

(65) Prior Publication Data
US 2018/0312471 A1 Nov. 1, 2018

Related U.S. Application Data

(60) Provisional application No. 62/254,564, filed on Nov. 12, 2015.

(51) Int. Cl.
| | |
|---|---|
| *C07D 221/20* | (2006.01) |
| *A61K 31/4747* | (2006.01) |
| *C07D 401/12* | (2006.01) |
| *C07D 409/12* | (2006.01) |
| *C07D 413/14* | (2006.01) |
| *C07D 211/26* | (2006.01) |
| *C07D 413/12* | (2006.01) |
| *C07D 211/58* | (2006.01) |
| *C07D 405/06* | (2006.01) |

(52) U.S. Cl.
CPC .......... *C07D 221/20* (2013.01); *C07D 211/26* (2013.01); *C07D 211/58* (2013.01); *C07D 401/12* (2013.01); *C07D 405/06* (2013.01); *C07D 409/12* (2013.01); *C07D 413/12* (2013.01); *C07D 413/14* (2013.01)

(58) Field of Classification Search
None
See application file for complete search history.

(56) References Cited

U.S. PATENT DOCUMENTS

2013/0065926 A1  3/2013  Pajouhesh et al.

FOREIGN PATENT DOCUMENTS

| WO | 200700261 A1 | 1/2007 | |
|---|---|---|---|
| WO | 2007002884 A2 | 1/2007 | |
| WO | 2012047703 A2 | 4/2012 | |
| WO | 2012125662 A1 | 9/2012 | |
| WO | 2013041457 A1 | 3/2013 | |
| WO | WO-2013041457 A1 * | 3/2013 | ........... C07D 401/14 |
| WO | 2013127269 A1 | 9/2013 | |
| WO | 2015000949 A1 | 1/2015 | |
| WO | 2015068773 A1 | 5/2015 | |

OTHER PUBLICATIONS

International Search Report issued to EP16865345 (dated Apr. 3, 2019).
Tringham et al., T-Type Calcium Channel Blockers that Attenuate Thalamic Burst Firing and Suppress Absence Seizures, www.sciencetranslationmedicine.org, Feb. 15, 2012, vol. 4, Issue 121.
International Preliminary Report issued to PCT/US2016/061918 (dated Nov. 14, 2016).

* cited by examiner

*Primary Examiner* — Zinna Northington Davis
(74) *Attorney, Agent, or Firm* — Wei Zhang; Intelink Law Group PC

(57) ABSTRACT

The present invention is directed towards new chemical entities which primarily inhibit the human T-type calcium channels and differentially modulate other key ion channels to control cell excitability, and abnormal neuronal activity particularly involved in the development and maintenance of persistent or chronic pain, and/or neurological disorders. These novel compounds are useful in the treatment and prevention of neurological and psychiatric disorders and diseases in which these ion channels are involved. The invention is also directed towards pharmaceutical formulations comprising these compounds and the uses of these compounds.

23 Claims, 12 Drawing Sheets

ION CHANNEL INHIBITORY COMPOUNDS, PHARMACEUTICAL FORMULATIONS, AND USES

CROSS-REFERENCE TO RELATED APPLICATIONS

This application claims the benefit of U.S. Provisional Patent Application No. 62/254,564, filed Nov. 12, 2015, which is incorporated by reference in its entirety for all purposes.

STATEMENT OF GOVERNMENT RIGHTS

This invention was made with Government support under Grant 1 R44 NS086343-01 awarded by the National Institute of Neurological Disorders and Stroke, National Institute of Health. The Government has certain rights in this invention.

FIELD OF THE INVENTION

The field of the present invention relates to ion channel modulators (inhibitors or antagonists of one type ion channel and/or combination of inhibition of multiple ion channels), compositions including ion channel modulators, and methods of treating conditions and disorders using the compounds and compositions. A more particular field involves compounds having selective T-type $Ca_{v3}$ channel inhibitory effects for mitigating neuropathic and/or inflammatory pain, pharmaceutical formulations including such compounds, and methods for selective treatment of neuropathic and inflammatory pain, other neurological disorders, such epilepsy, essential tremor, migraine and Parkinson disease, and psychiatric disorders, e.g., anxiety, depression and schizophrenia.

BACKGROUND OF THE INVENTION

Voltage-gated calcium ($Ca^{2+}$) channels (VGCC) play an integral role in the regulation of membrane ion conductance, cellular excitability and neurotransmitter release. VGCC are composed of the pore-forming α1 subunit and auxiliary α2δ ppm and β subunits that modulate channel expression and function. Among the low voltage activated channels is the $Ca_{v3}$ channel subtype, which mediates T-type calcium currents that may be targeted for treatment of epilepsy, especially children absence epilepsy and chronic pain (Huguenard, 1998, Cribbs et al., 2000, Perez-Reyes et al., 2009, Perez-Reyes, 2010).

The T-type or "low voltage-activated" calcium channels are so named because they open for shorter duration (T=transient) than the L-type (L=long lasting) calcium channels. T-type channels are activated at relatively negative membrane potentials (~−60 mV). In many types of neurons, $Ca^{2+}$ influx through T channels triggers low-threshold $Ca^{2+}$ spikes, which in turn elicit a burst of action potentials mediated by voltage-gated sodium ($Na^+$) channels. Brief burst firing is thought to play an important role in the synchronized activity of the thalamus and neuronal pacemaker under physiological conditions, but it also underlies a wide range of thalamocortical dysrhythmias under pathological conditions such as neuropathic pain or seizures, T channels can be activated by mild depolarization of the cell membrane (Talley et al., 1999, Perez-Reyes, 2003, Perez-Reyes, 2010, Pexton et al., 2011, Todorovic and Jevtovic-Todorovic, 2011).

Molecular cloning has revealed three distinct T channel proteins, designated $Ca_{v3.1}$, $Ca_{v3.2}$ and $Ca_{v3.3}$. The $Ca_{v3.1}$ and $Ca_{v3.3}$ channels are expressed predominantly, though not exclusively, in the CNS. In contrast, the $Ca_{v3.2}$ channel is not only present in the CNS, but also expressed in peripheral nerve cell bodies and nerve endings of afferent fibers (Huguenard, 1998, Cribbs et al., 2000, Perez-Reyes et al., 2009, Perez-Reyes, 2010). The $Ca_{v3.2}$ channel is highly expressed in dorsal root ganglion (DRG) neurons, whereas little $Ca_{v3.1}$ and virtually no $Ca_{v3.3}$ are expressed in the small diameter DRG neurons (Nelson et al., 1992). The $Ca_{v3.2}$ channels are also expressed at a lower level in several non-neuronal tissues, including heart, liver, kidney, and pituitary. Both diabetic neuropathy and chronic constriction injury models in rats lead to DRG neuron-specific upregulation of the $Ca_{v3.2}$ channel and the T current density. This pathological adaptation results in enhanced excitability of sensory neurons and causes hyperalgesia and allodynia (Jagodic et al., 2007, Jagodic et al., 2008, Latham et al., 2009, Messinger et al., 2009, Yue et al., 2013). Conversely, knockout or antisense knockdown of the $Ca_{v3.2}$ isoform produces analgesic effects (Messinger et al., 2009).

T-type channel inhibitors have two known uses in the clinic. The anti-absence seizure effects of ethosuximide and lamotrigine are thought to be mediated by the inhibition of T channel activity in the thalamus (Gomora et al., 2001, Huguenard, 2002). However, both drugs are weak and not specific against the T channel (Xie et al., 1995, Zhang et al., 1996). The antihypertensive effect of mibefradil is conventionally attributed to its inhibition of the T channel. However, mibefradil has poor selectivity with about 3-10 times more potent inhibition of the T-type than of the L-type $Ca^{2+}$ current or the voltage-gated $Na^+$ current (Avdonin et al., 2000). Because there are no selective T channel blockers, it is unclear whether and to what extend the inhibition of T channel activity at therapeutically relevant concentrations contributes to the therapeutic usefulness of a wide range of drugs, such as analgesics, antiepileptics, neuroprotectants, antipsychotics, antidepressants, antiarrhythmics and antihypertensives.

Targeting a T-channel, particularly the $Ca_{v3.2}$ isoform, would be highly useful in reduction of thermal hyperalgesia and mechanical allodynia under pathological conditions, for example diabetic neuropathy. Several efforts to discover potent and selective T-type $Ca^{2+}$ channels have been described in the literature, as exemplified below.

1,4-Substituted piperidines, for example, "compound 30" (3,5-dichloro-N-{[1-(3,3-dimethylbutyl)-3-fluoropiperidin-4-yl]methyl}benzamide) and "TTA-P2" (3,5-dichloro-N-((1-((2,2-dimethyltetrahydro-2H-pyran-4-yl)methyl)-4-fluoropiperidin-4-yl)methyl)benzamide) were synthesized by Merck and found to potently block the T-Type Cav3.2 channel [J. Med. Chem. 51, 3692, (2008); J. Med. Chem. 51, 6471, (2008); US 2010/0222387; US 2013/8501773]. TTA-A2 suppresses active wake, promotes slow-wave sleep (Kraus et al., 2010), and prevents weight gain in mice on a high-fat diet (Uebele et al., 2009).

A scaffold hopping approach afforded ML218 (3,5-Dichloro-N-[[(1α,5α,6-exo,6α)-3-(3,3-dimethylbutyl)-3-azabicyclo[3.1.0]hex-6-yl]methyl]benzamide, CID 45115620) a selective T-Type $Ca^{2+}$ inhibitor. ML218 possess acceptable in vivo rat PK and was efficacious in a preclinical Parkinson model. Thus, ML218 is a useful new biologic probe to study T-Type $Ca^{2+}$ function in vitro and in vivo (Xie et al., 2010, Xiang et al., 2011).

Certain lactam acetamides have been described by Abbott and others as $Ca_{v2.2}$ and $Ca_{v3.2}$ calcium channel blockers, and ABT-639 has been reported as a $Ca_{v3.2}$ calcium channel blocker for treatment of diabetic neuropathic pain through peripheral action, because ABT-639 is presumed to not penetrate the blood brain barrier (Jarvis et al., 2014).

N-Piperidinyl acetamide derivatives as calcium channel blockers have been described by Zalicus Pharmaceuticals, Ltd. [U.S. Pat. No. 8,569,344 (2013); U.S. Pat. No. 8,377,968 (2013)]. A piperidine-based compound, Z944, inhibits $Ca_{v3}$ channels in a voltage-dependent manner and is able to attenuate thalamic burst firing and suppress absence seizures in rats (Tringham et al., 2012). Z944 has shown promising results in clinical Phase I studies of pain in humans (Lee, 2014).

Despite the fact that many T-type $Ca^{2+}$ channel inhibitors have been discovered and have advanced to different stages of development, no FDA-approved selective T-type channel inhibitory compounds are available for clinical applications.

SUMMARY OF THE INVENTION

The current invention provides compounds, formulations and methods of useful for the treatment and prevention of neurological and psychiatric disorders and diseases, especially neuropathic pain and inflammatory pain, in which key ion channels, particularly the T-type $Ca^{2+}$ channels are involved. The compounds and methods can be used in both human and veterinary medicine.

Some embodiments described herein are recited as "comprising" or "comprises" with respect to their various elements. In alternative embodiments, those elements can be recited with the transitional phrase "consisting essentially of" or "consists essentially of" as applied to those elements. In further alternative embodiments, those elements can be recited with the transitional phrase "consisting of" or "consists of" as applied to those elements. Thus, for example, if a compound, formulation or method is disclosed herein as comprising A and B, the alternative embodiment for that compound, formulation or method of "consisting essentially of A and B" and the alternative embodiment for that compound, formulation or method of "consisting of A and B" are also considered to have been disclosed herein. Likewise, embodiments recited as "consisting essentially of" or "consisting of" with respect to their various elements can also be recited as "comprising" as applied to those elements. Finally, embodiments recited as "consisting essentially of" with respect to their various elements can also be recited as "consisting of" as applied to those elements, and embodiments recited as "consisting of" with respect to their various elements can also be recited as "consisting essentially of" as applied to those elements.

When a compound or formulation is described as "consisting essentially of" the listed components, the compound or formulation contains the components expressly listed, and may contain other components which do not substantially affect the condition being treated. That is, the compound or formulation either does not contain any other components which do substantially affect the condition being treated other than those components expressly listed; or, if the compound or formulation does contain extra components other than those listed which substantially affect the condition being treated, the compound or formulation does not contain a sufficient concentration or amount of those extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed.

DETAILED DESCRIPTION OF THE INVENTION

Figure 1A:
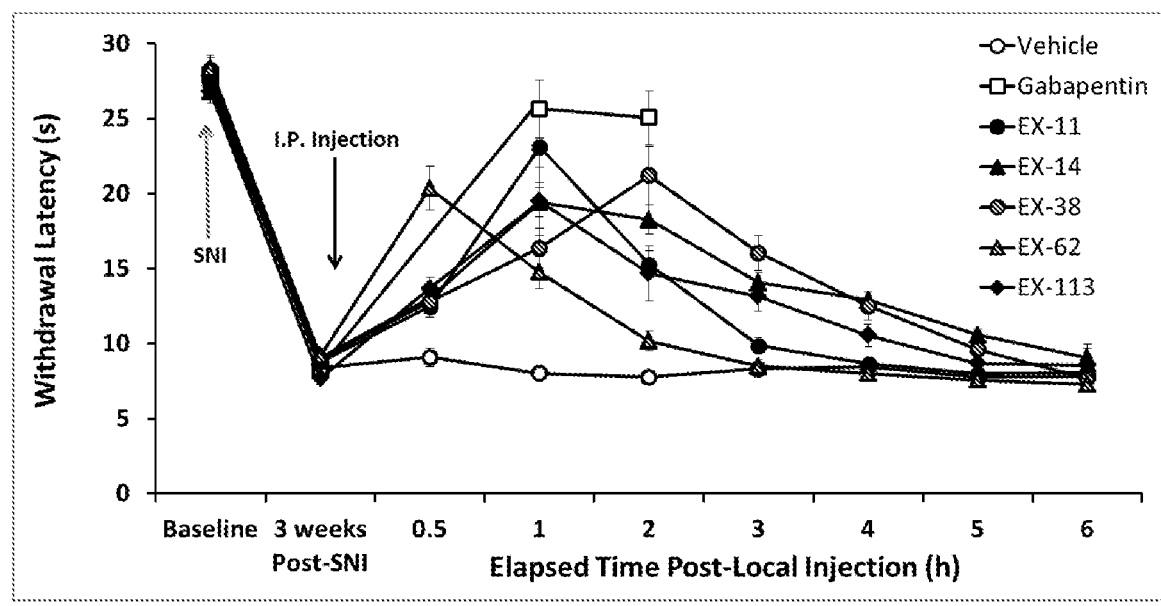
FIG. 1A. Examples of compounds that mitigate neuropathic pain induced by Spared Nerve Injury (SNI) in mice. The withdrawal latencies of the mice's left hindpaws (injured site) in response to thermal stimulation (Hargreaves test). Each SNI mouse received either EXAMPLE (EX)-11, -14, -38, -62, or 113, or gabapentin, as benchmark (each 30 mg/kg, 0.2 mL I.P.), or vehicle (0.2 mL I.P. 2% DMSO in 0.5% Hydroxyl Propyl Cellulose, HPC). Application of EXAMPLE-11, -14, -38, -62, or 113 (or gabapentin) reduced hyperalgesia, while the SNI-vehicle group remained in a hyperalgesic state. 40 seconds were cut off in order to prevent tissue damage (n=8 per group).

"Compound of the invention," as used herein, refers to the compounds discussed herein and salts (e.g. pharmaceutically acceptable salts) of these compounds.

"Alkyl" is intended to embrace a univalent saturated linear or branched hydrocarbon chain having the number of carbon atoms specified, or if no number is specified, having 1 to 8 carbon atoms. "Alkylene" refers to a similar group, which is divalent. "Optionally substituted" alkyl refers to either an unsubstituted alkyl group, or an alkyl group substituted with one or more substituents (such as one, two, three, four, or five substituents) selected from the group consisting of —OH, —($C_1$-$C_4$ alkyl)-OH, halo, fluoro, chloro, bromo, iodo, —($C_1$-$C_4$ alkyl), —($C_1$-$C_4$) haloalkyl, —($C_1$-$C_4$) perhaloalkyl, —O—($C_1$-$C_4$ alkyl), —O—($C_1$-$C_4$ haloalkyl), —O—($C_1$-$C_4$ perhaloalkyl), —($C_1$-$C_4$) perfluoroalkyl, —(C=O)—($C_1$-$C_4$) alkyl, —(C=O)—($C_1$-$C_4$) haloalkyl, —(C=O)—($C_1$-$C_4$) perhaloalkyl, —$NH_2$, —NH($C_1$-$C_4$ alkyl), —N($C_1$-$C_4$ alkyl)($C_1$-$C_4$ alkyl) (where each $C_1$-$C_4$ alkyl is chosen independently of the other), —$NO_2$, —CN, isocyano (NC—), oxo (=O), —C(=O)H, —C(=O)—($C_1$-$C_4$ alkyl), —COOH, —C(=O)—O—($C_1$-$C_4$ alkyl), —C(=O)$NH_2$, —C(=O)NH($C_1$-$C_4$ alkyl), —C(=O)N($C_1$-$C_4$ alkyl)($C_1$-$C_4$ alkyl) (where each $C_1$-$C_4$ alkyl is chosen independently of the other), —SH, —($C_1$-$C_4$ alkyl)-SH, —S—($C_1$-$C_4$ alkyl), —S(=O)—($C_1$-$C_4$ alkyl), —$SO_2$—($C_1$-$C_4$ alkyl), and —$SO_2$—($C_1$-$C_4$ perfluoroalkyl). Examples of such substituents are —$CH_3$, —$CH_2CH_3$, —$CF_3$, —$CH_2CF_3$, —$CF_2CF_3$, —$OCH_3$, —NH($CH_3$), —N($CH_3$)$_2$, —$SCH_3$, and $SO_2CH_3$. "Optionally substituted alkylene" groups can be unsubstituted, or substituted in the same manner as substituted alkyl groups.

"Cycloalkyl" is intended to embrace a univalent saturated cyclic hydrocarbon chain having the number of carbon atoms specified, or if no number is specified, having 3 to 10 carbon atoms, or 3 to 8 carbon atoms, preferably 3 to 6 carbon atoms. "Cycloalkylene" refers to a similar group, which is divalent. Cycloalkyl and cycloalkylene groups can be unsubstituted, or substituted in the same manner as substituted alkyl groups.

"Alkenyl" is intended to embrace a univalent linear or branched hydrocarbon chain having at least one carbon-carbon double bond, and having the number of carbon atoms specified, or if no number is specified, having 2 to 8 carbon atoms. "Alkenylene" refers to a similar group, which is divalent. Alkenyl and alkenylene groups can be unsubstituted, or substituted in the same manner as substituted alkyl groups where chemically possible.

"Cycloalkenyl" is intended to embrace a univalent cyclic hydrocarbon chain having at least one carbon-carbon double bond and having the number of carbon atoms specified, or if no number is specified, having 4 to 10 carbon atoms, or 4 to 8 carbon atoms, or 4 to 6 carbon atoms. "Cycloalkenylene" refers to a similar group, which is divalent. Cycloalkenyl and cycloalkenylene groups can be unsubstituted, or substituted in the same manner as substituted alkyl groups where chemically possible.

"Alkynyl" is intended to embrace a univalent linear or branched hydrocarbon chain having at least one carbon-carbon triple bond, and having the number of carbon atoms specified, or if no number is specified, having 2 to 8 carbon atoms. "Alkynylene" refers to a similar group, which is divalent. Alkynyl and alkynylene groups can be unsubstituted, or substituted in the same manner as substituted alkyl groups where chemically possible.

"Aryl" is defined as a univalent aromatic ring system. Aryl groups include monocyclic aromatic rings and polycyclic aromatic ring systems containing the number of carbon atoms specified, or if no number is specified, containing six to twenty carbon atoms. In other embodiments, aryl groups may contain six to ten carbon atoms. Non-limiting examples of aryl and heteroaryl groups include phenyl, 1-naphthyl, 2-naphthyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

In some embodiments, aryl groups can be unsubstituted. In other embodiments, aryl groups can be substituted with, for example, one, two, three or more substituents independently selected from the group consisting of —OH, —($C_1$-$C_4$ alkyl)-OH, halo, fluoro, chloro, bromo, iodo, —($C_1$-$C_4$ alkyl), —($C_1$-$C_4$) haloalkyl, —($C_1$-$C_4$) perhaloalkyl, —O—($C_1$-$C_4$ alkyl), —O—($C_1$-$C_4$ haloalkyl), —O—($C_1$-$C_4$ perhaloalkyl), —($C_1$-$C_4$) perfluoroalkyl, —(C=O)—($C_1$-$C_4$) alkyl, —(C=O)—($C_1$-$C_4$) haloalkyl, —(C=O)—($C_1$-$C_4$) perhaloalkyl, —NH$_2$, —NH($C_1$-$C_4$ alkyl), —N($C_1$-$C_4$ alkyl)($C_1$-$C_4$ alkyl) (where each $C_1$-$C_4$ alkyl is chosen independently of the other), —NO$_2$, —CN, (NC—), —C(=O)H, —C(=O)—($C_1$-$C_4$ alkyl), —COOH, —C(=O)—O—($C_1$-$C_4$ alkyl), —C(=O)NH$_2$, —C(=)ONH($C_1$-$C_4$ alkyl), —C(=O)N($C_1$-$C_4$ alkyl)($C_1$-$C_4$ alkyl) (where each $C_1$-$C_4$ alkyl is chosen independently of the other), —SH, —($C_1$-$C_4$ alkyl)-SH and —S—$C_1$-$C_4$ alkyl. In some embodiments, any of the aryl and heteroaryl groups is optionally substituted, e.g., with one or more groups referred to herein as an "aryl group substituent". "Arylene" refers to a similar group, which is divalent.

The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom.

"Hydrocarbyl" is defined as a univalent hydrocarbon group, that is, a group comprised of hydrogen and carbon, whether aliphatic or aromatic, acyclic or cyclic, or any combination of, or all of, aliphatic, aromatic, acyclic and cyclic. Hydrocarbyl groups have the number of carbon atoms specified, or if no number is specified, having 1 to 10 carbon atoms. "Hydrocarbylene" refers to a similar group, which is divalent. Hydrocarbyl and hydrocarbylene groups can be unsubstituted, or substituted in the same manner as substituted alkyl groups where chemically possible.

"Heterocycle" or a "heterocyclic group" is defined as a ring system which contains the number of carbon atoms specified, and one or more heteroatoms (such as one to six heteroatoms, or one to three heteroatoms, or one heteroatom), where heteroatoms include, but are not limited to, oxygen, nitrogen, sulfur, and phosphorus. "Heteroaryl" is defined as an aromatic ring system which contains the number of carbon atoms specified, and one or more heteroatoms (such as one to six heteroatoms, or one to three heteroatoms, or one heteroatom), where heteroatoms include, but are not limited to, oxygen, nitrogen, sulfur, and phosphorus; heteroaryl groups are a subset of heterocyclic groups. In some embodiments, heteroatoms for heterocyclyl and heteroaryl groups are selected from the group consisting of oxygen and nitrogen. In various embodiments, heterocyclic groups may contain two to twenty carbon atoms and one to six heteroatoms, two to twelve carbon atoms and one to four heteroatoms, two to twelve carbon atoms and one to three heteroatoms, two to ten carbon atoms and one to three heteroatoms, two to six carbon atoms and one to three heteroatoms, or two to six carbon atoms and two to four heteroatoms. In some embodiments, heterocyclic groups can be unsubstituted. In other embodiments, heterocyclic groups can be substituted on any chemically possible valence with for example, one, two, or three substituents independently selected from the group consisting of —OH, —($C_1$-$C_4$ alkyl)-OH, halo, fluoro, chloro, bromo, iodo, —($C_1$-$C_4$ alkyl), —($C_1$-$C_4$) haloalkyl, —($C_1$-$C_4$) perhaloalkyl, —O—($C_1$-$C_4$ alkyl), —O—($C_1$-$C_4$ haloalkyl), —O—($C_1$-$C_4$ perhaloalkyl), —($C_1$-$C_4$) perfluoroalkyl, —(C=O)—($C_1$-$C_4$) alkyl, —(C=O)—($C_1$-$C_4$) haloalkyl, —(C=O)—($C_1$-$C_4$) perhaloalkyl, —NH$_2$, —NH($C_1$-$C_4$ alkyl), —N($C_1$-$C_4$ alkyl)($C_1$-$C_4$ alkyl) (where each $C_1$-$C_4$ alkyl is chosen independently of the other), —NO$_2$, —CN, (NC—), —C(=O)H, —C(=O)—($C_1$-$C_4$ alkyl), —COOH, —C(=O)—O—($C_1$-$C_4$ alkyl), —C(=O)NH$_2$, —C(=)ONH($C_1$-$C_4$ alkyl), —C(=O)N($C_1$-$C_4$ alkyl)($C_1$-$C_4$ alkyl) (where each $C_1$-$C_4$ alkyl is chosen independently of the other), —SH, —($C_1$-$C_4$ alkyl)-SH and —S—$C_1$-$C_4$ alkyl. Examples of heterocycles include aziridine, oxirane, oxetane, azetidine, pyrrolidine, pyrrole, tetrahydrofuran, furan, thiolane, thiophene, imidazolidine, imidazole, pyrazolidine, pyrazole, 1,2,3-triazole, 1,2,4-triazole, piperidine, pyridine, pyran, piperazine, and morpholine.

A "heteroalkyl" group is defined as a univalent hydrocarbyl group, where one or more of the carbon atoms have been independently replaced by a heteroatom at any chemically possible location, where heteroatoms include, but are not limited to, oxygen, nitrogen, sulfur, and phosphorus. Heteroalkyl groups have the number of carbon atoms specified, or if no number is specified, having 1 to 10 carbon atoms, and also at least one heteroatom, such as 1 to 5 heteroatoms, 1 to 4 heteroatoms, 1 to 3 heteroatoms, 1 to 2 heteroatoms, or one heteroatom. "Heteroalkylene" refers to a similar group, which is divalent. Heteroalkyl and heteroalkylene groups can be unsubstituted, or substituted in the same manner as substituted alkyl groups where chemically possible. Examples of heteroalkyl and heteroalkylene groups include, but are not limited to, ethylene glycol and polyethylene glycol moieties, such as $(—CH_2CH_2—O)_n—H$ (a monovalent heteroalkyl group) and $(—CH_2CH_2—O—)_n$ (a divalent heteroalkylene group) where n is an integer from 1 to 12 inclusive, and propylene glycol and polypropylene glycol moieties, such as $(—CH_2CH(CH_3)—O—)_n—H$ (a monovalent heteroalkyl group) and $(—CH_2CH(CH_3)—O—)_n—$ (a divalent heteroalkylene group) where n is an integer from 1 to 12 inclusive. The heteroatom(s) O, N and S and Si may be placed at any interior position of the heteroalkyl group or at the position at which the alkyl group is attached to the remainder of the molecule. Examples include, but are not limited to, $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2—,$ $—S(O)—CH_3$, $—CH_2—CH_2—S(O)_2—CH_3$, $—CH=CH—O—CH_3$, $—Si(CH_3)_3$, $—CH_2—CH=N—OCH_3$, and $—CH=CH—N(CH_3)—CH_3$. Up to two heteroatoms may be consecutive, such as, for example, $—CH_2—NH—OCH_3$ and $—CH_2—O—Si(CH_3)_3$. Similarly, the term "heteroalkylene" by itself or as part of another substituent means a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—CO_2R'—$ represents both $—C(O)OR'$ and $—OC(O)R'$.

The various groups described above can be attached to the remainder of the molecule at any chemically possible location on the fragment, including attachment via a substituent when the group is substituted. For the purposes of drawing the structures, groups are typically attached by replacement of a hydrogen, hydroxyl, methyl, or methoxy group on a "complete" molecule to generate the appropriate fragment, and a bond is drawn from the open valence on the fragment to the remainder of the molecule. For example, attachment of the heteroalkyl group $—CH_2—O—CH_3$ proceeds by removal of a hydrogen from one of the methyl groups of $CH_3—O—CH_3$, to generate the heteroalkyl fragment $—CH_2—O—CH_3$, from which a bond is drawn from the open valence to the remainder of the molecule.

Reference to "about" a value or parameter herein includes (and describes) variations that are directed to that value or parameter per se. For example, description referring to "about X" includes description of "X".

The terms "a" or "an," as used in herein means one or more, unless the context clearly indicates otherwise.

By "subject," "individual," or "patient" is meant an individual organism, preferably a vertebrate, more preferably a mammal, most preferably a human.

The description is intended to embrace all salts of the compounds described herein, as well as methods of using such salts of the compounds. In one embodiment, the salts of the compounds comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N'-dibenzylethylenediamine, and triethylamine salts. Salts of acidic compounds with amino acids, such as lysine salts, can also be prepared. For lists of pharmaceutically acceptable salts, see, for example, P. H. Stahl and C. G. Wermuth (eds.) "Handbook of Pharmaceutical Salts, Properties, Selection and Use" Wiley-VCH, 2011 (ISBN: 978-3-90639-051-2). Several pharmaceutically acceptable salts are also disclosed in Berge, J. Pharm. Sci. 66:1 (1977).

The phrase "therapeutically effective amount" as used herein means that amount of a compound, material, or formulation comprising a compound of the present invention which is effective for producing some desired therapeutic effect by inhibition of a T-Channel in at least a subpopulation of cells in an animal, thereby blocking or lessening the biological consequences of that pathway in the treated cells, at a reasonable benefit/risk ratio applicable to any medical treatment.

Below are definitions of representative types of pain and neurological disorders in which the compounds, pharmaceutical formulations and methods find use in treating.

The term "neurological disorder" refers to any condition of the central or peripheral nervous system of a mammal. The term "neurological disorder" includes neurodegenerative diseases (e.g., Alzheimer's disease, Parkinson's disease and amyotrophic lateral sclerosis), neuropsychiatric diseases (e.g. Schizophrenia and anxieties, such as general anxiety disorder). Exemplary neurological disorders include MLS (cerebellar ataxia), Huntington's disease, Down syndrome, multi-infarct dementia, status epilepticus, contusive injuries (e.g. spinal cord injury and head injury), viral infection induced neurodegeneration, (e.g. AIDS, encephalopathies), epilepsy, benign forgetfulness, closed head injury, sleep disorders, depression (e.g., bipolar disorder), dementias, movement disorders, psychoses, alcoholism, post-traumatic stress disorder and the like. "Neurological disorder" also includes any condition associated with the disorder. For instance, a method of treating a neurodegenerative disorder includes methods of treating loss of memory and/or loss of cognition associated with a neurodegenerative disorder.

Such method would also include treating or preventing loss of neuronal function characteristic of neurodegenerative disorder.

"Pain" is an unpleasant sensory and emotional experience. Pain classifications have been based on duration, etiology or pathophysiology, mechanism, intensity, and symptoms. The term "pain" as used herein refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic peripheral neuropathic pain (see, e.g., Harrison's Principles of Internal Medicine, pp. 93-98 (Wilson et al., eds., 12th ed. 1991); Williams et al., J. of Med. Chem. 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia.

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Neuropathic pain" is a heterogeneous group of neurological conditions that result from damage to the nervous system. "Neuropathic" pain, as described above, refers to pain resulting from injury to or dysfunctions of peripheral and/or central sensory pathways, and from dysfunctions of the nervous system, where the pain often occurs or persists without an obvious noxious input. This includes pain related to peripheral neuropathies as well as central neuropathic pain. Common types of peripheral neuropathic pain include diabetic neuropathy (also called diabetic peripheral neuropathic pain, or DN, DPN, or DPNP), post-herpetic neuralgia (PHN), and trigeminal neuralgia (TGN). Central neuropathic pain, involving damage to the brain or spinal cord, can occur following stroke, spinal cord injury, and as a result of multiple sclerosis. Other types of pain that are meant to be included in the definition of neuropathic pain include pain from spinal cord injury, neuropathic cancer pain, HIV/AIDS induced pain, phantom limb pain, and complex regional pain syndrome. In a preferred embodiment, the compounds of the invention are of use for treating neuropathic pain. An exemplary compound of use in this embodiment is a compound according to Formula I in which each of $R^1$-$R^3$ is hydrogen, and $R^4$ is selected such that the compound is a free acid or salt thereof.

Common clinical features of neuropathic pain include sensory loss, allodynia (non-noxious stimuli produce pain), hyperalgesia and hyperpathia (delayed perception, summation, and painful aftersensation). Pain is often a combination of nociceptive and neuropathic types, for example, mechanical spinal pain and radiculopathy or myelopathy.

"Acute pain", is the normal, predicted physiological response to a noxious chemical, thermal or mechanical stimulus typically associated with invasive procedures, trauma and disease. It is generally time-limited, and may be viewed as an appropriate response to a stimulus that threatens and/or produces tissue injury. "Acute pain", as described above, refers to pain, which is marked by short duration or sudden onset.

"Chronic pain" occurs in a wide range of disorders, for example, trauma, malignancies and chronic inflammatory diseases such as rheumatoid arthritis. Chronic pain usually lasts more than about six months. In addition, the intensity of chronic pain may be disproportionate to the intensity of the noxious stimulus or underlying process. "Chronic pain", as described above, refers to pain associated with a chronic disorder, or pain that persists beyond resolution of an underlying disorder or healing of an injury, and that is often more intense than the underlying process would predict. It may be subject to frequent recurrence.

"Inflammatory pain" is pain in response to tissue injury and the resulting inflammatory process. Inflammatory pain is adaptive in that it elicits physiologic responses that promote healing. However, inflammation may also affect neuronal function. Inflammatory mediators, including $PGE_2$ induced by the COX2 enzyme, bradykinins, and other substances, bind to receptors on pain-transmitting neurons and alter their function, increasing their excitability and thus increasing pain sensation. Much chronic pain has an inflammatory component. "Inflammatory pain", as described above, refers to pain, which is produced as a symptom or a result of inflammation or an immune system disorder.

"Visceral pain", as described above, refers to pain, which is located in an internal organ.

"Mixed etiology" pain, as described above, refers to pain that contains both inflammatory and neuropathic components.

"Dual mechanism" pain, as described above, refers to pain that is amplified and maintained by both peripheral and central sensitization.

"Causalgia", as described above, refers to a syndrome of sustained burning, allodynia, and hyperpathia after a traumatic nerve lesion, often combined with vasomotor and sudomotor dysfunction and later trophic changes.

"Central" pain, as described above, refers to pain initiated by a primary lesion or dysfunction in the central nervous system.

"Hyperesthesia", as described above, refers to increased sensitivity to stimulation, excluding the special senses.

"Hyperpathia", as described above, refers to a painful syndrome characterized by an abnormally painful reaction to a stimulus, especially a repetitive stimulus, as well as an increased threshold. It may occur with allodynia, hyperesthesia, hyperalgesia, or dysesthesia.

"Dysesthesia", as described above, refers to an unpleasant abnormal sensation, whether spontaneous or evoked. Special cases of dysesthesia include hyperalgesia and allodynia, "Hyperalgesia", as described above, refers to an increased response to a stimulus that is normally painful. It reflects increased pain on suprathreshold stimulation.

"Allodynia", as described above, refers to pain due to a stimulus that does not normally provoke pain.

The term "pain" includes pain resulting from dysfunction of the nervous system: organic pain states that share clinical features of neuropathic pain and possible common pathophysiology mechanisms, but are not initiated by an identifiable lesion in any part of the nervous system.

The term "Diabetic Peripheral Neuropathic Pain" (DPNP, also called diabetic neuropathy, DN or diabetic peripheral neuropathy) refers to chronic pain caused by neuropathy associated with diabetes mellitus. The classic presentation of DPNP is pain or tingling in the feet that can be described not only as "burning" or "shooting" but also as severe aching pain. Less commonly, patients may describe the pain as itching, tearing, or like a toothache. The pain may be accompanied by allodynia and hyperalgesia and an absence of symptoms, such as numbness.

The term "Post-Herpetic Neuralgia", also called "Postherpetic Neuralgia" (PHN), is a painful condition affecting nerve fibers and skin. It is a complication of shingles, a second outbreak of the varicella zoster virus (VZV), which initially causes chickenpox.

The term "neuropathic cancer pain" refers to peripheral neuropathic pain as a result of cancer, and can be caused directly by infiltration or compression of a nerve by a tumor, or indirectly by cancer treatments such as radiation therapy and chemotherapy (chemotherapy-induced neuropathy).

The term "HIV/AIDS peripheral neuropathy" or "HIV/AIDS-related neuropathy" refers to peripheral neuropathy caused by HIV/AIDS, such as acute or chronic inflammatory demyelinating neuropathy (AIDP and CIDP, respectively), as well as peripheral neuropathy resulting as a side effect of drugs used to treat HIV/AIDS.

The term "Phantom Limb Pain" refers to pain appearing to come from where an amputated limb used to be. Phantom limb pain can also occur in limbs following paralysis. It is usually chronic in nature. It is similar in nature to the limb pain experienced by patients with paralysis following spinal cord injury.

The term "Trigeminal Neuralgia" (TN) refers to a disorder of the fifth cranial (trigeminal) nerve that causes episodes of intense, stabbing, electric-shock-like pain in the areas of the face where the branches of the nerve are distributed (lips, eyes, nose, scalp, forehead, upper jaw, and lower jaw). It is also known as the "suicide disease".

The term "Complex Regional Pain Syndrome (CRPS)," formerly known as Reflex Sympathetic Dystrophy (RSD), is a chronic pain condition. The key symptom of CRPS is continuous, intense pain out of proportion to the severity of the injury, which gets worse rather than better over time. CRPS is divided into type 1, which includes conditions caused by tissue injury other than peripheral nerve, and type 2, in which the syndrome is provoked by major nerve injury, and is sometimes called causalgia.

The term "Fibromyalgia" refers to a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

The term "convulsion" refers to a CNS disorder and is used interchangeably with "seizure," although there are many types of seizure, some of which have subtle or mild symptoms instead of convulsions. Seizures of all types may be caused by disorganized and sudden electrical activity in the brain. Convulsions are a rapid and uncontrollable shaking. During convulsions, the muscles contract and relax repeatedly.

The following are definitions of representative methods in which the compounds and formulations of the invention find use.

The term "method of treating pain" means relief from the symptoms or the prevention of pain, which includes the descriptions of pain provided herein. Additional examples include, but are not limited to, migraine, chronic back pain, phantom limb pain, neuropathic pain such as diabetic neuropathy, and post herpetic neuropathy.

The term "method of treating anxiety disorders" as used herein means relief from the symptoms or the prevention of anxiety disorders, which include, but are not limited to, panic disorder with or without agoraphobia, agoraphobia without history of panic disorder, animal or other phobias including social phobias, obsessive-compulsive disorder, stress disorders including post-traumatic and acute stress disorder, situational anxiety, generalized anxiety disorder and substance-induced anxiety disorder.

The term "method of treating psychotic disorders" as used herein means relief from the symptoms or the prevention of psychotic disorders, which include, but are not limited to, schizophrenia, schizophreniform disorder, schizoaffective disorder, delusional disorder, brief psychotic disorder, shared psychotic disorder, psychotic disorder due to general medical condition, substance-induced psychotic disorder, or psychotic disorder not otherwise specified (*Diagnostic and Stastistical Manual of Mental Disorders*, (Ed. 4$^{th}$) American Psychiatric Association, Washington, D.C. (1994)).

The term "method of treating convulsive disorders" means relief from the symptoms or the prevention of epilepsy, which include, but are not limited to, altered consciousness, altered motor activity, autonomic responses, inappropriate behavior patterns seizures including tonic or clonic jerking of extremities, emotional stress, sense of terror, uneasiness, nervousness, headache, fatigue, auditory hallucinations, aggressive outbursts, acute skeletal muscle spasm, and spasticity.

The term "method of treating depressive or bipolar disorders", as used herein, means relief from the symptoms or the prevention of depressive disorders, which include, but are not limited to, single-episode or recurrent major depressive disorder, seasonal affective disorder (SAD), dysthymic disorder, bipolar I and bipolar II manic disorders, and cyclothymic disorder.

The term "method of treating cognitive disorders" means relief from the symptoms or the prevention of cognitive disorders, which includes, but is not limited to delirium, dementia, amnesic disorders, and cognitive deficits, including age-related memory deficits, due to traumatic injury, stroke, Parkinson's disease, attention deficit disorder and Downs Syndrome. Any of these conditions may be attributable to substance abuse or withdrawal. Examples of dementia include dementia of the Alzheimer's type with early or late onset, and vascular dementia, any of which may be uncomplicated or accompanied by delirium, delusions or depressed mood; and dementia due to HIV virus, head trauma, Parkinson's disease or Creutzfeldt-Jakob disease.

The term "method of treating sleeping disorders", as used herein, means relief from the symptoms or the prevention of sleep disorders or states that affect a subject's ability to sleep, which includes, but are not limited to, insomnia, sleep apnea, REM sleep interruptions, parasomnia, jet-lag syndrome, hypersomnia, shift workers' sleep disturbances, dysomnias, night terror, narcolepsy, disturbed sleep patterns, disturbed biological or circadian rhythms, sleep disturbances associated with such diseases as neurological disorders, neuropathic pain and restless leg syndrome, or providing sleep induction before surgical procedures or in disturbed or anxious states.

The term "method of treating neurodegenerative eye diseases", as used herein, means relief of symptoms or the prevention of neurodegenerative eye diseases, which includes, but is not limited to retinoschisis, vascular diseases of the retina, diseases caused by venous and/or arterial vascular occlusions, macular degenerations, traumatic retinal changes such as contusion of the eye, perforating eye injuries, siderosis/hemidosis, chalcosis, burns, retinopathia traumatica and/or injury to the retina from light, diseases of the choroid, diseases of the optic nerve, anterior ischemic optic neuropathy, optic atrophy, glaucoma, glaucoma simplex, secondary glaucoma and/or ocular hypertension.

The term "method of treating emesis" means relief from the symptoms or the prevention of emesis, which includes, but is not limited to, acute, delayed and anticipatory emesis, emesis induced by chemotherapy or radiation, as well as motion sickness, and postoperative nausea and vomiting.

The term "method of treating eating disorders" means relief from the symptoms or the prevention of eating disorders, which include, but are not limited to, anorexia nervosa, bulimia nervosa, obesity, weight-gain after smoking cessation, snacking and binge eating.

The term "benzodiazepine receptor" as used herein, includes the benzodiazepine receptor/GABA receptor/chloride channel complex (benzodiazepine receptor complex) and benzodiazepine receptor-agonist binding sites at or near the receptor complex. Both central nervous system ("central") and peripheral benzodiazepine receptors ("peripheral") are encompassed by the use of this term.

In an exemplary embodiment, the invention provides a method for treating a condition described herein in a mammal, the method comprises administering to the mammal a therapeutically effective amount of a compound described herein, or a compound according to a formula described herein, or a pharmaceutically acceptable salt thereof, sufficient to treat the condition, thereby treating the condition. In an exemplary embodiment, according to any method described herein, the mammal is in need of treatment with the compound. In an exemplary embodiment, according to any method described herein, the mammal is not otherwise in need of treatment with the compound. In an exemplary embodiment, according to any method described herein, the mammal is a mouse or a rat. In an exemplary embodiment, according to any method described herein, the mammal is a human.

In an exemplary embodiment, the invention provides a method for treating a condition described herein in a mammal, the method comprises administering to the mammal a therapeutically effective amount of a pharmaceutical formulation described herein, sufficient to treat the condition, thereby treating the condition. In an exemplary embodiment, according to any method described herein, the mammal is in need of treatment with the pharmaceutical formulation. In an exemplary embodiment, according to any method described herein, the mammal is not otherwise in need of treatment with the pharmaceutical formulation. In an exemplary embodiment, according to any method described herein, the mammal is a mouse or a rat. In an exemplary embodiment, according to any method described herein, the mammal is a human.

Pain

In an exemplary embodiment, the invention provides a method for treating pain in a mammal, the method comprises administering to the mammal a therapeutically effective amount of a compound described herein, or a compound according to a formula described herein, or a pharmaceutically acceptable salt thereof, sufficient to treat the pain, thereby treating the pain. In an exemplary embodiment, according to any method described herein, the mammal is in need of treatment with the compound. In an exemplary embodiment, according to any method described herein, the mammal is not otherwise in need of treatment with the compound. In an exemplary embodiment, the mammal is a mouse or a rat. In an exemplary embodiment, the mammal is a human.

In an exemplary embodiment, the invention provides a method for treating pain in a mammal, the method comprises administering to the mammal a therapeutically effective amount of a pharmaceutical formulation described herein, sufficient to treat the pain, thereby treating the pain. In an exemplary embodiment, according to any method described herein, the mammal is in need of treatment with the pharmaceutical formulation. In an exemplary embodiment, according to any method described herein, the mammal is not otherwise in need of treatment with the pharmaceutical formulation. In an exemplary embodiment, the mammal is a mouse or a rat. In an exemplary embodiment, the mammal is a human.

Epilepsy

In an exemplary embodiment, the invention provides a method for treating epilepsy in a mammal, the method comprises administering to the mammal a therapeutically effective amount of a compound described herein, or a compound according to a formula described herein, or a pharmaceutically acceptable salt thereof, sufficient to treat the epilepsy, thereby treating the epilepsy. In an exemplary embodiment, according to any method described herein, the mammal is in need of treatment with the compound. In an exemplary embodiment, according to any method described herein, the mammal is not otherwise in need of treatment with the compound. In an exemplary embodiment, the epilepsy is child absence epilepsy. In an exemplary embodiment, the mammal is a mouse or a rat. In an exemplary embodiment, the mammal is a human.

In an exemplary embodiment, the invention provides a method for treating epilepsy in a mammal, the method comprises administering to the mammal a therapeutically effective amount of a pharmaceutical formulation described herein, sufficient to treat the epilepsy, thereby treating the epilepsy. In an exemplary embodiment, according to any method described herein, the mammal is in need of treatment with the pharmaceutical formulation. In an exemplary embodiment, according to any method described herein, the mammal is not otherwise in need of treatment with the pharmaceutical formulation. In an exemplary embodiment, the epilepsy is child absence epilepsy. In an exemplary embodiment, the mammal is a mouse or a rat. In an exemplary embodiment, the mammal is a human.

Essential Tremor

In an exemplary embodiment, the invention provides a method for treating essential tremor in a mammal, the method comprises administering to the mammal a therapeutically effective amount of a compound described herein, or a compound according to a formula described herein, or a pharmaceutically acceptable salt thereof, sufficient to treat the essential tremor, thereby treating the essential tremor. In an exemplary embodiment, according to any method described herein, the mammal is in need of treatment with the compound. In an exemplary embodiment, according to any method described herein, the mammal is not otherwise in need of treatment with the compound. In an exemplary embodiment, the mammal is a mouse or a rat. In an exemplary embodiment, the mammal is a human.

In an exemplary embodiment, the invention provides a method for treating essential tremor in a mammal, the method comprises administering to the mammal a therapeutically effective amount of a pharmaceutical formulation described herein, sufficient to treat the essential tremor, thereby treating the essential tremor. In an exemplary embodiment, according to any method described herein, the mammal is in need of treatment with the pharmaceutical formulation. In an exemplary embodiment, according to any method described herein, the mammal is not otherwise in need of treatment with the pharmaceutical formulation. In an exemplary embodiment, the mammal is a mouse or a rat. In an exemplary embodiment, the mammal is a human.

The term "$IC_{50}$" refers to the concentration causing a 50% inhibition of the specific binding of the control substance.

The following abbreviations may be used herein:
~ about
+ve or pos. ion positive ion
Δ heat
Ac Acetyl
ACN acetonitrile
$Ac_2O$ acetic anhydride
aq aqueous
AcOH acetic acid
Bn benzyl
Boc tert-butyloxycarbonyl
BOP-Cl Bis(2-oxo-3-oxazolidinyl)phosphinic chloride
BSA bovine serum albumin
Bu butyl
Bz benzoyl
Calcd or Calc'd calculated
Cbz carboxybenzyloxy, benzylcarbamate
Conc. concentrated
δ NMR, chemical shift in parts per million (ppm)
D day(s) or doublet (NMR)
DBU 1,8-diazabicyclo[5.4.0]undec-7-ene
DCE dichloroethane
DCM dichloromethane
DDQ 2,3-dichloro-5,6-dicyano-1,4-benzoquinone
DEA diethylamine
DIEA or DIPEA diisopropylethylamine
DMAP 4-dimethylaminopyridine
DME 1,2-dimethoxyethane
DMF N,N-dimethylformamide
DMP Dess-Martin periodinane; 1,1,1-triacetoxy-1,1-dihydro-1,2-benziodoxol-3(1H)-one
DMSO dimethyl sulfoxide
DPPA Diphenylphosphoryl azide
DRG Dorsal Root Ganglion
EDC or EDCI N-ethyl-N'-(3-dimethylaminopropyl)carbodiimide
EGTA ethylene glycol tetraacetic acid
eq equivalent
ESI or ES electrospray ionization
Et ethyl
$Et_2O$ diethyl ether
$Et_3N$ triethylamine
EtOAc ethyl acetate
EtOH ethyl alcohol
g gram(s)
h hour(s)
HATU O-(7-azabenzotriazol-1-yl)-N,N,N',N'-tetramethyluronium hexafluorophosphate
HBTU O-benzotriazole-N,N,N',N'-tetramethyl-uronium-hexafluorophosphate
HEPES 4-(2-hydroxyethyl)-1-piperazineethanesulfonic acid
Hex hexanes
HMPA hexamethylphosphoramide
HOAt 1-hydroxy-7-azabenzotriazole
HOBT hydroxybenzotriazole
HPLC high pressure liquid chromatography
IPA or iPrOH isopropyl alcohol
KOAc potassium acetate
LCMS, LC-MS or LC/MS liquid chromatography mass spectrometry
LDA lithium diisopropylamide
LHMDS or LiHMDS lithium hexamethyldisilazide
M molar (mol $L^{-1}$)
Me methyl
MeCN acetonitrile
MeI iodomethane
MeOH methyl alcohol
mg milligram(s)
min minute(s)
mL milliliter(s)
M mole(s)
MS mass spectrometry
MsCl methanesulfonyl chloride
MTBE or MtBE methyl tert-butyl ether
m/z mass-to-charge ratio
NaHMDS sodium hexamethyldisilazide
NaOtBu sodium tert-butoxide
NBS N-bromosuccinimide
nBuLi n-butyl lithium
NMO N-methylmorpholine-N-oxide
NMP 1-methyl-2-pyrrolidinone
NMR nuclear magnetic resonance
PBS phosphate buffered saline
PMB paramethoxybenzyl
Pr propyl
Prep-HPLC Preparative high pressure liquid chromatography
ppm parts per million
p-tol para-toluoyl
PTZ pentylenetetrazole
rac racemic
RP-HPLC or RPHPLC reversed phase high pressure liquid chromatography
RT or rt or r.t. room temperature
sat or sat'd or satd Saturated
SNI Spared nerve injury
SNL Spinal nerve ligation
TBAF tetrabutylammonium fluoride
TBDMS tert-butyldimethylsilyl
TBDMS-Cl tert-butyldimethylsilyl chloride
TBDPS tert-butyldiphenylsilyl
TEMPO (2,2,6,6-tetramethylpiperidin-1-yl)oxidanyl
tert or t tertiary
TFA or TFAA triflouroacetic acid
THF tetrahydrofuran
TLC thin layer chromatography
TMS trimethylsilyl or trimethylsilane
tR retention time
tBuOH tert-butyl alcohol
v/v volume per volume In one aspect the invention provides a compound of the invention. In an exemplary embodiment, the invention provides a compound described herein, or a salt thereof. In an exemplary embodiment, the salt of a compound described herein is a pharmaceutically acceptable salt. In an exemplary embodiment, the invention provides a compound described herein, or a pharmaceutically acceptable salt thereof. In an exemplary embodiment, the invention provides a compound described in a formula provided herein. In an exemplary embodiment, the invention provides a compound described herein.

One object of the present invention is to provide a compound, or a pharmaceutically acceptable salt thereof, of the general structure:

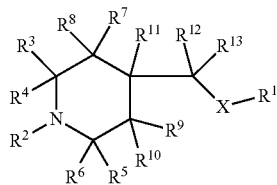

(I)

wherein $R^1$ is substituted or unsubstituted alkyl, substituted or unsubstituted aryl or substituted or unsubstituted heteroaryl; X is selected from —N($R^{14}$)—C(=O)—, or —N($R^{14}$)—S(=O)$_k$—, or —CH$_2$—N($R^{14}$)—C(=O)—, or —CH$_2$—N($R^{14}$)—S(=O)$_k$—, or C(=O)—N($R^{14}$), and —CH$_2$—C(=O)—N($R^{14}$), or CH$_2$—N($R^{14}$); k is selected from 1 and 2; and $R^{14}$ is H or substituted or unsubstituted $C_1$-$C_6$ alkyl or substituted or unsubstituted cycloalkyl, or substituted or unsubstituted heteroalkyl; $R^2$ is selected from substituted or unsubstituted alkyl and substituted or unsubstituted heteroalkyl; $R^3$, $R^4$, $R^5$, $R^6$ are each independently hydrogen, substituted or unsubstituted —$C_{1-6}$ alkyl, substituted or unsubstituted —$C_{1-6}$ haloalkyl, a 3-, 4-, 5- or 6-membered substituted or unsubstituted cycloalkyl or substituted or unsubstituted heterocycloalkyl group, wherein $R^3$ and $R^4$ along with the carbon to which they are attached optionally form a 3- to 6-membered substituted or unsubstituted cycloalkyl or substituted or unsubstituted heterocycloalkyl group, said heterocycloalkyl group optionally containing 1 or 2 heteroatoms independently selected from O, N or S, and said substituted cycloalkyl or substituted heterocycloalkyl group is optionally substituted with 1, 2, or 3 substituents independently selected from F, —$C_{1-6}$ alkyl, and —$CF_3$. $R^5$ and $R^6$, together with the carbon to which they are attached, optionally form a 3-, 4-, 5- or 6-membered substituted or unsubstituted cycloalkyl or substituted or unsubstituted heterocycloalkyl group, said heterocycloalkyl group optionally containing 1 or 2 heteroatoms independently selected from O, N or S, and said cycloalkyl or heterocycloalkyl group is optionally substituted with from 1, 2 or 3 substituents independently selected from F, —$C_{1-6}$ alkyl, and —$CF_3$. $R^7$, $R^8$, $R^9$, and $R^{10}$ are each independently hydrogen, fluorine, substituted or unsubstituted-$C_{1-6}$ alkyl, substituted or unsubstituted-$C_{1-6}$ haloalkyl, a 3-, 4-, 5- or 6-membered substituted or unsubstituted cycloalkyl or substituted or unsubstituted heterocycloalkyl group, wherein $R^7$ and $R^8$, together with the carbon to which they are attached, optionally form a 3-, 4-, 5-, or 6-membered substituted or unsubstituted cycloalkyl or substituted or unsubstituted heterocycloalkyl group, said heterocycloalkyl group optionally containing 1 or 2 heteroatoms independently selected from O, N or S, and said substituted cycloalkyl or substituted heterocycloalkyl group is optionally substituted with 1, 2 or 3 substituents independently selected from F, —$C_{1-6}$ alkyl, or —$CF_3$; $R^9$ and $R^{10}$, together with the carbon to which they are attached, optionally form a 3-, 4-, 5- or 6-membered substituted or unsubstituted cycloalkyl or substituted or unsubstituted heterocycloalkyl group, said heterocycloalkyl group containing from 1 or 2 heteroatoms independently selected from O, N or S, and the substituted cycloalkyl or substituted heterocycloalkyl group is optionally substituted with 1, 2, or 3 substituents independently selected from F, —$C_{1-6}$ alkyl, or —$CF_3$; $R^{11}$, $R^{12}$ and $R^{13}$ are each independently hydrogen, fluorine, substituted or unsubstituted-$C_{1-6}$ alkyl, substituted or unsubstituted-$C_{1-6}$ haloalkyl, a 3-, 4-, 5- or 6-membered substituted or unsubstituted cycloalkyl or substituted or unsubstituted heterocycloalkyl group, wherein $R^{11}$ and either $R^{12}$ or $R^{13}$, together with the carbons to which they are attached, optionally form a 3-, 4-, 5-, 6- or 7-membered substituted or unsubstituted cycloalkyl or substituted or unsubstituted heterocycloalkyl group.

In an exemplary embodiment, wherein $R^2$, $R^3$, $R^4$, $R^5$, $R^6$, $R^7$, $R^8$, $R^9$, $R^{10}$, $R^{11}$, $R^{12}$, $R^{13}$, and X are as described herein, $R^1$ is selected from substituted or unsubstituted benzyl or a substituted or unsubstituted polycyclic cycloalkyl ring, e.g., adamantyl. In an exemplary embodiment, wherein $R^2$, $R^3$, $R^4$, $R^5$, $R^6$, $R^7$, $R^8$, $R^9$, $R^{10}$, $R^{11}$, $R^{12}$, $R^{13}$, and X are as described herein, $R^1$ is substituted adamantyl. In an exemplary embodiment, wherein $R^2$, $R^3$, $R^4$, $R^5$, $R^6$, R, $R^8$, $R^9$, $R^{10}$, $R^{11}$, $R^{12}$, $R^{13}$, and X are as described herein, $R^1$ is substituted adamant-1-yl. In an exemplary embodiment, wherein $R^2$, $R^3$, $R^4$, $R^5$, $R^6$, $R^7$, $R^8$, $R^9$, $R^{10}$, $R^{11}$, $R^{12}$, $R^{13}$, and X are as described herein, $R^1$ is unsubstituted adamantyl. In an exemplary embodiment, wherein $R^2$, $R^3$, $R^4$, $R^5$, $R^6$, $R^7$, $R^8$, $R^9$, $R^{10}$, $R^{11}$, $R^{12}$, $R^{13}$, and X are as described herein, $R^1$ is unsubstituted adamant-1-yl.

In an exemplary embodiment, wherein $R^2$, $R^3$, $R^4$, $R^5$, $R^6$, $R^7$, $R^8$, $R^9$, $R^{10}$, $R^{11}$, $R^{12}$, $R^{13}$, and X are as described herein, $R^1$ is substituted by 1, 2, 3 or 4 non-hydrogen substituents selected from halo, haloalkyl, substituted or unsubstituted alkoxy, and cyano.

In an exemplary embodiment, the compounds of the invention have a structure according to Formula I, wherein $R^2$, $R^3$, $R^4$, $R^5$, $R^6$, $R^7$, $R^8$, $R^9$, $R^{10}$, $R^{11}$, $R^{12}$, $R^{13}$, and X are as described herein, $R^1$ is of the formula:

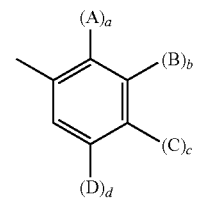

wherein A, B, C and D are independently selected from "aryl group substituents"; and the indices a, b, c, and d are independently selected from 0 and 1.

In an exemplary embodiment, the compounds of the invention have a structure according to Formula I, wherein $R^2$, $R^3$, $R^4$, $R^5$, $R^6$, $R^7$, $R^8$, $R^9$, $R^{10}$, $R^{11}$, $R^{12}$, $R^{13}$, and X are as described herein, A, B, C and D are independently selected from CN, Cl, Br, F, substituted or unsubstituted $C_1$-$C_6$ alkyl, substituted or unsubstituted $C_1$-$C_6$ heteroalkyl, substituted or unsubstituted $C_1$-$C_6$ haloalkyl, and substituted or unsubstituted $C_1$-$C_6$ alkoxy.

In an exemplary embodiment, wherein $R^1$, $R^3$, $R^4$, $R^5$, $R^6$, $R^7$, $R^8$, $R^9$, $R^{10}$, $R^{11}$, $R^{12}$, $R^{13}$, and X are as described herein, $R^2$ is selected from $C_1$-$C_{10}$ straight chain or branched substituted or unsubstituted $C_1$-$C_6$ alkyl, and $C_1$-$C_{10}$ substituted or unsubstituted $C_1$-$C_6$ alkyl heteroalkyl. In an exemplary embodiment, wherein $R^1$, $R^3$, $R^4$, $R^5$, $R^6$, $R^7$, $R^8$, $R^9$, $R^{10}$, $R^{11}$, $R^{12}$, $R^{13}$, and X are as described herein, $R^2$ includes substituted alkyl or substituted heteroalkyl groups, which are substituted with amide, oxo, substituted or unsubstituted aryl or substituted or unsubstituted heterocycloalkyl. Exemplary substituted aryl groups include substituted or unsubstituted phenyl, and an exemplary heterocycloalkyl moiety is an oxygen-containing heterocycle.

In an exemplary embodiment, a compound of the invention has the formula:

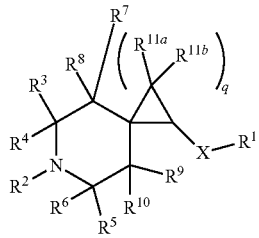

wherein $R^1$, $R^2$, $R^3$, $R^4$, $R^5$, $R^6$, $R^7$, $R^8$, $R^9$, $R^{10}$, $R^{11a}$, $R^{11b}$, and X are as described herein, wherein q is an integer selected from 1, 2, 3, 4 and 5. In an exemplary embodiment, wherein $R^1$, $R^2$, $R^3$, $R^4$, $R^5$, $R^6$, $R^7$, $R^8$, $R^9$, $R^{10}$, and X are as described herein, wherein $R^{11a}$ and $R^{11b}$ are members each independently selected from H, methyl, and fluorine. In an exemplary embodiment, wherein $R^1$, $R^2$, $R^3$, $R^4$, $R^5$, $R^6$, $R^7$, $R^8$, $R^9$, $R^{10}$, and X are as described herein, q is 1, $R^{11a}$ is H and $R^{11b}$ is F. In an exemplary embodiment, wherein $R^1$, $R^2$, $R^3$, $R^4$, $R^5$, $R^6$, $R^7$, $R^8$, $R^9$, $R^{10}$, and X are as described herein, q is 1, $R^{11a}$ is F and $R^{11b}$ is F.

In an exemplary embodiment, a compound of the invention has the formula:

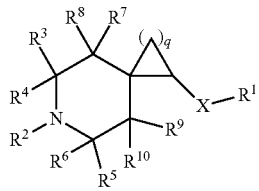

wherein $R^1$, $R^2$, $R^3$, $R^4$, $R^5$, $R^6$, $R^7$, $R^8$, $R^9$, $R^{10}$, and X are as described herein, q is an integer selected from 1, 2, 3, 4 and 5.

In an exemplary embodiment, a compound of the invention has the formula:

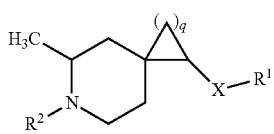

wherein X, $R^1$, and $R^2$ are as described herein, and q is 1 or 2.

In an exemplary embodiment, a compound of the invention has the formula:

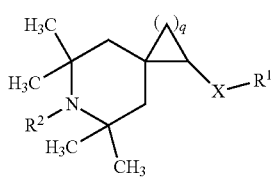

wherein X, $R^1$, and $R^2$ are as described herein, and q is 1 or 2.

In an exemplary embodiment, a compound of the invention has the formula:

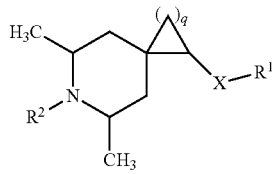

wherein X, $R^1$, and $R^2$ are as described herein, and q is 1 or 2.

In an exemplary embodiment, a compound of the invention has the formula:

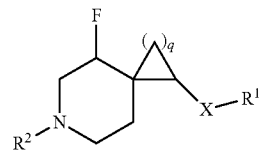

wherein X, $R^1$, and $R^2$ are as described herein, and q is 1 or 2.

In an exemplary embodiment, a compound of the invention has the formula:

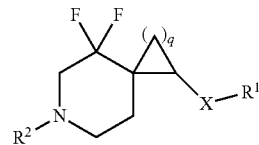

wherein X, $R^1$, and $R^2$ are as described herein, and q is 1 or 2.

In an exemplary embodiment, wherein q, $R^2$, $R^3$, $R^4$, $R^5$, $R^6$, $R^7$, $R^8$, $R^9$, $R^{10}$, and X are as described herein, wherein $R^1$ is substituted or unsubstituted benzyl or substituted or unsubstituted adamantyl. In an exemplary embodiment, wherein q, $R^2$, $R^3$, $R^4$, $R^5$, $R^6$, $R^7$, $R^8$, $R^9$, $R^{10}$, and X are as described herein, wherein $R^1$ is substituted phenyl. In an exemplary embodiment, wherein q, $R^2$, $R^3$, $R^4$, $R^5$, $R^6$, $R^7$, $R^8$, $R^9$, $R^{10}$, and X are as described herein, wherein $R^1$ is unsubstituted phenyl. In an exemplary embodiment, wherein q, $R^2$, $R^3$, $R^4$, $R^5$, $R^6$, $R^7$, $R^8$, $R^9$, $R^{10}$, and X are as described herein, wherein $R^1$ is substituted or unsubstituted adamantyl. In an exemplary embodiment, wherein q, $R^2$, $R^3$, $R^4$, $R^5$, $R^6$, $R^7$, $R^8$, $R^9$, $R^{10}$, and X are as described herein, wherein $R^1$ is

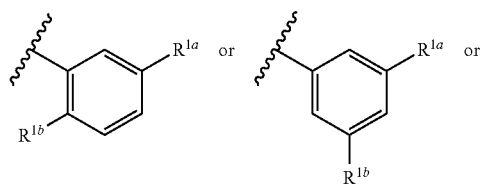

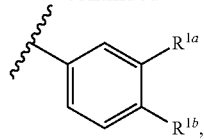

wherein ⸹ represents the covalent link between $R^1$ and X; and $R^{1a}$ and $R^{1b}$ are members each independently selected from halo, haloalkyl, substituted or unsubstituted alkoxy, and cyano. In an exemplary embodiment, wherein q, $R^2$, $R^3$, $R^4$, $R^5$, $R^6$, $R^7$, $R^8$, $R^9$, $R^{10}$, and X are as described herein, wherein $R^1$ is

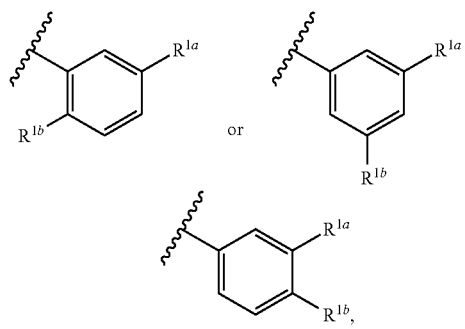

wherein ⸹ represents the covalent link between $R^1$ and X; and $R^{1a}$ and $R^{1b}$ are members each independently selected from F, Cl, Br, $CF_3$, methoxy, methyl, and CN. In an exemplary embodiment, wherein q, $R^2$, $R^3$, $R^4$, $R^5$, $R^6$, $R^7$, $R^8$, $R^9$, $R^{10}$, and X are as described herein, wherein $R^1$ is

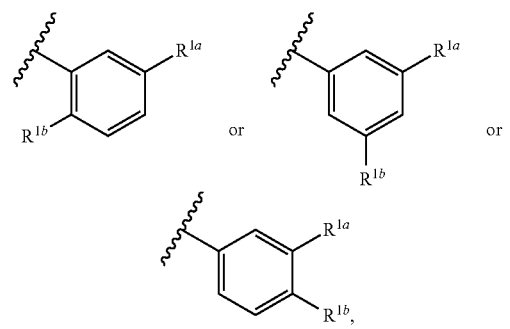

wherein ⸹ represents the covalent link between $R^1$ and X; and $R^{1a}$ and $R^{1b}$ are members each independently selected from F, Cl, and $CF_3$.

In an exemplary embodiment, wherein q, $R^2$, $R^3$, $R^4$, $R^5$, $R^6$, $R^7$, $R^8$, $R^9$, $R^{10}$, and X are as described herein, wherein $R^2$ is substituted or unsubstituted alkyl. In an exemplary embodiment, wherein q, $R^2$, $R^3$, $R^4$, $R^5$, $R^6$, $R^7$, $R^8$, $R^9$, $R^{10}$, and X are as described herein, wherein $R^2$ is substituted or unsubstituted heteroalkyl. In an exemplary embodiment, wherein q, $R^2$, $R^3$, $R^4$, $R^5$, $R^6$, $R^7$, $R^8$, $R^9$, $R^{10}$, and X are as described herein, wherein $R^2$ is

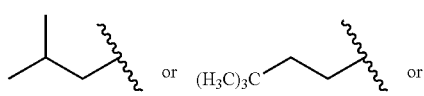

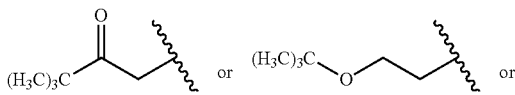

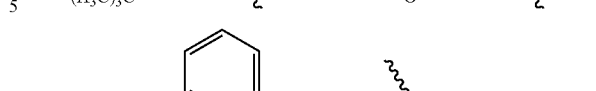

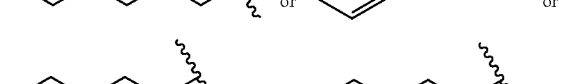

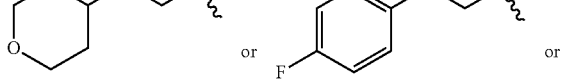

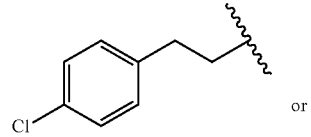

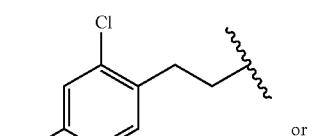

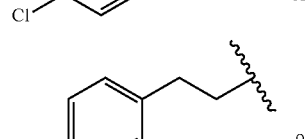

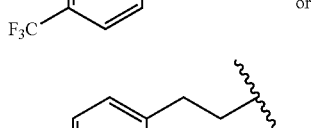

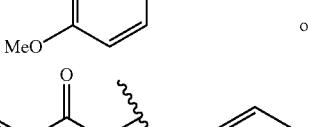

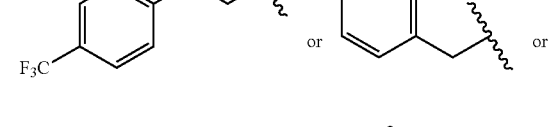

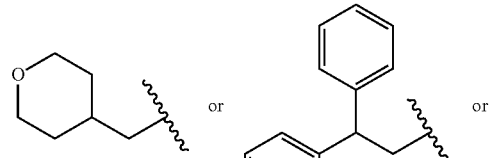

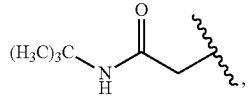

wherein ⸹ represents the covalent link between $R^2$ and the piperidine nitrogen.

In an exemplary embodiment, the compound has the following formula:

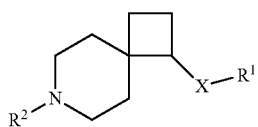

wherein X, R², and R¹ are as described herein.

In an exemplary embodiment, the compound has the following formula:

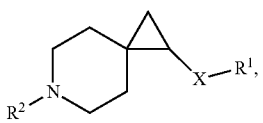

where X, R², and R¹ are as described herein. In an exemplary embodiment, the compound is according to a formula described herein, and R¹ is phenyl substituted with one to three substituents, each of which is a member selected from the group consisting of F, Cl, and CF₃. In an exemplary embodiment, the compound is according to a formula described herein, and R¹ is phenyl substituted with one substituent which is a member selected from the group consisting of F, Cl, and CF₃. In an exemplary embodiment, the compound is according to a formula described herein, and R¹ is phenyl substituted with two substituents which are members each individually selected from the group consisting of F, Cl, and CF₃. In an exemplary embodiment, the compound is according to a formula described herein, and R¹ is phenyl substituted with the substituents which are members each individually selected from the group consisting of F, Cl, and CF₃. In an exemplary embodiment, the compound has the following formula:

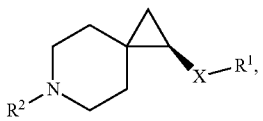

wherein X, R², and R¹ are as described herein. In an exemplary embodiment, the compound has the following formula:

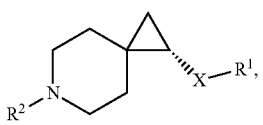

wherein X, R², and R¹ are as described herein.

In an exemplary embodiment, the compound is

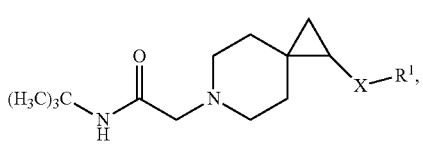

wherein X and R¹ are as described herein. In an exemplary embodiment, the compound is

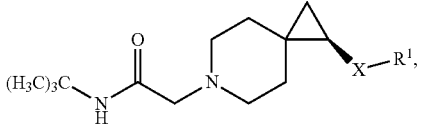

wherein X and R¹ are as described herein. In an exemplary embodiment, the compound is

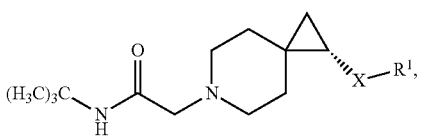

wherein X and R¹ are as described herein. In an exemplary embodiment, the compound is

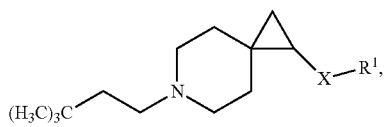

wherein X and R¹ are as described herein. In an exemplary embodiment, the compound is

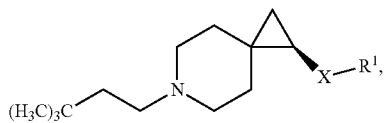

wherein X and R¹ are as described herein. In an exemplary embodiment, the compound is

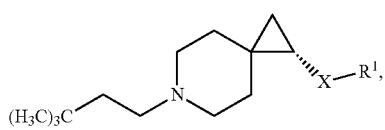

wherein X and R¹ are as described herein.

In an exemplary embodiment, the compound is

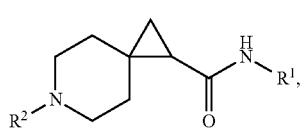

wherein R¹ and R² are as described herein. In an exemplary embodiment, the compound is

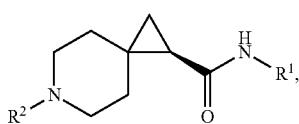

wherein R¹ and R² are as described herein. In an exemplary embodiment, the compound is

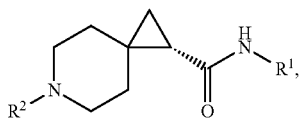

wherein R¹ and R² are as described herein. In an exemplary embodiment, the compound is

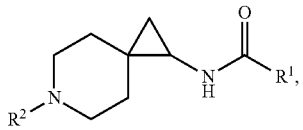

wherein R¹ and R² are as described herein. In an exemplary embodiment, the compound is

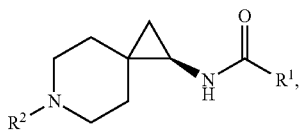

wherein R¹ and R² are as described herein. In an exemplary embodiment, the compound is

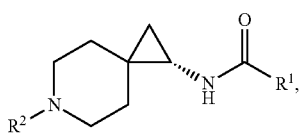

wherein R¹ and R² are as described herein.

In an exemplary embodiment, the compound is

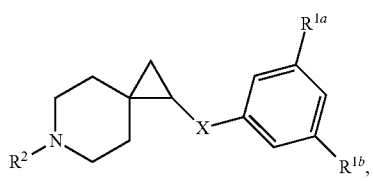

wherein X and R² are as described herein, $R^{1a}$ and $R^{1b}$ are members each independently selected from the group consisting of F, Cl, and $CF_3$.

In an exemplary embodiment, the compound is

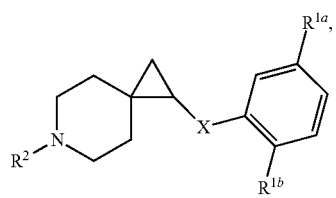

wherein X and R² are as described herein, $R^{1a}$ and $R^{1b}$ are members each independently selected from the group consisting of F, Cl, and $CF_3$.

In an exemplary embodiment, the compound is

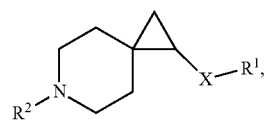

wherein X and R² are as described herein, R¹ is as described herein. In an exemplary embodiment, the compound is

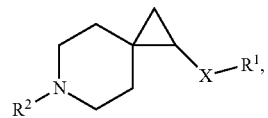

wherein X and R² are as described herein, R¹ is unsubstituted adamantyl. In an exemplary embodiment, the compound is

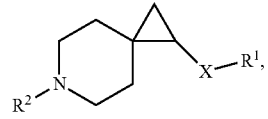

wherein X and R² are as described herein, R¹ is unsubstituted adamant-1-yl.

In an exemplary embodiment, the compound is

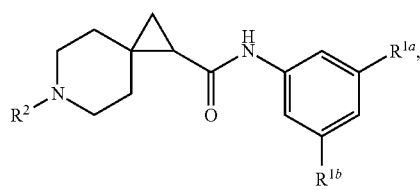

wherein R², $R^{1a}$ and $R^{1b}$ are as described herein. In an exemplary embodiment, the compound is according to a formula described herein which contains $R^{1a}$ and $R^{1b}$, wherein $R^{1a}$ and $R^{1b}$ are members each independently selected from the group consisting of F, Cl, and $CF_3$. In an exemplary embodiment, the compound is according to a formula described herein which contains $R^{1a}$ and $R^{1b}$, wherein $R^{1a}$ and $R^{1b}$ are members each independently selected from the group consisting of F, Cl, and $CF_3$. In an exemplary embodiment, the compound is according to a formula described herein which contains $R^{1a}$ and $R^{1b}$, wherein $R^{1a}$ is as described herein, and $R^{1b}$ is F. In an exemplary embodiment, the compound is according to a formula described herein which contains $R^{1a}$ and $R^{1b}$, wherein $R^{1a}$ is as described herein, and $R^{1b}$ is Cl. In an exemplary embodiment, the compound is according to a formula described herein which contains $R^{1a}$ and $R^{1b}$, wherein $R^{1a}$ is as described herein, and $R^{1b}$ is $CF_3$. In an exemplary embodiment, the compound is according to a formula described herein which contains $R^{1a}$ and $R^{1b}$, wherein $R^{1b}$ is as described herein, and $R^{1a}$ is F. In an exemplary embodiment, the compound is according to a formula described herein which contains $R^{1a}$ and $R^{1b}$, wherein $R^{1b}$ is as described herein, and $R^{1a}$ is Cl. In an exemplary embodiment, the compound is according to a formula described herein which contains $R^{1a}$ and $R^{1b}$, wherein $R^{1b}$ is as described herein, and $R^{1a}$ is $CF_3$. In an exemplary embodiment, the compound is

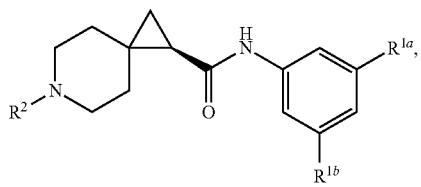

wherein $R^2$, $R^{1a}$ and $R^{1b}$ are as described herein. In an exemplary embodiment, the compound is

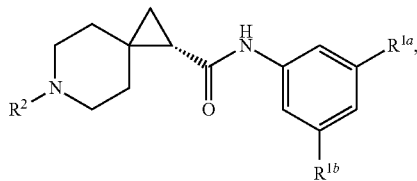

wherein $R^2$, $R^{1a}$ and $R^{1b}$ are as described herein. In an exemplary embodiment, the compound is

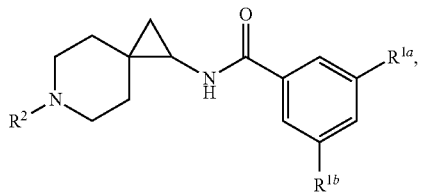

wherein $R^2$, $R^{1a}$ and $R^{1b}$ are as described herein. In an exemplary embodiment, the compound is

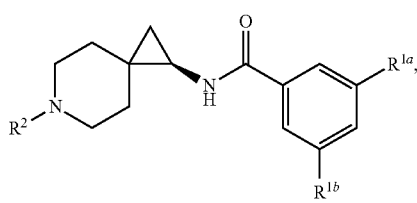

wherein $R^2$, $R^{1a}$ and $R^{1b}$ are as described herein. In an exemplary embodiment, the compound is

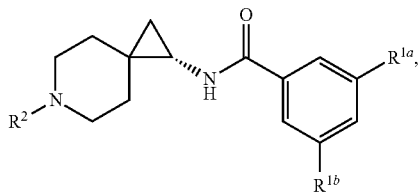

wherein $R^2$, $R^{1a}$ and $R^{1b}$ are as described herein.
In an exemplary embodiment, the compound is

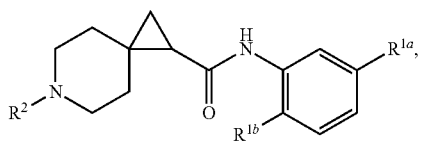

wherein $R^2$, $R^{1a}$ and $R^{1b}$ are as described herein. In an exemplary embodiment, the compound is according to a formula described herein which contains $R^{1a}$ and $R^{1b}$, wherein $R^{1a}$ and $R^{1b}$ are members each independently selected from the group consisting of F, Cl, and $CF_3$. In an exemplary embodiment, the compound is according to a formula described herein which contains $R^{1a}$ and $R^{1b}$, wherein $R^{1a}$ and $R^{1b}$ are members each independently selected from the group consisting of F, Cl, and $CF_3$. In an exemplary embodiment, the compound is according to a formula described herein which contains $R^{1a}$ and $R^{1b}$, wherein $R^{1a}$ is as described herein, and $R^{1b}$ is F. In an exemplary embodiment, the compound is according to a formula described herein which contains $R^{1a}$ and $R^{1b}$, wherein $R^{1a}$ is as described herein, and $R^{1b}$ is Cl. In an exemplary embodiment, the compound is according to a formula described herein which contains $R^{1a}$ and $R^{1b}$, wherein $R^{1a}$ is as described herein, and $R^{1b}$ is $CF_3$. In an exemplary embodiment, the compound is according to a formula described herein which contains $R^{1a}$ and $R^{1b}$, wherein $R^{1b}$ is as described herein, and $R^{1a}$ is F. In an exemplary embodiment, the compound is according to a formula described herein which contains $R^{1a}$ and $R^{1b}$, wherein $R^{1b}$ is as described herein, and $R^{1a}$ is Cl. In an exemplary embodiment, the compound is according to a formula described herein which contains $R^{1a}$ and $R^{1b}$, wherein $R^{1b}$ is as described herein, and $R^{1a}$ is $CF_3$. In an exemplary embodiment, the compound is

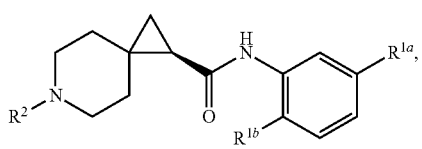

wherein $R^2$, $R^{1a}$ and $R^{1b}$ are as described herein. In an exemplary embodiment, the compound is

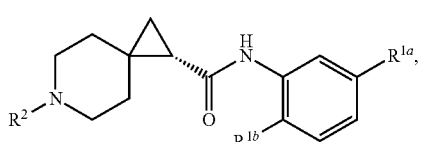

wherein $R^2$, $R^{1a}$ and $R^{1b}$ are as described herein. In an exemplary embodiment, the compound is

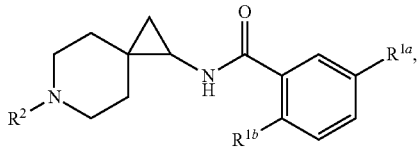

wherein $R^2$, $R^{1a}$ and $R^{1b}$ are as described herein. In an exemplary embodiment, the compound is

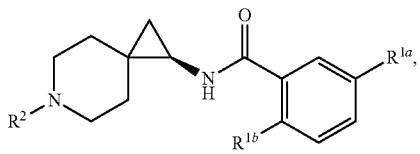

wherein $R^2$, $R^{1a}$ and $R^{1b}$ are as described herein. In an exemplary embodiment, the compound is

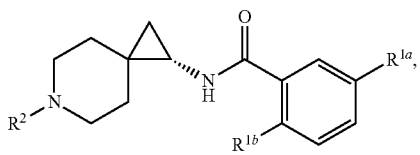

wherein $R^2$, $R^{1a}$ and $R^{1b}$ are as described herein.

In an exemplary embodiment, the compound is

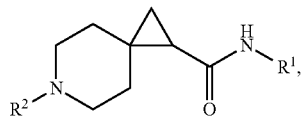

wherein $R^2$ is as described herein, and $R^1$ is unsubstituted adamantyl. In an exemplary embodiment, the compound is

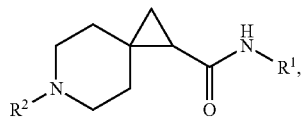

wherein $R^2$ is as described herein, and $R^1$ is unsubstituted adamant-1-yl. In an exemplary embodiment, the compound is

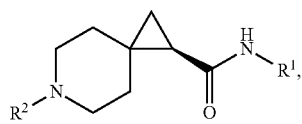

wherein $R^2$ is as described herein, and $R^1$ is unsubstituted adamantyl. In an exemplary embodiment, the compound is

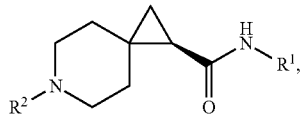

wherein $R^2$ is as described herein, and $R^1$ is unsubstituted adamant-1-yl. In an exemplary embodiment, the compound is

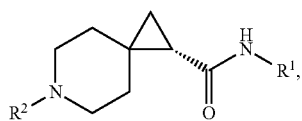

wherein $R^2$ is as described herein, and $R^1$ is unsubstituted adamantyl. In an exemplary embodiment, the compound is

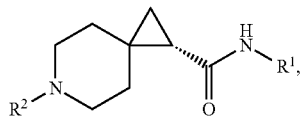

wherein $R^2$ is as described herein, and $R^1$ is unsubstituted adamant-1-yl.

In an exemplary embodiment, the compound is

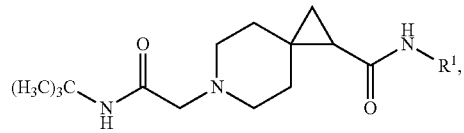

wherein $R^1$ is as described herein. In an exemplary embodiment, the compound is

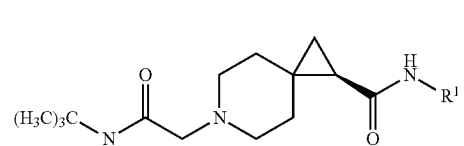

wherein $R^1$ is as described herein. In an exemplary embodiment, the compound is

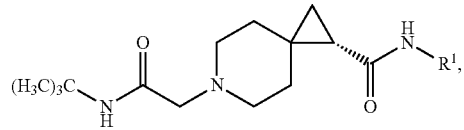

wherein $R^1$ is as described herein. In an exemplary embodiment, the compound is

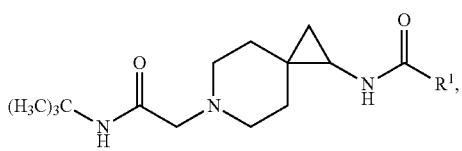

wherein R¹ is as described herein. In an exemplary embodiment, the compound is

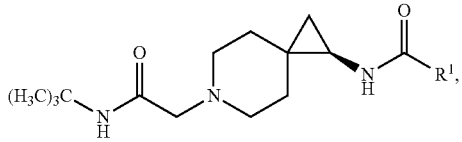

wherein R¹ is as described herein. In an exemplary embodiment, the compound is

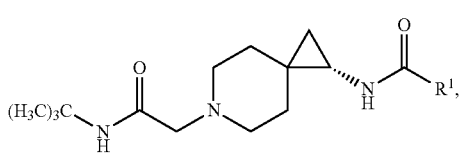

wherein R¹ is as described herein. In an exemplary embodiment, the compound is

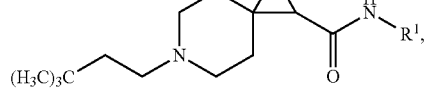

wherein R¹ is as described herein. In an exemplary embodiment, the compound is

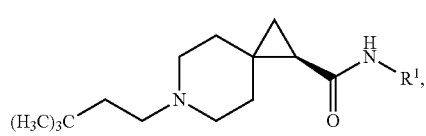

wherein R¹ is as described herein. In an exemplary embodiment, the compound is

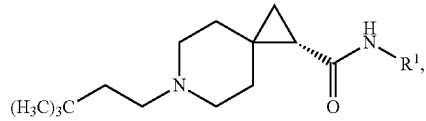

wherein R¹ is as described herein. In an exemplary embodiment, the compound is

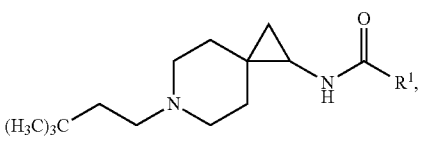

wherein R¹ is as described herein. In an exemplary embodiment, the compound is

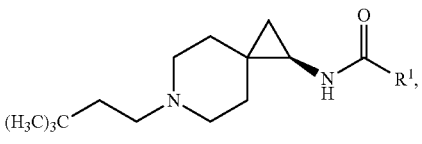

wherein R¹ is as described herein. In an exemplary embodiment, the compound is

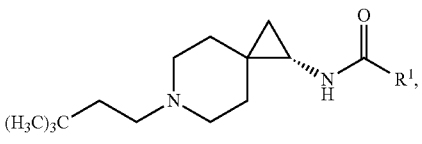

wherein R¹ is as described herein.
In an exemplary embodiment, the compound is

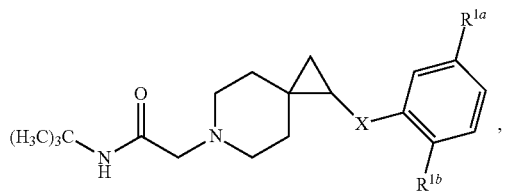

wherein X, R$^{1a}$ and R$^{1b}$ are as described herein. In an exemplary embodiment, the compound is

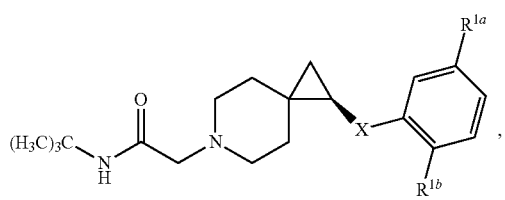

wherein X, R$^{1a}$ and R$^{1b}$ are as described herein. In an exemplary embodiment, the compound is

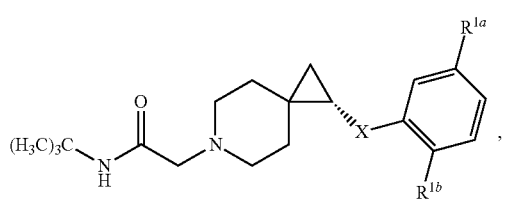

wherein X, R$^{1a}$ and R$^{1b}$ are as described herein.

In an exemplary embodiment, the compound is

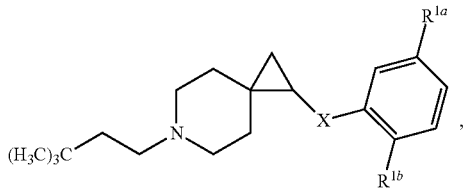

wherein X, $R^{1a}$ and $R^{1b}$ are as described herein. In an exemplary embodiment, the compound is

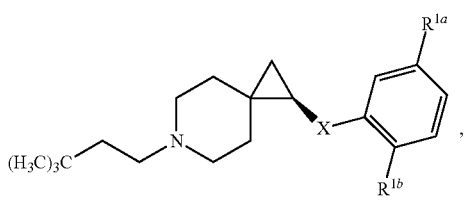

wherein X, $R^{1a}$ and $R^{1b}$ are as described herein. In an exemplary embodiment, the compound is

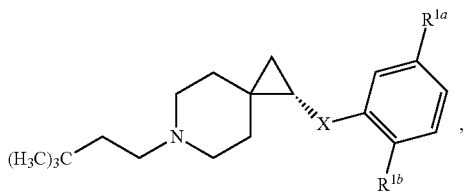

wherein X, $R^{1a}$ and $R^{1b}$ are as described herein.

In an exemplary embodiment, the compound is

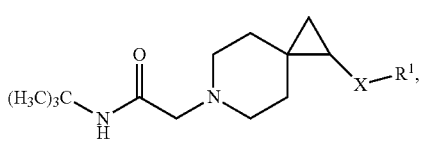

wherein X is as described herein, and $R^1$ is unsubstituted adamantyl. In an exemplary embodiment, the compound is

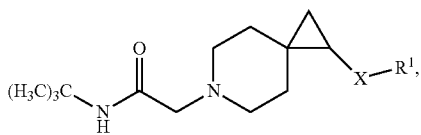

wherein X is as described herein, and $R^1$ is unsubstituted adamant-1-yl. In an exemplary embodiment, the compound is

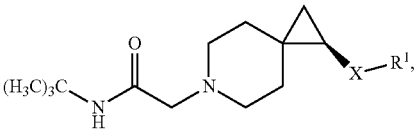

wherein X is as described herein, and $R^1$ is unsubstituted adamantyl. In an exemplary embodiment, the compound is

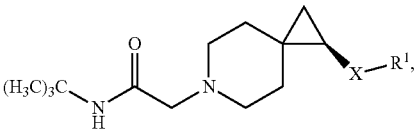

wherein X is as described herein, and $R^1$ is unsubstituted adamant-1-yl. In an exemplary embodiment, the compound is

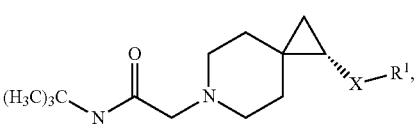

wherein X is as described herein, and $R^1$ is unsubstituted adamantyl. In an exemplary embodiment, the compound is

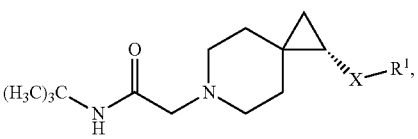

wherein X is as described herein, and $R^1$ is unsubstituted adamant-1-yl. In an exemplary embodiment, the compound is

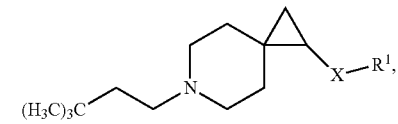

wherein X is as described herein, and $R^1$ is unsubstituted adamantyl. In an exemplary embodiment, the compound is

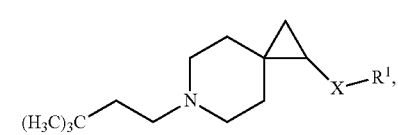

wherein X s as described herein, and $R^1$ is unsubstituted adamant-1-yl. In an exemplary embodiment, the compound is

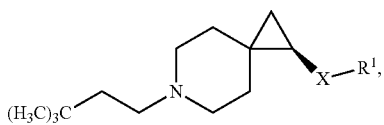

wherein X is as described herein, and R¹ is unsubstituted adamantyl. In an exemplary embodiment, the compound is

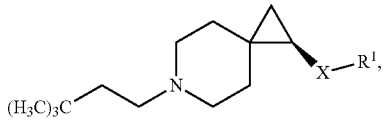

wherein X is as described herein, and R¹ is unsubstituted adamant-1-yl. In an exemplary embodiment, the compound is

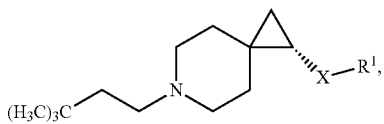

wherein X is as described herein, and R¹ is unsubstituted adamantyl. In an exemplary embodiment, the compound is

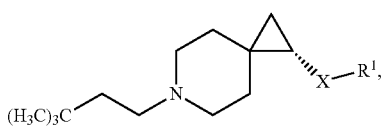

wherein X is as described herein, and R¹ is unsubstituted adamant-1-yl.

In an exemplary embodiment, the compound is

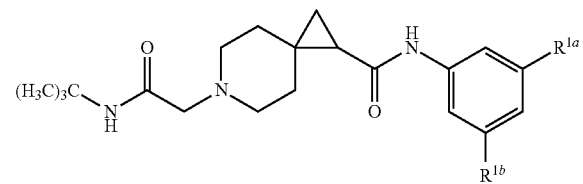

wherein $R^{1a}$ and $R^{1b}$ are members each independently selected from the group consisting of F, Cl, and $CF_3$. In an exemplary embodiment, the compound is

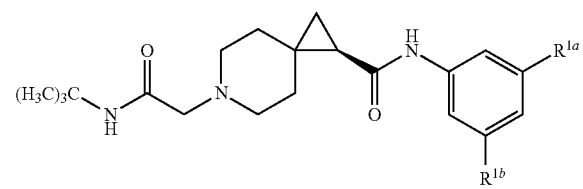

wherein $R^{1a}$ and $R^{1b}$ are members each independently selected from the group consisting of F, Cl, and $CF_3$. In an exemplary embodiment, the compound is

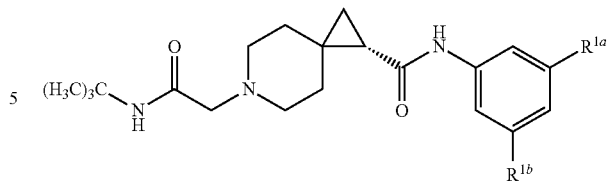

wherein $R^{1a}$ and $R^{1b}$ are members each independently selected from the group consisting of F, Cl, and $CF_3$. In an exemplary embodiment, the compound is

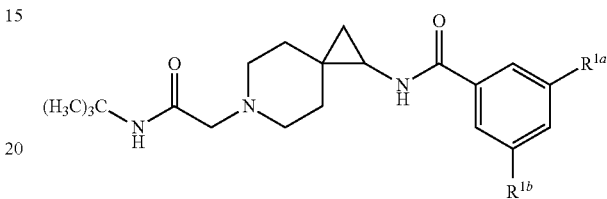

wherein $R^{1a}$ and $R^{1b}$ are members each independently selected from the group consisting of F, Cl, and $CF_3$. In an exemplary embodiment, the compound is

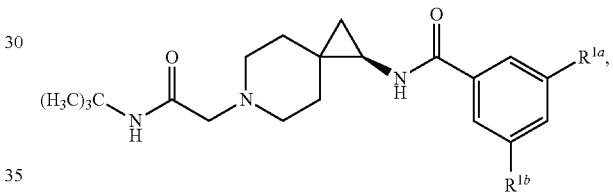

wherein $R^{1a}$ and $R^{1b}$ are members each independently selected from the group consisting of F, Cl, and $CF_3$. In an exemplary embodiment, the compound is

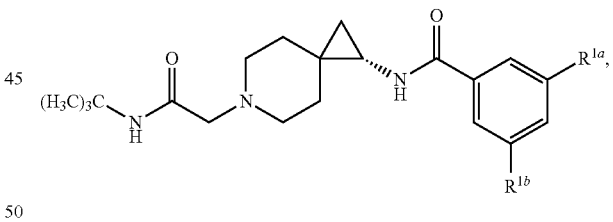

wherein $R^{1a}$ and $R^{1b}$ are members each independently selected from the group consisting of F, Cl, and $CF_3$. In an exemplary embodiment, the compound is

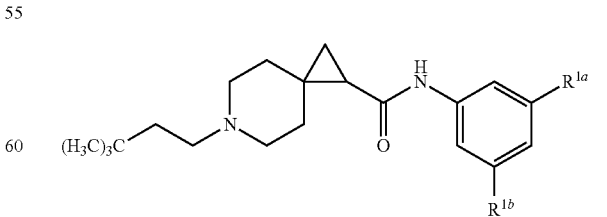

wherein $R^{1a}$ and $R^{1b}$ are members each independently selected from the group consisting of F, Cl, and $CF_3$. In an exemplary embodiment, the compound is

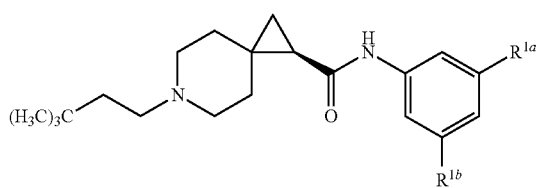

wherein $R^{1a}$ and $R^{1b}$ are members each independently selected from the group consisting of F, Cl, and $CF_3$. In an exemplary embodiment, the compound is

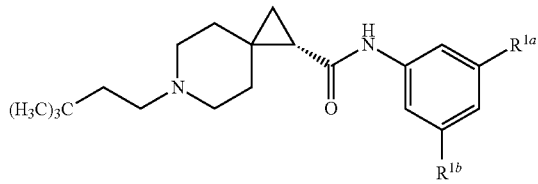

wherein $R^{1a}$ and $R^{1b}$ are members each independently selected from the group consisting of F, Cl, and $CF_3$.
In an exemplary embodiment, the compound is

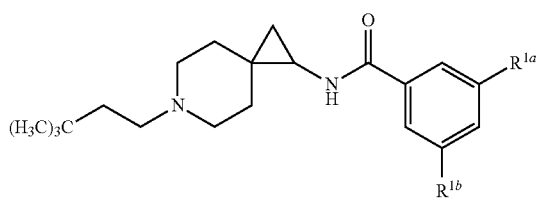

wherein $R^{1a}$ and $R^{1b}$ are members each independently selected from the group consisting of F, Cl, and $CF_3$. In an exemplary embodiment, the compound is

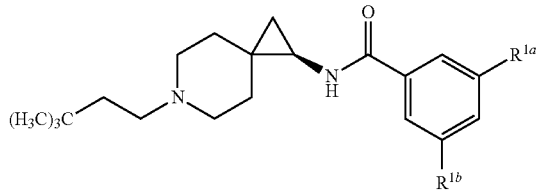

wherein $R^{1a}$ and $R^{1b}$ are members each independently selected from the group consisting of F, Cl, and $CF_3$. In an exemplary embodiment, the compound is

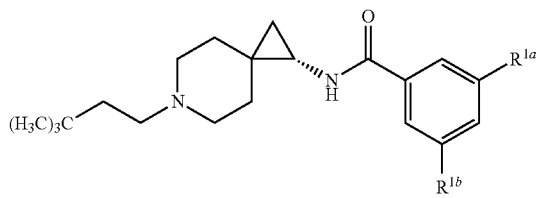

wherein $R^{1a}$ and $R^{1b}$ are members each independently selected from the group consisting of F, Cl, and $CF_3$.

In an exemplary embodiment, the compound is

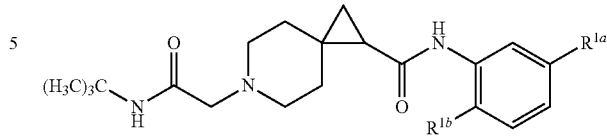

wherein $R^{1a}$ and $R^{1b}$ are members each independently selected from the group consisting of F, Cl, and $CF_3$. In an exemplary embodiment, the compound is

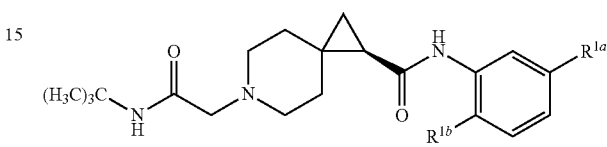

wherein $R^{1a}$ and $R^{1b}$ are members each independently selected from the group consisting of F, Cl, and $CF_3$. In an exemplary embodiment, the compound is

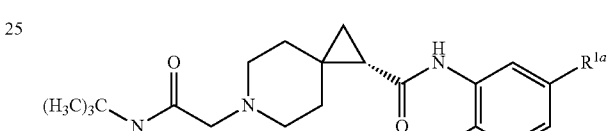

wherein $R^{1a}$ and $R^{1b}$ are members each independently selected from the group consisting of F, Cl, and $CF_3$. In an exemplary embodiment, the compound is

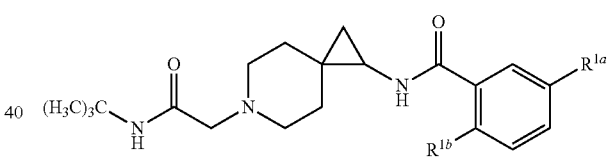

wherein $R^{1a}$ and $R^{1b}$ are members each independently selected from the group consisting of F, Cl, and $CF_3$. In an exemplary embodiment, the compound is

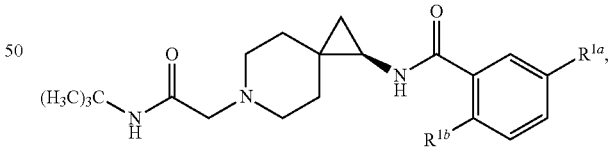

wherein $R^{1a}$ and $R^{1b}$ are members each independently selected from the group consisting of F, Cl, and $CF_3$. In an exemplary embodiment, the compound is

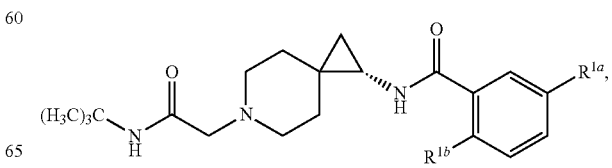

wherein $R^{1a}$ and $R^{1b}$ are members each independently selected from the group consisting of F, Cl, and $CF_3$. In an exemplary embodiment, the compound is

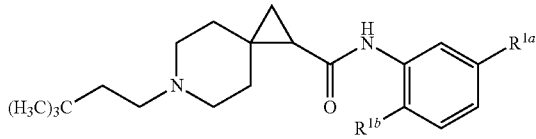

wherein $R^{1a}$ and $R^{1b}$ are members each independently selected from the group consisting of F, Cl, and $CF_3$. In an exemplary embodiment, the compound is

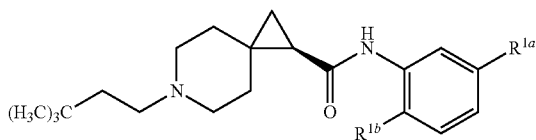

wherein $R^{1a}$ and $R^{1b}$ are members each independently selected from the group consisting of F, Cl, and $CF_3$. In an exemplary embodiment, the compound is

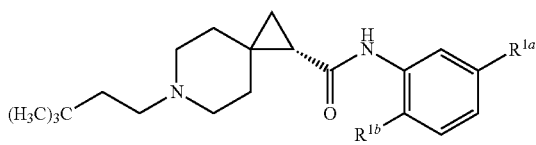

wherein $R^{1a}$ and $R^{1b}$ are members each independently selected from the group consisting of F, Cl, and $CF_3$. In an exemplary embodiment, the compound is

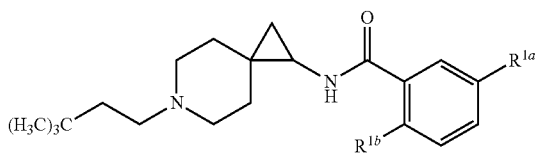

wherein $R^{1a}$ and $R^{1b}$ are members each independently selected from the group consisting of F, Cl, and $CF_3$. In an exemplary embodiment, the compound is

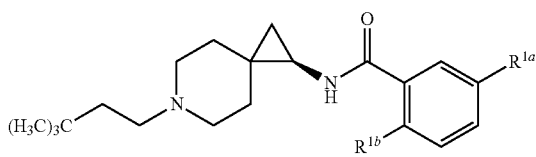

wherein $R^{1a}$ and $R^{1b}$ are members each independently selected from the group consisting of F, Cl, and $CF_3$. In an exemplary embodiment, the compound is

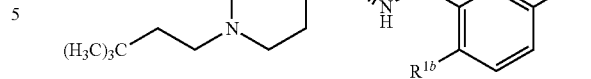

wherein $R^{1a}$ and $R^{1b}$ are members each independently selected from the group consisting of F, Cl, and $CF_3$.

In an exemplary embodiment, the compound is

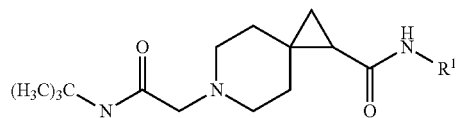

wherein $R^1$ is unsubstituted adamantyl. In an exemplary embodiment, the compound is

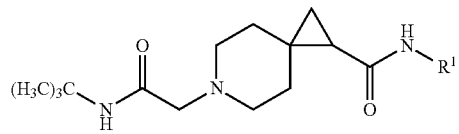

wherein $R^1$ is unsubstituted adamant-1-yl. In an exemplary embodiment, the compound is

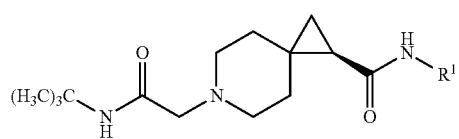

wherein $R^1$ is unsubstituted adamantyl. In an exemplary embodiment, the compound is

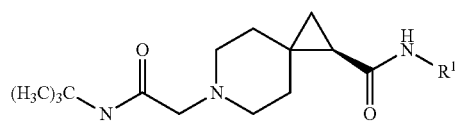

wherein $R^1$ is unsubstituted adamant-1-yl. In an exemplary embodiment, the compound is

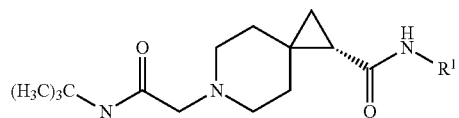

wherein $R^1$ is unsubstituted adamantyl. In an exemplary embodiment, the compound is

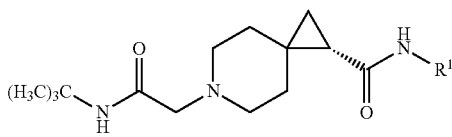

wherein R¹ is unsubstituted adamant-1-yl. In an exemplary embodiment, the compound is

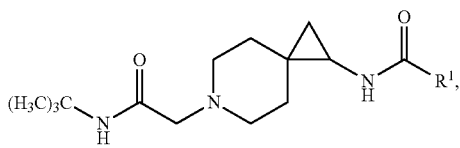

wherein R¹ is unsubstituted adamantyl. In an exemplary embodiment, the compound is

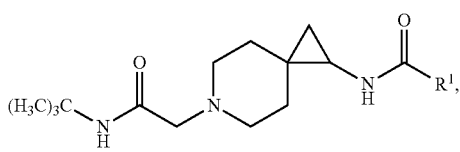

wherein R¹ is unsubstituted adamant-1-yl.
In an exemplary embodiment, the compound is

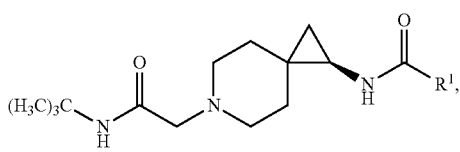

wherein R¹ is unsubstituted adamantyl. In an exemplary embodiment, the compound is

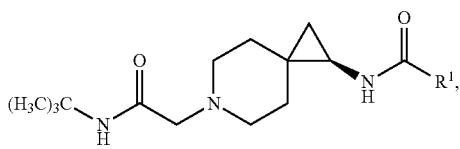

wherein R¹ is unsubstituted adamant-1-yl.
In an exemplary embodiment, the compound is

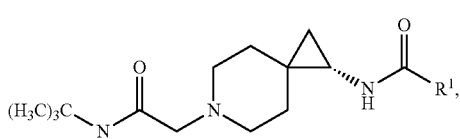

wherein R¹ is unsubstituted adamantyl. In an exemplary embodiment, the compound is

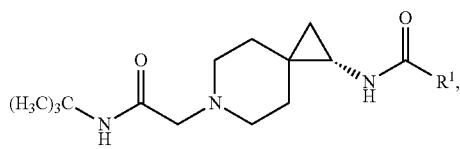

wherein R¹ is unsubstituted adamant-1-yl.
In an exemplary embodiment, the compound is

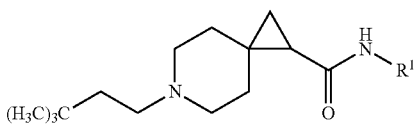

wherein R¹ is unsubstituted adamantyl. In an exemplary embodiment, the compound is

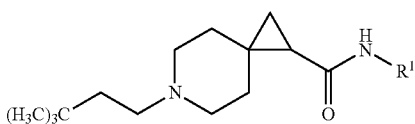

wherein R¹ is unsubstituted adamant-1-yl. In an exemplary embodiment, the compound is

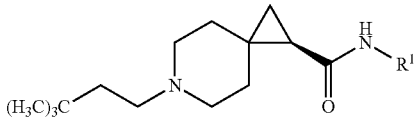

wherein R¹ is unsubstituted adamantyl. In an exemplary embodiment, the compound is

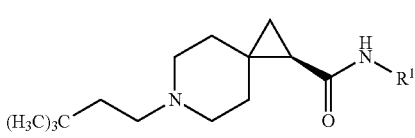

wherein R¹ is unsubstituted adamant-1-yl.
In an exemplary embodiment, the compound is

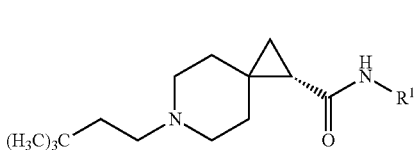

wherein R¹ is unsubstituted adamantyl. In an exemplary embodiment, the compound is

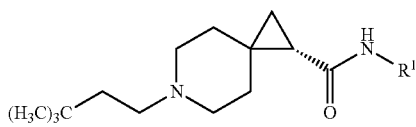

(wherein R¹ is unsubstituted adamant-1-yl. In an exemplary embodiment, the compound is

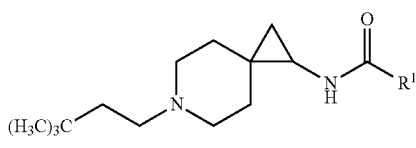

wherein R¹ is unsubstituted adamantyl. In an exemplary embodiment, the compound is

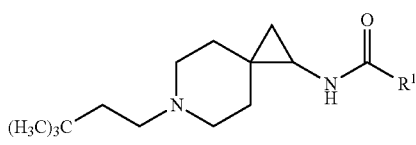

wherein R¹ is unsubstituted adamant-1-yl. In an exemplary embodiment, the compound is

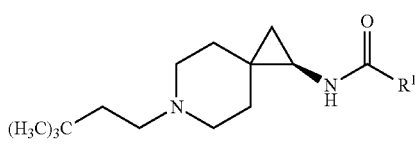

wherein R¹ is unsubstituted adamantyl. In an exemplary embodiment, the compound is

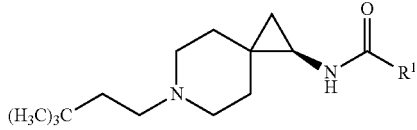

wherein R¹ is unsubstituted adamantyl. In an exemplary embodiment, the compound is

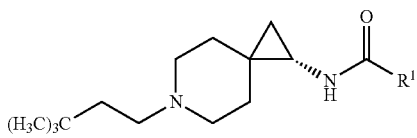

wherein R¹ is unsubstituted adamant-1-yl.

In an exemplary embodiment, the compound is

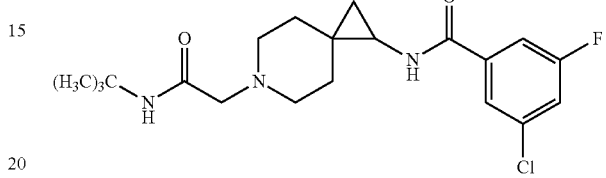

or a pharmaceutically acceptable salt thereof. In an exemplary embodiment, the compound is

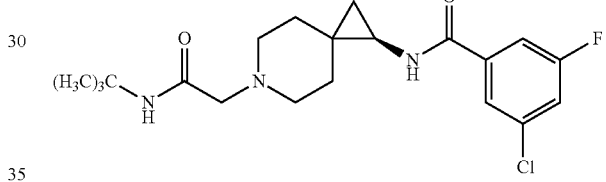

or a pharmaceutically acceptable salt thereof. In an exemplary embodiment, the compound is

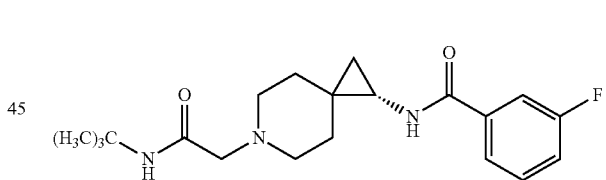

or a pharmaceutically acceptable salt thereof.

In an exemplary embodiment, the compound is

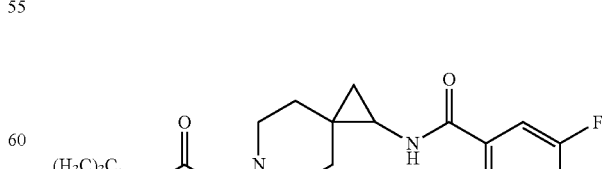

or a pharmaceutically acceptable salt thereof.

In an exemplary embodiment, the compound is

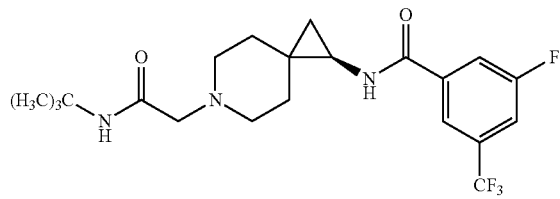 [SMILES: CC(C)(C)NC(=O)CN1CCC2(CC1)C[C@H]2NC(=O)c1cc(F)cc(C(F)(F)F)c1]

or a pharmaceutically acceptable salt thereof. In an exemplary embodiment, the compound is

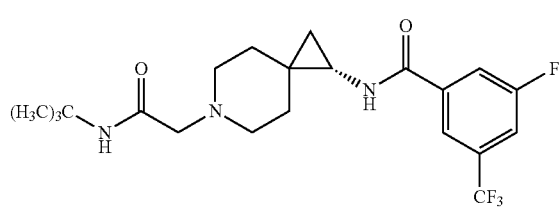 [SMILES: CC(C)(C)NC(=O)CN1CCC2(CC1)C[C@@H]2NC(=O)c1cc(F)cc(C(F)(F)F)c1]

or a pharmaceutically acceptable salt thereof.

In an exemplary embodiment, the compound is

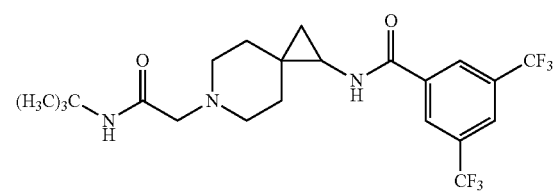

or a pharmaceutically acceptable salt thereof. In an exemplary embodiment, the compound is

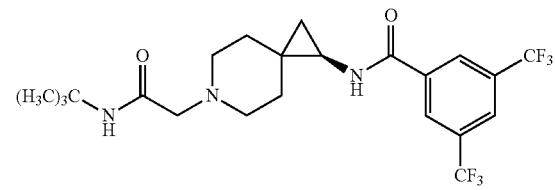 [SMILES: CC(C)(C)NC(=O)CN1CCC2(CC1)C[C@H]2NC(=O)c1cc(C(F)(F)F)cc(C(F)(F)F)c1]

or a pharmaceutically acceptable salt thereof. In an exemplary embodiment, the compound is

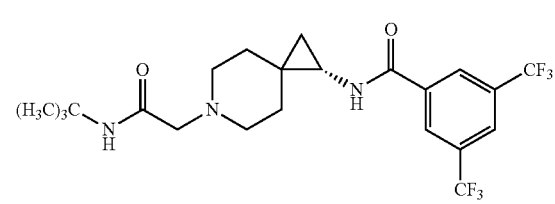 [SMILES: CC(C)(C)NC(=O)CN1CCC2(CC1)C[C@@H]2NC(=O)c1cc(C(F)(F)F)cc(C(F)(F)F)c1]

or a pharmaceutically acceptable salt thereof.

In an exemplary embodiment, the compound is

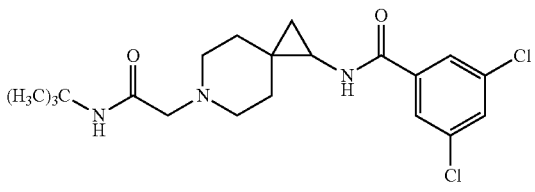 [SMILES: CC(C)(C)NC(=O)CN1CCC2(CC1)CC2NC(=O)c1cc(Cl)cc(Cl)c1]

or a pharmaceutically acceptable salt thereof. In an exemplary embodiment, the compound is

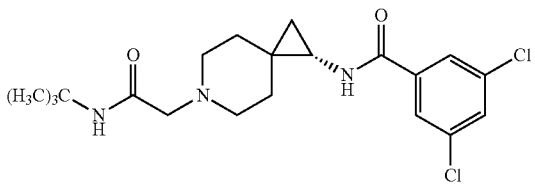

or a pharmaceutically acceptable salt thereof. In an exemplary embodiment, the compound is

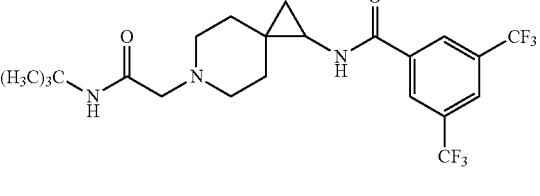

or a pharmaceutically acceptable salt thereof.

In an exemplary embodiment, the compound is

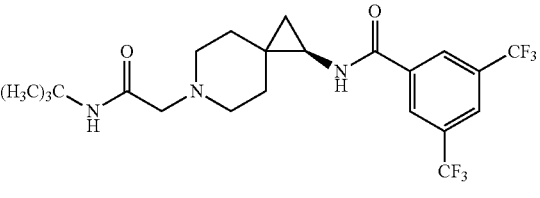 [SMILES: CC(C)(C)NC(=O)CN1CCC2(CC1)C[C@H]2NC(=O)c1cc(C(F)(F)F)cc(C(F)(F)F)c1]

or a pharmaceutically acceptable salt thereof. In an exemplary embodiment, the compound is or a pharmaceutically acceptable salt thereof.

In an exemplary embodiment, the compound is or a pharmaceutically acceptable salt thereof. In an exemplary embodiment, the compound is or a pharmaceutically acceptable salt thereof. In an exemplary embodiment, the compound is or a pharmaceutically acceptable salt thereof.

In an exemplary embodiment, the compound is or a pharmaceutically acceptable salt thereof. In an exemplary embodiment, the compound is or a pharmaceutically acceptable salt thereof. In an exemplary embodiment, the compound is or a pharmaceutically acceptable salt thereof.

In an exemplary embodiment, the compound is or a pharmaceutically acceptable salt thereof. In an exemplary embodiment, the compound is or a pharmaceutically acceptable salt thereof. In an exemplary embodiment, the compound is or a pharmaceutically acceptable salt thereof.

In exemplary embodiment, the compound is

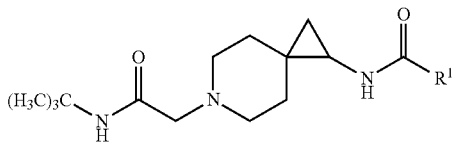

or a pharmaceutically acceptable salt thereof, wherein R¹ is unsubstituted adamant-1-yl. In an exemplary embodiment, the compound is

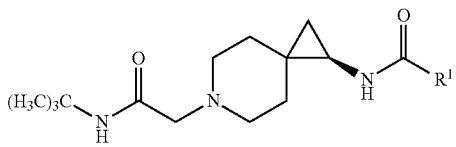

or a pharmaceutically acceptable salt thereof, wherein R¹ is unsubstituted adamant-1-yl. In an exemplary embodiment, the compound is

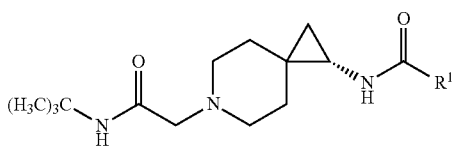

or a pharmaceutically acceptable salt thereof, wherein R¹ is unsubstituted adamant-1-yl.

In an exemplary embodiment, the compound is

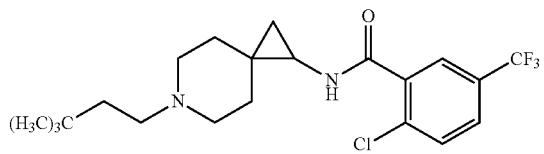 [SMILES: CC(C)(C)CCN1CCC2(CC1)CC2NC(=O)c1cc(C(F)(F)F)ccc1Cl]

or a pharmaceutically acceptable salt thereof. In an exemplary embodiment, the compound is

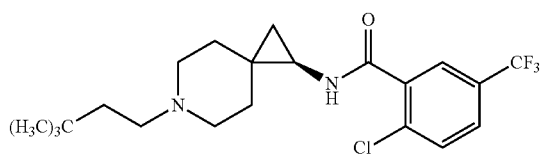 [SMILES: CC(C)(C)CCN1CCC2(CC1)C[C@H]2NC(=O)c1cc(C(F)(F)F)ccc1Cl]

or a pharmaceutically acceptable salt thereof. In an exemplary embodiment, the compound is

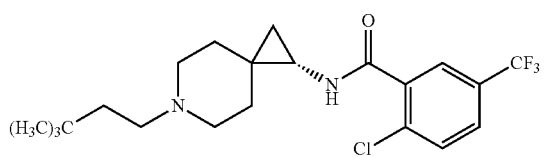 [SMILES: CC(C)(C)CCN1CCC2(CC1)C[C@@H]2NC(=O)c1cc(C(F)(F)F)ccc1Cl]

or a pharmaceutically acceptable salt thereof.

The invention is of a scope including any compound disclosed herein whether it is or is not covered by Formula I.

The invention also provides a pharmaceutical formulation comprising a therapeutically effective amount of a compound according to Formula I or individually disclosed herein. The formulation further includes a pharmaceutically acceptable carrier.

The invention also provides a method for treating pain responsive to selective inhibition of the T Channel known as the $Ca_{v3.2}$ channel comprising administering to a mammal a therapeutically effective amount of a compound according to Formula I or individually disclosed herein.

The present invention provides compounds which are selective T-Channel inhibitory compounds useful for relief of neuropathic and/or inflammatory pain, and epilepsy.

The invention also includes, where chemically possible, all stereoisomers and geometric isomers of the compounds, including diastereomers, enantiomers, and cis/trans (E/Z) isomers. The invention also includes mixtures of stereoisomers and/or geometric isomers in any ratio, including, but not limited to, racemic mixtures. Unless stereochemistry is explicitly indicated in a structure, the structure is intended to embrace all possible stereoisomers of the compound depicted. If stereochemistry is explicitly indicated for one portion or portions of a molecule, but not for another portion or portions of a molecule, the structure is intended to embrace all possible stereoisomers for the portion or portions where stereochemistry is not explicitly indicated.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention. Unless a specific isotope is indicated, the invention includes all isotopologues of the compounds disclosed herein, such as, for example, deuterated derivatives of the compounds (where H can be $^2$H, i.e., D).

In the context of the present invention, compounds that are considered to possess activity as T-Channel inhibitors are those displaying 50% inhibition of the $Ca^{++}$ voltage ($IC_{50}$) at a concentration of not higher than about 100 μM, preferably, not higher than about 10 μM, more preferably not higher than about 1 μM and most preferably not higher than about 100 nM.

Chemical Synthesis

Terminology related to "protecting", "deprotecting" and "protected" functionalities occurs throughout this application. Such terminology is well understood by persons of skill in the art and is used in the context of processes that involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as "Greene's Protective Groups in Organic Synthesis: Fifth Edition" by Peter G. M. Wuts, [John Wiley & Sons, New York, 2014], DOI: 10.1002/9781118905074, which is incorporated herein by reference.

A comprehensive list of abbreviations utilized by organic chemists appears in the first issue of each volume of the *Journal of Organic Chemistry*. The list, which is typically presented in a table entitled "Standard List of Abbreviations", is incorporated herein by reference.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here. The starting materials, for example in the case of suitably substituted benzimidazole ring compounds, are either commercially available, synthesized as described in the examples or may be obtained by the methods well known to persons of skill in the art.

Pharmaceutical Formulations

The present invention further provides pharmaceutical formulations comprising as active agents, the compounds described herein.

In an exemplary embodiment, the invention is a pharmaceutical formulation comprising a therapeutically effective amount of a compound described herein, or a pharmaceutically acceptable salt thereof. In an exemplary embodiment, the invention is a pharmaceutical formulation comprising a therapeutically effective amount of a compound of a formula described herein, or a pharmaceutically acceptable salt thereof.

In an exemplary embodiment, the invention is a pharmaceutical formulation comprising a therapeutically effective amount of a compound described herein, or a pharmaceutically acceptable salt thereof, and a pharmaceutically acceptable carrier. In an exemplary embodiment, the invention is a pharmaceutical formulation comprising a therapeutically effective amount of a compound of a formula described herein, or a pharmaceutically acceptable salt thereof, and a pharmaceutically acceptable carrier.

In an exemplary embodiment, the invention is a pharmaceutical formulation described herein, wherein the formulation is in a unit dosage form.

As used herein a "pharmaceutical formulation" refers to a preparation of one or more of the compounds described herein, or physiologically acceptable salts or solvates (including hydrates) thereof, with other chemical components such as physiologically suitable carriers and excipients.

Pharmaceutical formulations containing compounds of Formulas I, and, any compound described herein may be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof. The magnitude of a prophylactic or therapeutic dose typically varies with the nature and severity of the condition to be treated and the route of administration. The dose, and perhaps the dose frequency, will also vary according to the age, body weight and response of the individual patient. In general, a dose ranges from about 0.1 mg to about 7000 mg, preferably about 1 mg to about 100 mg, and more preferably, about 25 mg to about 50 mg, in single or divided doses. In some embodiments, a dose may range from about 50 mg to about 500 mg, and preferably, about 100 mg to about 500 mg. Such doses may be administered 1, 2, 3, 4, 5, 6 or more times in a day. It may be recommended that children, patients over 65 years old, and those with impaired renal or hepatic function, initially receive low doses and that the dosage is titrated based on individual responses and/or blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

Pharmaceutical formulations for use in accordance with the present invention thus may be formulated in a conventional manner using one or more physiologically acceptable carriers comprising excipients and auxiliaries, which facilitate processing of the active compounds into preparations which, can be used pharmaceutically. The carriers must be acceptable in the sense of being compatible with the other ingredients of the formulation and not deleterious to the recipient thereof. Proper formulation is dependent upon the route of administration chosen.

Compounds that inhibit T-Channels can be formulated as pharmaceutical formulations and administered to a mammalian subject, such as a human patient in a variety of forms adapted to the chosen route of administration, i.e., oral, rectal, topical (including dermal, buccal, sublingual, and intraocular), or parenteral, by intravenous, intramuscular, topical, transdermal, intradermal, intraarticular, or subcutaneous routes.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as crosslinked polyvinyl pyrrolidone, agar or alginic acid or a salt thereof such as sodium alginate.

In addition, an enteric coating may be useful as it is may be desirable to prevent exposure of the compounds of the invention to the gastric environment.

Pharmaceutical formulations, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia. All formulations for oral administration should be in dosages suitable for the chosen route of administration.

For injection, the compounds of the invention may be formulated in aqueous solutions, preferably in physiologically compatible buffers such as Hank's or Ringer's solution or physiological saline buffer. For transmucosal and transdermal administration, penetrants appropriate to the barrier to be permeated may be used in the formulation. Such penetrants, including for example DMSO or polyethylene glycol, are known in the art.

For administration by inhalation, the compounds for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Pharmaceutical formulations for parenteral administration include aqueous and non-aqueous sterile injection solutions, which may contain anti-oxidants, buffers, bacteriostats and solutes, which render the formulation isotonic with the blood of the intended recipient. Formulations also include aqueous and non-aqueous sterile suspensions, which may include suspending agents and thickening agents. Pharmaceutical formulations for parenteral administration in an aqueous solution contain the active ingredients in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds, to allow for the preparation of highly concentrated solutions.

The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

The compounds of the present invention may also be formulated in rectal formulations such as suppositories or retention enemas, using, e.g., conventional suppository bases such as cocoa butter, polyethylene glycol, or other glycerides.

Depending on the severity and responsiveness of the condition to be treated, dosing can also be a single administration of a slow release formulations, with course of treatment lasting from several days to several weeks or until cure is effected or diminution of the disease state is achieved. The amount of a formulation to be administered will, of course, be dependent on many factors including the subject being treated, the severity of the affliction, the manner of administration, the judgment of the prescribing physician. The compounds of the invention may be administered orally or via injection at a dose from 0.001 to 250 mg/kg per day. The dose range for adult humans is generally from 0.5 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As used herein, and as would be understood by the person of skill in the art, the recitation of "a compound" is intended to include salts, solvates and inclusion complexes of that compound. The term "solvate" refers to a compound described herein and/or from Formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Inclusion complexes are described in Remington: The Science and Practice of Pharmacy 19th Ed. (1995) volume 1, page 176-177, which is incorporated herein by reference. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenedi amine, meglumine (N-methylglucamine) and procaine.

The term "preventing" as used herein refers to administering a medicament beforehand to forestall or obtund an attack. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended herein.

It should be understood that in addition to the ingredients particularly mentioned above, the formulations of this invention may include other agents conventional in the art having regard to the type of formulation in question, for example those suitable for oral administration may include flavoring agents.

The formulations may be presented in a packaging device or dispenser, which may contain one or more unit dosage forms containing the active ingredient. Examples of a packaging device include metal or plastic foil, such as a blister pack and a nebulizer for inhalation. The packaging device or dispenser may be accompanied by instructions for administration. Formulations comprising a compound of the present invention formulated in a compatible pharmaceutical carrier may also be placed in an appropriate container and labeled for treatment of an indicated condition.

The following examples are provided to illustrate, but not limit, the invention.

EXAMPLES

Synthetic Examples

Example 01

N-(6-Isobutyl-6-azaspiro[2.5]octan-1-yl)benzamide

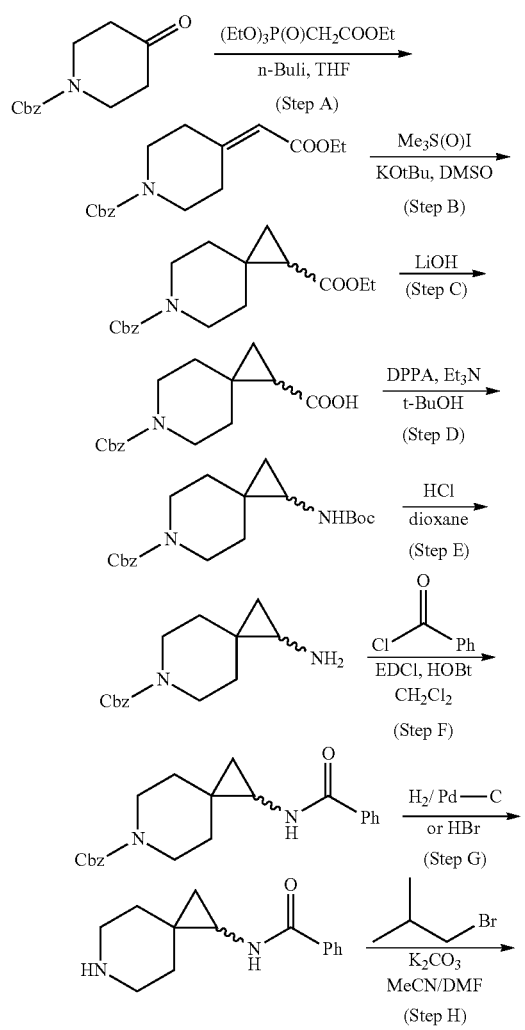

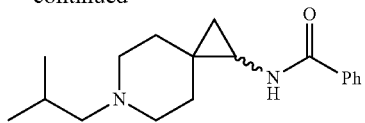

Step A.

To ethyl 2-(diethoxyphosphoryl)acetate (4.68 mL, 23.38 mmol) in THF (50 mL) at −78° C. was added n-BuLi (2.5M in hexanes, 9.43 mL, 23.58 mmol) and the reaction mixture was stirred for 10 min. To this mixture was added benzyl 4-oxopiperidine-1-carboxylate (5.00 g, 21.44 mmol) and the mixture was allowed to warm to RT and stirred for 30 min. The solvent was removed and the resulting solids were triturated with 100 mL hexanes. The mixture was filtered through Celite® (J.T. Baker, Phillipsberg, N.J., diatomaceous earth). The filtrate was concentrated in vacuo and the resulting oil dried under high vacuum to give benzyl 4-(2-ethoxy-2-oxoethylidene)piperidine-1-carboxylate (5.52 g, 85% yield) as a clear oil which was carried forward without further purification. Mass Spectrum (ESI) m/z=326 (M+23). $^1$H NMR (400 MHz, CDCl$_3$) δ ppm 1.28 (t, J=6.95 Hz, 3H) 2.30 (t, J=5.27 Hz, 2H) 2.96 (t, J=5.69 Hz, 2H) 3.57 (q, J=6.32 Hz, 4H) 4.15 (q, J=7.17 Hz, 2H) 5.15 (s, 2H) 5.72 (s, 1H) 7.28-7.47 (m, 5H).

Step B.

Potassium tert-butoxide (8.43 g, 75.1 mmol) was added to a solution of trimethylsulfoxonium iodide (17.5 g, 79.5 mmol) in DMSO (100 mL) in one portion. The mixture was stirred at RT for 2 h, after which benzyl 4-(2-ethoxy-2-oxoethylidene)piperidine-1-carboxylate (13.4 g, 44.2 mmol) in DMSO (50 mL) was added. The mixture was stirred at RT overnight and then slowly added to a sat. aq. NH$_4$Cl solution at 0° C. with stirring. The mixture was extracted with ether. The combined organic layers were washed with sat. aq. NaHCO$_3$ solution and concentrated under reduced pressure. The residue was taken up in EtOAc (100 mL). Aqueous KMnO$_4$ (2.0 g in 200 mL H$_2$O) and NaHCO$_3$ (1.5 g) were added and the mixture was stirred overnight. The mixture was then filtered through Celite® (J.T. Baker, Phillipsberg, N.J., diatomaceous earth) and extracted with EtOAc. The organic layer was washed with brine and dried over Na$_2$SO$_4$. The crude residue was purified by silica gel column chromatography (hexanes:EtOAc 5:1 to 4:1) to afford 6-benzyl 1-ethyl 6-azaspiro[2.5]octane-1,6-dicarboxylate (10.52 g, 75% yield). Mass Spectrum (ESI) m/z=340 (M+23). $^1$H NMR (400 MHz, CDCl$_3$): δ ppm 0.93 (1H, dd, J=8.0, 4.6 Hz), 1.17 (1H, t, J=5.0 Hz), 1.26 (3H, t, J=7.1 Hz), 1.40-1.46 (2H, m), 1.56 (1H, dd, J=8.0, 5.4 Hz), 1.69-1.74 (2H, m), 3.31-3.39 (1H, m), 3.46-3.61 (3H, m), 4.13 (2H, q, J=7.1 Hz), 5.13 (2H, s), 7.30-7.36 (5H, m).

Step C.

6-Benzyl 1-ethyl 6-azaspiro[2.5]octane-1,6-dicarboxylate (4.06 mmol, 1.29 g) was dissolved in MeOH (8 mL), THF (8 mL), and H$_2$O (8 mL). LiOH was added (8.13 mmol, 0.33 g), and the reaction was stirred overnight at room temperature. After the reaction was complete, the mixture was acidified to pH 1 with 1 N HCl and extracted with EtOAc. The combined organics were dried over MgSO$_4$, filtered, and concentrated in vacuo to give 6-(benzyloxycarbonyl)-6-azaspiro[2.5]octane-1-carboxylic acid as a white solid (1.10 g, 94% yield). Mass Spectrum (ESI) m/z=290 (M+1). $^1$H NMR (400 MHz, CDCl$_3$): δ ppm 0.83-0.94 (m, 1H), 1.09-1.15 (m, 1H), 1.30-1.40 (m, 2H), 1.46-1.52 (m, 1H), 1.61-1.70 (m, 2H), 3.23-3.54 (m, 4H), 5.06 (s, 2H), 7.20-7.28 (m, 5H).

Step D.

To a solution of 6-(benzyloxycarbonyl)-6-azaspiro[2.5]octane-1-carboxylic acid (1.9 g, 6.6 mmol) in t-BuOH (19 mL) was added DPPA (2.7 g, 9.8 mmol) and triethylamine (2 g, 19.6 mmol). The reaction mixture was stirred at reflux temperature for 6 h, then concentrated under reduced pressure. The crude residue was purified by silica gel column chromatography (hexanes:EtOAc 10:1 to 5:1) to afford 6-benzyloxycarbonyl-1-(tert-butoxycarbonyl)amino-6-azaspiro[2.5]octane (1.0 g, 44% yield). Mass Spectrum (ESI) m/z=383 (M+23).

Step E.

A solution of 6-benzyloxycarbonyl-1-(tert-butoxycarbonyl)amino-6-azaspiro[2.5]octane (1 g, 2.8 mmol) in HCl in dioxane (4M, 10 mL) was stirred at RT for 1 h, then concentrated in vacuo to give 6-benzyloxycarbonyl-1-amino-6-azaspiro[2.5]octane hydrochloride (0.8 g, 44% yield). Mass Spectrum (ESI) m/z=261 (M+1).

Step F.

To a solution of 6-benzyloxycarbonyl-1-amino-6-azaspiro[2.5]octane hydrochloride (0.8 g, 2.7 mmol) in DCM was added EDCI (0.78 g, 4.05 mmol), HOBT (0.55 g, 4.05 mmol), DIPEA (1.04 g, 8.1 mmol) and benzoyl chloride (0.57 g, 4.05 mmol). The reaction mixture was stirred at RT for 12 h, then diluted with DCM, and washed successively with sat. $NH_4Cl$ solution, sat. $NaHCO_3$ solution, water and brine. The organic phase was concentrated under reduced pressure and the crude residue purified by silica gel column chromatography (hexanes:EtOAc 3:1 to 1:1) to afford N-(6-benzyloxycarbonyl-6-azaspiro[2.5]octan-1-yl)benzamide (0.82 g, 84% yield). Mass Spectrum (ESI) m/z=365 (M+1).

Step G.

To a solution of N-(6-benzyloxycarbonyl-6-azaspiro[2.5]octan-1-yl)benzamide (1 g, 2.7 mmol) in MeOH was added Pd/C. The flask was purged and back-filled with $H_2$ 3 times, and then stirred at RT under an $H_2$ atmosphere for 2 h. The mixture was then filtered through a Celite® (J.T. Baker, Phillipsberg, N.J., diatomaceous earth) pad, and the filtrate was concentrated to give the crude product N-(6-azaspiro[2.5]octan-1-yl)benzamide (0.6 g, 95% yield), which was used in next step without purification.

Alternatively, the following procedure can be applied:

To a solution of N-(6-azaspiro[2.5]octan-1-yl)benzamide (1 g, 2.7 mmol) in AcOH (10 mL) was added HBr in AcOH (33%, 3 mL) at RT. The resulting mixture was stirred at RT for 2 h and then concentrated in vacuo. The residue was poured into water (10 mL), adjusted to pH 12 by addition of $NaHCO_3$ (sat. aq.), then extracted with ethyl acetate (2×20 mL). The combined organic layers were dried over sodium sulfate, filtered and concentrated to give the crude product N-(6-azaspiro[2.5]octan-1-yl)benzamide (0.6 g, 95% yield), which was used in next step without purification. Mass Spectrum (ESI) m/z=231 (M+1).

Step H.

A solution of N-(6-azaspiro[2.5]octan-1-yl)benzamide (76 mg, 0.33 mmol), 1-bromo-2-methylpropane (55 mg, 0.44 mmol) and $K_2CO_3$ (91 mg, 0.66 mmol) in DMF/$CH_3CN$ (1:1, 3 mL) was stirred at 60° C. for 16 h. Then 10 mL of water was added and the solution was extracted with EtOAc (20 mL×3). The combined organic layers were washed with brine, dried over $Na_2SO_4$ and concentrated in vacuo. The residue was purified by silica gel chromatography eluting with 5% DCM/MeOH to give N-(6-Isobutyl-6-azaspiro[2.5]octan-1-yl)benzamide as a yellow solid (50 mg, 53%).

$^1$H NMR (400 MHz, MeOD) δ ppm 7.82-7.80 (m, 2H), 7.55-7.53 (m, 1H), 7.49-7.45 (m, 2H), 2.79-2.76 (m, 1H), 2.68-2.66 (m, 1H), 2.53-2.46 (m, 3H), 2.21-2.20 (d, J=7.1 Hz, 2H), 1.91-1.84 (m, 1H), 1.60-1.59 (m, 4H), 0.95-0.94 (dd, J=6.6, 0.8 Hz, 6H), 0.84 (m, 1H), 0.74-0.66 (m, 1H). Mass Spectrum (ESI) m/z=287 (M+1).

Examples 02 to 18 were also prepared by procedures similar to the one described in Example 01, replacing benzoyl chloride in step F and/or 1-bromo-2-methylpropane in step H with the designated reagents.

| Example | R¹ | R² | Reagent used in Step F | Reagent used in Step H |
| --- | --- | --- | --- | --- |
| 02 | phenyl | neopentyl | Benzoyl chloride | 1-Bromo-3,3-dimethylbutane |
| 03 | phenyl | phenethyl | Benzoyl chloride | (2-Bromoethyl)benzene |
| 04 | phenyl | tert-butylcarbamoylmethyl | Benzoyl chloride | 2-Bromo-N-(tert-butyl)acetamide |

-continued

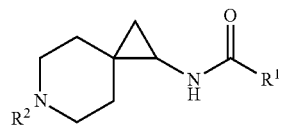

| Example | R¹ | R² | Reagent used in Step F | Reagent used in Step H |
|---|---|---|---|---|
| 05 | phenyl | Ph-CH₂- (benzyl) | Benzoyl chloride | Benzylbromide |
| 06 | 3,4-dichlorophenyl | isobutyl (2-methylpropyl) | 3,4-Dichlorobenzoyl chloride | 1-Bromo-2-methylpropane |
| 07 | 3,4-dichlorophenyl | 3,3-dimethylbutyl | 3,4-Dichlorobenzoyl chloride | 1-Bromo-3,3-dimethylbutane |
| 08 | 3,4-dichlorophenyl | 2-phenylethyl | 3,4-Dichlorobenzoyl chloride | (2-Bromoethyl)benzene |
| 09 | 3,4-dichlorophenyl | -CH₂C(O)NH-tBu | 3,4-Dichlorobenzoyl chloride | 2-Bromo-N-(tert-butyl)acetamide |
| 10 | 3,4-dichlorophenyl | Ph-CH₂- (benzyl) | 3,4-Dichlorobenzoyl chloride | Benzylbromide |
| 11 | 3,5-dichlorophenyl | isobutyl (2-methylpropyl) | 3,4-Dichlorobenzoyl chloride | 1-Bromo-2-methylpropane |
| 12 | 3,5-dichlorophenyl | 3,3-dimethylbutyl | 3,4-Dichlorobenzoyl chloride | 1-Bromo-3,3-dimethylbutane |

-continued

| Example | R¹ | R² | Reagent used in Step F | Reagent used in Step H |
|---|---|---|---|---|
| 13 | 3,5-dichlorophenyl | 2-phenylethyl | 3,4-Dichlorobenzoyl chloride | (2-Bromoethyl)benzene |
| 14 | 3,5-dichlorophenyl | -CH₂C(O)NH-tBu | 3,4-Dichlorobenzoyl chloride | 2-Bromo-N-(tert-butyl)acetamide |
| 15 | 3,5-dichlorophenyl | PhCH₂- (benzyl) | 3,4-Dichlorobenzoyl chloride | Benzylbromide |
| 16 | 3,5-bis(trifluoromethyl)phenyl | -CH₂C(O)NH-tBu | 3,5-Bis(trifluoromethyl)benzoyl chloride | 2-Bromo-N-(tert-butyl)acetamide |
| 17 | 3-chloro-5-fluorophenyl | -CH₂C(O)NH-tBu | 3-Chloro-5-fluorobenzoyl chloride | 2-Bromo-N-(tert-butyl)acetamide |
| 18 | 3-fluoro-5-(trifluoromethyl)phenyl | -CH₂C(O)NH-tBu | 3-Fluoro-5-(trifluoromethyl)benzoyl chloride | 2-Bromo-N-(tert-butyl)acetamide |

Example 02

N-(6-(3,3-Dimethylbutyl)-6-azaspiro[2.5]octan-1-yl)benzamide $^1$H NMR (400 MHz, MeOD) δ ppm 7.83-7.81 (d, J=7.7 Hz, 2H), 7.56-7.54 (d, J=6.1 Hz, 1H), 7.50-7.48 (d, J=6.9 Hz, 2H), 2.88 (s, 1H), 2.80-2.79 (d, J=3.3 Hz, 2H), 2.71 (m, 1H), 2.62 (m, 3H), 1.70 (m, 2H), 1.54-1.50 (m, 4H), 0.96 (s, 9H), 0.92-0.90 (m, 1H), 0.76 (m, 1H). Mass Spectrum (ESI) m/z=315 (M+1).

Example 03

N-(6-Phenethyl-6-azaspiro[2.5]octan-1-yl)benzamide $^1$H NMR (400 MHz, MeOD) δ ppm 7.83-7.81 (d, J=7.9 Hz, 2H), 7.57-7.46 (m, 3H), 7.31-7.18 (m, 5H), 2.85-2.66 (m, 9H), 1.68-1.64 (m, 4H), 0.90-0.87 (m, 1H), 0.75-0.74 (m, 1H). Mass Spectrum (ESI) m/z=335 (M+1).

Example 04

N-(6-(2-(tert-Butylamino)-2-oxoethyl)-6-azaspiro[2.5]octan-1-yl)benzamide $^1$H NMR (400 MHz, MeOD) δ ppm 7.82-7.80 (m, 2H), 7.55-7.46 (m, 3H), 2.93 (s, 2H), 2.77-2.75 (m, 2H), 2.56-2.49 (m, 3H), 1.62-1.53 (m, 4H), 1.37 (s, 9H), 0.84 (m, 1H), 0.72 (m, 1H). Mass Spectrum (ESI) m/z=344 (M+1).

Example 05

N-(6-Benzyl-6-azaspiro[2.5]octan-1-yl)benzamide $^1$H NMR (400 MHz, MeOD) δ ppm 7.91-7.80 (m, 2H), 7.53-7.44 (m, 8H), 4.39 (s, 2H), 3.55-3.35 (m, 3H), 3.20-3.15 (m, 1H), 3.05-2.99 (m, 1H), 2.89-2.81 (m, 1H), 2.25-2.01 (m, 2H), 1.68-1.25 (m, 2H), 1.06-1.02 (m, 1H), 0.92-0.91 (m, 1H). Mass Spectrum (ESI) m/z=321 (M+1).

Example 06

3,4-Dichloro-N-(6-isobutyl-6-azaspiro[2.5]octan-1-yl)benzamide $^1$H NMR (400 MHz, MeOD) δ ppm 8.06-8.02 (m, 1H), 7.92-7.73 (m, 1H), 7.69-7.66 (m, 1H), 3.68-3.38 (m, 3H), 3.15-2.96 (m, 3H), 2.86-2.80 (m, 1H), 2.34-1.97 (m, 3H), 1.63-1.48 (m, 2H), 1.06 (s, 6H), 1.04-1.03 (m, 1H), 0.92-0.86 (m, 1H). Mass Spectrum (ESI) m/z=355 (M+1).

Example 07

3,4-Dichloro-N-(6-(3,3-dimethylbutyl)-6-azaspiro[2.5]octan-1-yl)benzamide $^1$H NMR (400 MHz, MeOD) δ ppm 8.06 (s, 1H), 7.80 (m, 1H), 7.69-7.67 (d, J=8.4 Hz, 1H), 3.62-3.34 (m, 3H), 3.32-3.19 (m, 2H), 2.83-2.68 (m, 2H), 2.25-2.03 (m, 2H), 1.70-1.66 (m, 2H), 1.52-1.42 (m, 2H), 1.08 (m, 1H), 1.02 (s, 9H), 0.90-0.86 (m, 1H). Mass Spectrum (ESI) m/z=383 (M+1).

Example 08

3,4-Dichloro-N-(6-phenethyl-6-azaspiro[2.5]octan-1-yl)benzamide $^1$H NMR (400 MHz, MeOD) δ ppm 8.07-8.02 (m, 1H), 7.82-7.77 (m, 1H), 7.69-7.66 (m, 1H), 7.35-7.27 (m, 5H), 3.74-3.67 (m, 1H), 3.40-3.37 (m, 3H), 3.23-3.17 (m, 1H), 3.17-3.13 (m, 2H), 3.04-2.99 (m, 1H), 2.87-2.82 (m, 1H), 2.32-2.01 (m, 2H), 1.61-1.38 (m, 2H), 1.08-1.05 (m, 1H), 0.93-0.87 (m, 1H). Mass Spectrum (ESI) m/z=403 (M+1).

Example 09

N-(6-(2-(tert-Butylamino)-2-oxoethyl)-6-azaspiro[2.5]octan-1-yl)-3,4-dichlorobenzamide $^1$H NMR (400 MHz, MeOD) δ ppm 8.03-8.02 (m, 1H), 7.79-7.77 (m, 1H), 7.69-7.66 (m, 1H), 3.74-3.35 (m, 2H), 3.30-3.15 (m, 3H), 2.87-2.82 (m, 2H), 1.64-1.38 (m, 4H), 1.31 (s, 9H), 0.98 (m, 1H), 0.82 (m, 1H). Mass Spectrum (ESI) m/z=412 (M+1).

Example 10

N-(6-Benzyl-6-azaspiro[2.5]octan-1-yl)-3,4-dichlorobenzamide $^1$H NMR (400 MHz, MeOD) δ ppm 8.07-8.02 (m, 1H), 7.82-7.77 (m, 1H), 7.69-7.66 (m, 1H), 7.35-7.27 (m, 5H), 4.41-4.36 (m, 2H), 3.54-3.33 (m, 2H), 3.17-3.15 (m, 1H), 3.00-2.95 (m, 1H), 2.85-2.80 (m, 1H), 2.19-2.01 (m, 2H), 1.51-1.37 (m, 2H), 1.08-1.05 (m, 1H), 0.93-0.87 (m, 1H). Mass Spectrum (ESI) m/z=389 (M+1).

Example 11

3,5-Dichloro-N-(6-isobutyl-6-azaspiro[2.5]octan-1-yl)benzamide $^1$H NMR (400 MHz, MeOD) δ ppm 7.86-7.85 (s, 2H), 7.85-7.82 (s, 1H), 7.69-7.68 (s, 1H), 3.33-2.95 (m, 2H), 3.15-2.96 (m, 3H), 2.86-2.80 (m, 2H), 2.34-1.97 (m, 3H), 1.51-1.38 (m, 2H), 1.09 (s, 6H), 1.04-1.03 (m, 1H), 0.92-0.88 (m, 1H). Mass Spectrum (ESI) m/z=355 (M+1).

Example 12

3,5-Dichloro-N-(6-(3,3-dimethylbutyl)-6-azaspiro[2.5]octan-1-yl)benzamide $^1$H NMR (400 MHz, MeOD) δ ppm 7.86 (s, 1H), 7.82 (s, 1H), 7.69-7.67 (d, J=8.4 Hz, 1H), 3.62-3.34 (m, 3H), 3.32-3.19 (m, 2H), 2.83-2.68 (m, 2H), 2.25-2.03 (m, 2H), 1.70-1.66 (m, 2H), 1.52-1.42 (m, 2H), 1.08 (m, 1H), 1.02 (s, 9H), 0.90-0.86 (m, 1H). Mass Spectrum (ESI) m/z=383 (M+1).

Example 13

3,5-Dichloro-N-(6-phenethyl-6-azaspiro[2.5]octan-1-yl)benzamide $^1$H NMR (400 MHz, MeOD) δ ppm 7.87-7.82 (m, 2H), 7.70-7.68 (m, 1H), 7.39-7.27 (m, 5H), 3.74-3.67 (m, 1H), 3.40-3.37 (m, 3H), 3.23-3.17 (m, 1H), 3.17-3.13 (m, 2H), 3.04-2.99 (m, 1H), 2.87-2.82 (m, 1H), 2.32-2.01 (m, 2H), 1.61-1.38 (m, 2H), 1.08-1.05 (m, 1H), 0.93-0.87 (m, 1H). Mass Spectrum (ESI) m/z=403 (M+1).

Example 14

N-(6-(2-(tert-Butylamino)-2-oxoethyl)-6-azaspiro[2.5]octan-1-yl)-3,5-dichlorobenzamide $^1$H NMR (400 MHz, MeOD) δ ppm 7.86-7.82 (m, 2H), 7.69-7.66 (m, 1H), 3.74-3.35 (m, 2H), 3.30-3.15 (m, 3H), 2.87-2.82 (m, 2H), 1.64-1.38 (m, 4H), 1.31 (s, 9H), 0.98 (m, 1H), 0.82 (m, 1H). Mass Spectrum (ESI) m/z=412 (M+1).

Example 15

N-(6-Benzyl-6-azaspiro[2.5]octan-1-yl)-3,5-dichlorobenzamide $^1$H NMR (400 MHz, MeOD) δ ppm 7.85-7.80 (m, 2H), 7.70-7.68 (m, 1H), 7.55-7.51 (m, 5H), 4.41-4.35 (m, 2H), 3.34-3.31 (m, 3H), 3.23-3.17 (m, 1H), 3.17-3.13 (m, 1H), 2.99-2.81 (m, 1H), 2.24-1.99 (m, 2H), 1.61-1.38 (m, 2H), 1.08-1.05 (m, 1H), 0.93-0.87 (m, 1H). Mass Spectrum (ESI) m/z=389 (M+1).

Example 16

N-(6-(2-(tert-Butylamino)-2-oxoethyl)-6-azaspiro[2.5]octan-1-yl)-3,5-bis(trifluoromethyl)benzamide $^1$H NMR (400 MHz, MeOD) δ ppm 8.50 (s, 2H), 8.22 (s, 1H), 3.84 (s, 2H), 3.54 (d, J=49.4 Hz, 3H), 3.02 (s, 1H), 2.88 (s, 1H), 2.24 (s, 2H), 1.54-1.42 (m, 2H), 1.40 (d, J=14.4 Hz, 9H), 1.17-1.03 (m, 1H), 0.94 (s, 1H). Mass Spectrum (ESI) m/z=480 (M+1).

Example 17

N-(6-(2-(tert-Butylamino)-2-oxoethyl)-6-azaspiro[2.5]octan-1-yl)-3-chloro-5-fluorobenzamide $^1$H NMR (400 MHz, MeOD) δ ppm 7.70 (dd, J=2.3, 1.0 Hz, 1H), 7.54 (ddd, J=9.1, 2.4, 1.4 Hz, 1H), 7.42 (dt, J=8.4, 2.1 Hz, 1H), 2.94 (s, 2H), 2.74 (m, 2H), 2.62-2.37 (m, 3H), 1.73-1.41 (m, 4H), 1.43-1.29 (s, 9H), 0.86 (dd, J=8.0, 5.7 Hz, 1H), 0.80-0.63 (m, 1H). Mass Spectrum (ESI) m/z=396 (M+1).

Example 18

N-{6-[(tert-Butylcarbamoyl)methyl]-6-azaspiro[2.5]octan-1-yl}-3-fluoro-5-(trifluoromethyl)benzamide $^1$H NMR (400 MHz, MeOD) δ 8.01 (s, 1H), 7.88 (dd, J=9.0, 1.8 Hz, 1H), 7.68 (d, J=8.3 Hz, 1H), 2.99 (s, 2H), 2.83-2.71 (m, 2H), 2.55 (m, 3H), 1.78-1.45 (m, 4H), 1.34 (s, 9H), 0.88 (dd, J=8.0, 5.7 Hz, 1H), 0.81-0.60 (m, 1H). Mass Spectrum (ESI) m/z=430 (M+H).

Examples 19 to 36 can also prepared by procedures similar to the one described in Example 01, replacing benzoyl chloride in step F with the appropriate acyl chloride.

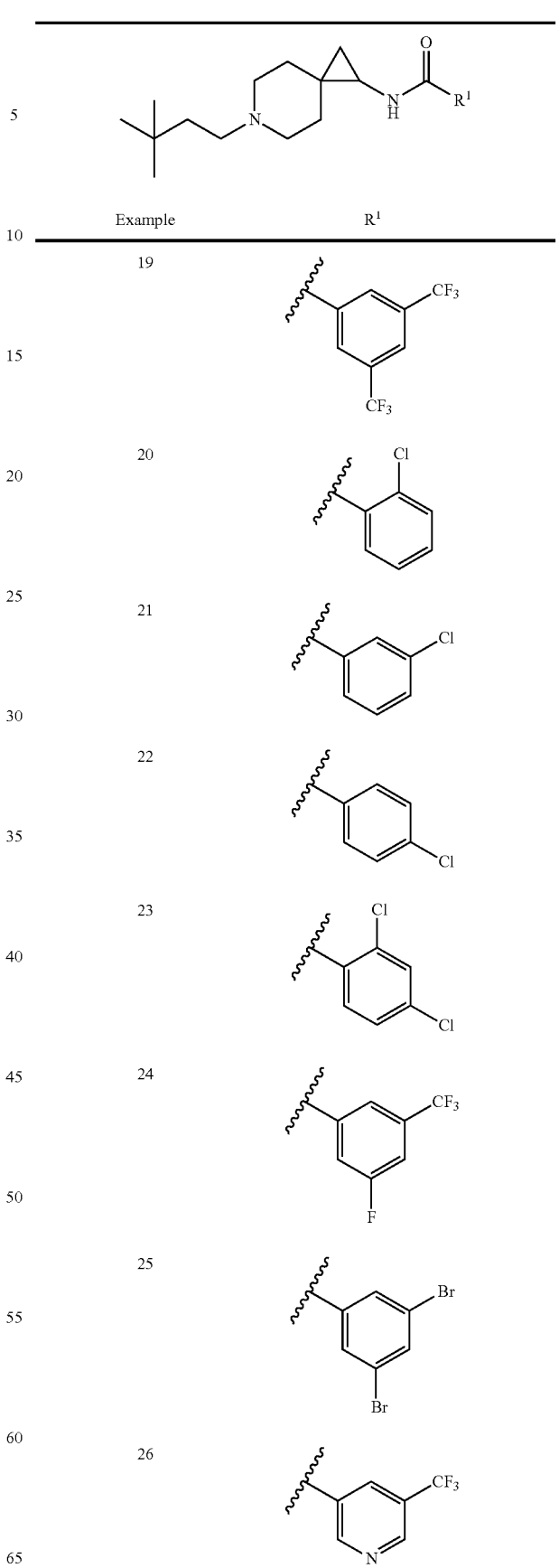

| Example | R$^1$ |
| --- | --- |
| 19 | 3,5-bis(CF$_3$)phenyl |
| 20 | 2-Cl-phenyl |
| 21 | 3-Cl-phenyl |
| 22 | 4-Cl-phenyl |
| 23 | 2,4-diCl-phenyl |
| 24 | 3-CF$_3$-5-F-phenyl |
| 25 | 3,5-diBr-phenyl |
| 26 | 3-CF$_3$-pyridin-5-yl |

-continued

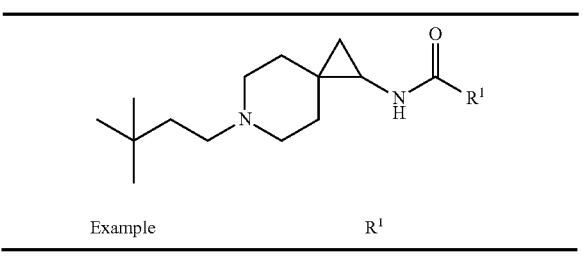

| Example | R¹ |
|---|---|
| 27 | 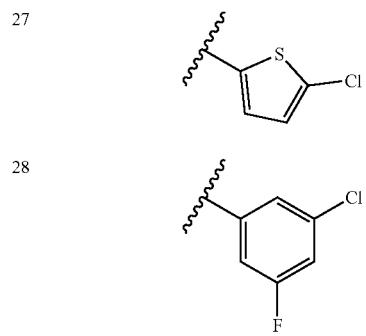 (5-chlorothiophen-2-yl) |
| 28 | 3-chloro-5-fluorophenyl |
| 29 | 3-(trifluoromethyl)phenyl |
| 30 | adamantyl |
| 31 | 3,5-bis(trifluoromethyl)benzyl |
| 32 | 3,5-dimethylphenyl |
| 33 | 3,5-dimethoxyphenyl |
| 34 | 3-cyanobenzyl |

-continued

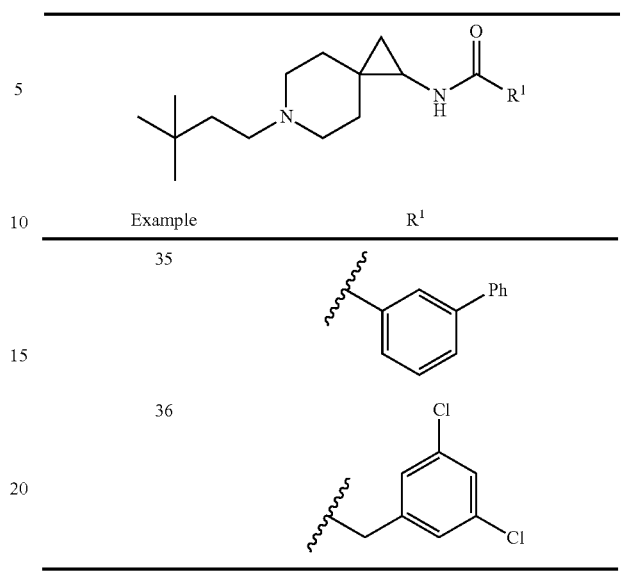

| Example | R¹ |
|---|---|
| 35 | 3-phenylphenyl |
| 36 | 3,5-dichlorobenzyl |

Example 19

N-(6-(3,3-Dimethylbutyl)-6-azaspiro[2.5]octan-1-yl)-3,5-bis(trifluoromethyl)benzamide $^1$H NMR (400 MHz, MeOD) δ ppm 8.52 (s, 2H), 8.23 (s, 1H), 3.63 (s, 1H), 3.45 (s, 2H), 3.19 (d, J=5.5 Hz, 3H), 2.92 (d, J=28.2 Hz, 2H), 2.22 (d, J=36.4 Hz, 2H), 1.79-1.61 (m, 1H), 1.47 (dd, J=45.5, 14.6 Hz, 2H), 1.09 (dd, J=7.9, 6.3 Hz, 1H), 1.02 (s, 9H), 0.94 (s, 1H). Mass Spectrum (ESI) m/z=451 (M+1).

Example 20

2-Chloro-N-(6-(3,3-dimethylbutyl)-6-azaspiro[2.5]octan-1-yl)benzamide $^1$H NMR (400 MHz, MeOD) δ ppm 7.59-7.36 (m, 4H), 3.46 (s, 3H), 3.26-3.07 (m, 2H), 2.84 (dd, J=8.2, 4.7 Hz, 1H), 2.04 (d, J=37.2 Hz, 2H), 1.70 (dd, J=11.2, 4.8 Hz, 3H), 1.10-0.96 (m, 10H), 0.79 (dd, J=7.5, 3.2 Hz, 1H). Mass Spectrum (ESI) m/z=349 (M+1).

Example 21

3-Chloro-N-(6-(3,3-dimethylbutyl)-6-azaspiro[2.5]octan-1-yl)benzamide $^1$H NMR (400 MHz, MeOD) δ ppm 7.88 (d, J=9.7 Hz, 1H), 7.80 (d, J=7.8 Hz, 1H), 7.60 (d, J=8.2 Hz, 1H), 7.50 (t, J=7.9 Hz, 1H), 3.83-3.38 (m, 3H), 3.26-3.10 (m, 2H), 3.00 (d, J=11.4 Hz, 1H), 2.83 (dd, J=8.1, 4.7 Hz, 1H), 2.37-1.98 (m, 2H), 1.80-1.65 (m, 2H), 1.49 (d, J=47.6 Hz, 2H), 1.12-0.97 (m, 10H), 0.89 (dd, J=14.0, 8.4 Hz, 1H). Mass Spectrum (ESI) m/z=349 (M+1).

Example 22

4-Chloro-N-(6-(3,3-dimethylbutyl)-6-azaspiro[2.5]octan-1-yl)benzamide $^1$H NMR (400 MHz, MeOD) δ ppm 7.85 (t, J=7.9 Hz, 2H), 7.61-7.42 (m, 2H), 3.45 (s, 3H), 3.24-3.00 (m, 3H), 2.83 (dd, J=8.1, 4.7 Hz, 1H), 2.44-1.89 (m, 2H), 1.81-1.59 (m, 2H), 1.55 (s, 2H), 1.12-0.96 (m, 10H), 0.88 (dd, J=12.7, 7.3 Hz, 1H). Mass Spectrum (ESI) m/z=349 (M+1).

Example 23

2,4-Dichloro-N-(6-(3,3-dimethylbutyl)-6-azaspiro[2.5]octan-1-yl)benzamide $^1$H NMR (400 MHz, MeOD) δ ppm 7.60 (dd, J=7.8, 1.7 Hz, 1H), 7.51 (d, J=8.2 Hz, 1H), 7.49-7.44 (m, 1H), 3.73-3.53 (m, 2H), 3.40 (d, J=13.0 Hz, 1H), 3.19 (ddd, J=31.3, 19.8, 8.6 Hz, 3H), 2.90-2.81 (m, 1H), 2.33-2.15 (m, 2H), 1.76-1.59 (m, 3H), 1.39 (d, J=15.0 Hz, 1H), 1.12-0.94 (m, 10H), 0.82-0.73 (m, 1H). Mass Spectrum (ESI) m/z=383 (M+1).

Example 24

N-(6-(3,3-Dimethylbutyl)-6-azaspiro[2.5]octan-1-yl)-3-fluoro-5-(trifluoromethyl)benzamide $^1$H NMR (400 MHz, MeOD) δ ppm 8.06 (s, 1H), 7.93 (d, J=9.0 Hz, 1H), 7.72 (d, J=8.1 Hz, 1H), 3.77-3.36 (m, 3H), 3.19 (dd, J=11.2, 6.1 Hz, 2H), 2.86 (dd, J=8.1, 4.7 Hz, 2H), 2.24 (s, 2H), 1.67 (dt, J=60.5, 25.6 Hz, 4H), 1.14-0.94 (m, 10H), 0.92 (s, 1H). Mass Spectrum (ESI) m/z=401 (M+1).

Example 25

3,5-Dibromo-N-(6-(3,3-dimethylbutyl)-6-azaspiro[2.5]octan-1-yl)benzamide $^1$H NMR (400 MHz, MeOD) δ ppm 8.02 (dd, J=19.1, 1.7 Hz, 2H), 7.99-7.95 (m, 1H), 3.62 (d, J=9.3 Hz, 1H), 3.43 (dd, J=24.0, 12.1 Hz, 2H), 3.25-3.09 (m, 3H), 2.96-2.80 (m, 1H), 2.33-1.97 (m, 2H), 1.75-1.65 (m, 2H), 1.44 (dd, J=40.0, 16.9 Hz, 2H), 1.10-0.99 (m, 10H), 0.88 (dd, J=13.8, 4.9 Hz, 1H). Mass Spectrum (ESI) m/z=471 (M+1).

Example 26

N-(6-(3,3-dimethylbutyl)-6-azaspiro[2.5]octan-1-yl)-5-(trifluoromethyl)nicotinamide $^1$H NMR (400 MHz, MeOD) δ ppm 9.32 (d, J=13.0 Hz, 1H), 9.12 (d, J=15.4 Hz, 1H), 8.68 (s, 1H), 3.64 (d, J=10.0 Hz, 1H), 3.43 (dd, J=27.7, 13.5 Hz, 2H), 3.26-3.07 (m, 2H), 3.03-2.85 (m, 2H), 2.17 (dd, J=65.8, 24.0 Hz, 2H), 1.70 (d, J=5.4 Hz, 2H), 1.57 (t, J=14.6 Hz, 2H), 1.43 (t, J=17.6 Hz, 1H), 1.09 (dd, J=8.0, 6.3 Hz, 1H), 1.02 (s, 9H), 0.93 (d, J=4.8 Hz, 1H). Mass Spectrum (ESI) m/z=384 (M+1).

Example 27

5-Chloro-N-(6-(3,3-dimethylbutyl)-6-azaspiro[2.5]octan-1-yl)thiophene-2-carboxamide $^1$H NMR (400 MHz, MeOD) δ ppm 7.54 (d, J=4.0 Hz, 1H), 7.03 (d, J=4.0 Hz, 1H), 2.87-2.57 (m, 7H), 1.72-1.47 (m, 6H), 1.31 (s, 1H), 0.96 (s, 9H), 0.73 (t, J=5.0 Hz, 1H). Mass Spectrum (ESI) m/z=355 (M+1).

Example 28

3-Chloro-N-(6-(3,3-dimethylbutyl)-6-azaspiro[2.5]octan-1-yl)-5-fluorobenzamide $^1$H NMR (400 MHz, MeOD) δ ppm 7.75 (s, 1H), 7.59 (d, J=9.0 Hz, 1H), 7.46 (d, J=8.3 Hz, 1H), 3.47 (d, J=27.1 Hz, 3H), 3.24-3.01 (m, 3H), 2.88-2.79 (m, 1H), 2.31-1.94 (m, 2H), 1.71-1.63 (m, 2H), 1.47 (d, J=41.2 Hz, 2H), 1.13-0.97 (m, 10H), 0.89 (t, J=9.8 Hz, 1H). Mass Spectrum (ESI) m/z=367 (M+1).

Example 29

N-(6-(3,3-Dimethylbutyl)-6-azaspiro[2.5]octan-1-yl)-3-(trifluoromethyl)benzamide $^1$H NMR (400 MHz, MeOD) δ ppm 8.29-8.08 (m, 2H), 7.90 (d, J=7.7 Hz, 1H), 7.72 (t, J=7.8 Hz, 1H), 3.46 (s, 3H), 3.25-2.93 (m, 3H), 2.86 (dd, J=8.1, 4.7 Hz, 1H), 2.40-1.98 (m, 2H), 1.73-1.64 (m, 2H), 1.58-1.19 (m, 2H), 1.13-0.97 (m, 10H), 0.94 (d, J=15.4 Hz, 1H). Mass Spectrum (ESI) m/z=383 (M+1).

Example 30

N-[6-(3,3-Dimethylbutyl)-6-azaspiro[2.5]octan-1-yl]adamantane-1-carboxamide $^1$H NMR (400 MHz, MeOD) δ ppm 2.66 (s, 2H), 2.55 (s, 1H), 2.50-2.37 (m, 4H), 1.92 (s, 3H), 1.76 (s, 5H), 1.65 (t, J=10.1 Hz, 6H), 1.51 (s, 2H), 1.41-1.30 (m, 4H), 1.19 (s, 1H), 0.84 (s, 9H), 0.70-0.62 (m, 1H), 0.53 (t, J=5.0 Hz, 1H). Mass Spectrum (ESI) m/z=373 (M+1).

Example 31

2-(3,5-Bis(trifluoromethyl)phenyl)-N-(6-(3,3-dimethylbutyl)-6-azaspiro[2.5]octan-1-yl)acetamide $^1$H NMR (400 MHz, MeOD) δ ppm 7.98-7.88 (m, 3H), 3.77 (d, J=14.8 Hz, 2H), 3.67-3.49 (m, 1H), 3.28-3.02 (m, 4H), 2.67 (ddd, J=12.7, 8.4, 4.4 Hz, 2H), 2.15 (dd, J=23.6, 14.1 Hz, 2H), 1.70-1.55 (m, 2H), 1.48-1.26 (m, 2H), 1.01 (dd, J=17.3, 13.6 Hz, 10H), 0.72 (s, 1H). Mass Spectrum (ESI) m/z=465 (M+1).

Example 32

N-(6-(3,3-Dimethylbutyl)-6-azaspiro[2.5]octan-1-yl)-3,5-dimethylbenzamide $^1$H NMR (400 MHz, MeOD) δ 7.35 (s, 2H), 7.11 (s, 1H), 3.39 (m, 3H), 3.07 (dd, J=11.4, 6.0 Hz, 2H), 2.84 (s, 1H), 2.69 (dd, J=8.1, 4.7 Hz, 1H), 2.26 (s, 6H), 2.11 (s, 2H), 1.57 (m, 2H), 1.40 (s, 2H), 0.91 (m, 10H), 0.78 (s, 1H). Mass Spectrum (ESI) m/z=343 (M+1).

Example 33

N-(6-(3,3-Dimethylbutyl)-6-azaspiro[2.5]octan-1-yl)-3,5-dimethoxybenzamide $^1$H NMR (400 MHz, MeOD) δ 7.01 (dd, J=14.5, 1.9 Hz, 2H), 6.69 (t, J=4.8 Hz, 1H), 3.82 (m, 6H), 3.64 (m, 1H), 3.43 (m, 1H), 3.16 (m, 3H), 2.94 (t, J=11.2 Hz, 1H), 2.82 (m, 1H), 2.17 (m, 2H), 1.69 (m, 2H), 1.47 (m, 2H), 1.03 (m, 10H), 0.91 (m, 1H). Mass Spectrum (ESI) m/z=375 (M+1).

Example 34

3-Cyano-N-(6-(3,3-dimethylbutyl)-6-azaspiro[2.5]octan-1-yl)benzamide $^1$H NMR (400 MHz, MeOD) δ 8.18 (m, 2H), 7.95 (m, 1H), 7.70 (t, J=7.9 Hz, 1H), 3.53 (m, 3H), 3.19 (m, 6.0 Hz, 3H), 2.85 (dd, J=8.1, 4.7 Hz, 1H), 2.17 (m, 2H), 1.69 (m, 2H), 1.37 (m, 2H), 1.08 (m, 1H), 1.04 (s, 9H), 0.91 (m, 1H). Mass Spectrum (ESI) m/z=340 (M+1).

Example 35

N-(6-(3,3-Dimethylbutyl)-6-azaspiro[2.5]octan-1-yl)-[1,1'-biphenyl]-3-carboxamide ¹H NMR (400 MHz, MeOD) δ 8.13 (s, 1H), 7.85 (d, J=6.8 Hz, 2H), 7.70 (d, J=7.3 Hz, 2H), 7.59 (t, J=7.6 Hz, 1H), 7.49 (t, J=7.3 Hz, 2H), 7.41 (d, J=7.1 Hz, 1H), 3.53 (m, 3H), 3.20 (s, 3H), 2.87 (m, 1H), 2.27 (s, 2H), 1.69 (m, 2H), 1.49 (m, 2H), 1.20 (m, 1H), 1.05 (s, 9H), 0.94 (m, 1H). Mass Spectrum (ESI) m/z=391 (M+1).

Example 36

2-(3,5-Dichlorophenyl)-N-(6-(3,3-dimethylbutyl)-6-azaspiro[2.5]octan-1-yl)acetamide ¹H NMR (400 MHz, MeOD) δ 7.41-7.29 (m, 3H), 3.60-3.51 (m, 3H), 3.26-3.06 (m, 3H), 2.70-2.59 (m, 2H), 2.29-2.02 (m, 2H), 1.70-1.58 (m, 2H), 1.45-1.23 (m, 2H), 1.05-0.92 (m, 11H), 0.73-0.71 (m, 1H). Mass Spectrum (ESI) m/z=397 (M+1).

Examples 37 to 50 were also prepared by procedures similar to the one described in Example 01, replacing 1-bromo-2-methylpropane in step H with the appropriate alkyl halide.

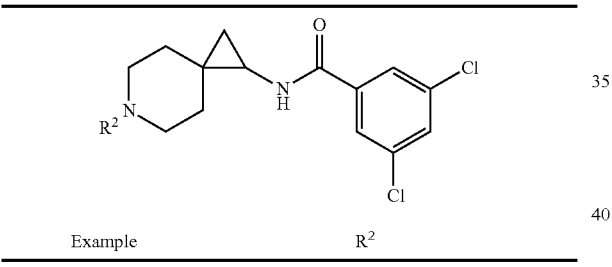

| Example | R² |
|---|---|
| 37 | 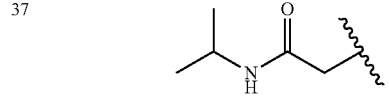 |
| 38 | 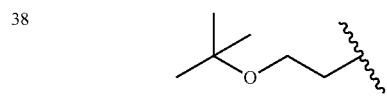 |
| 39 | 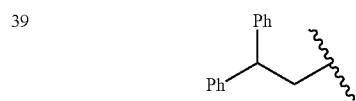 |
| 40 | 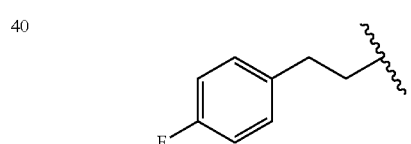 |
| 41 | 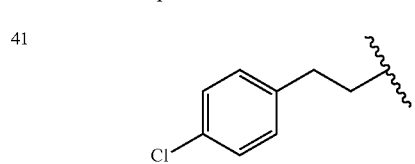 |

-continued

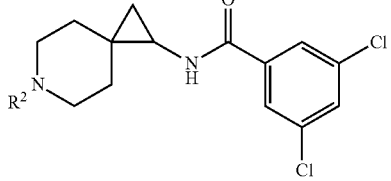

| Example | R² |
|---|---|
| 42 | 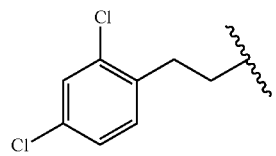 [SMILES: *CCc1ccc(Cl)cc1Cl] |
| 43 | 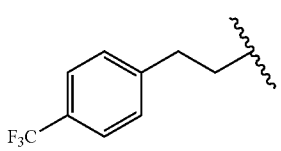 [SMILES: *CCc1ccc(C(F)(F)F)cc1] |
| 44 | 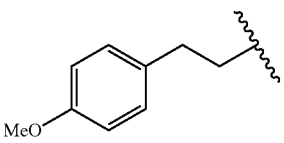 [SMILES: *CCc1ccc(OC)cc1] |
| 45 | 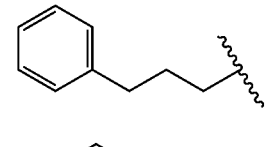 |
| 46 | 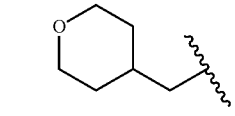 [SMILES: *CC1CCOCC1] |
| 47 | 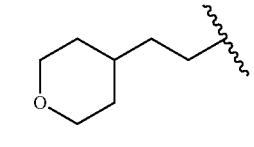 [SMILES: *CCC1CCOCC1] |
| 48 | 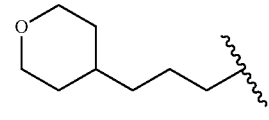 [SMILES: *CCCC1CCOCC1] |
| 49 | 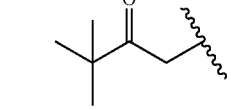 |
| 50 | 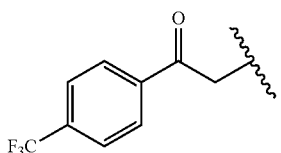 |

Example 37

3,5-Dichloro-N-(6-(2-(isopropylamino)-2-oxoethyl)-6-azaspiro[2.5]octan-1-yl)benzamide ¹H NMR (400 MHz, MeOD) δ ppm 7.80 (d, J=1.9 Hz, 2H), 7.66 (t, J=1.9 Hz, 1H), 4.08-3.98 (m, 1H), 3.14 (s, 2H), 2.84 (s, 1H), 2.77 (dd, J=8.0, 4.5 Hz, 1H), 2.62 (s, 3H), 1.61 (s, 4H), 1.18 (dd, J=6.6, 1.4 Hz, 6H), 0.89 (dd, J=8.0, 5.8 Hz, 1H), 0.81-0.68 (m, 1H). Mass Spectrum (ESI) m/z=398 (M+1).

Example 38

N-(6-(2-(tert-Butoxy)ethyl)-6-azaspiro[2.5]octan-1-yl)-3,5-dichlorobenzamide

¹H NMR (400 MHz, MeOD) δ ppm 8.54 (s, 0.3H), 7.83 (d, J=1.9 Hz, 1.7H), 7.68 (t, J=1.9 Hz, 1H), 3.73 (t, J=5.3 Hz, 2H), 3.22 (s, 3H), 2.82 (dd, J=8.1, 4.7 Hz, 1H), 2.68 (s, 1H), 1.93 (s, 3H), 1.64 (s, 3H), 1.26 (s, 9H), 1.02 (dd, J=8.0, 6.0 Hz, 1H), 0.88-0.83 (m, 1H). Mass Spectrum (ESI) m/z=399 (M+1).

Example 39

3,5-Dichloro-N-(6-(2,2-diphenylethyl)-6-azaspiro[2.5]octan-1-yl)benzamide

¹H NMR (400 MHz, MeOD) δ ppm 7.81 (d, J=22.3 Hz, 2H), 7.69 (d, J=10.4 Hz, 1H), 7.50-7.34 (m, 8H), 7.30 (d, J=6.5 Hz, 2H), 4.61 (s, 1H), 4.01 (d, J=7.4 Hz, 1H), 3.65-3.50 (m, 2H), 3.19 (d, J=26.5 Hz, 1H), 3.04-2.92 (m, 1H), 2.80 (dd, J=8.1, 4.7 Hz, 1H), 2.25-2.02 (m, 2H), 1.65-1.25 (m, 3H), 1.02 (dd, J=8.0, 6.2 Hz, 1H), 0.86 (s, 1H). Mass Spectrum (ESI) m/z=479 (M+1).

Example 40

3,5-Dichloro-N-(6-(4-fluorophenethyl)-6-azaspiro[2.5]octan-1-yl)benzamide

¹H NMR (400 MHz, MeOD) δ ppm 7.85 (d, J=1.6 Hz, 2H), 7.72-7.66 (m, 1H), 7.35 (dd, J=8.0, 5.6 Hz, 2H), 7.10 (t, J=8.8 Hz, 2H), 3.66-3.27 (m, 5H), 3.19-3.02 (m, 2H), 2.84 (dd, J=8.1, 4.7 Hz, 1H), 2.00 (s, 2H), 1.67 (s, 2H), 1.07 (dd, J=8.1, 6.1 Hz, 1H), 0.98-0.87 (m, 1H). Mass Spectrum (ESI) m/z=421 (M+1).

Example 41

3,5-Dichloro-N-(6-(4-chlorophenethyl)-6-azaspiro[2.5]octan-1-yl)benzamide

¹H NMR (400 MHz, MeOD) δ 7.85 (d, J=1.7 Hz, 2H), 7.69 (t, J=1.7 Hz, 1H), 7.35 (q, J=8.5 Hz, 4H), 3.51 (d, J=6.9 Hz, 2H), 3.36 (dd, J=10.6, 6.3 Hz, 4H), 3.14-3.06 (m, 2H), 2.84 (dd, J=8.1, 4.7 Hz, 1H), 2.03 (s, 2H), 1.67 (s, 2H), 1.06 (dd, J=7.9, 6.2 Hz, 1H), 0.90 (t, J=5.3 Hz, 1H). Mass Spectrum (ESI) m/z=437 (M+1).

Example 42

3,5-Dichloro-N-(6-(2,4-dichlorophenethyl)-6-azaspiro[2.5]octan-1-yl)benzamide

¹H NMR (400 MHz, MeOD) δ 7.84 (d, J=1.9 Hz, 2H), 7.69 (t, J=1.9 Hz, 1H), 7.55 (d, J=2.1 Hz, 1H), 7.43 (d, J=8.3 Hz, 1H), 7.37 (dd, J=8.3, 2.1 Hz, 1H), 3.53 (s, 3H), 3.27-3.15 (m, 5H), 2.84 (dd, J=8.1, 4.7 Hz, 1H), 2.02 (s, 2H), 1.69 (s, 2H), 1.06 (dd, J=8.1, 6.1 Hz, 1H), 0.93-0.87 (m, 1H). Mass Spectrum (ESI) m/z=471 (M+1).

Example 43

3,5-Dichloro-N-(6-(4-(trifluoromethyl)phenethyl)-6-azaspiro[2.5]octan-1-yl)benzamide ¹H NMR (400 MHz, MeOD) δ 7.84 (d, J=1.9 Hz, 2H), 7.69 (t, J=1.9 Hz, 1H), 7.55 (d, J=2.1 Hz, 1H), 7.43 (d, J=8.3 Hz, 1H), 7.37 (dd, J=8.3, 2.1 Hz, 1H), 3.53 (s, 3H), 3.27-3.15 (m, 5H), 2.84 (dd, J=8.1, 4.7 Hz, 1H), 2.02 (s, 2H), 1.69 (s, 2H), 1.06 (dd, J=8.1, 6.1 Hz, 1H), 0.93-0.87 (m, 1H). Mass Spectrum (ESI) m/z=471 (M+1).

Example 44

3,5-Dichloro-N-(6-(4-methoxyphenethyl)-6-azaspiro[2.5]octan-1-yl)benzamide

¹H NMR (400 MHz, MeOD) δ 7.85 (d, J=1.8 Hz, 2H), 7.69 (t, J=1.9 Hz, 1H), 7.24 (d, J=8.6 Hz, 2H), 6.95-6.88 (m, 2H), 3.79 (s, 3H), 3.51 (dd, J=14.1, 7.0 Hz, 2H), 3.42-3.33 (m, 4H), 3.04 (dd, J=9.9, 6.9 Hz, 2H), 2.84 (dd, J=8.1, 4.7 Hz, 1H), 2.02 (s, 2H), 1.65 (s, 2H), 1.06 (dd, J=8.1, 6.1 Hz, 1H), 0.94-0.86 (m, 1H). Mass Spectrum (ESI) m/z=433 (M+1).

Example 45

3,5-Dichloro-N-(6-(3-phenylpropyl)-6-azaspiro[2.5]octan-1-yl)benzamide

¹H NMR (400 MHz, MeOD) δ ppm 7.83 (d, J=1.7 Hz, 2H), 7.69 (t, J=1.9 Hz, 1H), 7.38-7.17 (m, 5H), 3.59-3.34 (m, 4H), 3.21-3.06 (m, 3H), 2.86-2.64 (m, 4H), 2.21-1.99 (m, 3H), 1.20 (t, J=7.0 Hz, 1H), 1.04 (dd, J=8.0, 6.2 Hz, 1H), 0.93-0.82 (m, 1H). Mass Spectrum (ESI) m/z=417 (M+1).

Example 46

3,5-Dichloro-N-(6-((tetrahydro-2H-pyran-4-yl)methyl)-6-azaspiro[2.5]octan-1-yl)benzamide ¹H NMR (400 MHz, MeOD) δ ppm 7.79 (d, J=1.9 Hz, 2H), 7.66 (t, J=1.9 Hz, 1H), 3.95 (dd, J=11.3, 3.9 Hz, 2H), 3.44 (td, J=11.9, 1.8 Hz, 2H), 2.90-2.71 (m, 3H), 2.62 (s, 2H), 2.45 (s, 2H), 1.97-1.86 (m, 1H), 1.78-1.50 (m, 6H), 1.41-1.22 (m, 2H), 0.94-0.84 (m, 1H), 0.79-0.71 (m, 1H). Mass Spectrum (ESI) m/z=397 (M+1).

Example 47

3,5-Dichloro-N-(6-(2-(tetrahydro-2H-pyran-4-yl)ethyl)-6-azaspiro[2.5]octan-1-yl)benzamide ¹H NMR (400 MHz, MeOD) δ ppm 7.86/7.82 (d, J=1.9 Hz, 2H), 7.69/7.67 (t, J=1.9 Hz, 1H), 3.95 (dd, J=11.2, 4.1 Hz, 2H), 3.63 (t, J=11.9 Hz, 2H), 3.51-3.37 (m, 3H), 3.29-3.05 (m, 3H), 2.92 (td, J=12.9, 3.4 Hz, 1H), 2.86-2.78 (m, 1H), 2.31-2.25 (m, 1H), 2.20-2.10 (m, 1H), 1.79-1.60 (m, 5H), 1.55-1.29 (m, 4H), 1.06 (dd, J=8.2, 6.2 Hz, 1H), 0.96-0.84 (m, 1H). Mass Spectrum (ESI) m/z=411 (M+1).

Example 48

3,5-Dichloro-N-(6-(3-(tetrahydro-2H-pyran-4-yl)propyl)-6-azaspiro[2.5]octan-1-yl)benzamide $^1$H NMR (400 MHz, MeOD) δ ppm 7.85/7.82 (d, J=1.8 Hz, 2H), 7.69 (dd, J=4.2, 2.4 Hz, 1H), 3.95 (dd, J=11.1, 4.3 Hz, 2H), 3.68-3.55 (m, 1H), 3.42 (dd, J=16.7, 6.8 Hz, 3H), 3.20-3.06 (m, 2H), 3.01-2.89 (m, 1H), 2.88-2.77 (m, 1H), 2.18 (dd, J=40.2, 17.6 Hz, 2H), 2.06-1.93 (m, 1H), 1.80 (dd, J=18.9, 13.1 Hz, 2H), 1.68 (d, J=13.2 Hz, 2H), 1.69-1.59 (m, 2H), 1.49 (d, J=15.3 Hz, 1H), 1.44-1.22 (m, 4H), 1.06 (dt, J=11.4, 5.7 Hz, 1H), 0.93-0.82 (m, 1H). Mass Spectrum (ESI) m/z=425 (M+1).

Example 49

3,5-Dichloro-N-(6-(3,3-dimethyl-2-oxobutyl)-6-azaspiro[2.5]octan-1-yl)benzamide $^1$H NMR (400 MHz, MeOD) δ 7.84 (dd, J=15.5, 1.9 Hz, 2H), 7.69 (dt, J=6.2, 1.9 Hz, 1H), 4.57-4.45 (m, 2H), 3.58-3.32 (m, 3H), 3.17 (dd, J=24.2, 11.8 Hz, 1H), 3.02-2.98 (m, 1H), 2.87-2.84 (m, 1H), 2.36-2.19 (m, 2H), 2.06-2.01 (m, 1H), 1.63-1.47 (m, 2H), 1.24 (s, 9H), 1.09-1.04 (m, 1H), 0.93-0.86 (m, 1H). Mass Spectrum (ESI) m/z=397 (M+1).

Example 50

3,5-Dichloro-N-(6-(2-oxo-2-(4-(trifluoromethyl)phenyl)ethyl)-6-azaspiro[2.5]octan-1-yl)benzamide $^1$H NMR (400 MHz, MeOD) δ 8.25 (d, J=8.2 Hz, H), 7.94 (d, J=8.3 Hz, 2H), 7.86 (s, 2H), 7.69 (s, 1H), 5.06 (s, 2H), 3.57 (m, 3H), 2.87 (dd, J=8.0, 4.8 Hz, 2H), 2.31 (s, 2H), 1.55 (s, 2H), 1.11-1.08 (m, 1H), 0.93 (s, 1H). Mass Spectrum (ESI) m/z=485 (M+1).

Examples 51 to 53 were also prepared by procedures similar to the one described in Example 01, replacing benzoyl chloride in step F with 3,5-dichlorobenzenesulfonyl chloride (CAS #705-21-5) and 1-bromo-2-methylpropane in step H with the designated reagents.

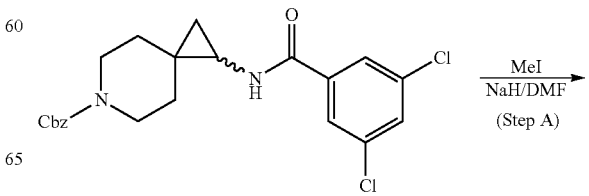

| Example | R² | Reagent used in Step H |
|---|---|---|
| 51 | (branched alkyl) | 1-Bromo-3,3-dimethylbutane |
| 52 | (phenethyl) | (2-Bromoethyl)benzene |

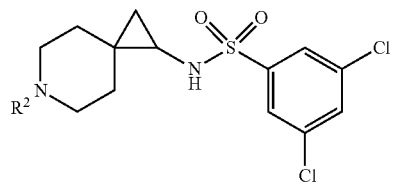

| Example | R² | Reagent used in Step H |
|---|---|---|
| 53 | (tert-butyl amide) | 2-Bromo-N-(tert-butyl)acetamide |

Example 51

3,5-Dichloro-N-(6-(3,3-dimethylbutyl)-6-azaspiro[2.5]octan-1-yl)benzenesulfonamide $^1$H NMR (400 MHz, MeOD) δ ppm 7.84-7.62 (m, 3H), 3.50-3.26 (m, 2H), 3.14-2.91 (m, 4H), 2.06 (dd, J=7.9, 4.0 Hz, 1H), 1.86 (s, 3H), 1.66-1.48 (m, 3H), 0.90 (s, 9H), 0.77 (dd, J=7.8, 6.0 Hz, 1H), 0.64 (dd, J=5.6, 4.2 Hz, 1H). Mass Spectrum (ESI) m/z=419 (M+1).

Example 52

3,5-Dichloro-N-(6-phenethyl-6-azaspiro[2.5]octan-1-yl)benzenesulfonamide $^1$H NMR (400 MHz, MeOD) δ ppm 7.94-7.69 (m, 3H), 7.42-7.15 (m, 5H), 3.51 (dd, J=14.1, 7.1 Hz, 2H), 3.35-3.16 (m, 3H), 3.07 (dd, J=10.3, 6.5 Hz, 2H), 2.18 (dd, J=7.8, 4.0 Hz, 1H), 1.97 (d, J=16.5 Hz, 2H), 1.66 (s, 2H), 1.20 (t, J=7.0 Hz, 1H), 0.88 (dd, J=7.7, 6.0 Hz, 1H), 0.80-0.61 (m, 1H). Mass Spectrum (ESI) m/z=439 (M+1).

Example 53

N-(tert-Butyl)-2-(1-(((3,5-dichlorophenyl)sulfonamido)-6-azaspiro[2.5]octan-6-yl)acetamide $^1$H NMR (400 MHz, MeOD) δ ppm 7.83 (d, J=1.9 Hz, 2H), 7.81-7.77 (m, 1H), 2.99 (d, J=20.0 Hz, 2H), 2.65 (d, J=29.7 Hz, 2H), 2.47 (s, 2H), 2.15-2.04 (m, 1H), 1.70-1.47 (m, 4H), 1.43-1.33 (m, 9H), 0.71 (dd, J=7.5, 5.7 Hz, 1H), 0.68-0.56 (m, 1H). Mass Spectrum (ESI) m/z=448 (M+1).

Example 54

3,5-Dichloro-N-(6-(3,3-dimethylbutyl)-6-azaspiro[2.5]octan-1-yl)-N-methylbenzamide

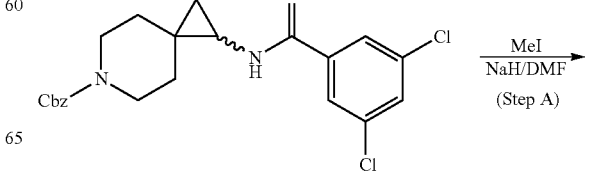

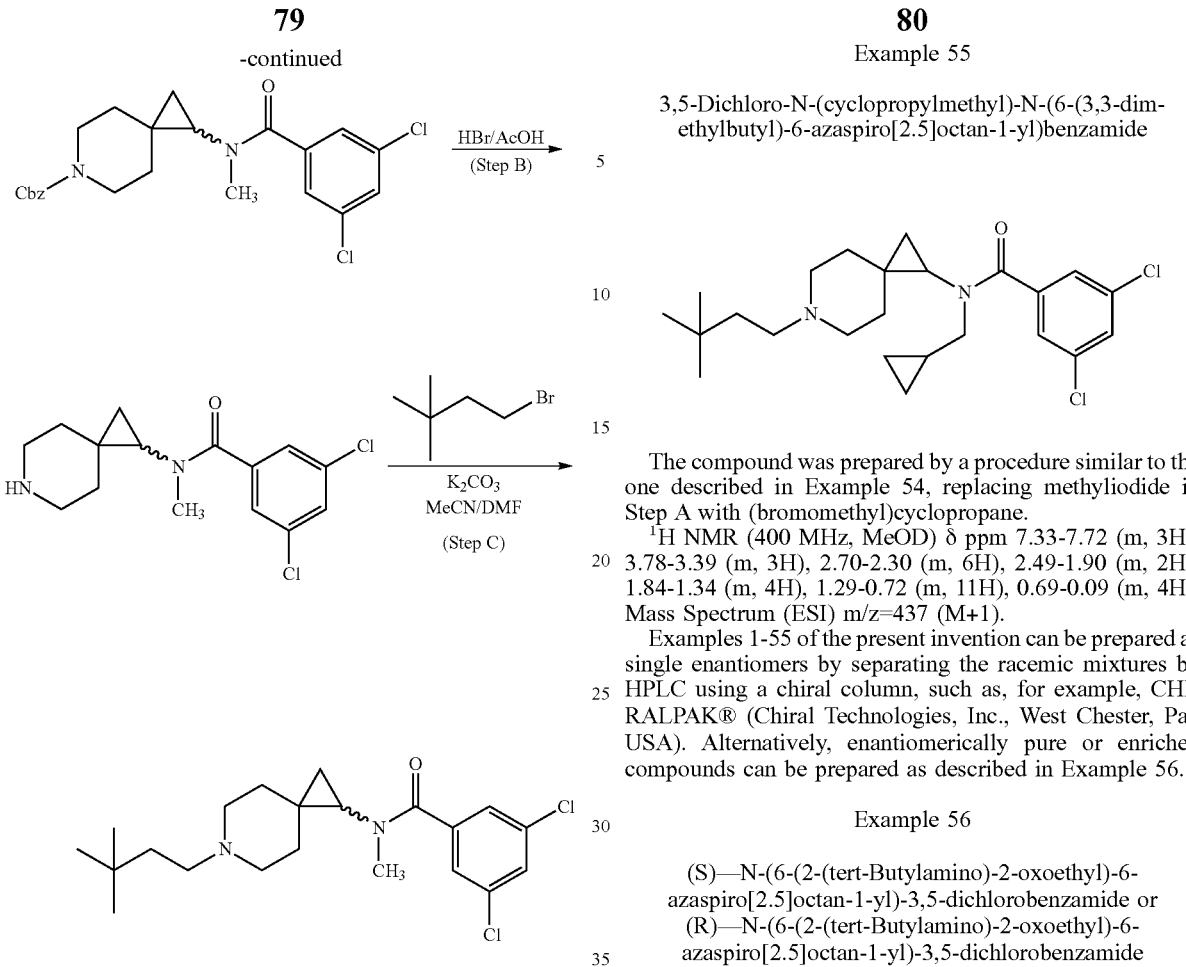

Example 55

3,5-Dichloro-N-(cyclopropylmethyl)-N-(6-(3,3-dimethylbutyl)-6-azaspiro[2.5]octan-1-yl)benzamide The compound was prepared by a procedure similar to the one described in Example 54, replacing methyliodide in Step A with (bromomethyl)cyclopropane.

$^1$H NMR (400 MHz, MeOD) δ ppm 7.33-7.72 (m, 3H), 3.78-3.39 (m, 3H), 2.70-2.30 (m, 6H), 2.49-1.90 (m, 2H), 1.84-1.34 (m, 4H), 1.29-0.72 (m, 11H), 0.69-0.09 (m, 4H). Mass Spectrum (ESI) m/z=437 (M+1).

Examples 1-55 of the present invention can be prepared as single enantiomers by separating the racemic mixtures by HPLC using a chiral column, such as, for example, CHIRALPAK® (Chiral Technologies, Inc., West Chester, Pa., USA). Alternatively, enantiomerically pure or enriched compounds can be prepared as described in Example 56.

Example 56

(S)—N-(6-(2-(tert-Butylamino)-2-oxoethyl)-6-azaspiro[2.5]octan-1-yl)-3,5-dichlorobenzamide or (R)—N-(6-(2-(tert-Butylamino)-2-oxoethyl)-6-azaspiro[2.5]octan-1-yl)-3,5-dichlorobenzamide

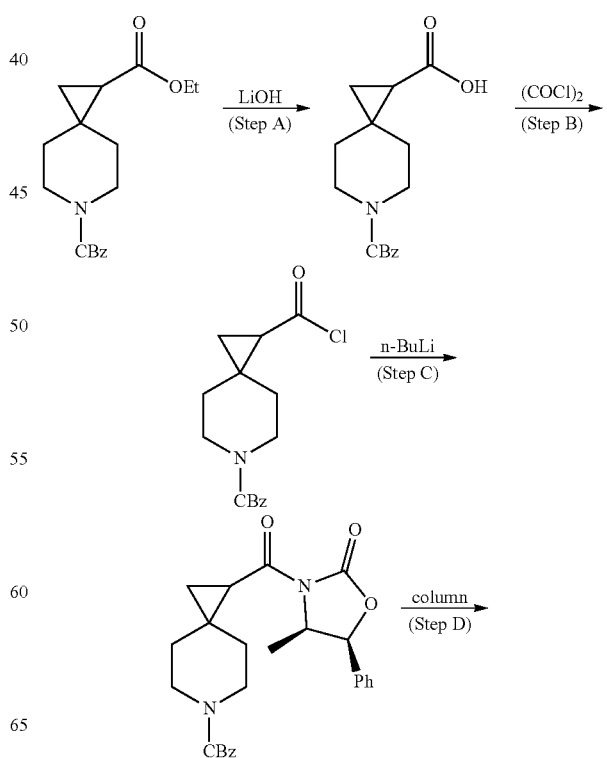

Step A.

Benzyl 1-(3,5-dichlorobenzamido)-6-azaspiro[2.5]octane-6-carboxylate, prepared by a procedure similar to the on described in Example 1, Step F, is alkylated with MeI in DMF in presence of a base, such as NaH to give benzyl 1-(3,5-dichloro-N-methylbenzamido)-6-azaspiro[2.5]octane-6-carboxylate.

Step B.

To a solution of benzyl 1-(3,5-dichloro-N-methylbenzamido)-6-azaspiro[2.5]octane-6-carboxylate from Step A in AcOH (10 mL) was added HBr in AcOH (33%, 3 mL) at rt. The resulting mixture was stirred at rt for 2 h. Solvent was removed, the residue was diluted with ethyl acetate (20 mL) and washed with sat. aq. NaHCO$_3$ (20 mL) and extracted with ethyl acetate (2×30 mL). The combined organic layers were dried over anhydrous sodium sulfate, filtered and concentrated to give a product that was used in next step without further purification.

Step C.

3,5-Dichloro-N-methyl-N-(6-azaspiro[2.5]octan-1-yl)benzamide obtained in Step B was converted to 3,5-dichloro-N-(6-(3,3-dimethylbutyl)-6-azaspiro[2.5]octan-1-yl)-N-methylbenzamide by a procedure similar to the one described in Example 1 Step H.

$^1$H NMR (400 MHz, MeOD) δ ppm 7.75-7.38 (m, 3H), 3.80-3.45 (m, 3H), 3.26-2.88 (m, 7H), 2.45-1.98 (m, 2H), 1.98-1.28 (m, 5H), 0.99 (s, 10H). Mass Spectrum (ESI) m/z=397 (M+1).

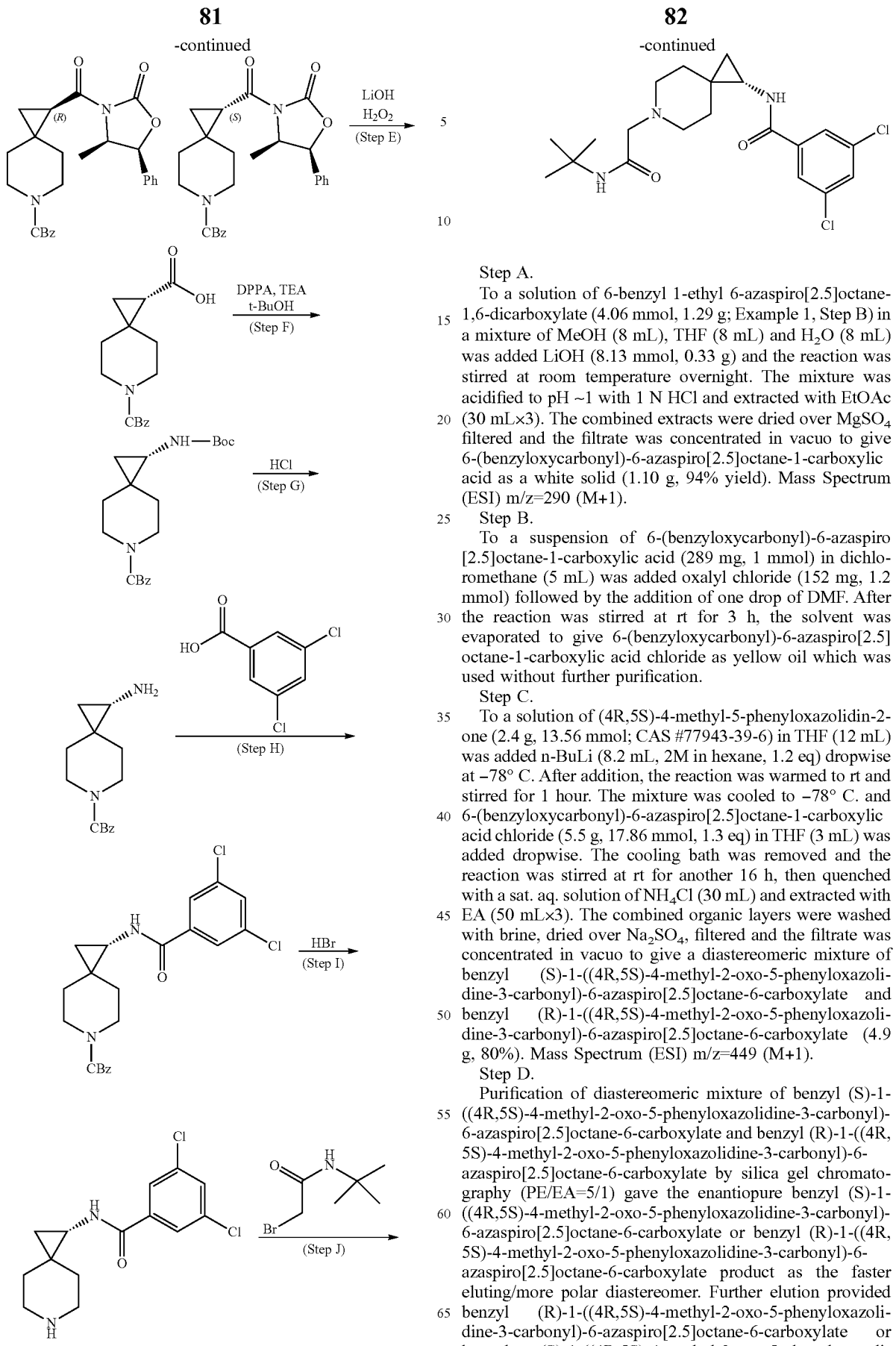

Step A.

To a solution of 6-benzyl 1-ethyl 6-azaspiro[2.5]octane-1,6-dicarboxylate (4.06 mmol, 1.29 g; Example 1, Step B) in a mixture of MeOH (8 mL), THF (8 mL) and H₂O (8 mL) was added LiOH (8.13 mmol, 0.33 g) and the reaction was stirred at room temperature overnight. The mixture was acidified to pH ~1 with 1 N HCl and extracted with EtOAc (30 mL×3). The combined extracts were dried over MgSO₄ filtered and the filtrate was concentrated in vacuo to give 6-(benzyloxycarbonyl)-6-azaspiro[2.5]octane-1-carboxylic acid as a white solid (1.10 g, 94% yield). Mass Spectrum (ESI) m/z=290 (M+1).

Step B.

To a suspension of 6-(benzyloxycarbonyl)-6-azaspiro[2.5]octane-1-carboxylic acid (289 mg, 1 mmol) in dichloromethane (5 mL) was added oxalyl chloride (152 mg, 1.2 mmol) followed by the addition of one drop of DMF. After the reaction was stirred at rt for 3 h, the solvent was evaporated to give 6-(benzyloxycarbonyl)-6-azaspiro[2.5]octane-1-carboxylic acid chloride as yellow oil which was used without further purification.

Step C.

To a solution of (4R,5S)-4-methyl-5-phenyloxazolidin-2-one (2.4 g, 13.56 mmol; CAS #77943-39-6) in THF (12 mL) was added n-BuLi (8.2 mL, 2M in hexane, 1.2 eq) dropwise at −78° C. After addition, the reaction was warmed to rt and stirred for 1 hour. The mixture was cooled to −78° C. and 6-(benzyloxycarbonyl)-6-azaspiro[2.5]octane-1-carboxylic acid chloride (5.5 g, 17.86 mmol, 1.3 eq) in THF (3 mL) was added dropwise. The cooling bath was removed and the reaction was stirred at rt for another 16 h, then quenched with a sat. aq. solution of NH₄Cl (30 mL) and extracted with EA (50 mL×3). The combined organic layers were washed with brine, dried over Na₂SO₄, filtered and the filtrate was concentrated in vacuo to give a diastereomeric mixture of benzyl (S)-1-((4R,5S)-4-methyl-2-oxo-5-phenyloxazolidine-3-carbonyl)-6-azaspiro[2.5]octane-6-carboxylate and benzyl (R)-1-((4R,5S)-4-methyl-2-oxo-5-phenyloxazolidine-3-carbonyl)-6-azaspiro[2.5]octane-6-carboxylate (4.9 g, 80%). Mass Spectrum (ESI) m/z=449 (M+1).

Step D.

Purification of diastereomeric mixture of benzyl (S)-1-((4R,5S)-4-methyl-2-oxo-5-phenyloxazolidine-3-carbonyl)-6-azaspiro[2.5]octane-6-carboxylate and benzyl (R)-1-((4R,5S)-4-methyl-2-oxo-5-phenyloxazolidine-3-carbonyl)-6-azaspiro[2.5]octane-6-carboxylate by silica gel chromatography (PE/EA=5/1) gave the enantiopure benzyl (S)-1-((4R,5S)-4-methyl-2-oxo-5-phenyloxazolidine-3-carbonyl)-6-azaspiro[2.5]octane-6-carboxylate or benzyl (R)-1-((4R,5S)-4-methyl-2-oxo-5-phenyloxazolidine-3-carbonyl)-6-azaspiro[2.5]octane-6-carboxylate product as the faster eluting/more polar diastereomer. Further elution provided benzyl (R)-1-((4R,5S)-4-methyl-2-oxo-5-phenyloxazolidine-3-carbonyl)-6-azaspiro[2.5]octane-6-carboxylate or benzyl (S)-1-((4R,5S)-4-methyl-2-oxo-5-phenyloxazolidine-3-carbonyl)-6-azaspiro[2.5]octane-6-carboxylate as the slower eluting/less polar diastereomer.

Step E.

To a solution of benzyl (R)-1-((4R,5S)-4-methyl-2-oxo-5-phenyloxazolidine-3-carbonyl)-6-azaspiro[2.5]octane-6-carboxylate or benzyl (S)-1-((4R,5S)-4-methyl-2-oxo-5-phenyloxazolidine-3-carbonyl)-6-azaspiro[2.5]octane-6-carboxylate (1.5 g, 3.4 mmol, slower eluting/less polar diastereomer) in THF (8 mL) and water (2 mL) was added LiOH (408 mg, 17 mmol, 5 eq), $H_2O_2$ (1.93 g, 17 mmol, 5 eq, 30% in water). The mixture was stirred at rt for 16 h. Then 15 mL of water was added and the mixture was extracted with EA (20 mL×3). The water phase was acidified with 1 N HCl to pH=1 and extracted with EA (30 mL×3). The combined organic layers were washed with brine, dried over $Na_2SO_4$, filtered and the filtrate was concentrated to give (S)-6-((benzyloxy)carbonyl)-6-azaspiro[2.5]octane-1-carboxylic acid or (R)-6-((benzyloxy)carbonyl)-6-azaspiro[2.5]octane-1-carboxylic acid as a white solid (850 mg, 87% yield). Mass Spectrum (ESI) m/z=290 (M+1).

Step F.

To a solution of (S)-6-((benzyloxy)carbonyl)-6-azaspiro[2.5]octane-1-carboxylic acid or (R)-6-((benzyloxy)carbonyl)-6-azaspiro[2.5]octane-1-carboxylic acid (850 mg, 2.94 mmol) in t-BuOH (20 mL) was added DPPA (1.21 g, 4.4 mmol) and tetraethylammonium chloride (TEA-Cl) (600 mg, 5.9 mmol). The reaction mixture was refluxed for 6 h, then concentrated to give the crude residue which was purified by silica gel chromatography (hexanes:EtOAc 10:1 to 5:1) to afford benzyl (S)-1-((tert-butoxycarbonyl)amino)-6-azaspiro[2.5]octane-6-carboxylate or benzyl (R)-1-((tert-butoxycarbonyl)amino)-6-azaspiro[2.5]octane-6-carboxylate (440 mg, 42% yield). Mass Spectrum (ESI) m/z=383 (M+23).

Step G.

A solution of benzyl (S)-1-((tert-butoxycarbonyl)amino)-6-azaspiro[2.5]octane-6-carboxylate or benzyl (R)-1-((tert-butoxycarbonyl)amino)-6-azaspiro[2.5]octane-6-carboxylate (440 mg, 1.2 mmol) in HCl in Dioxane (4M, 10 mL) was stirred at rt for 1 h. The solvent was removed and the residue (420 mg, crude) was used in the next step without further purification. Mass Spectrum (ESI) m/z=261 (M+1).

Step H.

To a solution of the crude product from Step G (420 mg, 1.4 mmol) in DCM (10 mL) was added EDCI (403 mg, 2.1 mmol), HOBT (284 mg, 2.1 mmol), DIPEA (542 mg, 4.2 mmol) and 3,5-dichlorobenzoic acid (401 mg, 2.1 mmol). The reaction mixture was stirred at rt for 12 h, then diluted with DCM (20 mL), washed successively with sat. aq. $NH_4Cl$ solution, sat. aq. $NaHCO_3$, water and brine and concentrated. The residue was purified by silica gel chromatography (hexanes/EtOAc 3:1 to 1:1) to afford the product benzyl (S)-1-(3,5-dichlorobenzamido)-6-azaspiro[2.5]octane-6-carboxylate or benzyl (R)-1-(3,5-dichlorobenzamido)-6-azaspiro[2.5]octane-6-carboxylate as a yellow oil (562 mg, 93% yield). Mass Spectrum (ESI) m/z=433 (M+1).

Step I.

To a solution of the compound from Step H (1 g, 2.7 mmol) in AcOH (10 mL) was added HBr in AcOH (33%, 3 mL) at rt. The resulting mixture was stirred at rt for 2 h. Solvent was removed, the residue was diluted with ethyl acetate (20 mL) and washed with sat. aq. $NaHCO_3$ (20 mL) and extracted with ethyl acetate (2×30 mL). The combined organic layers were dried over anhydrous sodium sulfate, filtered and concentrated to give a product (0.6 g, 95% yield) that was used in next step without further purification. Mass Spectrum (ESI) m/z=231 (M+1).

(S)—N-(6-(2-(tert-butylamino)-2-oxoethyl)-6-azaspiro[2.5]octan-1-yl)-3,5-dichlorobenzamide or (R)—N-(6-(2-(tert-butylamino)-2-oxoethyl)-6-azaspiro[2.5]octan-1-yl)-3,5-dichlorobenzamide

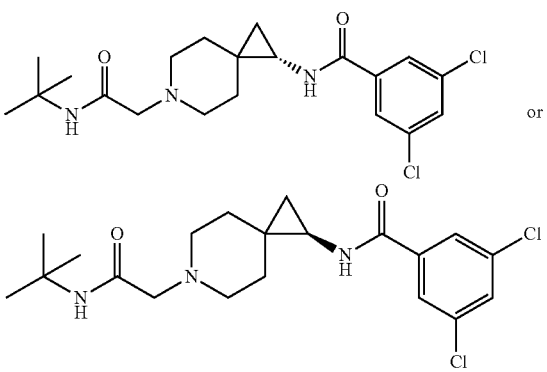

or

Step J.

A solution of the product from Step I (60 mg, 0.2 mmol), 2-bromo-N-tert-butylacetamide (35 mg, 0.18 mmol) and $K_2CO_3$ (83 mg, 0.6 mmol) in DMF/MeCN (1/1, 3 mL) was stirred at 60° C. for 16 h. 10 mL of water was added and the mixture was extracted with EA (20 mL×3). The combined organic layers were washed with brine, dried over $Na_2SO_4$ and concentrated. The residue was purified by chromatography on silica gel eluting with 5% DCM/MeOH to give (S)—N-(6-(2-(tert-butylamino)-2-oxoethyl)-6-azaspiro[2.5]octan-1-yl)-3,5-dichlorobenzamide or (R)—N-(6-(2-(tert-butylamino)-2-oxoethyl)-6-azaspiro[2.5]octan-1-yl)-3,5-dichlorobenzamide as a yellow solid (60 mg, 70%).

$^1$H NMR (400 MHz, MeOD) δ ppm 7.85 (d, J=1.9 Hz, 1.5H), 7.82 (d, J=1.9 Hz, 0.5H), 7.72-7.66 (m, 1H), 3.89 (s, 0.5H), 3.88-3.74 (m, 1.5H), 3.63 (dd, J=19.4, 12.0 Hz, 1H), 3.54-3.39 (m, 1H), 3.19 (d, J=11.5 Hz, 1H), 3.03-2.92 (m, 1H), 2.90-2.76 (m, 1H), 2.27 (dddd, J=37.0, 15.3, 13.0, 4.2 Hz, 2H), 2.07-1.92 (m, 0.5H), 1.62-1.44 (m, 1.5H), 1.40 (dd, J=10.8, 2.1 Hz, 9H), 1.06 (dt, J=12.5, 6.2 Hz, 1H), 0.96-0.84 (m, 1H). Mass Spectrum (ESI) m/z=412 (M+1).

Example 57

(R)—N-(6-(2-(tert-Butylamino)-2-oxoethyl)-6-azaspiro[2.5]octan-1-yl)-3,5-dichlorobenzamide or (S)—N-(6-(2-(tert-Butylamino)-2-oxoethyl)-6-azaspiro[2.5]octan-1-yl)-3,5-dichlorobenzamide

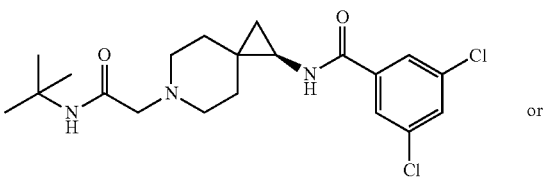

or

-continued

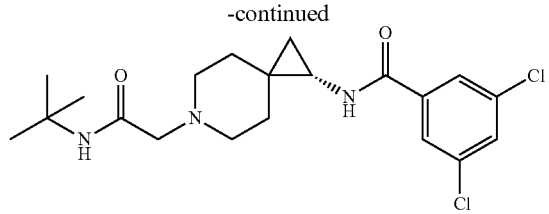

The title compound was prepared from enantiopure (S)-1-((4R,5S)-4-methyl-2-oxo-5-phenyloxazolidine-3-carbonyl)-6-azaspiro[2.5]octane-6-carboxylate or benzyl (R)-1-((4R,5S)-4-methyl-2-oxo-5-phenyloxazolidine-3-carbonyl)-6-azaspiro[2.5]octane-6-carboxylate (faster eluting/more polar diastereomer from Example 56, Step D) following Example 56 Steps E-J.

$^1$H NMR (400 MHz, MeOD) δ ppm 7.85/7.82 (d, J=1.9 Hz, 2H), 7.68 (dt, J=5.2, 1.9 Hz, 1H), 3.96-3.75 (m, 2H), 3.69-3.55 (m, 1H), 3.51-3.40 (m, 1H), 3.25-3.12 (m, 1H), 2.97 (td, J=12.7, 3.4 Hz, 1H), 2.89-2.77 (m, 1H), 2.36-2.24 (m, 1H), 2.24-2.16 (m, 1H), 2.06-1.95 (m, 1H), 1.65-1.44 (m, 2H), 1.44-1.33 (m, 8H), 1.06 (dt, J=12.8, 6.4 Hz, 1H), 0.95-0.84 (m, 1H). Mass Spectrum (ESI) m/z=412 (M+1).

Example 58

3,5-Dichloro-N-(6-(2-hydroxy-3,3-dimethylbutyl)-6-azaspiro[2.5]octan-1-yl)benzamide

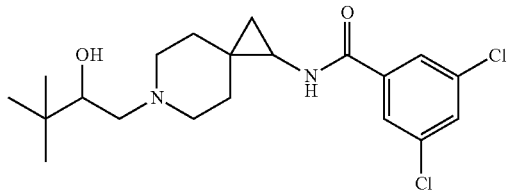 [SMILES: CC(C)(C)C(O)CN1CCC2(CC1)CC2NC(=O)c1cc(Cl)cc(Cl)c1]

To a solution of Example 49 in MeOH was added NaBH$_4$ at 0° C., and the resulting mixture was stirred at rt for 1 h. The solution was concentrated and the residue was diluted with ethyl acetate (30 mL) and washed with water (30 mL). The combined organic layers were dried over anhydrous sodium sulfate, filtered and concentrated. The crude product was purified by prep-TLC with DCM/MeOH to obtain the desired product as a white solid.

$^1$H NMR (400 MHz, CDCl3) δ 10.74 (s, 1H), 7.69 (s, 2H), 7.50 (s, 1H), 6.69 (s, 1H), 4.80 (s, 1H), 3.83 (s, 1H), 3.64 (m, 1H), 3.40 (m, 2H), 3.34 (s, 1H), 3.04 (s, 2.5H), 2.92 (s, 1.5H), 2.73 (s, 2H), 1.30 (m, 1H), 1.16 (s, 1H), 1.06 (s, 1H), 0.93 (s, 9H), 0.84 (s, 1H). Mass Spectrum (ESI) m/z=399 (M+1).

Example 59

3,5-Dichloro-N-(6-(2-hydroxy-2-(4-(trifluoromethyl)phenyl)ethyl)-6-azaspiro[2.5]octan-1-yl)benzamide

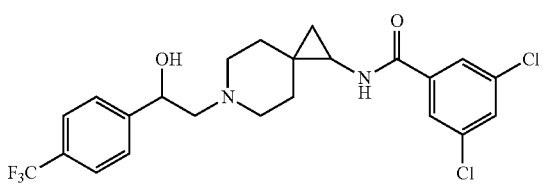 [SMILES: O=C(NC1CC12CCN(CC(O)c1ccc(C(F)(F)F)cc1)CC2)c1cc(Cl)cc(Cl)c1]

Example 59 can be prepared from Example 50 using a procedure sit ar to the one described in Example 58.

$^1$H NMR (400 MHz, MeOD) δ 7.61 (m, 7H), 4.98 (s, 1H), 2.83 (m, 7H), 1.62 (m, 4H), 0.84 (d, J=6.5 Hz, 1H), 0.70 (s, 1H). Mass Spectrum (ESI) m/z=487 (M+1).

Example 60

N-(7-Isobutyl-7-azaspiro[3.5]nonan-1-yl)benzamide

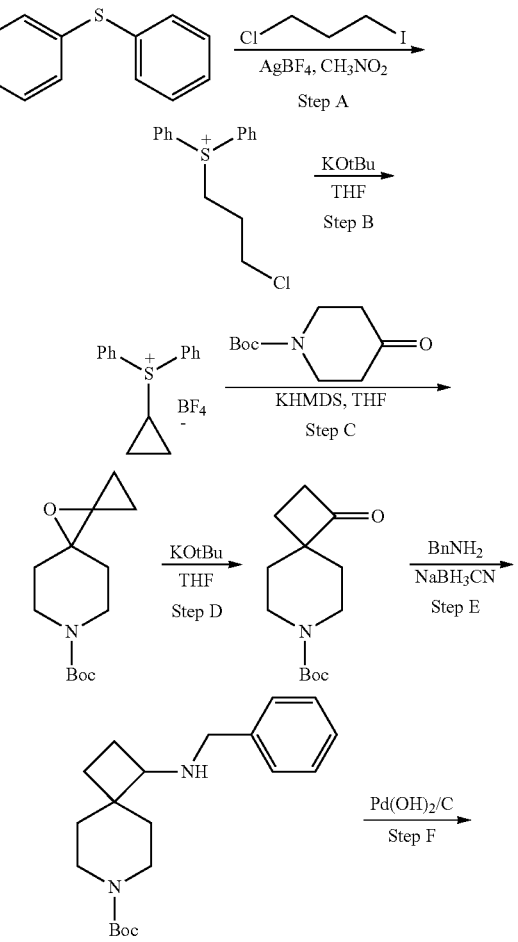

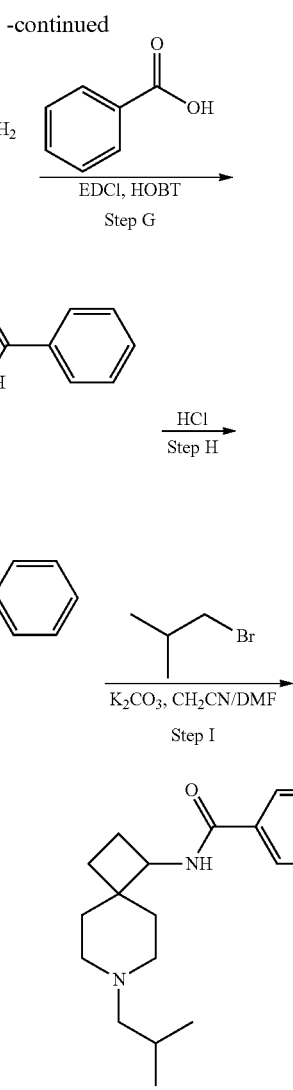

The synthesis of tert-butyl 1-oxo-7-azaspiro[3,5]-nonane-7-carboxylate has been described in the literature (a: Trost, B. M.; Bogdanowicz, M. J.; J. Am. Chem. Soc. 1973, 95, 5298-5307. b: Finke, P. E.; Loebach, J. L.; Parker, K. A.; Plummer, C. W.; Mills, S. G.; U.S. Pat. Appl. US 2005070609, 2005). The synthesis of tert-butyl 1,8-diazaspiro[5.6]decane-8-carboxylate from tert-butyl 1-oxo-7-azaspiro[3,5]-nonane-7-carboxylate has also been reported in the literature (J. Org. Chem. 2009, 74, 1304-1313).

Step A.

To a solution of diphenyl sulfide (7.44 g, 40 mmol) and 1-chloro-3-iodopropane (24.5 g, 120 mmol) in nitromethane (15 mL) at RT was added silver tetrafluoroborate (7.37 g, 38 mmol) in one portion. A yellow precipitate formed, and the reaction temperature initially rose to around 40-50° C., then gradually fell to RT. The reaction mixture was stirred at RT for 20 hr then diluted with dichloromethane (15 mL) and filtered through a sintered funnel packed with Celite® (J.T. Baker, Phillipsberg, N.J., diatomaceous earth) to remove all silver compounds. The yellow solid in the funnel was washed with dichloromethane (3×12 mL). The filtrate concentrated under reduced pressure until a precipitate appeared. The product was triturated with diethyl ether (100 mL) for 2 h, then filtered to give a white solid. The solid was washed with diethyl ether (3×12 mL), dried under suction for 5 min and then transferred to a container to dry overnight under reduced pressure to give 12 g of a white solid.

Mass Spectrum (ESI) m/z=264.2 (M+H). $^1$H NMR (400 MHz, CDCl$_3$) δ ppm 7.97 (d, J=7.4 Hz, 4H), 7.81-7.66 (m, 6H), 4.36-4.27 (m, 2H), 3.76 (t, J=5.9 Hz, 2H), 2.27 (dt, J=12.9, 6.3 Hz, 2H).

Step B.

To a slurry of 3-chloropropyldiphenylsulfonium fluoroborate (13 g, 37.2 mmol) in tetrahydrofuran (150 mL) was added a solution (1.28M) of potassium tert-butoxide (37.2 mol, 4.2 g) in dimethyl sulfoxide (29 mL) at RT over a period of 1 h. The reaction mixture turned a deep amber color when the base was added [the colour disappeared quickly after each addition, but at the end of the addition, the color remained amber]. The reaction mixture was diluted with dichloromethane (80 mL), stirred for 10 min then poured onto a mixture of dichloromethane/water (1:1, 100 mL). The phases were separated and the dichloromethane phase collected and evaporated to dryness. The residue was stirred in diethyl ether (1 L) for 1 hr and then decanted. The oily residue was crystallized using ethanol/diethyl ether to give the product (4.1 g, 13.1 mmol, 35%) as a white solid.

Mass Spectrum (ESI) m/z=315.1 (M+H). $^1$H NMR (400 MHz, CDCl$_3$) δ ppm 7.99 (d, J=7.6 Hz, 4H), 7.79-7.63 (m, 6H), 4.11-3.86 (m, 1H), 1.71 (d, J=7.2 Hz, 2H), 1.44 (d, J=3.8 Hz, 2H).

Step C.

To a solution of cyclopropyldiphenylsulfonium tetrafluoroborate (4 g, 12.74 mmol) in tetrahydrofuran (80 mL) at −40° C. was added potassium bis(trimethylsilyl)amide (14 mmol, 1 M in THF, 14 mL). The resulting yellow solution was stirred at −40° C. for a further 10 min, then 4-Boc-piperidone (12.54 mmol, 2.54 g) was added in one portion. The resulting solution was stirred at −40° C. for 30 min, allowed to warm to RT over 2 hr, and then stirred at RT for 1 hr. The reaction mixture was quenched with water (60 mL), then extracted with diethyl ether (100 mL×2). The combined ether extracts were dried and concentrated under reduced pressure to give crude product (6.2 g, 26 mmol) as a colourless liquid. The crude product, which contained diphenyl sulfide, was used without purification in the next step.

Mass Spectrum (ESI) m/z=262 (M+Na).

Step D.

Dried crude t-butyl 10-oxa-7-azadispiro[2.0.5.1]decane-7-carboxylate (6.2 g, 26 mmol) was dissolved in anhydrous toluene (60 mL). To this solution was added lithium tetrafluoroborate (122 mg) in one lot. The mixture was heated to 80° C. for 2 h. After cooling to RT, about 50 mL of toluene was removed under reduced pressure. The reaction mixture was then quenched with water (40 mL). The product was extracted with diethyl ether (3×50 mL), washed with brine (2×60 mL), dried over sodium sulfate and evaporated to dryness. The residue was purified by flash column chromatography on silica gel with ethyl acetate/hexane (20:80) to give tert-butyl 1-oxo-7-azaspiro[3,5]-nonane-7-carboxylate (2.96 g, 12.4 mmol) as a white solid.

Mass Spectrum (ESI) m/z=262 (M+Na). $^1$H NMR (400 MHz, CDCl$_3$) δ ppm 3.62-3.50 (m, 2H), 3.46-3.34 (m, 2H), 3.03 (t, J=8.4 Hz, 2H), 1.95-1.75 (m, 4H), 1.68-1.54 (m, 2H), 1.45 (s, 9H).

Step E.

To a solution of tert-butyl 1-oxo-7-azaspiro[3,5]-nonane-7-carboxylate (2.96 g, 12.4 mmol) in anhydrous 1,2-dichloroethane (35 mL) was added benzylamine (1.6 g, 14.9 mmol) followed by sodium triacetoxyborohydride (5.3 g, 24.8 mmol). The mixture was stirred at rt for 18 h and then quenched with saturated aqueous sodium bicarbonate and the product extracted with EtOAc (3×50 mL). The combined extracts were washed with water (2×40 mL) and brine (2×50 mL), dried over Na₂SO₄, and concentrated to dryness. The product was purified by silica gel chromatography eluting with 2% MeOH/DCM to give tert-butyl 1-(benzylamino)-7-azaspiro[3.5]nonane-7-carboxylate (3.48 g, 85%).

Mass Spectrum (ESI) m/z=331.2 (M+H).

Step F.

To a solution of tert-butyl 1-(benzylamino)-7-azaspiro [3.5]nonane-7-carboxylate (2.63 g, 7.96 mmol) in methanol (60 mL) was added Pd/C (260 mg) in one portion. The reaction mixture was stirred at rt under a hydrogen atmosphere (balloon) for 16 h, and then the catalyst was filtered off through a Celite® (J.T. Baker, Phillipsberg, N.J., diatomaceous earth)-packed funnel. The Celite® layer was washed with methanol (3×20 mL). The combined filtrate and washings were concentrated to dryness to afford tert-butyl 1,8-diazaspiro[5.6]decane-8-carboxylate as a yellow oil (1.9 g, 99%).

Mass Spectrum (ESI) m/z=241 (M+H).

Step G.

A solution of tert-butyl 1,8-diazaspiro[5.6]decane-8-carboxylate (600 mg, 2.5 mmol), benzoic acid (458 mg, 3.75 mmol), HOBT (675 mg, 5 mmol), EDCI (955 mg, 5 mmol) and diisopropylethylamine (968 g, 7.5 mmol) in DMF/DCM (2 mL/8 mL) was stirred at RT for 3 hours. Then 20 mL of water was added and the solution was extracted with DCM (30 mL×3). The combined organic layers were washed sequentially with NH₄Cl and brine, dried over Na₂SO₄ and concentrated in vacuo. The residue was purified by silica gel chromatography (40% PE/EtOAc) to give tert-butyl 1-(benzylamino)-7-azaspiro[3.5]nonane-7-carboxylate (700 mg, 80%).

Mass Spectrum (ESI) m/z=367 (M+Na). ¹H NMR (400 MHz, CDCl₃) δ ppm 7.74 (d, J=7.3 Hz, 2H), 7.47 (dt, J=14.9, 7.2 Hz, 3H), 6.13 (d, J=7.8 Hz, 1H), 4.39 (dd, J=16.8, 8.5 Hz, 1H), 3.83 (s, 2H), 3.02-2.82 (m, 2H), 2.41 (dd, J=17.8, 8.7 Hz, 1H), 1.98-1.73 (m, 4H), 1.62 (d, J=20.0 Hz, 2H), 1.43 (s, 9H).

Step H.

A solution of tert-butyl 1-(benzylamino)-7-azaspiro[3.5] nonane-7-carboxylate (500 mg, 1.45 mmol) in MeOH (8 mL) was added HCl/1,4-dioxane (4N, 3 mL), then the reaction was stirred at RT for 1 hours. The solution was concentrated to give N-(7-azaspiro[3.5]nonan-1-yl)benzamide as a white solid (340 mg, 95%). Mass Spectrum (ESI) m/z=245.2 (M+H).

Step I.

A solution of N-(7-azaspiro[3.5]nonan-1-yl)benzamide (80 mg, 0.33 mmol), 1-Bromo-2-methylpropane (55 mg, 0.44 mmol) and K₂CO₃ (91 mg, 0.66 mmol) in DMF/CH₃CN (1/1 3 mL) was stirred at 60° C. for 16 h. Then 10 mL of water was added and the solution was extracted with EA (20 mL×3). The combined organic layers were washed with brine, dried over Na₂SO₄ filtered and the filtrate was concentrated. The residue was purified by silica gel chromatography eluting with 5% DCM/MeOH to give the title compound as a yellow solid (42 mg, 42%).

Mass Spectrum (ESI) m/z=301.3 (M+H). ¹H NMR (400 MHz, MeOD) δ ppm 7.95-7.80 (m, 2H), 7.65-7.43 (m, 3H), 4.36 (t, J=6.6 Hz, 1H), 3.58-3.44 (m, 2H), 3.13-2.85 (m, 3.5H), 2.78-2.68 (m, 0.5H), 2.43-2.09 (m, 4H), 2.06-1.91 (m, 2H), 1.86-1.71 (m, 2H), 1.31 (s, 0.5H), 1.20 (t, J=7.0 Hz, 0.5H), 1.04 (dd, J=6.5, 4.6 Hz, 6H).

Examples 61 to 71 were also prepared by procedures similar to the one described in Example 60, replacing benzoic acid in step G and/or 1-bromo-2-methylpropane in step I with the designated reagents.

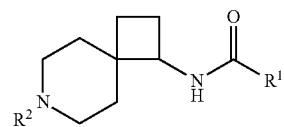

| Example | R¹ | R² | Reagent used in Step G | Reagent used in Step I |
|---|---|---|---|---|
| 61 | phenyl | neopentyl | Benzoic acid | 1-Bromo-3,3-dimethylbutane |
| 62 | phenyl | 2-phenylethyl | Benzoic acid | (2-Bromoethyl)benzene |
| 63 | phenyl | N-(tert-butyl)acetamide | Benzoic acid | 2-Bromo-N-(tert-butyl)acetamide |

-continued

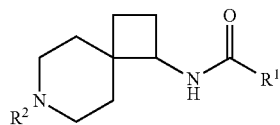

| Example | R¹ | R² | Reagent used in Step G | Reagent used in Step I |
|---|---|---|---|---|
| 64 | 3,4-dichlorophenyl | isobutyl | 3,4-Dichlorobenzoic acid | 1-Bromo-2-methylpropane |
| 65 | 3,4-dichlorophenyl | 3,3-dimethylbutyl | 3,4-Dichlorobenzoic acid | 1-Bromo-3,3-dimethylbutane |
| 66 | 3,4-dichlorophenyl | 2-phenylethyl | 3,4-Dichlorobenzoic acid | (2-Bromoethyl)benzene |
| 67 | 3,4-dichlorophenyl | -CH₂C(O)NH-tBu | 3,4-Dichlorobenzoic acid | 2-Bromo-N-(tert-butyl)acetamide |
| 68 | 3,5-dichlorophenyl | isobutyl | 3,5-Dichlorobenzoic acid | 1-Bromo-2-methylpropane |
| 69 | 3,5-dichlorophenyl | 3,3-dimethylbutyl | 3,5-Dichlorobenzoic acid | 1-Bromo-3,3-dimethylbutane |
| 70 | 3,5-dichlorophenyl | 2-phenylethyl | 3,5-Dichlorobenzoic acid | (2-Bromoethyl)benzene |
| 71 | 3,5-dichlorophenyl | -CH₂C(O)NH-tBu | 3,5-Dichlorobenzoic acid | 2-Bromo-N-(tert-butyl)acetamide |

Example 61

N-(6-(3,3-Dimethylbutyl)-6-azaspiro[2.5]octan-1-yl) benzamide

¹H NMR (400 MHz, MeOD) δ ppm 7.83 (d, J=7.8 Hz, 2H), 7.60-7.43 (m, 3H), 4.35 (t, J=8.7 Hz, 1H), 2.85 (s, 2H), 2.55-2.28 (m, 5H), 2.22-2.13 (m, 1H), 2.04-1.95 (m, 1H), 1.74-1.89 (m, 4H), 1.67-1.60 (m, 1H), 1.51-1.41 (m, 2H), 0.93 (s, 9H). Mass Spectrum (ESI) m/z=329.3 (M+H).

Example 62

N-(6-Phenethyl-6-azaspiro[2.5]octan-1-yl)benzamide

¹¹H NMR (400 MHz, CDCl₃) δ ppm 7.74 (d, J=7.8 Hz, 2H), 7.53-7.40 (m, 3H), 7.33-7.18 (m, 5H), 6.19 (d, J=6.7 Hz, 1H), 4.53-4.33 (m, 1H), 2.81 (s, 4H), 2.62 (d, J=25.7 Hz, 2H), 2.45-1.95 (m, 4H), 1.97-1.71 (m, 4H), 1.62-1.53 (m, 1H), 1.26 (s, 1H). Mass Spectrum (ESI) m/z=349.3 (M+H).

Example 63

N-(7-(2-(tert-Butylamino)-2-oxoethyl)-7-azaspiro [3.5]nonan-1-yl)benzamide

¹H NMR (400 MHz, MeOD) δ ppm 7.89-7.82 (m, 2H), 7.60-7.54 (m, 1H), 7.49 (t, J=7.4 Hz, 2H), 4.34 (t, J=8.9 Hz, 1H), 3.16-2.69 (m, 5H), 2.41-2.06 (m, 4H), 1.95-1.77 (m, 4H), 1.76-1.66 (m, 1H), 1.35 (s, 9H). Mass Spectrum (ESI) m/z=358.3 (M+H).

Example 64

3,4-Dichloro-N-(7-isobutyl-7-azaspiro[3.5]nonan-1-yl)benzamide

¹H NMR (400 MHz, MeOD) δ ppm 8.10 (d, J=2.0 Hz, 0.2H), 8.04 (d, J=2.0 Hz, 0.7H), 7.88-7.77 (m, 1H), 7.73-7.65 (m, 1H), 4.38-4.30 (m, 1H), 3.55-3.41 (m, 2H), 3.08 (t, J=11.7 Hz, 1H), 3.01-2.85 (m, 3H), 2.75-2.67 (m, 0.3H), 2.50-2.12 (m, 4.7H), 2.01-1.92 (m, 2H), 1.86-1.74 (m, 2H), 1.09-1.00 (m, 6H). Mass Spectrum (ESI) m/z=369.2 (M+H).

Example 65

3,4-Dichloro-N-(7-(3,3-dimethylbutyl)-7-azaspiro [3.5]nonan-1-yl)benzamide

¹H NMR (400 MHz, MeOD) δ ppm 8.01 (d, J=1.8 Hz, 1H), 7.77 (dd, J=8.4, 1.9 Hz, 1H), 7.66 (d, J=8.4 Hz, 1H), 4.31 (t, J=8.9 Hz, 1H), 2.85 (s, 2H), 2.55-2.23 (m, 5H), 2.21-2.12 (m, 1H), 2.03-1.95 (m, 1H), 1.89-1.66 (m, 4H), 1.67-1.59 (m, 1H), 1.50-1.45 (m, 2H), 0.93 (s, 9H). Mass Spectrum (ESI) m/z=397.2 (M+H).

Example 66

3,4-Dichloro-N-(7-phenethyl-7-azaspiro[3.5]nonan-1-yl)benzamide

¹H NMR (400 MHz, MeOD) δ ppm 8.01 (s, 1H), 7.77 (d, J=8.0 Hz, 1H), 7.66 (d, J=8.3 Hz, 1H), 7.33-7.14 (m, 5H), 4.32 (t, J=8.9 Hz, 1H), 2.95-2.78 (m, 4H), 2.67-2.58 (m, 2H), 2.41 (s, 1H), 2.29 (d, J=8.7 Hz, 2H), 2.21-2.12 (m, 1H), 2.05-1.97 (m, 1H), 1.87-1.76 (m, 3H), 1.67-1.56 (m, 1H), 1.31 (s, 1H). Mass Spectrum (ESI) m/z=417.2 (M+H).

Example 67

N-(7-(2-(tert-Butylamino)-2-oxoethyl)-7-azaspiro [3.5]nonan-1-yl)-3,4-dichlorobenzamide ¹H NMR (400 MHz, MeOD) δ ppm 8.83-8.61 (m, 1H), 8.10-7.75 (m, 3H), 7.68 (t, J=7.4 Hz, 1H), 4.43-4.30 (m, 1H), 3.95-3.53 (m, 4H), 3.30-2.85 (m, 3H), 2.37-2.12 (m, 3H), 2.03-1.93 (m, 2H), 1.86-1.70 (m, 2H), 1.40-1.33 (m, 9H). Mass Spectrum (ESI) m/z=426.2 (M+H).

Example 68

3,5-Dichloro-N-(7-isobutyl-7-azaspiro[3.5]nonan-1-yl)benzamide

¹H NMR (400 MHz, MeOD) δ ppm 7.81 (d, J=1.9 Hz, 2H), 7.66 (t, J=1.9 Hz, 1H), 4.30 (t, J=8.8 Hz, 1H), 2.76 (s, 2H), 2.35-2.10 (m, 6H), 1.98 (s, 1H), 1.90-1.69 (m, 5H), 1.65-1.57 (m, 1H), 0.93 (d, J=6.6 Hz, 6H). Mass Spectrum (ESI) m/z=369.2 (M+H).

Example 69

3,5-Dichloro-N-(7-(3,3-dimethylbutyl)-7-azaspiro [3.5]nonan-1-yl)benzamide

¹H NMR (400 MHz, MeOD) δ ppm 7.81 (s, 2H), 7.66 (s, 1H), 4.31 (t, J=8.9 Hz, 1H), 2.91 (s, 2H), 2.61-2.28 (m, 5H), 2.22-2.12 (m, 1H), 2.01 (t, J=10.6 Hz, 1H), 1.87-1.70 (m, 4H), 1.68-1.60 (m, 1H), 1.47 (dd, J=10.2, 6.7 Hz, 2H), 0.94 (s, 9H). Mass Spectrum (ESI) m/z=397.2 (M+H).

Example 70

3,5-Dichloro-N-(7-phenethyl-7-azaspiro[3.5]nonan-1-yl)benzamide

¹H NMR (400 MHz, MeOD) δ ppm 7.81 (d, J=1.7 Hz, 2H), 7.66 (s, 1H), 7.31-7.17 (m, 5H), 4.32 (t, J=8.9 Hz, 1H), 2.94-2.80 (m, 4H), 2.70-2.60 (m, 2H), 2.42 (s, 1H), 2.37-2.26 (m, 2H), 2.18 (dd, J=20.3, 10.5 Hz, 1H), 2.06-1.97 (m, 1H), 1.81 (dd, J=21.6, 11.8 Hz, 3H), 1.90-1.75 (m, 1H), 1.31 (s, 1H). Mass Spectrum (ESI) m/z=417.2 (M+H).

Example 71

N-(7-(2-(tert-Butylamino)-2-oxoethyl)-7-azaspiro [3.5]nonan-1-yl)-3,5-dichlorobenzamide ¹H NMR (400 MHz, MeOD) δ ppm 8.90-8.62 (m, 1H), 8.10-7.80 (m, 3H), 7.68 (s, 1H), 4.33 (s, 1H), 3.83-3.49 (m, 4H), 2.95 (d, J=53.1 Hz, 3H), 2.45-2.12 (m, 3H), 2.02-1.89 (m, 2H), 1.79 (s, 2H), 1.37 (s, 9H). Mass Spectrum (ESI) m/z=426.2 (M+H).

Example 72

N-(8-Isobutyl-8-azaspiro[4.5]decan-1-yl)benzamide

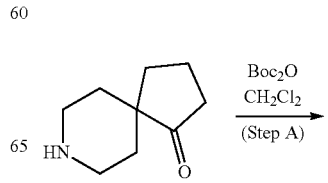

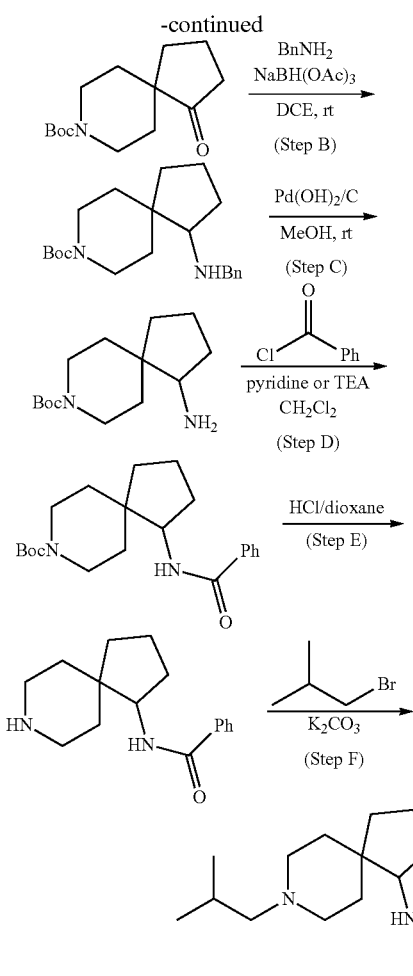

Step A.

8-Azaspiro[4.5]decan-1-one (CAS No. 198133-82-3) is commercially available or can be prepared as described in WO9737992. 8-Azaspiro[4.5]decan-1-one can be treated with (Boc)₂O in presence of a base to give tert-butyl 1-oxo-8-azaspiro[4.5]decane-8-carboxylate.

Step B.

tert-butyl 1-oxo-8-azaspiro[4.5]decane-8-carboxylate can be converted into tert-butyl 1-(benzylamino)-8-azaspiro[4.5]decane-8-carboxylate by a procedure similar to the one described in Example 58 Step E.

Step C.

tert-butyl 1-(benzylamino)-8-azaspiro[4.5]decane-8-carboxylate can be converted into tert-butyl 1-amino-8-azaspiro[4.5]decane-8-carboxylate by a procedure similar to the one described in Example 58 Step F.

Step D.

tert-butyl 1-amino-8-azaspiro[4.5]decane-8-carboxylate can be converted into tert-butyl 1-benzamido-8-azaspiro[4.5]decane-8-carboxylate by a procedure similar to the one described in Example 58 Step G.

Step E.

tert-butyl 1-benzamido-8-azaspiro[4.5]decane-8-carboxylate can be converted into N-(8-azaspiro[4.5]decan-1-yl)benzamide by a procedure similar to the one described in Example 58 Step H.

Step F.

N-(8-azaspiro[4.5]decan-1-yl)benzamide can be converted into N-(8-isobutyl-8-azaspiro[4.5]decan-1-yl)benzamide by a procedure similar to the one described in Example 16 Step I.

Examples 73 to 86 can also prepared by procedures similar to the one described in Example 70, replacing benzoylchloride in step D and/or 1-bromo-2-methylpropane in step F with the designated reagents.

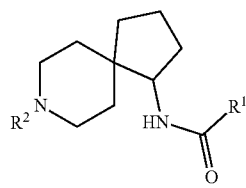

| Example | R¹ | R² | Reagent used in Step D | Reagent used in Step F |
|---|---|---|---|---|
| 73 | 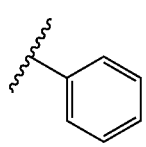 [SMILES: *c1ccccc1] | 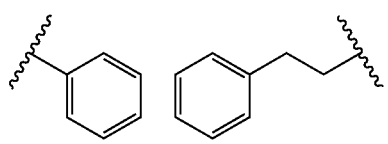 | Benzoyl chloride | 1-Bromo-3,3-dimethylbutane |
| 74 | (phenyl) | (phenethyl) | Benzoyl chloride | (2-Bromoethyl)benzene |

-continued

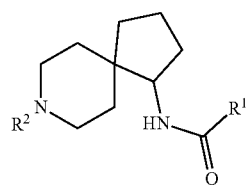

| Example | R¹ | R² | Reagent used in Step D | Reagent used in Step F |
|---------|----|----|------------------------|------------------------|
| 75 | phenyl | tert-butyl-NH-C(O)-CH₂- | Benzoyl chloride | 2-Bromo-N-(tert-butyl)acetamide |
| 76 | phenyl | PhCH₂- | Benzoyl chloride | Benzylbromide |
| 77 | 3,4-dichlorophenyl | isobutyl | 3,4-Dichlorobenzoyl chloride | 1-Bromo-2-methylpropane |
| 78 | 3,4-dichlorophenyl | 3,3-dimethylbutyl | 3,4-Dichlorobenzoyl chloride | 1-Bromo-3,3-dimethylbutane |
| 79 | 3,4-dichlorophenyl | 2-phenylethyl | 3,4-Dichlorobenzoyl chloride | (2-Bromoethyl)benzene |
| 80 | 3,4-dichlorophenyl | tert-butyl-NH-C(O)-CH₂- | 3,4-Dichlorobenzoyl chloride | 2-Bromo-N-(tert-butyl)acetamide |
| 81 | 3,4-dichlorophenyl | PhCH₂- | 3,4-Dichlorobenzoyl chloride | Benzylbromide |
| 82 | 3,5-dichlorophenyl | isobutyl | 3,5-Dichlorobenzoyl chloride | 1-Bromo-2-methylpropane |

-continued

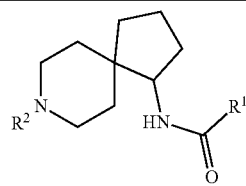

| Example | R¹ | R² | Reagent used in Step D | Reagent used in Step F |
|---|---|---|---|---|
| 83 | 3,5-dichlorophenyl | tert-butyl-CH₂CH₂- | 3,5-Dichlorobenzoyl chloride | 1-Bromo-3,3-dimethylbutane |
| 84 | 3,5-dichlorophenyl | PhCH₂CH₂- | 3,5-Dichlorobenzoyl chloride | (2-Bromoethyl)benzene |
| 85 | 3,5-dichlorophenyl | tBuNHC(O)CH₂- | 3,5-Dichlorobenzoyl chloride | 2-Bromo-N-(tert-butyl)acetamide |
| 86 | 3,5-dichlorophenyl | PhCH₂- | 3,5-Dichlorobenzoyl chloride | Benzylbromide |

Example 87

N-((6-(2-(tert-Butylamino)-2-oxoethyl)-6-azaspiro[2.5]octan-1-yl)methyl)-3,5-dichlorobenzamide

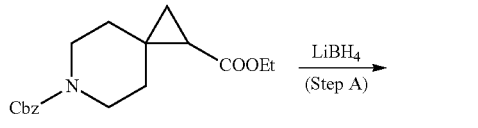

-continued

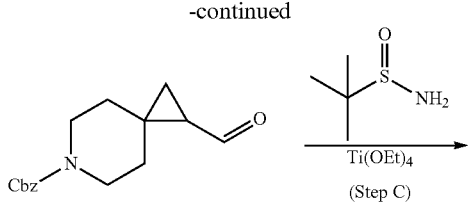

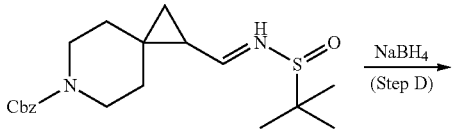

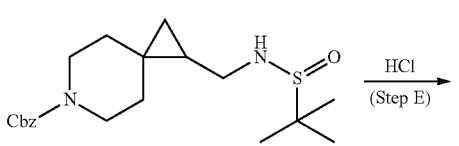

-continued

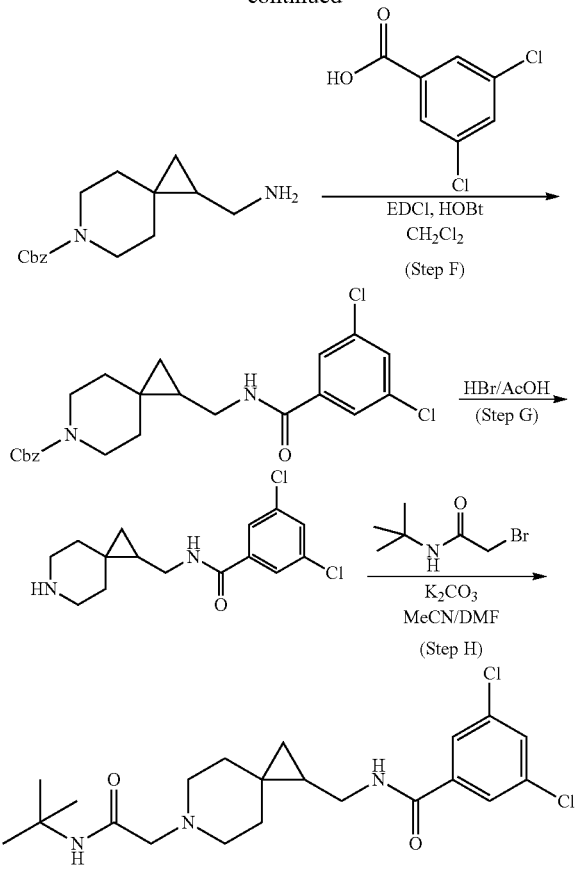

Step A.

To a solution of 6-benzyl 1-ethyl 6-azaspiro[2.5]octane-1,6-dicarboxylate (1.5 g, 4.8 mmol; Example 1, Step B) in THF (20 mL) was added LiBH₄ (1.1 g, 48 mmol) at 0° C. The mixture was stirred at RT for 2 hours. 1N HCl was added to quench the reaction at 0° C. The organic layer was separated; the aqueous layer was extracted with EA (30 mL×3). The combined organic layers were dried and concentrated to give the crude product as yellow oil which was used in the next step without further purification. Mass Spectrum (ESI) m/z=276 (M+H).

Step B.

To a solution of the product from Step A (1.5 g, 5.5 mmol) in DCM (20 mL) was added DMP (2.8 g, 6.6 mmol) at 0° C., then warmed to rt and stirred for 2 hours. The mixture was diluted with DCM (80 mL) and washed with 1M aq. Na₂S₂O₃ solution (30 mL), saturated aq. NaHCO₃ solution (30 m) and brine (30 mL). The organic layer was dried over MgSO4, filtered and the filtrate was concentrated in vacuo to give the crude product benzyl 1-formyl-6-azaspiro[2.5]octane-6-carboxylate (1.5 g) as yellow oil. Mass Spectrum (ESI) m/z=274 (M+H).

Step C.

To a solution of the product from Step B (1.6 g, 5.9 mmol) and 2-methylpropane-2-sulfinamide (860 mg, 7.1 mmol) in THF (25 mL) was added Ti(OEt)₄ (2 g, 8.9 mmol) dropwise at 0° C. The mixture was refluxed for 16 h. Then the solvent was removed, to give the crude product benzyl 1-(((tert-butylsulfinyl)-14-azanylidene)methyl)-6-azaspiro[2.5]octane-6-carboxylate which was used in the next step without further purification. Mass Spectrum (ESI) m/z=377.

Step D.

To a solution of benzyl 1-(((tert-butylsulfinyl)-14-azanylidene)methyl)-6-azaspiro[2.5]octane-6-carboxylate (1.1 g, 3 mmol) in THF (10 mL) was added NaBH₄ (2.2 g, 5.9 mmol) at 0° C., The reaction mixture was stirred at RT for 2 h, then diluted with EA (50 mL) washed with sat. aq. NH₄Cl solution (20 mL), sat. aq. NaHCO₃ solution (20 mL) and brine (20 mL) and concentrated under reduced pressure. The residue was purified by chromatography on silica gel (hexanes:EtOAc 3:1 to 1:1) to afford the benzyl 1-(((tert-butylsulfinyl)amino)methyl)-6-azaspiro[2.5]octane-6-carboxylate (2 g, 88% yield) as yellow oil. Mass Spectrum (ESI) m/z=379 (M+H).

Step E.

To a stirred solution of benzyl 1-(((tert-butylsulfinyl)amino)methyl)-6-azaspiro[2.5]octane-6-carboxylate (2 g, 5.3 mmol) in DCM (20 mL) was added 3M HCl (10 mL) at 0° C. and the mixture was stirred at RT for 2 hours. The solution was concentrated to give benzyl 1-(aminomethyl)-6-azaspiro[2.5]octane-6-carboxylate (1.4 g, 96%) as a white solid. Mass Spectrum (ESI) m/z=275 (M+H).

Step F.

To a stirred solution of benzyl 1-(aminomethyl)-6-azaspiro[2.5]octane-6-carboxylate (930 mg, 3 mmol) in DCM (15 mL) was added EDCI (864 mg, 1.5 mmol), HOBT (486 mg, 3.6 mmol), DIPEA (1.2 g, 9 mmol) and 3,5-dichlorobenzoic acid (688 mg, 3.6 mmol), The reaction mixture was stirred at RT for 12 h, then diluted with DCM (30 mL), washed with brine (30 mL) and extracted with DCM (30 mL×3). The combined extracts were concentrated under reduced pressure. The crude residue was purified by chromatography on silica gel (hexanes:EtOAc 3:1 to 1:1) to afford benzyl 1-((3,5-dichlorobenzamido)methyl)-6-azaspiro[2.5]octane-6-carboxylate (1 g, 73% yield) as yellow oil. Mass Spectrum (ESI) m/z=447 (M+H).

Step G.

To a stirred solution of benzyl 1-((3,5-dichlorobenzamido)methyl)-6-azaspiro[2.5]octane-6-carboxylate (900 mg, 3 mmol) in AcOH (10 mL) was added HBr in AcOH (33%, 4 mL) at rt. After the mixture was stirred at rt for 2 h, solvent was removed, the residue was diluted with ethyl acetate (30 mL) and washed with sat. aq NaHCO₃ solution (30 mL) and extracted with ethyl acetate (2×30 mL). The combined organic layers were dried over anhydrous sodium sulfate, filtered and concentrated to give the crude product N-((6-azaspiro[2.5]octan-1-yl)methyl)-3,5-dichlorobenzamide (0.45 g, 48% yield), which was used in the next step without further purification. Mass Spectrum (ESI) m/z=313 (M+H).

Step H.

A solution of N-((6-azaspiro[2.5]octan-1-yl)methyl)-3,5-dichlorobenzamide (120 mg, 0.39 mmol), 2-bromo-N-tert-butylacetamide (67 mg, 0.34 mmol) and K₂CO₃ (210 mg, 1.54 mmol) in DMF/MeCN (1/1, 3 mL) was stirred at 60° C. for 16 h. 10 mL of water was added and the solution was extracted with EA (20 mL×3). The combined organic layers were washed with brine, dried over Na₂SO₄ filtered and the filtrate was concentrated. The residue was purified by silica gel chromatography eluting with 5% DCM/MeOH to N-((6-(2-(tert-butylamino)-2-oxoethyl)-6-azaspiro[2.5]octan-1-yl)methyl)-3,5-dichlorobenzamide as a white solid (25 mg, 17%).

¹H NMR (400 MHz, MeOD) δ ppm 7.81 (d, J=1.9 Hz, 2H), 7.65 (t, J=1.9 Hz, 1H), 3.47 (dd, J=14.0, 7.7 Hz, 1H), 3.36 (d, J=7.4 Hz, 1H), 2.91 (s, 2H), 2.61 (d, J=5.2 Hz, 2H), 2.51 (s, 2H), 1.82-1.75 (m, 1H), 1.63 (s, 1H), 1.37 (s, 9H), 1.05 (td, J=13.0, 7.7 Hz, 1H), 0.59 (dd, J=8.5, 4.6 Hz, 1H), 0.30 (t, J=4.9 Hz, 1H). Mass Spectrum (ESI) m/z=426 (M+H).

Examples 88 and 89 can also prepared by procedures similar to the one described in Example 87, replacing 2-bromo-N-tert-butylacetamide in step H with the designated reagents.

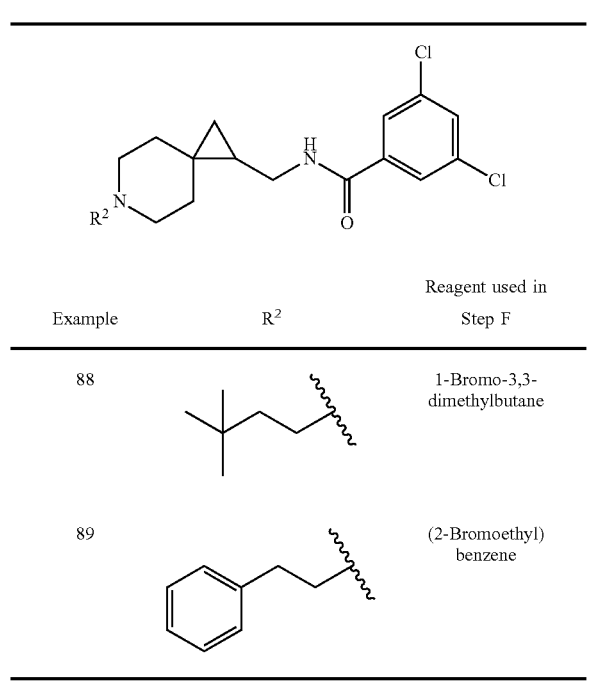

| Example | R² | Reagent used in Step F |
|---|---|---|
| 88 | (tert-butyl-CH₂CH₂-) | 1-Bromo-3,3-dimethylbutane |
| 89 | (phenyl-CH₂CH₂-) | (2-Bromoethyl)benzene |

Example 88

3,5-Dichloro-N-((6-(3,3-dimethylbutyl)-6-azaspiro[2.5]octan-1-yl)methyl)benzamide ¹H NMR (400 MHz, MeOD) δ ppm 7.81 (d, J=1.9 Hz, 2H), 7.66 (t, J=1.9 Hz, 1H), 3.47 (dd, J=14.1, 8.0 Hz, 1H), 3.41-3.34 (m, 1H), 2.86 (s, 2H), 2.76 (s, 2H), 2.73-2.62 (m, 2H), 1.86 (s, 1H), 1.68 (s, 2H), 1.58-1.48 (m, 2H), 1.41 (d, J=11.0 Hz, 1H), 1.22-1.05 (m, 1H), 0.96 (s, 9H), 0.66 (dd, J=8.6, 4.7 Hz, 1H), 0.36 (t, J=5.0 Hz, 1H). Mass Spectrum (ESI) m/z=397 (M+1).

Example 89

3,5-Dichloro-N-((6-phenethyl-6-azaspiro[2.5]octan-1-yl)methyl)benzamide

¹H NMR (400 MHz, MeOD) δ ppm 7.81 (d, J=1.9 Hz, 2H), 7.65 (d, J=1.3 Hz, 1H), 7.33-7.26 (m, 2H), 7.25-7.18 (m, 3H), 3.48 (dd, J=14.1, 7.9 Hz, 2H), 2.86-2.66 (m, 8H), 1.85 (s, 1H), 1.66 (s, 2H), 1.50-1.35 (m, 1H), 1.17-1.06 (m, 1H), 0.65 (dd, J=8.6, 4.7 Hz, 1H), 0.35 (t, J=4.9 Hz, 1H). Mass Spectrum (ESI) m/z=417 (M+1).

Example 90

N-((6-(2-(tert-Butylamino)-2-oxoethyl)-6-azaspiro[2.5]octan-1-yl)methyl)-3,5-dichlorobenzamide

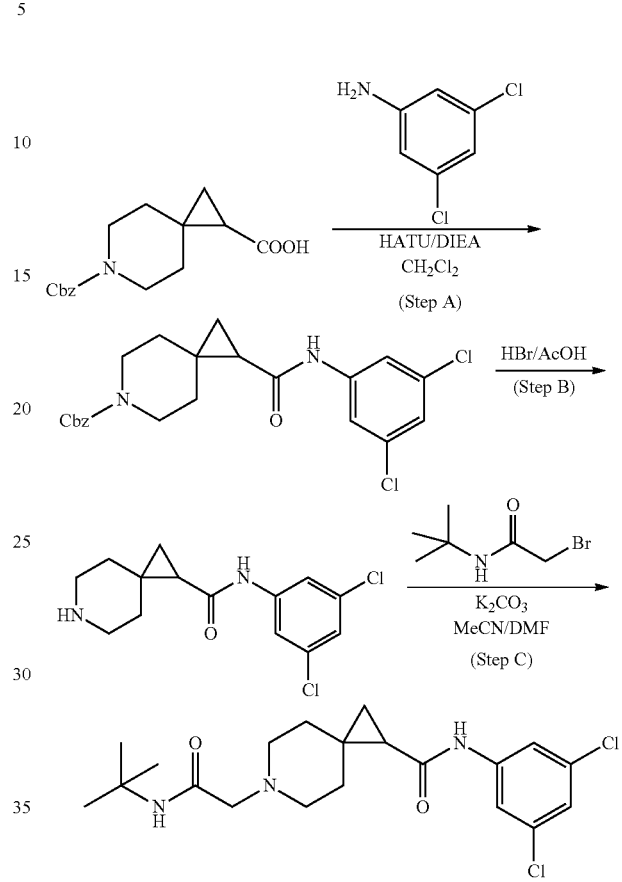

Step A.

A solution of 6-(Benzyloxycarbonyl)-6-azaspiro[2.5]octane-1-carboxylic acid (1 g, 3.46 mmol; Example 1, Step C), 3,5-dichlorobenzenamine (1.1 g, 6.92 mmol), HATU (2.6 g, 6.92 mmol), and DIEA (1.8 g, 13.8 mmol) in DCM/DMF (12 mL/3 mL) was stirred at RT for 1 h. 20 mL of water was added and the solution was extracted with DCM (30 mL×3). The combined organic layers were washed with brine, dried over Na₂SO₄ and concentrated in vacuo. The residue was purified by chromatography on silica gel (DCM/MeOH=10:1) to give benzyl 1-((3,5-dichlorophenyl)carbamoyl)-6-azaspiro[2.5]octane-6-carboxylate (1.4 g, 93%) as a yellow oil. Mass Spectrum (ESI) m/z=434 (M+H).

Step B.

To a solution of benzyl 1-((3,5-dichlorophenyl)carbamoyl)-6-azaspiro[2.5]octane-6-carboxylate (700 mg, 1.62 mmol) in AcOH (10 mL) was added HBr in AcOH (33%, 4 mL) at rt. After the reaction mixture was stirred at rt for 2 h, the solvent was concentrated, the residue was diluted with ethyl acetate (30 mL) and washed with saturated aq NaHCO₃ solution (30 mL) and extracted with ethyl acetate (2×30 mL). The combined organic layers were dried over anhydrous sodium sulfate, filtered and concentrated to give the crude product N-(3,5-dichlorophenyl)-6-azaspiro[2.5]octane-1-carboxamide (400 mg, 80% yield), which was used in next step without any purification. Mass Spectrum (ESI) m/z=299 (M+H).

Step C.

A solution of N-(3,5-dichlorophenyl)-6-azaspiro[2.5]octane-1-carboxamide (100 mg, 0.2 mmol), 2-bromo-N-tert-butylacetamide (80 mg, 0.41 mmol) and $K_2CO_3$ (188 mg, 1.36 mmol) in DMF/MeCN (1/1, 3 mL) was stirred at 60° C. for 16 h. Water (20 mL) was added and the solution was extracted with EA (30 mL×3). The combined organic layers were washed with brine, dried over $Na_2SO_4$ and concentrated. The residue was purified by chromatography on silica gel eluting with 5% DCM/MeOH to give 6-(2-(tert-butylamino)-2-oxoethyl)-N-(3,5-dichlorophenyl)-6-azaspiro[2.5]octane-1-carboxamide as a white solid (20 mg, 12%).

$^1$H NMR (400 MHz, MeOD) δ ppm 7.66 (s, 2H), 7.15 (s, 1H), 3.86 (s, 2H), 3.71-3.49 (m, 2H), 3.28-3.15 (m, 1H), 3.12-2.75 (m, 1H), 2.47-2.28 (m, 1H), 2.21-2.05 (m, 2H), 1.89 (s, 1H), 1.45-1.30 (m, 11H), 1.13 (s, 1H). Mass Spectrum (ESI) m/z=412 (M+H).

Examples 91 and 92 can also prepared by procedures similar to the one described in Example 90, replacing 2-bromo-N-tert-butylacetamide in step C with the designated reagents.

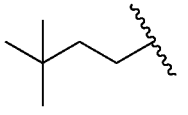 [SMILES: *CCC(C)(C)C]

| Example | $R^2$ | Reagent used in Step F |
|---|---|---|
| 91 | 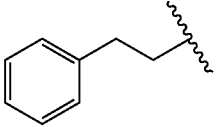 [SMILES: *CCc1ccccc1] | 1-Bromo-3,3-dimethylbutane |
| 92 | | (2-Bromoethyl)benzene |

Example 91

N-(3,5-Dichlorophenyl)-6-(3,3-dimethylbutyl)-6-azaspiro[2.5]octane-1-carboxamide $^1$H NMR (400 MHz, MeOD) δ ppm 7.65 (s, 2H), 7.17-7.13 (m, 1H), 3.64 (s, 2H), 3.18-3.09 (m, 2H), 2.95-2.63 (m, 1H), 2.40-2.05 (m, 3H), 1.95-1.89 (m, 1H), 1.75-1.62 (m, 2H), 1.51-1.28 (m, 2H), 1.13 (dd, J=7.7, 4.6 Hz, 1H), 1.01 (s, 10H). Mass Spectrum (ESI) m/z=383 (M+1).

Example 92

N-(3,5-Dichlorophenyl)-6-phenethyl-6-azaspiro[2.5]octane-1-carboxamide $^1$H NMR (400 MHz, MeOD) δ ppm 7.66 (s, 2H), 7.38-7.26 (m, 5H), 7.15 (dd, J=2.2, 1.4 Hz, 1H), 3.77-3.37 (m, 5H), 3.28-2.93 (m, 4H), 2.14 (s, 3H), 1.89 (t, J=5.5 Hz, 1H), 1.34 (t, J=5.0 Hz, 1H), 1.14 (dd, J=8.0, 4.6 Hz, 1H). Mass Spectrum (ESI) m/z=403 (M+1).

Example 93

6-(2-(tert-Butylamino)-2-oxoethyl)-N-(3,5-dichlorophenyl)-6-azaspiro[2.5]octane-1-carboxamide

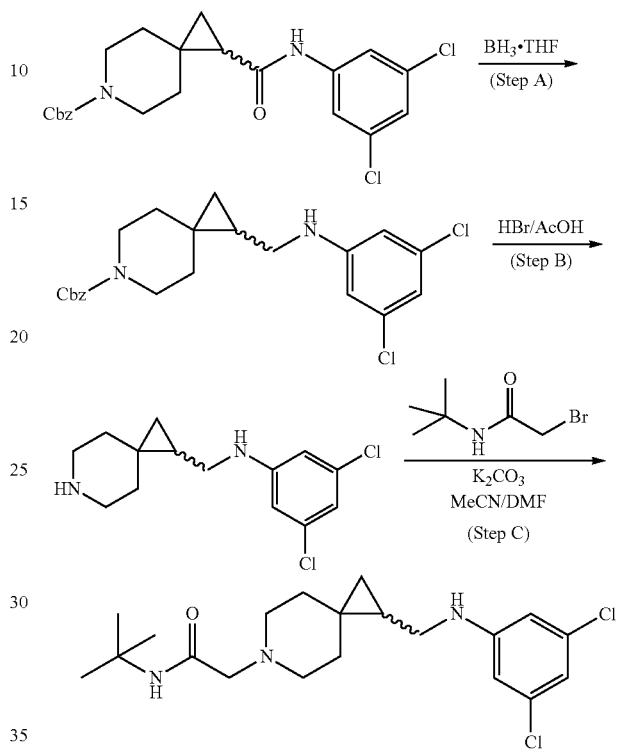

Step A.

To a stirred solution of benzyl 1-((3,5-dichlorophenyl)carbamoyl)-6-azaspiro[2.5]octane-6-carboxylate (500 mg, 1.23 mmol; Example 90, Step A) in anhydrous THF (10 mL) was added a solution of $BH_3$-THF complex (1 M in THF, 5 mL) at 0° C. The reaction was warmed to rt and stirred for 16 h. Then the reaction was quenched by addition of a saturated aq. solution of $NH_4Cl$ (20 mL) until gas evolution ceased, and extracted with EtOAc (30 mL×3). The combined organic layers were washed with brine (50 mL), dried over $Na_2SO_4$ filtered and the filtrate was concentrated to give benzyl 1-(((3,5-dichlorophenyl)amino)methyl)-6-azaspiro[2.5]octane-6-carboxylate as a colourless oil, which was used in the next step without further purification. Mass Spectrum (ESI) m/z=419 (M+H).

Step B.

N-((6-Azaspiro[2.5]octan-1-yl)methyl)-3,5-dichloroaniline was prepared from benzyl 1-(((3,5-dichlorophenyl)amino)methyl)-6-azaspiro[2.5]octane-6-carboxylate as described in Example 90, Step B and was used in the next step without further purification. Mass Spectrum (ESI) m/z=285 (M+H).

Step C.

N-((6-Azaspiro[2.5]octan-1-yl)methyl)-3,5-dichloroaniline was alkylated with 2-bromo-N-tert-butylacetamide as described in Example 90, Step C. The product was purified by silica gel chromatography eluting with 5% DCM/MeOH to give 6-(2-(tert-butylamino)-2-oxoethyl)-N-(3,5-dichlorophenyl)-6-azaspiro[2.5]octane-1-carboxamide as a yellow solid (30 mg, 22%).

¹H NMR (400 MHz, MeOD) δ ppm 7.01 (d, J=20.8 Hz, 3H), 3.87 (d, J=10.7 Hz, 2H), 3.69-3.50 (m, 2H), 3.32-3.26 (m, 3H), 3.17 (dd, J=12.6, 9.9 Hz, 2H), 2.39-2.09 (m, 2H), 1.75 (d, J=14.7 Hz, 0.5H), 1.60-1.51 (m, 0.5H), 1.47-1.32 (m, 8.5H), 1.22 (dd, J=15.2, 9.2 Hz, 1.2H), 0.85 (d, J=5.6 Hz, 1H), 0.60-0.50 (m, 1H). Mass Spectrum (ESI) m/z=398 (M+H).

Examples 94 and 95 can also prepared by procedures similar to the one described in Example 93, replacing 2-bromo-N-tert-butylacetamide in step C with the designated reagents.

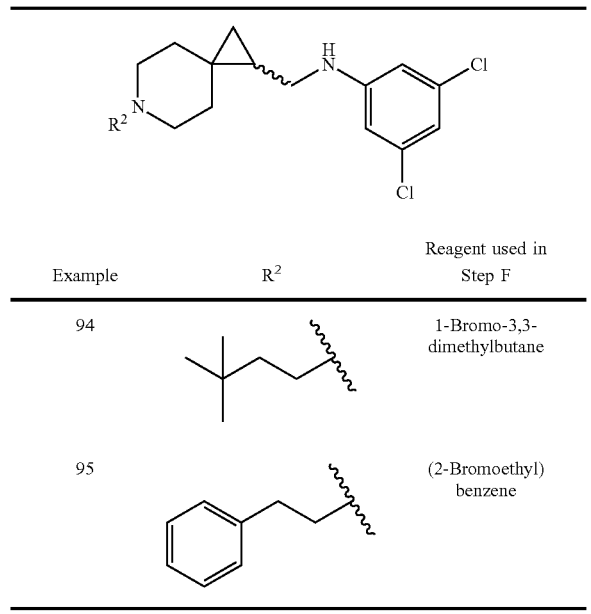

| Example | R² | Reagent used in Step F |
|---|---|---|
| 94 | (tert-butyl-like group) | 1-Bromo-3,3-dimethylbutane |
| 95 | (phenethyl group) | (2-Bromoethyl)benzene |

Example 94

N-(3,5-Dichlorophenyl)-6-(3,3-dimethylbutyl)-6-azaspiro[2.5]octane-1-carboxamide ¹H NMR (400 MHz, MeOD) δ ppm 7.44-7.13 (m, 3H), 3.70-3.55 (m, 2H), 3.44-3.35 (m, 1H), 3.23-3.17 (m, 2H), 3.14-3.03 (m, 1.5H), 2.69 (s, 2.5H), 2.34-2.08 (m, 2H), 1.71-1.66 (m, 1.5H), 1.54 (dd, J=14.5, 2.5 Hz, 0.5H), 1.37-1.30 (m, 0.5H), 1.28-1.17 (m, 1.5H), 1.08-0.95 (m, 9H), 0.93-0.84 (m, 1H), 0.59 (dt, J=8.6, 5.0 Hz, 1H). Mass Spectrum (ESI) m/z=369 (M+1).

Example 95

N-(3,5-Dichlorophenyl)-6-phenethyl-6-azaspiro[2.5]octane-1-carboxamide

¹H NMR (400 MHz, MeOD) δ ppm 7.43-7.24 (m, 5H), 6.93-6.76 (m, 3H), 3.67 (dt, J=11.1, 10.0 Hz, 2H), 3.40 (ddd, J=13.1, 8.4, 4.3 Hz, 2H), 3.31-3.08 (m, 6H), 2.37-2.13 (m, 2H), 1.75 (dd, J=15.4, 2.2 Hz, 0.5H), 1.58 (dd, J=14.5, 2.4 Hz, 0.5H), 1.40-1.30 (m, 0.5H), 1.28-1.15 (m, 1.5H), 0.88-0.79 (m, 1H), 0.56-0.50 (m, 1H). Mass Spectrum (ESI) m/z=389 (M+1).

Example 96

N-((1-(2-(tert-Butylamino)-2-oxoethyl)piperidin-4-yl)methyl)benzamide

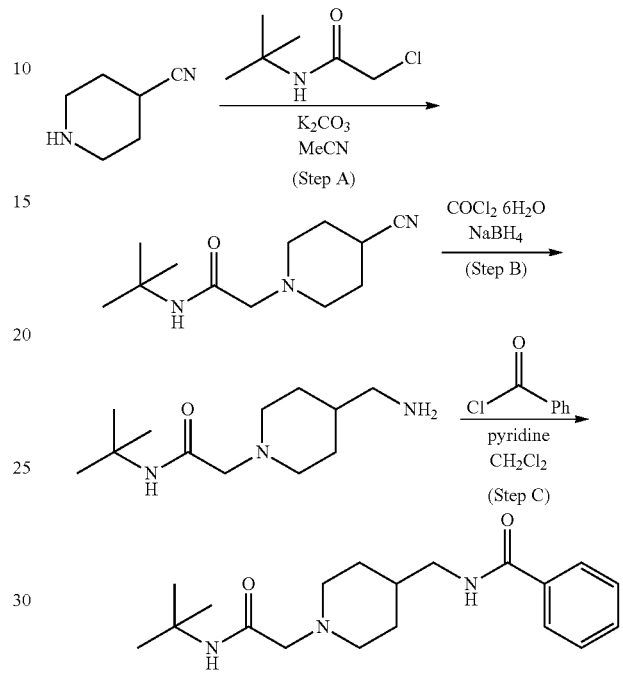

Step A.

A mixture of 4-cyano piperidine (1 g, 9.1 mmol), N-tert-butyl-2-chloroacetamide (1.35 g, 9.1 mmol), and potassium carbonate (2.5 g, 18.2 mmol) in acetonitrile (30 mL) was heated to reflux under argon for 9 hours. The resulting mixture was cooled and filtered through a layer of potassium carbonate. The filtrate was concentrated and crystallized from ethyl ether to give N-tert-butyl-2-(4-cyanopiperidin-1-yl)acetamide (1.82 g, 90% yield) as a white solid.

Step B.

To a cold solution of N-tert-butyl-2-(4-cyanopiperidin-1yl)acetamide (Example 43, Step A) (0.7 g, 3.1 mmol) and MeOH (20 mL), cobalt (II) chloride hexahydrate (0.37 g, 1.6 mmol) was added followed by the addition of sodium borohydride (0.53 g, 14.1 mmol). After stirring for 15 hours at 25° C., the reaction solution was diluted with 25 mL of 5% aqueous ammonium hydroxide and extracted three times with dichloromethane. The combined organic layer was washed with brine, dried over anhydrous Na₂SO₄ and concentrated to give 2-(4-(aminomethyl)piperidin-1-yl)-N-(tert-butyl)acetamide (0.65 g, 90% yield) as a crude product, which was used in the next step without further purification.

Step C.

To a cold solution of 0.20 g (0.88 mmol) of 2-(4-(aminomethyl)piperidin-1-yl)-N-(tert-butyl)acetamide in freshly distilled dichloromethane under argon, pyridine (1.3 mmol) was added followed by the addition of 0.12 g (0.88 mmol) of benzoyl chloride. The reaction was stirred at 0° C. for 30 min. and 25° C. for 2 hours. The reaction solution was diluted with 20 mL of aqueous sodium bicarbonate and extracted three times with DCM. The combined organic layer was washed with brine, dried (anhydrous Na₂SO₄), concentrated, and column chromatographed on silica gel using a mixture of dichloromethane and MeOH (10:1) as eluant to give the title compound, N-((1-(2-(tert-butylamino)-2-oxoethyl)piperidin-4-yl)methyl)benzamide, (0.15 g, 51% yield) as a white solid.

$^1$H NMR (400 MHz, CDCl$_3$) δ=7.77 (d, J=7.4 Hz, 2H), 7.49 (t, 1H), 7.45 (t, 2H), 7.1 (s, 1H), 6.38 (br. s., 1H), 3.37 (t, J=6.4 Hz, 2H), 2.79-2.90 (m, 6H), 2.12 (t, J=11.3 Hz, 2H), 1.77 (d, J=12.5 Hz, 2H), 1.55-1.67 (m, 1H), 1.36 (s, 9H). MS (ESI) m/z=354 (M+Na)$^+$.

Examples 97 to 106 can also prepared by procedures similar to the one described in Example 96, replacing N-tert-butyl-2-chloroacetamide in step A and/or benzoyl chloride in step C with the designated reagents.

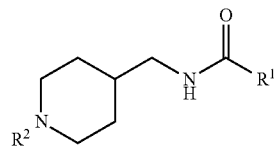

| Example | R$^1$ | R$^2$ | Reagent used in Step A | Reagent used in Step C |
|---|---|---|---|---|
| 97 | 5-chlorothiophen-2-yl | 2-cyclopropylethyl | (2-Bromoethyl) cyclopropane | 5-Chlorothiophene-2-carbonyl chloride |
| 98 | 5-chlorothiophen-2-yl | CH$_2$C(O)NH-tBu | N-tert-butyl-2-chloroacetamide | 5-Chlorothiophene-2-carbonyl chloride |
| 99 | 2-(3-chlorophenyl)ethyl | CH$_2$C(O)NH-tBu | N-tert-butyl-2-chloro acetamide | 3-(3-Chlorophenyl) propanoyl chloride |
| 100 | phenyl | CH$_2$C(O)NH-cyclohexyl | N-cyclohexyl-2-chloro acetamide | Benzoylchloride |
| 101 | phenyl | CH$_2$C(O)NH-phenyl | N-phenyl-2-chloro acetamide | Benzoylchloride |
| 102 | 4-hydroxyphenyl | CH$_2$C(O)NH-phenyl | N-phenyl-2-chloro acetamide | 4-Hydroxybenzoyl chloride |
| 103 | 2-fluorophenyl | CH$_2$C(O)NH-tBu | N-tert-butyl-2-chloro acetamide | 2-Fluoro-benzoyl chloride |

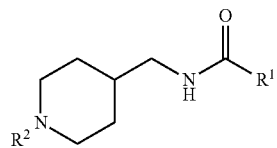

| Example | R¹ | R² | Reagent used in Step A | Reagent used in Step C |
|---------|----|----|------------------------|------------------------|
| 104 | 3,5-dimethoxyphenyl | N-tert-butyl acetamide group | N-tert-butyl-2-chloro acetamide | 3,5-Dimethoxy-benzoyl chloride |
| 105 | pyrazinyl | N-phenyl acetamide group | N-phenyl-2-chloro acetamide | Pyrazine-2-carbonyl chloride |
| 106 | 1-(1H-pyrrol-2-yl)ethanone group | N-phenyl acetamide group | N-phenyl-2-chloro acetamide | 2-Bromo-1-(1H-pyrrol-2-yl)ethan-1-one |

Example 97

5-Chloro-N-((1-(2-cyclopropylethyl)piperidin-4-yl)methyl)thiophene-2-carboxamide $^1$H NMR (400 MHz, CDCl$_3$) δ=7.15 (d, J=3.9 Hz, 1H), 7.07 (d, J=3.9 Hz, 1H), 3.54-3.66 (m, 2H), 3.29-3.36 (m, 2H), 2.84-3.03 (m, 2H), 1.46-1.85 (m, 9H), 0.81-0.93 (m, 1H), 0.44-0.53 (m, 2H), 0.04-0.10 (m, 2H). MS (ESI) m/z=327.1.

Example 98

N-((1-(2-(tert-Butylamino)-2-oxoethyl)piperidin-4-yl)methyl)-5-chlorothiophene-2-carboxamide $^1$H NMR (400 MHz, CDCl$_3$) δ=7.26 (d, J=3.5 Hz, 1H), 7.05 (br. s., 1H), 6.91 (d, J=3.9 Hz, 1H), 5.94 (br. s., 1H), 3.34 (t, J=6.4 Hz, 2H), 2.88 (s, 2H), 2.84 (s, 2H), 2.14 (m, 2H), 1.76 (m, 2H), 1.6 (m, 3H), 1.36 (s, 9H). MS (ESI) m/z=393.9 (M+Na)$^+$.

Example 99

N-((1-(2-(tert-Butylamino)-2-oxoethyl)piperidin-4-yl)methyl)-3-(3-chlorophenyl)propanamide $^1$H NMR (400 MHz, CDCl$_3$) δ=7.15-7.23 (m, 3H), 7.05-7.14 (m, 1H), 5.55 (s, 1H), 3.25 (s, 1H), 3.1 (t, 2H), 2.95 (t, 2H), 2.85 (s, 2H), 2.8 (s, 2H), 2.46 (t, J=7.4 Hz, 2H), 2.05-2.12 (m, 3H), 1.5-1.6 (m, 4H), 1.36 (s, 9H). MS (ESI) m/z=416.1 (M+Na)$^+$.

Example 100

N-((1-(2-(Cyclohexylamino)-2-oxoethyl)piperidin-4-yl)methyl)benzamide $^1$H NMR (400 MHz, CDCl$_3$) δ 7.77 (d, J=7.4 Hz, 2H), 7.49 (t, 1H), 7.45 (t, 2H), 6.19 (br. s., 1H), 3.8 (br. s., 1H), 3.41 (t, J=6.4 Hz, 2H), 2.98 (br. s., 2H), 2.89 (br. s., 2H), 1.77-1.97 (m, 4H), 1.53-1.75 (m, 6H), 1.16-1.48 (m, 8H). MS (ESI) m/z=380.4 (M+Na)$^+$.

Example 101

N-((1-(2-Oxo-2-(phenylamino)ethyl)piperidin-4-yl)methyl)benzamide $^1$H NMR (400 MHz, CDCl$_3$) δ 7.76-7.81 (m, 2H), 7.59 (d, J=7.4 Hz, 2H), 7.50-7.55 (m, 1H), 7.43-7.48 (m, 2H), 7.32-7.37 (m, 2H), 7.12 (t, J=7.4 Hz, 1H), 6.24 (br. s., 1H), 3.43 (t, J=6.4 Hz, 2H), 3.15 (br. s., 2H), 2.98 (br. s., 2H), 2.30 (br. s., 2H), 1.85 (d, J=12.9 Hz, 2H), 1.71 (br. s., 1H), 1.45 (d, J=8.2 Hz, 2H). MS (ESI) m/z=373.9 (M+Na)$^+$.

Example 102

4-Hydroxy-N-((1-(2-oxo-2-(phenylamino)ethyl)piperidin-4-yl)methyl)benzamide $^1$H NMR (400 MHz, CDCl$_3$) δ ppm 9.17 (br. s., 1H), δ ppm 7.68 (d, J=8.59 Hz, 2H), 7.57 (d, J=7.42 Hz, 2H), 7.35 (d, J=7.42 Hz, 2H), 7.09-7.15 (m, 1H), 6.88 (d, J=8.59 Hz, 2H), 6.17 (d, J=5.86 Hz, 1H), 3.39 (t, J=6.44 Hz, 2H), 3.11 (s, 2H), δ ppm 2.93 (d, J=11.33 Hz, 2H), 2.25 (t, J=10.74 Hz, 2H), 1.81 (d, J=11.33 Hz, 2H), 1.67 (d, J=7.03 Hz, 2H), 1.37-1.43 (m, 2H); MS (ESI) m/z=368.4 (M+H)$^+$.

Example 103

N-((1-(2-(tert-butylamino)-2-oxoethyl)piperidin-4-yl)methyl)-2-fluorobenzamide $^1$H NMR (400 MHz, CDCl$_3$) δ ppm 8.02 (dt, J=1.95, 7.62 Hz, 2H), 7.52-7.59 (m, 2H), 7.23 (t, J=7.42 Hz, 2H), 7.16 (dd, J=8.98, 10.54 Hz, 2H), 7.03-7.09 (m, 1H), 3.06 (s, 2H), 2.82 (d, J=3.91 Hz, 2H), 2.64-2.72 (m, 1H), 2.52 (br. s., 2H), 1.99-2.07 (m, 3H), 1.93 (dt, J=4.10, 8.69 Hz, 3H), 1.36 (s, 9H). $^{13}$C NMR (100 MHz, CDCl$_3$) δ ppm 168.83, 163.84, 161.25, 135.16, 135.07, 132.81, 124.19, 121.28, 117.28, 117.06, 61.94, 51.61, 51.07, 28.79, 28.74, 25.60; MS (ESI) m/z=350.2 (M+H)$^+$.

Example 104

N-((1-(2-(tert-butylamino)-2-oxoethyl)piperidin-4-yl)methyl)-3,5-dimethoxybenzamide $^1$H NMR (400 MHz, CDCl$_3$) δ ppm 7.24 (d, J=1.95 Hz, 1H), 6.92 (d, J=2.34 Hz, 1H), 6.58-6.69 (m, 1H), 3.81-3.87 (m, 2H), 3.75 (s, 1H), 2.93 (s, 1H), 2.74 (d, J=4.30 Hz, 1H), 2.63 (d, J=10.15 Hz, 1H), 2.53 (s, 1H), 2.40 (br. s., 1H), 1.94-2.02 (m, 1H), 1.78-1.94 (m, 1H), 1.25-1.40 (m, 9H); MS (ESI) m/z=393.6 (M+2H)$^+$.

Example 105

N-((1-(2-Oxo-2-(phenylamino)ethyl)piperidin-4-yl)methyl)pyrazine-2-carboxamide $^1$H NMR (400 MHz, CDCl$_3$) δ 9.42 (s, 1H), 9.15 (br. s., 1H), 8.77 (d, J=2.34 Hz, 1H), 8.53 (s, 1H), 7.87-7.98 (m, 1H), 7.56 (d, J=7.81 Hz, 2H), 7.33 (t, J=7.81 Hz, 2H), 7.11 (t, J=7.42 Hz, 1H), 3.44 (t, J=6.64 Hz, 1H), 3.11 (s, 2H), 2.95 (d, J=11.33 Hz, 2H), 2.17-2.33 (m, 2H), 1.84 (d, J=12.50 Hz, 2H), 1.69 (ddd, J=3.91, 7.42, 14.84 Hz, 2H), 1.38-1.48 (m, 2H). $^{13}$C NMR (100 MHz, CDCl$_3$) δ ppm 168.74, 163.26, 147.50, 144.62, 142.63, 137.71, 129.17, 124.31, 119.55, 62.44, 53.95, 44.85, 35.92, 30.47, 29.84. MS (ESI), m/z=354.3 (M+H)$^+$.

Example 106

2-(4-(((2-Oxo-2-(1H-pyrrol-2-yl)ethyl)amino)methyl)piperidin-1-yl)-N-phenylacetamide $^1$H-NMR (400 MHz, CDCl$_3$) δ ppm 1.13-1.47 (m, 2H), 1.62 (br. s, 1H, NH), 1.84 (d, J=11.72 Hz, 2H), 2.23 (t, J=10.74 Hz, 2H), 2.38 (s, 1H), 2.64 (d, J=6.64 Hz, 2H), 2.90 (d, J=11.33 Hz, 2H), 3.18 (s, 2H), 3.89 (s, 2H), 6.27 (dd, J=1.00 Hz, 1H), 6.93 (d, J=3.51 Hz, 1H), 7.06 (br. s., 1H) 7.10 (t, J=7.42 Hz, 1H), 7.33 (t, J=1.00 Hz, 2H), 7.53 (d, J=1.00 Hz, 2H), 9.19 (br. s., 1H, NH), 9.96 (br. s., 1H, NH). $^{13}$C-NMR (100 MHz, CDCl$_3$) δ ppm ppm 31.04 (2C), 35.98, 54.31 (2C), 55.00, 55.88, 62.59, 111.03, 116.03, 119.61 (2C), 124.31, 124.89, 129.21 (2C), 130.62, 137.85, 169.07, 188.59. MS (ESI) m/z=355.4 (M+H)$^+$, 377.5 (M+Na)$^+$.

Example 107

N-((1-(2-(tert-butylamino)-2-oxoethyl)-4-methylpiperidin-4-yl)methyl)benzamide

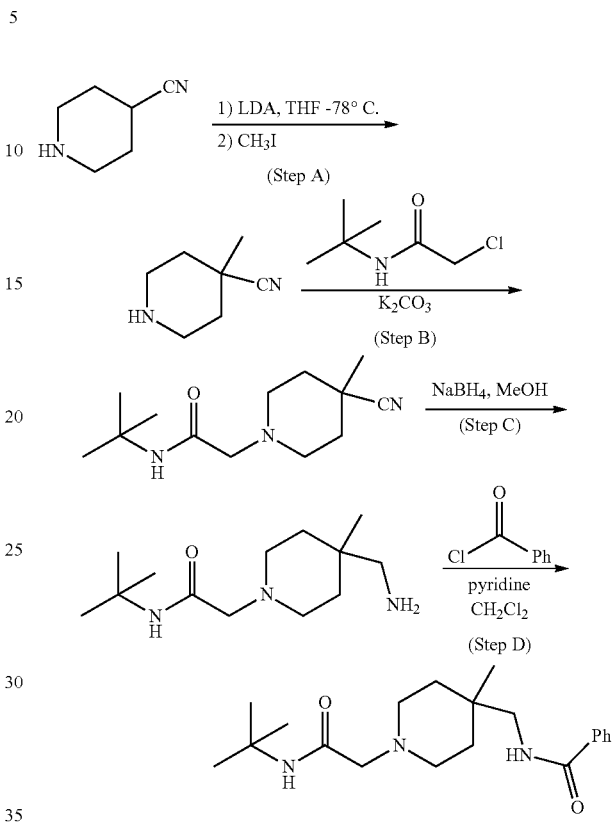

Step A.

A solution of 4-cyanopiperidine 0.5 g (4.54 mmol) was dissolved in 25 mL of dry THF and cooled to −78° C. LDA (0.227 M in 20 mL, 4.54 mmol) was slowly added to the above solution over 30 min at −78° C. under argon. A pale brown solution was obtained. Stirring continued for 2 h at −78° C. and iodomethane (0.64 g, 4.54 mmol) was added dropwise into the reaction while keeping the temperature at −78° C. The solution was stirred at −78° C. for 2 h, diluted with 5 mL of saturated NH$_4$Cl solution at −78° C. and allowed to warm up to room temperature. The organic layer was removed and the aqueous layer was extracted three times (100 mL each) with dichloromethane. The combined organic layers were washed with brine (100 mL), dried (Na$_2$SO$_4$), concentrated and purified by chromatography on silica gel using a gradient mixture of CH$_2$Cl$_2$ and MeOH as eluant to give 4-methylpiperidine-4-carbonitrile, 352 mg (62% yield) as a white solid.

Step B.

To a solution of 4-methylpiperidine-4-carbonitrile (0.19 g, 1.50 mmol) in dry CH$_3$CN (8 mL), 2-chloro-N-(1,1-dimethylethyl)acetamide (0.22 g, 1.50 mmol) and anhydrous K$_2$CO$_3$ (0.41 g, 3.0 mmol) were added and refluxed at 85° C. for 8 h. The reaction mixture was filtered and evaporated to obtain a yellow oil, which was purified by column chromatography on silica gel using a mixture of EtOAc and hexane (5:1) as eluant to give N-(tert-butyl)-2-(4-cyano-4-methylpiperidin-1-yl)acetamide, 0.35 g (97% yield).

Step C.

To a solution of N-(tert-butyl)-2-(4-cyano-4-methylpiperidin-1-yl)acetamide (0.23 g, 1.06 mmol) in 8 mL of methanol, CoCl₂·6H₂O (0.13 g, 0.53 mmol) was added and stirred. The reaction mixture was cooled to 0° C. and sodium borohydride (0.18 g, 4.77 mmol) was added in several portions over 30 min. The resulting solution was stirred for 18 h at rt, diluted with 15 mL of cold saturated NH₄Cl and 15 mL of water, and extracted three times with ethyl acetate. The combined organic layers were washed with brine (10 mL), dried (Na₂SO₄), filtered, and concentrated to yield 0.19 g (74% yield) of 2-(4-(aminomethyl)-4-methylpiperidin-1-yl)-N-(tert-butyl)acetamide, as a light yellow oil.

Step D.

To a solution of 2-(4-(aminomethyl)-4-methylpiperidin-1-yl)-N-(tert-butyl)acetamide (0.15 g, 0.625 mmol) in freshly distilled dichloromethane (7.5 mL) dry pyridine (81 µL, 0.625 mmol) was added and the resulting solution was stirred at 0° C. To this mixture benzoyl chloride (88 mg, 0.625 mmol) was added and the reaction mixture was stirred for 3 h at rt. The reaction mixture was partitioned between dichloromethane and water and basified to pH 8 using NaHCO₃. The organic layer was removed and the aqueous layer was extracted three times with dichloromethane. The combined organic layers were washed with brine, dried (Na₂SO₄), filtered, concentrated, and purified by column chromatography on silica gel using a gradient mixture of CH₂Cl₂ and MeOH as eluant to obtain 0.15 g (70% yield) of N-((1-(2-(tert-butylamino)-2-oxoethyl)-4-methylpiperidin-4-yl)methyl)benzamide as a white solid.

¹H NMR (400 MHz, CDCl₃) δ 7.77 (d, J=7.4 Hz, 2H), 7.5 (t, 1H), 7.45 (t, 2H), 6.98-7.12 (br. s., 1H), 6.19 (br. s., 1H), 3.39 (d, J=6.3 Hz, 2H), 2.9 (s, 2H), 2.61 (m, 2H), 2.43 (m, 2H), 1.58 (m, 2H), 1.39-1.48 (m, 3H), 1.28-1.37 (s, 11H). MS (ESI) m/z=368 (M+Na)⁺.

Example 108

N-((1-(2-(tert-butylamino)-2-oxoethyl)-4-methylpiperidin-4-yl)methyl)-3-methoxybenzamide

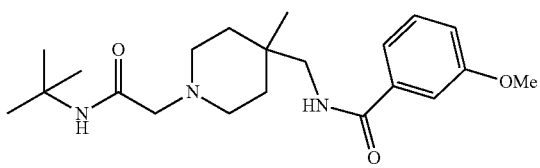 [SMILES: COc1cccc(C(=O)NCC2(C)CCN(CC(=O)NC(C)(C)C)CC2)c1]

To a solution of 2-(4-(aminomethyl)-4-methylpiperidin-1-yl)-N-(tert-butyl)acetamide (Example 54, Step C; 0.19 g, 0.78 mmol) in distilled dichloromethane (10 mL) was added dry pyridine (130 µL, 1.558 mmol) and stirred at 0° C. To this 3-methoxybenzoyl chloride (0.13 g, 0.78 mmol) was added and the mixture was stirred for 3 h at rt. The reaction mixture was partitioned between dichloromethane and water and basified to pH 8 using NaHCO₃. The organic layer was removed and the aqueous layer was extracted three times with dichloromethane. The combined organic layers were washed with brine, dried (Na₂SO₄), filtered, concentrated, and purified by column chromatography on silica gel using a gradient mixture of CH₂Cl₂ and MeOH as eluant to obtain 0.23 g (78% yield) of the title compound as a white solid.

¹H NMR (400 MHz, CDCl₃) δ ppm 1.01 (s, 3H), 1.29-1.37 (m, 10H), 1.52-1.63 (m, 4H), 2.40 (t, J=10.54 Hz, 2H), 2.61 (m, 2H), 2.89 (s, 2H), 3.37 (d, J=6.64 Hz, 2H) 3.86 (s, 3H), 6.15 (br.s., 1 NH), 7.01-7.07 (m, 2H), 7.30-7.39 (m, 2H). MS (ESI) m/z=376.3 (M+H)⁺.

Example 109

(4-((2-Fluorobenzamido)methyl)-1-(2-oxo-2-(phenylamino)ethyl)piperidin-4-yl)methyl Benzoate

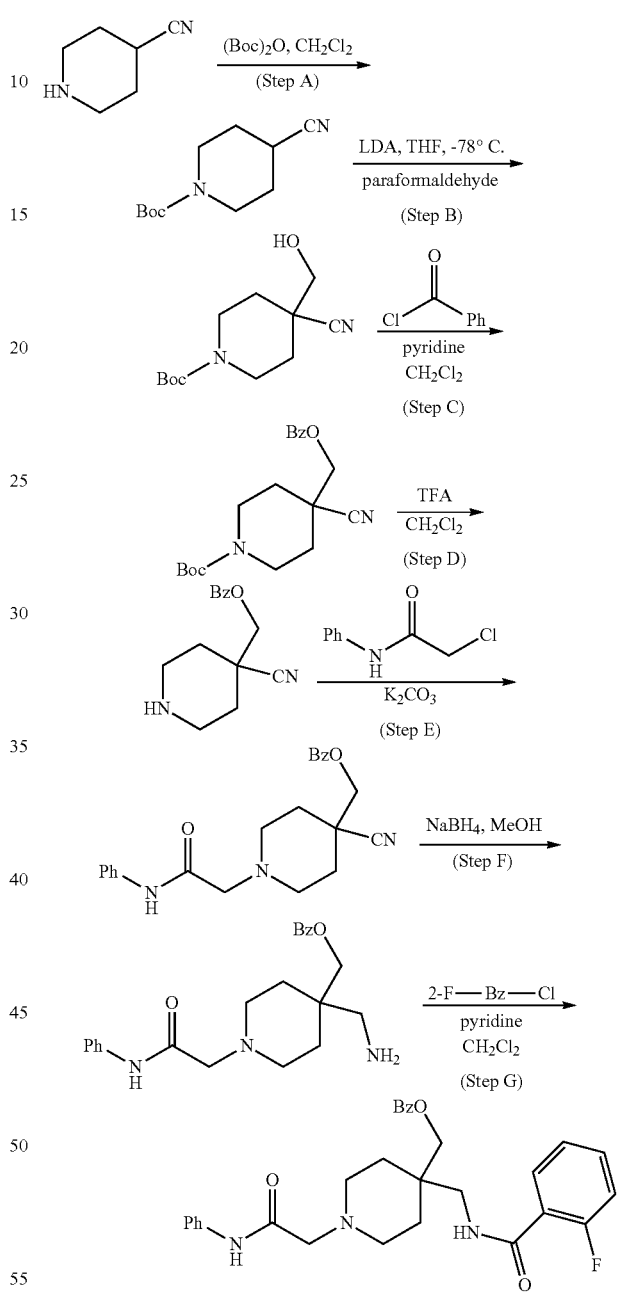

Step A.

To a solution of piperidine-4-carbonitrile (0.5 g, 4.54 mmol) in 25 mL of distilled dichloromethane under argon, distilled triethylamine (1.3 mL, 9.08 mmol) was added. While stirring, the solution was cooled to 0° C. and di-tert-butyl dicarbonate (1.19 g, 5.4 mmol) was added in several portions over 15 min (bubbling observed). The resulting mixture was stirred at rt for 12 h, then solvent was evaporated and the residue was purified by column chromatography on silica gel using a mixture of CH₂Cl₂ and MeOH (30:1) as an eluant to give tert-butyl 4-cyanopiperidine-1-carboxylate, 0.95 g (100% yield) as a colorless thick oil, that solidifies on standing.

Step B.

A solution of tert-butyl 4-cyanopiperidine-1-carboxylate 0.95 g (4.54 mmol) was dissolved in 25 mL of dry THF and cooled to −78° C. LDA (0.23 M in 20 mL, 4.54 mmol) was slowly added to the reaction over 30 min at −78° C. under argon. A pale brown solution was obtained. Stirring continued for 2 h at −78° C., and a solution of paraformaldehyde (0.16 g, 5.4 mmol) in 25 mL of freshly distilled THF was added slowly into the reaction solution while keeping the temperature at −78° C. The reaction mixture was allowed to reach room temperature while stirred for 15 h under argon. The reaction mixture was diluted in 100 mL of water, saturated NaCl (50 mL) was added, and extracted with DCM three times (250 mL each). The combined organic layers were washed with brine (100 mL), dried ($Na_2SO_4$), concentrated, and column chromatographed on silica gel using a gradient mixture of hexane and ethyl acetate as eluant to give tert-butyl 4-cyano-4-(hydroxymethyl)piperidine-1-carboxylate, 0.78 g (72% yield) as a white solid.

Step C.

To a solution of tert-butyl 4-cyano-4-(hydroxymethyl) piperidine-1-carboxylate (0.49 g, 2.0 mmol) in DCM (8 mL), pyridine (0.24 mL, 3.03 mmol) was added and the mixture was stirred at 0° C. To this mixture, benzoyl chloride (0.25 mL, 2.0 mmol) was added and the reaction mixture was stirred for 8 h at rt. The reaction mixture was partitioned between dichloromethane and water and basified to pH 8 using $NaHCO_3$. The organic layer was separated, and the aqueous layer was extracted three times with dichloromethane. The combined organic layers were washed with brine (10 mL), dried ($Na_2SO_4$), filtered, concentrated, and purified by column chromatography on silica gel using a mixture of $CH_2Cl_2$ and MeOH (30:1) to obtain 0.21 g (86% yield) of tert-butyl 4-((benzoyloxy)methyl)-4-cyanopiperidine-1-carboxylate as a yellow solid.

Step D.

A solution of 4-((benzoyloxy)methyl)-4-cyanopiperidine-1-carboxylate (1.12 mmol) in 2 mL dichloromethane containing 10% trifluoroacetic acid (TFA) was stirred at room temperature for 1 h. The solvent was removed and the remaining solid was kept under high vacuum to yield 0.27 g (>95% yield) of (4-cyanopiperidin-4-yl)methyl benzoate as a yellow solid.

Step E.

To a solution of (4-cyanopiperidin-4-yl)methyl benzoate (0.10 g, 0.41 mmol) in dry $CH_3CN$, N-(chloromethyl)-benzamide (57 mg, 0.41 mmol) and anhydrous $K_2CO_3$ (0.17 g, 1.23 mmol) were added and refluxed at 85° C. for 12 h. The reaction mixture was filtered and evaporated to yield a yellow oil that was purified by column chromatography on silica gel using a mixture of $CH_2Cl_2$ and MeOH (30:1) as eluant to give (4-cyano-1-(2-oxo-2-(phenylamino)ethyl)piperidin-4-yl)methyl benzoate, 0.15 g (97% yield).

Step F.

To a solution of (4-cyano-1-(2-oxo-2-(phenylamino) ethyl)piperidin-4-yl)methyl benzoate (0.16 g, 0.42 mmol) in 5 mL of methanol, $CoCl_2.6H_2O$ (51 mg 0.21 mmol) was added and stirred. The reaction mixture was cooled to 0° C. and sodium borohydride (86 mg, 2.27 mmol) was added in several portions over 30 min. The resulting solution was stirred for 18 h at room temperature, diluted with 15 mL of cold saturated $NH_4Cl$, 15 mL of water and extracted three times with ethyl acetate. The combined organic layers were washed with brine (10 mL), dried ($Na_2SO_4$), filtered, and concentrated to yield 0.13 g (78% yield) of (4-(aminomethyl)-1-(2-oxo-2-(phenylamino)ethyl)piperidin-4-yl) methyl benzoate, as a white solid.

Step G.

To a solution of (4-(aminomethyl)-1-(2-oxo-2-(phenylamino)ethyl) piperidin-4-yl)methyl benzoate (50 mg, 0.13 mmol) in dichloromethane (5 mL) was added dry pyridine (19 μL, 0.17 mmol) and the mixture was stirred at 0° C. To the reaction solution, 2-fluorobenzoyl chloride (27 mg, 017 mmol) was added and the mixture was stirred for 3 h at room temperature. The reaction mixture was partitioned between dichloromethane and water, and basified to pH 8 using $NaHCO_3$. The organic layer was separated, and the aqueous layer was extracted three times with dichloromethane. The combined organic layers were washed with brine (10 mL), dried ($Na_2SO_4$), filtered, concentrated, and purified by column chromatography on silica gel using a mixture of $CH_2Cl_2$ and MeOH (30:1) as eluant to obtained 48 mg (69% yield) of (4-((2-fluorobenzamido)methyl)-1-(2-oxo-2-(phenylamino)ethyl)piperidin-4-yl)methyl benzoate, as a white solid.

$^1$H NMR (400 MHz, $CDCl_3$) δ ppm 9.67 (br. s., 1H), δ ppm 7.99 (d, J=4.69 Hz, 2H), 7.82 (d, J=7.42 Hz, 2H), 7.41-7.61 (m, 6H), 7.29-7.34 (m, 1H), 7.21 (d, J=7.81 Hz, 1H), 7.10-7.16 (m, 3H), 6.09 (br. s., 1H), 4.25-4.53 (m, 2H), 3.61 (d, J=6.25 Hz, 2H), 3.47 (br. s., 2H), 2.86-3.11 (m, 4H), 1.84 (br. s., 4H); $^{13}$C NMR (100 MHz, $CDCl_3$) δ ppm ppm 168.10, 166.80, 165.15, 161.15, 137.72, 135.31, 134.76, 132.72, 132.51, 131.84, 129.10, 128.77, 127.15, 124.52, 124.11, 119.91, 117.17, 76.84, 69.37, 61.68, 49.40, 42.44, 36.71, 29.89; MS (ESI) m/z=504.2 (M+H)$^+$.

Example 110

2-fluoro-N-((4-(hydroxymethyl)-1-(2-oxo-2-(phenylamino)ethyl)piperidin-4-yl)methyl)benzamide

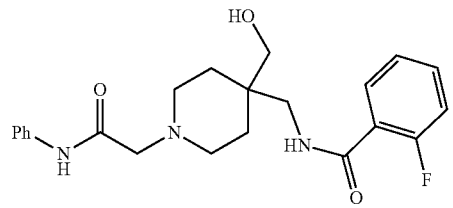 [SMILES: O=C(CN1CCC(CO)(CNC(=O)c2ccccc2F)CC1)Nc1ccccc1]

To a solution of (4-((2-fluorobenzamido)methyl)-1-(2-oxo-2-(phenylamino)ethyl)piperidin-4-yl)methyl benzoate (Example 56; 30 mg, 0.06 mmol) in methanol, $K_2CO_3$ was added and the slurry was stirred for 2 h. The reaction mixture was filtered and purified by column chromatography on silica gel using a mixture of DCM and MeOH (30:1) as eluant to give 13 mg (55% yield) of the title compound, as a white solid.

$^1$H NMR (400 MHz, $CDCl_3$) δ ppm 9.11 (br. s., 1H), δ ppm 7.78 (d, J=7.42 Hz, 2H), 7.56 (d, J=7.81 Hz, 2H), 7.42-7.50 (m, 2H), 7.30-7.40 (m, 2H), 7.07-7.22 (m, 1H), 6.78 (d, J=5.47 Hz, 1H), 3.40-3.64 (m, 4H), 3.14 (s, 2H), 2.60-2.66 (m, 2H), 1.62-1.74 (m, 4H); $^{13}$C NMR (100 MHz, $CDCl_3$) δ ppm 169.27, 168.63, 137.66, 133.89, 132.09, 129.20, 128.88, 127.12, 124.43, 119.66, 65.99, 62.47, 49.90, 37.16, 31.07. MS (ESI) m/z=400.0 (M+H)$^+$.

Examples 60-71 of the present invention can be prepared as single enantiomers by separating the racemic mixtures by HPLC using a chiral column, such as, for example, CHIRALPAK® (Chiral Technologies, Inc., West Chester, Pa., USA). Alternatively, enantiomerically pure or enriched compounds can be prepared as described in Example 111.

Example 111

(R)—N-(7-Phenethyl-7-azaspiro[3.5]nonan-1-yl)benzamide

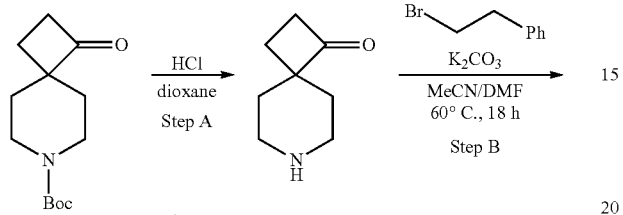

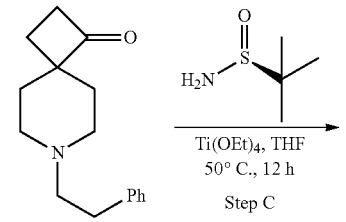

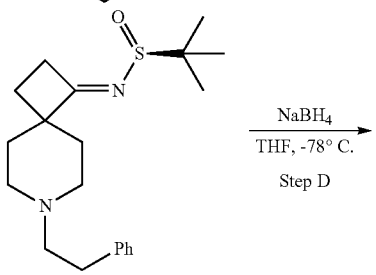

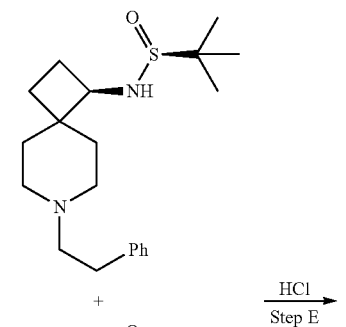

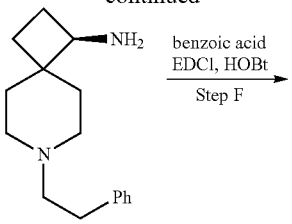

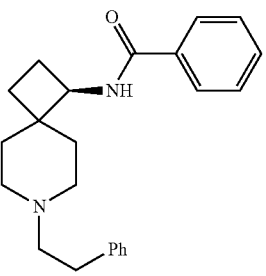

tert-Butyl 1-oxo-7-azaspiro[3,5]-nonane-7-carboxylate was prepared as described in Example 60.

Step A.

The Boc group of tert-butyl 1-oxo-7-azaspiro[3,5]-nonane-7-carboxylate was removed as described in Example 60, Step H to give 7-azaspiro[3.5]nonan-1-one.

Step B.

7-Azaspiro[3.5]nonan-1-one was alkylated with phenethylbromide to give 7-phenethyl-7-azaspiro[3.5]nonan-1-one by a procedure similar to the one described in Example 60, Step I.

Step C.

7-Phenethyl-7-azaspiro[3.5]nonan-1-one was converted to (S)-2-methyl-N-(7-phenethyl-7-azaspiro[3.5]nonan-1-ylidene)propane-2-sulfinamide using the commercially available (S)-2-methyl-2-propanesulfinamide (Sigma-Aldrich, Milwaukee, Order No.: 513210) by a procedure similar to the one described by e.g. Liu, G.; Cogan, D. A.; Owens, T. D.; Tang, T. P.; Ellman, J. A., J. Org. Chem., 64, 1278-1284, (1999).

Step D.

(S)-2-methyl-N-(7-phenethyl-7-azaspiro[3.5]nonan-1-ylidene)propane-2-sulfinamide was reduced with NaBH$_4$ in THF to give a mixture of (S)-2-methyl-N—((R)-7-phenethyl-7-azaspiro[3.5]nonan-1-yl)propane-2-sulfinamide and (S)-2-methyl-N—((S)-7-phenethyl-7-azaspiro[3.5]nonan-1-yl)propane-2-sulfinamide which was separated by chromatography on silica gel to give (S)-2-methyl-N—((R)-7-phenethyl-7-azaspiro[3.5]nonan-1-yl)propane-2-sulfinamide as the major isomer.

Step E.

Treatment of (S)-2-methyl-N—((R)-7-phenethyl-7-azaspiro[3.5]nonan-1-yl)propane-2-sulfinamide with HCl gave (R)-7-phenethyl-7-azaspiro[3.5]nonan-1-amine.

Step F.

(R)-7-phenethyl-7-azaspiro[3.5]nonan-1-amine was acylated with benzoic acid using a procedure similar to the one described in Example 60, Step G to give (R)—N-(7-phenethyl-7-azaspiro[3.5]nonan-1-yl)benzamide.

Example 112

(S)—N-(7-Phenethyl-7-azaspiro[3.5]nonan-1-yl)benzamide

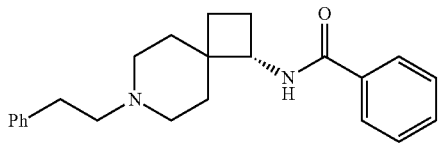 [SMILES: O=C(N[C@H]1CCC12CCN(CCc1ccccc1)CC2)c1ccccc1]

The compound was prepared by a procedure similar to the one described in Example 103, using the commercially available (R)-2-methyl-2-propanesulfinamide (Sigma-Aldrich, Milwaukee, Order No.: 497401) in Step C.

Example 113

(R)—N-(7-(2-(tert-Butylamino)-2-oxoethyl)-7-azaspiro[3.5]nonan-1-yl)-3,5-dichlorobenzamide

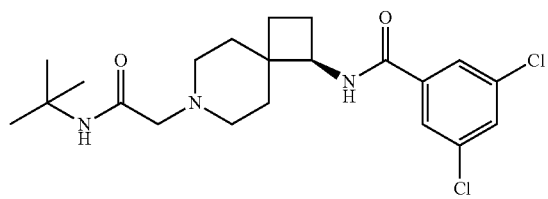 [SMILES: CC(C)(C)NC(=O)CN1CCC2(CC[C@H]2NC(=O)c2cc(Cl)cc(Cl)c2)CC1]

The compound was prepared by a procedure similar to the one described in Example 111, using 2-bromo-N-(tert-butyl)acetamide in Step B and 3,5-dichlorobenzoic acid in Step F.

Example 114

(R)—N-(7-(2-(tert-Butylamino)-2-oxoethyl)-7-azaspiro[3.5]nonan-1-yl)-3,5-dichlorobenzamide

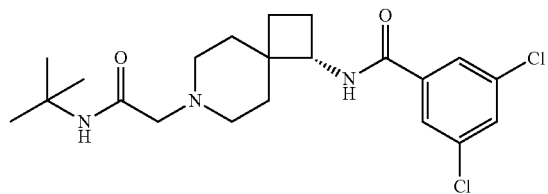 [SMILES: CC(C)(C)NC(=O)CN1CCC2(CC[C@@H]2NC(=O)c2cc(Cl)cc(Cl)c2)CC1]

The compound was prepared by a procedure similar to the one described in Example 112, using 2-bromo-N-(tert-butyl)acetamide in Step B and 3,5-dichlorobenzoic acid in Step F.

Example 115 (Synthesis of Oxadiazoles)

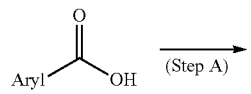

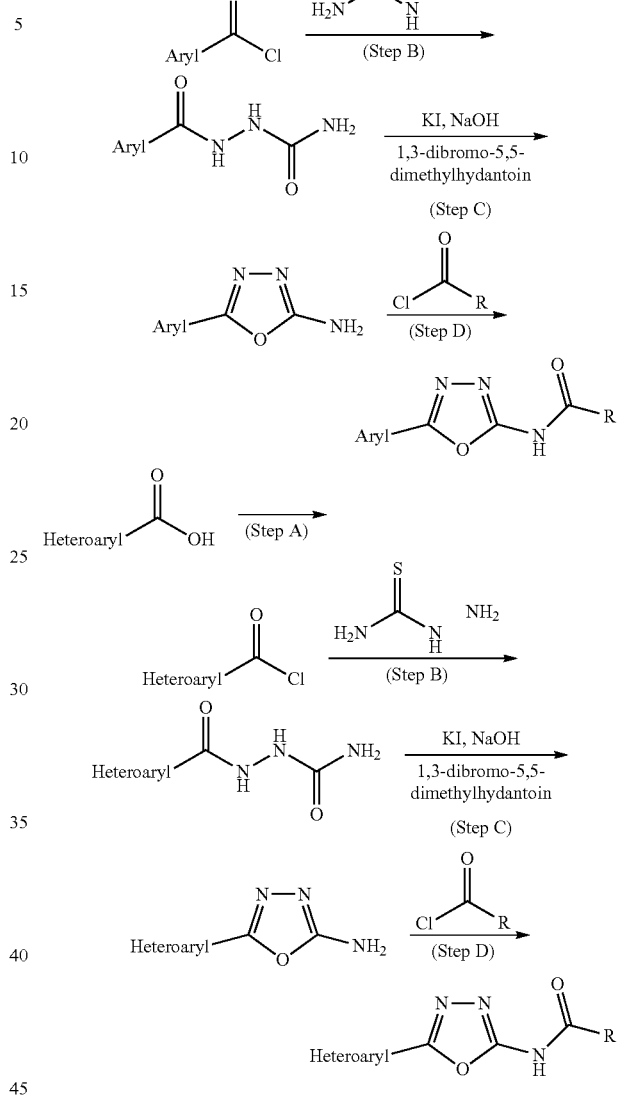

5-Aryl-1,3,4-oxadiazol-2-yl)-2-carboxamides or 5-heteroaryl-1,3,4-oxadiazol-2-yl)-2-carboxamides can be synthesized by a variety of methods well known to well known to the practitioner in the art. For example, an arylacetic acid or heteroarylacetic acid can be converted to an acid chloride using $SOCl_2$, $POCl_3$, $(COCl)_2$ or the like (Step A). The acid chloride can be converted to an acylthiosemicarbazide by reaction with hydrazine carbothioamide (Step B). The acylthiosemicarbazide can be cyclized to give the 5-aryl-1,3,4-oxadiazol-2-amine or 5-heteroaryl-1,3,4-oxadiazol-2-amine by a variety of methods well known to those skilled in the art (Step C). For example, 1,3-dibromo-5,5-dimethylhydantoin is an effective agent for this cyclization reaction (Rivera, N. R.; Balsells, J.; Hansen, K. B., Tetrahedron Lett., 47, 4889, (2006)). Condensation of the 5-aryl-1,3,4-oxadiazol-2-amine or 5-heteroaryl-1,3,4-oxadiazol-2-amine with an acid chloride in presence of a base, such as pyridine or triethylamine, will give 5-aryl-1,3,4-oxadiazol-2-yl)-2-carboxamides or 5-heteroaryl-1,3,4-oxadiazol-2-yl)-2-carboxamides.

5-Chloro-N-(5-phenyl-1,3,4-oxadiazol-2-yl)thiophene-2-carboxamide

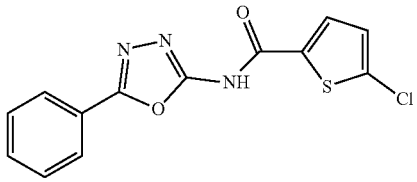 [SMILES: O=C(Nc1nnc(-c2ccccc2)o1)c1ccc(Cl)s1]

5-Phenyl-1,3,4-oxadiazol-2-amine (CAS No. 1612-76-6) is commercially available (e.g. Sigma-Aldrich, Milwaukee, US; Catalog No. 663395).

To a solution of 0.20 g (1.24 mmol) of 5-phenyl-1,3,4-oxadiazol-2-amine in 2 mL of DCM at 25° C., pyridine (1.86 mmol) and 0.22 g (1.24 mmol) of 5-chlorothiophene-2-carbonyl chloride were added. The reaction solution was stirred at 25° C. for 4 h, diluted with 20 mL of aqueous sodium bicarbonate, and extracted three times with DCM. The combined organic layer was washed with brine, dried over anhydrous Na$_2$SO$_4$, concentrated, and the residue was purified by column chromatography on silica gel using a mixture of ethyl acetate and hexane (1:1) as eluant to give 0.20 g (53% yield) of the title compound as a white solid.

$^1$H NMR (400 MHz, CDCl$_3$) δ ppm 12.3 (d, J=3.9 Hz, 1H), 8.00 (d, J=7.4 Hz, 2H), 7.60-7.66 (m, 1H), 7.52-7.59 (m, 2H), 7.08 (d, J=4.3 Hz, 1H). MS (ESI) m/z=327.8 (M+Na)$^+$.

Example 116

5,6-Dichloro-N-(5-(5-chlorothiophen-2-yl)-1,3,4-oxadiazol-2-yl)-1,3-dioxoisoindoline-2-carboxamide

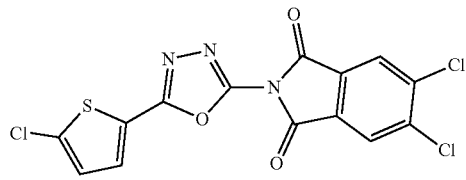 [SMILES: O=C1c2cc(Cl)c(Cl)cc2C(=O)N1c1nnc(-c2ccc(Cl)s2)o1]

The title compound was prepared by reacting 5-(5-chlorothiophen-2-yl)-1,3,4-oxadiazol-2-amine (CAS No. 1105193-79-0) with 4,5-dichlorophthaloyl dichloride in presence of pyridine in DCM at rt. MS (ESI) m/z=464.9 (M+Na)$^+$.

Examples 117 to 130 can also be prepared by procedures similar to the one described in Example 115 using the reagents indicated in the table below.

| Example | R$^1$ | R$^2$ | 1,3,4-oxadiazol-2-amines used in Step D | Acyl chloride used in Step D |
|---|---|---|---|---|
| 117 | 5-chlorothiophen-2-yl | phenyl | 5-(5-Chlorothiophen-2-yl)-1,3,4-oxadiazol-2-amine | Benzoyl chloride |
| 118 | 5-chlorothiophen-2-yl | 2-(3-chlorophenyl)ethyl | 5-(5-Chlorothiophen-2-yl)-1,3,4-oxadiazol-2-amine | 3-(3-Chlorophenyl)propanoyl chloride |
| 119 | phenyl | 2-(3-chlorophenyl)ethyl | 5-Phenyl-1,3,4-oxadiazol-2-amine | 3-(3-Chlorophenyl)propanoyl chloride |
| 120 | 5-chlorothiophen-2-yl | 2-(3,4-dichlorophenyl)ethyl | 5-(5-Chlorothiophen-2-yl)-1,3,4-oxadiazol-2-amine | 3-(3,4-Dichlorophenyl)propanoyl chloride |

-continued

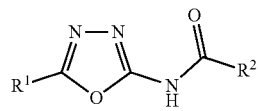

| Example | R¹ | R² | 1,3,4-oxadiazol-2-amines used in Step D | Acyl chloride used in Step D |
|---|---|---|---|---|
| 121 | 5-chlorothiophen-2-yl | 3-chlorobenzyl | 5-(5-Chlorothiophen-2-yl)-1,3,4-oxadiazol-2-amine | 2-(3-Chlorophenyl)acetyl chloride |
| 122 | phenyl | 5-methylisoxazol-3-yl | 5-Phenyl-1,3,4-oxadiazol-2-amine | 5-Methylisoxazole-3-carbonyl chloride |
| 123 | phenyl | (phenylamino)methyl | 5-Phenyl-1,3,4-oxadiazol-2-amine | Phenylglycinoyl chloride |
| 124 | phenyl | pyrazin-2-yl | 5-Phenyl-1,3,4-oxadiazol-2-amine | Pyrazine-2-carbonyl chloride |
| 125 | 2-fluorophenyl | 5-chlorothiophen-2-yl | 5-(2-Fluorophenyl)-1,3,4-oxadiazol-2-amine | 5-Chlorothiophene-2-carbonyl chloride |
| 126 | 2-fluorophenyl | 5-methylisoxazol-3-yl | 5-(2-Fluorophenyl)-1,3,4-oxadiazol-2-amine | 5-Methylisoxazole-3-carbonyl chloride |
| 127 | 2-fluorophenyl | pyrazin-2-yl | 5-(2-Fluorophenyl)-1,3,4-oxadiazol-2-amine | Pyrazine-2-carbonyl chloride |

Example 117

N-(5-(5-Chlorothiophen-2-yl)-1,3,4-oxadiazol-2-yl)benzamide $^1$H NMR (400 MHz, DMSO-d$_6$) δ 7.27-7.39 (m, 1H), 7.47-7.59 (m, 2H), 7.59-7.73 (m, 3H), 7.98-8.10 (m, 2H). MS (ESI) m/z=327.8 (M+Na)$^+$.

Example 118

3-(3-Chlorophenyl)-N-(5-(5-chlorothiophen-2-yl)-1,3,4-oxadiazol-2-yl)propanamide $^1$H NMR (400 MHz, CDCl$_3$) δ 7.55 (d, J=3.9 Hz, 1H), 7.31 (s, 1H), 7.16-7.25 (m, 3H), 7.01 (d, J=3.9 Hz, 1H), 2.90-3.16 (m, 4H). MS (ESI) m/z=389.8 (M+Na)$^+$.

Example 119

3-(3-Chlorophenyl)-N-(5-phenyl-1,3,4-oxadiazol-2-yl)propanamide $^1$H NMR (400 MHz, CDCl$_3$) δ 7.89-7.95 (m, 2H), 7.48-7.55 (m, 2H), 7.29 (s, 1H), 7.13-7.26 (m, 4H), 3.17-3.23 (m, 2H), 3.04-3.10 (m, 2H). MS (ESI) m/z=349.7 (M+Na)$^+$.

Example 120

N-(5-(5-Chlorothiophen-2-yl)-1,3,4-oxadiazol-2-yl)-3-(3,4-dichlorophenyl)propanamide $^1$H NMR (400 MHz, CDCl$_3$) δ 7.55 (d, J=3.91 Hz, 1H), 7.34-7.42 (m, 2H), 7.11 (d, J=8.20 Hz, 1H), 7.00 (d, J=3.51 Hz, 1H), 2.98-3.17 (m, 4H). MS (ESI) m/z=403.9 (M+H)$^+$.

Example 121

2-(3-Chlorophenyl)-N-(5-(5-chlorothiophen-2-yl)-1,3,4-oxadiazol-2-yl)acetamide $^1$H NMR (400 MHz, CDCl$_3$) δ 7.45 (br. s., 1H), 7.38 (d, J=3.91 Hz, 1H), 7.31 (s, 2H), 6.99 (d, J=3.91 Hz, 1H), 6.96 (d, J=3.91 Hz, 1H), 3.92 (s, 2H). MS (ESI) m/z=375.8 (M+Na)$^+$.

Example 122

5-Methyl-N-(5-phenyl-1,3,4-oxadiazol-2-yl)isoxazole-3-carboxamide $^1$H NMR (400 MHz, CDCl$_3$) δ ppm 9.01 (br. s., 1H), 7.89 (br. s., 1H), 7.47 (br. s., 1H), 6.65 (br. s., 1H), 6.43 (br. s., 1H), 2.49 (br. s., 3H). MS (ESI) m/z=293.2 (M+H)$^+$.

Example 123

N-(5-Phenyl-1,3,4-oxadiazol-2-yl)-2-(phenylamino)acetamide $^1$H NMR (400 MHz, DMSO-d$_6$) δ 10.21-10.32 (m, 1H), 7.87-7.94 (m, 2H), 7.75-7.85 (m, 2H), 7.42-7.55 (m, 3H), 7.31-7.40 (m, 2H), 6.99-7.11 (m, 1H), 4.43-4.56 (m, 2H); MS (ESI) m/z=295.4 (M+H$^+$).

Example 124

N-(5-Phenyl-1,3,4-oxadiazol-2-yl)pyrazine-2-carboxamide $^1$H NMR (400 MHz, DMSO-d$_6$) δ ppm 7.35-7.58 (m, 1H), 7.77-8.03 (m, 2H), 8.13-8.42 (m, 2H), 8.66-8.78 (m, 1H), 8.80-8.91 (m, 1H), 9.15-9.21 (m, 1H). MS (ESI) m/z=268.1 (M+H)$^+$.

Example 125

5-Chloro-N-(5-(2-fluorophenyl)-1,3,4-oxadiazol-2-yl)thiophene-2-carboxamide $^1$H NMR (400 MHz, CDCl$_3$) δ ppm 8.23 (br. s., 1H), 8.17 (d, J=4.30 Hz, 1H), 7.90-7.96 (m, 1H), 7.58-7.65 (m, 1H), 7.31-7.38 (m, 1H), 7.27-7.31 (m, 1H), 7.07 (d, J=4.30 Hz, 1H); MS (ESI) m/z, 295.4 (M+H)+; MS, m/z=346.3 (M+Na)$^+$.

Example 126

N-(5-(2-Fluorophenyl)-1,3,4-oxadiazol-2-yl)-5-methylisoxazole-3-carboxamide $^1$H NMR (400 MHz, CDCl$_3$) δ ppm 9.46-9.59 (m, 1H), 8.07 (t, J=6.64 Hz, 1H), 7.55 (dd, J=6.83, 12.69 Hz, 2H), 7.30 (d, J=7.81 Hz, 1H), 6.60 (s, 1H), 2.55 (s, 3H).

Example 127

N-(5-(2-Fluorophenyl)-1,3,4-oxadiazol-2-yl)pyrazine-2-carboxamide $^1$H NMR (400 MHz, DMSO-d$_6$) δ ppm 7.32-7.50 (m, 1H), 7.51-7.65 (m, 1H), 7.80-7.95 (m, 1H), 8.21-8.37 (m, 1H), 8.67-8.76 (m, 1H), 8.86 (d, J=1.56 Hz, 1H) 9.18 (s, 1H).

Example 128

(S)—N-(6-(2-(tert-Butylamino)-2-oxoethyl)-6-azaspiro[2.5]octan-1-yl)-3-chloro-5-fluorobenzamide or (R)—N-(6-(2-(tert-Butylamino)-2-oxoethyl)-6-azaspiro[2.5]octan-1-yl)-3-chloro-5-fluorobenzamide

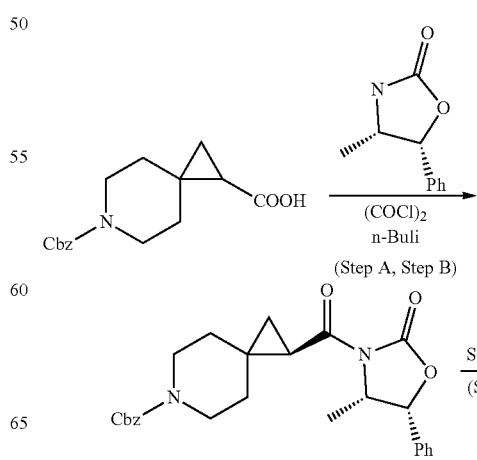

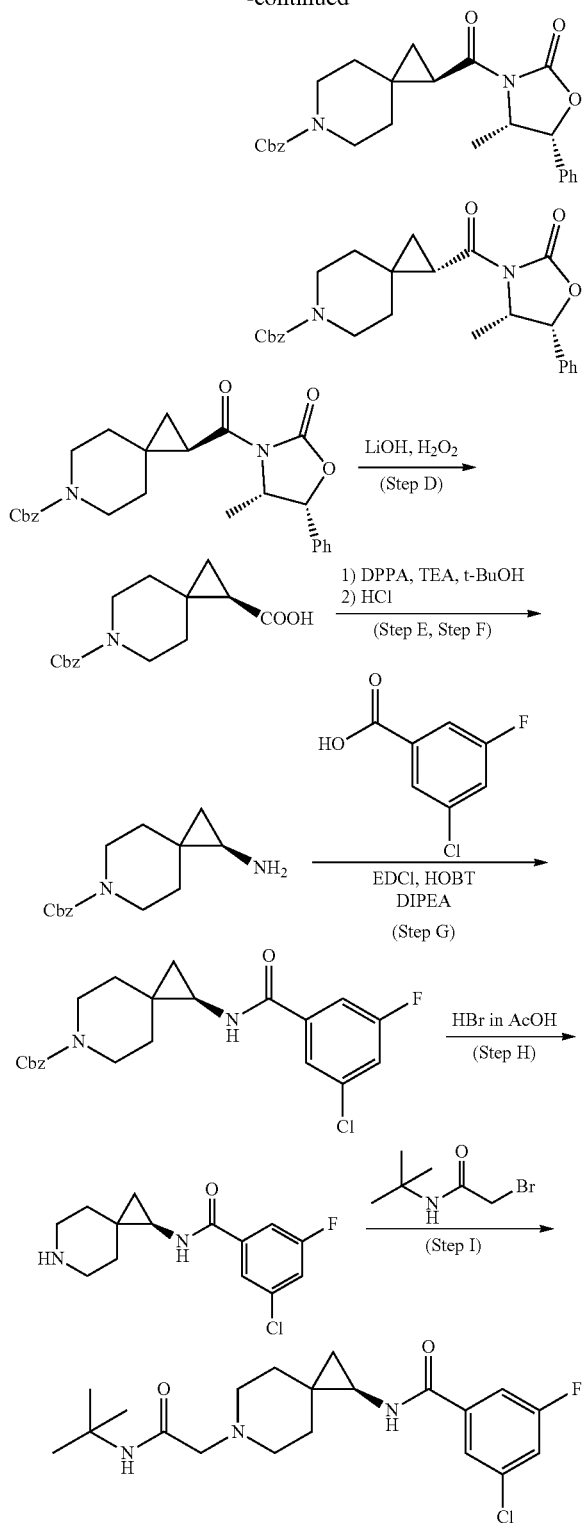

Step A.

To a suspension of 6-(benzyloxycarbonyl)-6-azaspiro[2.5]octane-1-carboxylic acid (Example 56, Step A; 14.5 g, 50 mmol) in dichloromethane (250 mL) was added oxalyl chloride (16 g, 125 mmol) followed by the addition of 1 mL of DMF. After the reaction was stirred at rt for 3 h, the solvent was evaporated to give 6-(benzyloxycarbonyl)-6-azaspiro[2.5]octane-1-carboxylic acid chloride as yellow oil which was used without further purification.

Step B.

To a solution of (4S,5R)-4-methyl-5-phenyloxazolidin-2-one (5.9 g, 33 mmol; CAS #16251-45-9) in THF (200 mL) was added n-BuLi (20 mL, 2M in hexane, 1.2 eq) dropwise at −78° C. After addition, the reaction was warmed to rt and stirred for 1 hour. The mixture was cooled to −78° C. and 6-(benzyloxycarbonyl)-6-azaspiro[2.5]octane-1-carboxylic acid chloride (15.3 g, 50 mmol) in THF (50 mL) was added dropwise. The cooling bath was removed and the reaction was stirred at rt for another 16 h, then quenched with a sat. aq. solution of NH$_4$Cl (100 mL) and extracted with EA (200 mL×3). The combined organic layers were washed with brine, dried over Na$_2$SO$_4$, filtered and the filtrate was concentrated in vacuo to give a diastereomeric mixture of benzyl (R)-1-((4S,5R)-4-methyl-2-oxo-5-phenyloxazolidine-3-carbonyl)-6-azaspiro[2.5]octane-6-carboxylate and benzyl (S)-1-((4S,5R)-4-methyl-2-oxo-5-phenyloxazolidine-3-carbonyl)-6-azaspiro[2.5]octane-6-carboxylate.
Mass Spectrum (ESI) m/z=449 (M+1).

Step C.

Purification of diastereomeric mixture of benzyl (R)-1-((4S,5R)-4-methyl-2-oxo-5-phenyloxazolidine-3-carbonyl)-6-azaspiro[2.5]octane-6-carboxylate and benzyl (S)-1-((4S,5R)-4-methyl-2-oxo-5-phenyloxazolidine-3-carbonyl)-6-azaspiro[2.5]octane-6-carboxylate by silica gel chromatography (PE/EA=3/1) gave the enantiopure benzyl (R)-1-((4S,5R)-4-methyl-2-oxo-5-phenyloxazolidine-3-carbonyl)-6-azaspiro[2.5]octane-6-carboxylate or benzyl (S)-1-((4S,5R)-4-methyl-2-oxo-5-phenyloxazolidine-3-carbonyl)-6-azaspiro[2.5]octane-6-carboxylate as the major/faster eluting/more polar diastereomer. Further elution provided the minor/slower eluting/less polar diastereomer.

Step D.

To a solution of benzyl (R)-1-((4S,5R)-4-methyl-2-oxo-5-phenyloxazolidine-3-carbonyl)-6-azaspiro[2.5]octane-6-carboxylate or benzyl (S)-1-((4S,5R)-4-methyl-2-oxo-5-phenyloxazolidine-3-carbonyl)-6-azaspiro[2.5]octane-6-carboxylate (3 g, 6.7 mmol, major diastereomer) in THF (8 mL) and water (2 mL) was added LiOH (804 mg, 33.5 mmol, 5 eq), H$_2$O$_2$ (3.8 g, 33.5 mmol, 5 eq, 30% in water). The mixture was stirred at rt for 16 h. Then 100 mL of water was added and the mixture was extracted with EA (100 mL×3). The water phase was acidified with 1 N HCl to pH=1 and extracted with EA (100 mL×3). The combined organic layers were washed with brine, dried over Na$_2$SO$_4$, filtered and the filtrate was concentrated to give (S)-6-((benzyloxy)carbonyl)-6-azaspiro[2.5]octane-1-carboxylic acid or (R)-6-((benzyloxy)carbonyl)-6-azaspiro[2.5]octane-1-carboxylic acid as a white solid (1.5 g, 78% yield). Mass Spectrum (ESI) m/z=290 (M+1).

Step E.

To a solution of (S)-6-((benzyloxy)carbonyl)-6-azaspiro[2.5]octane-1-carboxylic acid or (R)-6-((benzyloxy)carbonyl)-6-azaspiro[2.5]octane-1-carboxylic acid (1.5 g, 5.2 mmol) in t-BuOH (30 mL) was added DPPA (2.1 g, 7.8 mmol) and TEA (1.1 g, 10.4 mmol). The reaction mixture was refluxed for 6 h, then concentrated to give the crude residue which was purified by silica gel chromatography (hexanes:EtOAc 10:1 to 5:1) to afford benzyl (S)-1-((tert-butoxycarbonyl)amino)-6-azaspiro[2.5]octane-6-carboxylate or benzyl (R)-1-((tert-butoxycarbonyl)amino)-6-azaspiro[2.5]octane-6-carboxylate (650 mg, 35% yield). Mass Spectrum (ESI) m/z=383 (M+23).

Step F.

A solution of benzyl (S)-1-((tert-butoxycarbonyl)amino)-6-azaspiro[2.5]octane-6-carboxylate or benzyl (R)-1-((tert-butoxycarbonyl)amino)-6-azaspiro[2.5]octane-6-carboxylate (650 mg, 1.8 mmol) in HCl in Dioxane (4M, 10 mL) was stirred at rt for 1 h. The solvent was removed and the residue (500 mg, crude) was used in the next step without further purification. Mass Spectrum (ESI) m/z=261 (M+1).

Step G.

To a solution of the crude product from Step F (500 mg) in DCM (15 mL) was added EDCI (522 mg, 2.7 mmol), HOBT (366 mg, 2.7 mmol), DIPEA (464 mg, 3.6 mmol) and 3-chloro-5-fluorobenzoic acid (470 mg, 2.7 mmol). The reaction mixture was stirred at rt for 12 h, then diluted with DCM (100 mL), washed successively with sat. aq. NH$_4$Cl solution, sat. aq. NaHCO$_3$, water and brine and concentrated. The residue was purified by silica gel chromatography (hexanes/EtOAc=2:1) to afford the product benzyl (R)-1-(3-chloro-5-fluorobenzamido)-6-azaspiro[2.5]octane-6-carboxylate or benzyl (S)-1-(3-chloro-5-fluorobenzamido)-6-azaspiro[2.5]octane-6-carboxylate as a yellow oil (600 mg, 80% yield). Mass Spectrum (ESI) m/z=417 (M+1).

Step H.

To a solution of the compound from Step G (600 mg, 1.4 mmol) in AcOH (10 mL) was added HBr in AcOH (33%, 3 mL) at rt. The resulting mixture was stirred at rt for 2 h. The solvent was removed, the residue was diluted with ethyl acetate (20 mL) and washed with sat. aq. NaHCO$_3$ solution (100 mL) and extracted with ethyl acetate (3×100 mL). The combined organic layers were dried over anhydrous sodium sulfate, filtered and concentrated to give a product (0.4 g, 98% yield) that was used in next step without further purification. Mass Spectrum (ESI) m/z=283 (M+1).

Step I.

(S)—N-(6-(2-(tert-butylamino)-2-oxoethyl)-6-azaspiro[2.5]octan-1-yl)-3-chloro-5-fluorobenzamide or (R)—N-(6-(2-(tert-butylamino)-2-oxoethyl)-6-azaspiro[2.5]octan-1-yl)-3-chloro-5-fluorobenzamide

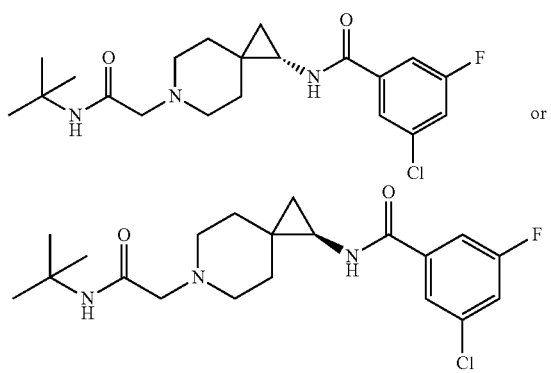

or

A solution of the product from Step H (400 mg, 1.4 mmol), 2-bromo-N-tert-butylacetamide (231 mg, 1.2 mmol), KI (232 mg, 1.4 mmol), and K$_2$CO$_3$ (386 mg, 2.8 mmol) in DMF/MeCN (1/1, 6 mL) was stirred at 60° C. for 16 h. 10 mL of water was added and the mixture was extracted with EA (20 mL×3). The combined organic layers were washed with brine, dried over Na$_2$SO$_4$ and concentrated. The residue was purified by chromatography on silica gel eluting with 5% DCM/MeOH to give (S)—N-(6-(2-(tert-butylamino)-2-oxoethyl)-6-azaspiro[2.5]octan-1-yl)-3-chloro-5-fluorobenzamide or (R)—N-(6-(2-(tert-butylamino)-2-oxoethyl)-6-azaspiro[2.5]octan-1-yl)-3-chloro-5-fluorobenzamide as a white solid (300 mg, 38%). $^1$H NMR (400 MHz, MeOD) δ ppm 7.70 (dd, J=2.3, 1.0 Hz, 1H), 7.54 (ddd, J=9.1, 2.4, 1.4 Hz, 1H), 7.42 (dt, J=8.4, 2.1 Hz, 1H), 2.94 (s, 2H), 2.74 (m, 2H), 2.62-2.37 (m, 3H), 1.73-1.41 (m, 4H), 1.43-1.29 (s, 9H), 0.86 (dd, J=8.0, 5.7 Hz, 1H), 0.80-0.63 (m, 1H). Mass Spectrum (ESI) m/z=396 (M+1).

Example 129

(R)—N-(6-(2-(tert-Butylamino)-2-oxoethyl)-6-azaspiro[2.5]octan-1-yl)-3-chloro-5-fluorobenzamide or (S)—N-(6-(2-(tert-Butylamino)-2-oxoethyl)-6-azaspiro[2.5]octan-1-yl)-3-chloro-5-fluorobenzamide

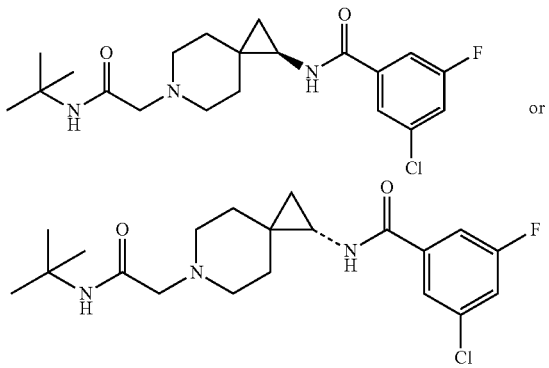

The title compound was prepared from enantiopure benzyl (S)-1-((4S,5R)-4-methyl-2-oxo-5-phenyloxazolidine-3-carbonyl)-6-azaspiro[2.5]octane-6-carboxylate or benzyl (R)-1-((4S,5R)-4-methyl-2-oxo-5-phenyloxazolidine-3-carbonyl)-6-azaspiro[2.5]octane-6-carboxylate (minor/slower eluting/less polar diastereomer from Example 128, Step c, following Example 128 Steps D-I.

$^1$H NMR (400 MHz, MeOD) δ ppm 7.70 (dd, J=2.3, 1.0 Hz, 1H), 7.54 (ddd, J=9.1, 2.4, 1.4 Hz, 1H), 7.42 (dt, J=8.4, 2.1 Hz, 1H), 2.94 (s, 2H), 2.74 (m, 2H), 2.62-2.37 (m, 3H), 1.73-1.41 (m, 4H), 1.43-1.29 (s, 9H), 0.86 (dd, J=8.0, 5.7 Hz, 1H), 0.80-0.63 (m, 1H). Mass Spectrum (ESI) m/z=396 (M+1).

Example 130

(R)—N-(6-(2-(tert-Butylamino)-2-oxoethyl)-6-azaspiro[2.5]octan-1-yl)-3-fluoro-5-(trifluoromethyl)benzamide or (S)—N-(6-(2-(tert-Butylamino)-2-oxoethyl)-6-azaspiro[2.5]octan-1-yl)-3-fluoro-5-(trifluoromethyl)benzamide

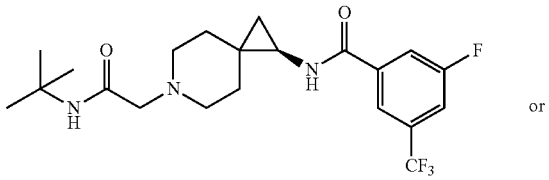

or

133
-continued

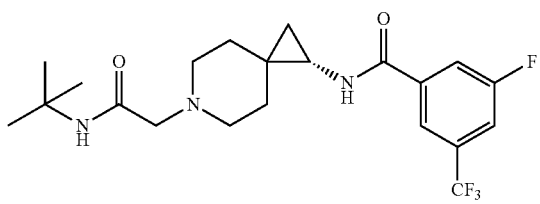

Example 130 can be prepared as described in Example 128, replacing 3-chloro-5-fluorobenzoic acid in Step G with 3-fluoro-5-(trifluoromethyl)benzoic acid. Mass Spectrum (ESI) m/z=430 (M+H). $^1$H NMR (400 MHz, MeOD) δ 8.01 (s, 1H), 7.88 (dd, J=9.0, 1.8 Hz, 1H), 7.68 (d, J=8.3 Hz, 1H), 2.99 (s, 2H), 2.83-2.71 (m, 2H), 2.55 (m, 3H), 1.78-1.45 (m, 4H), 1.34 (s, 9H), 0.88 (dd, J=8.0, 5.7 Hz, 1H), 0.81-0.60 (m, 1H).

Example 131

(3S,5S,7S)—N—((R)-6-(2-(tert-Butylamino)-2-oxo-ethyl)-6-azaspiro[2.5]octan-1-yl)-3,5,7-trifluoroadamantane-1-carboxamide or (3S,5S,7S)—N—((S)-6-(2-(tert-Butylamino)-2-oxoethyl)-6-azaspiro[2.5]octan-1-yl)-3,5,7-trifluoroadamantane-1-carboxamide

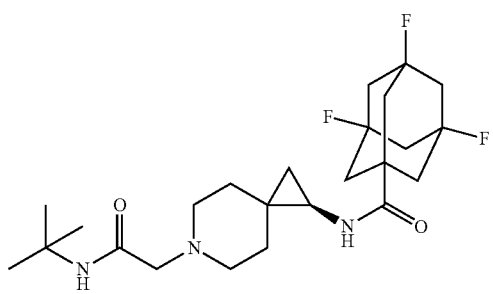

or

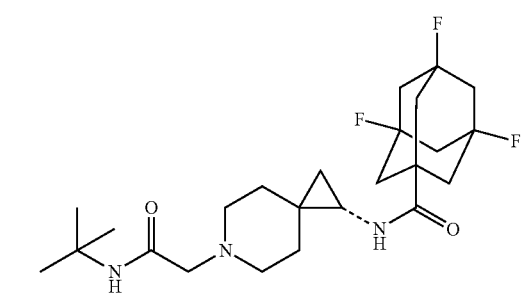

Example 131 can be prepared as described in Example 128, replacing 3-chloro-5-fluorobenzoic acid in Step G with (3s,5s,7s)-3,5,7-trifluoroadamantane-1-carboxylic acid.

Mass Spectrum (ESI) m/z=456 (M+H). $^1$H NMR (400 MHz, MeOD) δ 3.96-3.74 (m, 2H), 3.64-3.37 (m, 2H), 3.17 (dd, J=14.0, 5.9 Hz, 1H), 2.99-2.79 (m, 1H), 2.63 (m, 1H), 2.32-2.03 (m, 8H), 2.02-1.85 (m, 6H), 1.57-1.27 (m, 11H), 0.97 (dt, J=10.3, 5.2 Hz, 1H), 0.81 (dd, J=11.8, 6.4 Hz, 1H).

Example 132

(R)—N-(3,5-Bis(trifluoromethyl)phenyl)-6-(2-(tert-butylamino)-2-oxoethyl)-6-azaspiro[2.5]octane-1-carboxamide or (S)—N-(3,5-Bis(trifluoromethyl)phenyl)-6-(2-(tert-butylamino)-2-oxoethyl)-6-azaspiro[2.5]octane-1-carboxamide

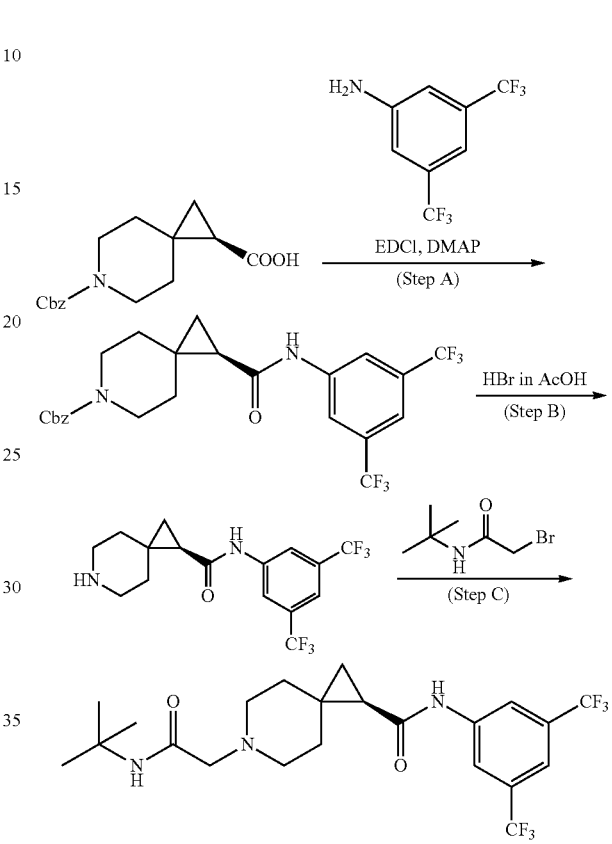

Step A.

To a solution of (R)-6-((benzyloxy)carbonyl)-6-azaspiro[2.5]octane-1-carboxylic acid or (S)-6-((benzyloxy)carbonyl)-6-azaspiro[2.5]octane-1-carboxylic acid (Example 128, Step D; 800 mg, 4.2 mmol) in DCM (30 mL) was added DMAP (340 mg, 2.77 mmol), EDCI (556 mg, 4.16 mmol), and 3,5-bis(trifluoromethyl)aniline (600 mg, 4.16 mmol), then the reaction mixture was stirred at rt for 12 h. The mixture was diluted with DCM (100 mL) and washed with water (30 mL×2). The organic layer was concentrated to give the crude residue which was purified by silica gel chromatography (PE/EtOAc=2/1) to afford benzyl (R)-1-((3,5-bis(trifluoromethyl)phenyl)carbamoyl)-6-azaspiro[2.5]octane-6-carboxylate or benzyl (S)-1-((3,5-bis(trifluoromethyl)phenyl)carbamoyl)-6-azaspiro[2.5]octane-6-carboxylate as yellow oil (1.0 g, 72% yield). Mass Spectrum (ESI) m/z=501 (M+H).

Step B.

To a solution of benzyl (R)-1-((3,5-bis(trifluoromethyl)phenyl)carbamoyl)-6-azaspiro[2.5]octane-6-carboxylate or benzyl (S)-1-((3,5-bis(trifluoromethyl)phenyl) carbamoyl)-6-azaspiro[2.5]octane-6-carboxylate (1.0 g, 2.0 mmol) in AcOH (30 mL) was added HBr in AcOH (33%, 10 mL) at rt. The resulting mixture was stirred at rt for 2 h. The mixture was concentrated. The residue was diluted with ethyl acetate (100 mL) and washed with sat'd. NaHCO$_3$ solution (50 mL×2). The organic layer was dried over anhydrous sodium sulfate, filtered and concentrated to give the crude product (600 mg, 82% yield) which was used in next step without any purification. Mass Spectrum (ESI) m/z=367 (M+H).

Step C.

(R)—N-(3,5-bis(trifluoromethyl)phenyl)-6-(2-(tert-butylamino)-2-oxoethyl)-6-azaspiro[2.5]octane-1-carboxamide or (S)—N-(3,5-bis(trifluoromethyl)phenyl)-6-(2-(tert-butylamino)-2-oxoethyl)-6-azaspiro[2.5]octane-1-carboxamide

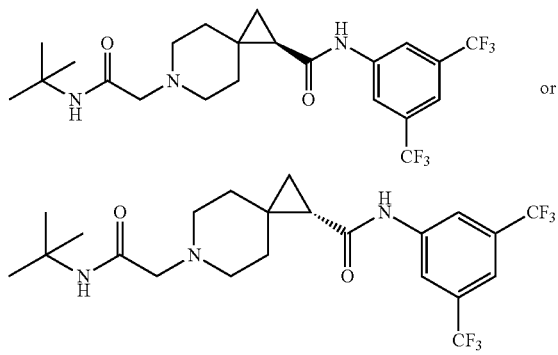

A solution of the product from Step B (600 mg, 1.64 mmol), 2-bromo-N-tert-butylacetamide (286 mg, 1.48 mmol), KI (272 mg, 1.64 mmol), and K$_2$CO$_3$ (453 mg, 3.28 mmol) in DMF/CH$_3$CN (1/1, 10 mL) was stirred at 60° C. for 16 h. The mixture was diluted with water (50 mL) and extracted with EA (100 mL*3). The combined organic layers were washed with brine, dried over Na$_2$SO$_4$ and concentrated. The residue was purified by silica gel chromatography (DCM/MeOH=20/1) to give the title compound as a white solid (400 mg, 51%). Mass Spectrum (ESI) m/z=480 (M+H). $^1$H NMR (400 MHz, MeOD) δ 8.23 (s, 2H), 7.62 (s, 1H), 2.95 (s, 2H), 2.75-2.48 (m, 3H), 2.43 (s, 1H), 1.84 (t, J=5.4 Hz, 2H), 1.79-1.43 (m, 3H), 1.39-1.31 (m, 9H), 1.32-1.24 (m, 1H), 0.99 (dd, J=7.9, 4.4 Hz, 1H).

Example 133

(R)-6-(2-(tert-Butylamino)-2-oxoethyl)-N-(3-fluoro-5-(trifluoromethyl)phenyl)-6-azaspiro[2.5]octane-1-carboxamide or (S)-6-(2-(tert-Butylamino)-2-oxoethyl)-N-(3-fluoro-5-(trifluoromethyl)phenyl)-6-azaspiro[2.5]octane-1-carboxamide

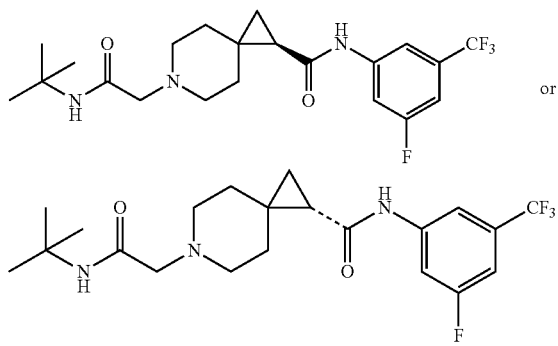

Example 133 can be prepared as described in Example 132, replacing 3,5-bis(trifluoromethyl)aniline in Step A with 3-fluoro-5-(trifluoromethyl)aniline. Mass Spectrum (ESI) m/z=430 (M+H). $^1$H NMR (400 MHz, MeOD) δ 7.89-7.56 (m, 2H), 7.13 (d, J=8.4 Hz, 1H), 2.93 (s, 2H), 2.73-2.31 (m, 4H), 1.90-1.42 (m, 5H), 1.33 (s, 9H), 1.23 (dd, J=12.6, 7.6 Hz, 1H), 0.97 (dd, J=7.9, 4.4 Hz, 1H).

Example 134

(R)-3-Chloro-N-(6-(3,3-dimethyl-2-oxobutyl)-6-azaspiro[2.5]octan-1-yl)-5-fluorobenzamide or (S)-3-Chloro-N-(6-(3,3-dimethyl-2-oxobutyl)-6-azaspiro[2.5]octan-1-yl)-5-fluorobenzamide

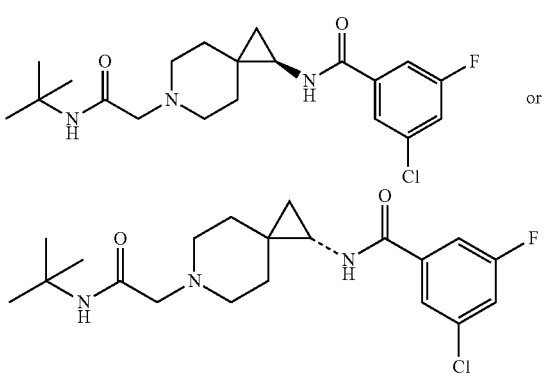

To a solution of (R)-3-chloro-5-fluoro-N-(6-azaspiro[2.5]octan-1-yl)benzamide or (S)-3-chloro-5-fluoro-N-(6-azaspiro[2.5]octan-1-yl)benzamide (Example 128, Step H; 70 mg, 0.25 mmol) and K$_2$CO$_3$ (69 mg, 0.50 mmol) in CH$_3$CN (5 mL) was added 1-bromo-3,3-dimethylbutan-2-one (45 mg, 0.25 mmol) at rt, the resulting mixture was stirred at rt for 2 h. The resulting solution was concentrated and the residue was diluted with ethyl acetate (50 mL) and washed with water (30 mL). The combined organic layers was dried over anhydrous sodium sulfate, filtered and concentrated to give the crude product. It was purified by prep-TLC with DCM/MeOH (20/1) to get the desired product as a white solid (60 mg, 63% yield). Mass Spectrum (ESI) m/z=381 (M+H). $^1$H NMR (400 MHz, MeOD) δ 7.70 (s, 1H), 7.55-7.52 (m, 1H), 7.44-7.41 (m, 1H), 3.53 (m, 2H), 2.77-2.45 (m, 5H), 1.75-1.48 (m, 4H), 1.13 (s, 9H), 0.85 (m, 1H), 0.71-0.68 (m, 1H).

Example 135

3-Chloro-5-fluoro-N-((1R)-6-(2-hydroxy-3,3-dimethylbutyl)-6-azaspiro[2.5]octan-1-yl)benzamide or 3-Chloro-5-fluoro-N-((1S)-6-(2-hydroxy-3,3-dimethylbutyl)-6-azaspiro[2.5]octan-1-yl) benzamide

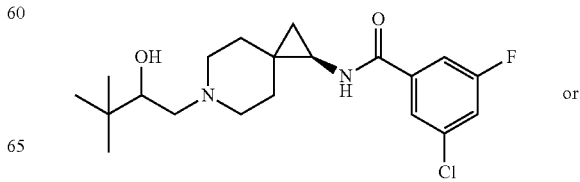

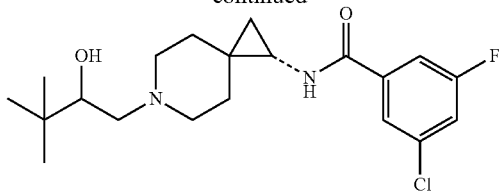

To a solution of (R)-3-chloro-N-(6-(3,3-dimethyl-2-oxobutyl)-6-azaspiro[2.5]octan-1-yl)-5-fluorobenzamide or (S)-3-chloro-N-(6-(3,3-dimethyl-2-oxobutyl)-6-azaspiro[2.5]octan-1-yl)-5-fluorobenzamide (Example 133; 40 mg, 0.1 mmol) in MeOH (5 mL) was added NaBH₄ (11 mg, 0.3 mmol) at 0° C., the resulting mixture was stirred at rt for 1 h. The resulting solution was concentrated and the residue was diluted with ethyl acetate (30 mL) and washed with water (30 mL). The combined organic layers were dried over anhydrous sodium sulfate, filtered and concentrated to give the crude product which was purified by prep-TLC with DCM/MeOH (10/1) to get the desired product as a white solid (17 mg, 45% yield). Mass Spectrum (ESI) m/z=383 (M+H). ¹H NMR (400 MHz, MeOD) δ 7.61 (s, 1H), 7.46 (d, J=9.1 Hz, 1H), 7.33 (dd, J=6.4, 1.9 Hz, 1H), 3.57-3.38 (m, 1H), 3.16-2.62 (m, 6H), 1.74-1.2 (m, 4H), 0.88-0.59 (m, 12H).

Example 136

(R)-3-Chloro-5-fluoro-N-(6-(2-oxo-2-(4-(trifluoromethyl)phenyl)ethyl)-6-azaspiro[2.5]octan-1-yl)benzamide or (S)-3-Chloro-5-fluoro-N-(6-(2-oxo-2-(4-(trifluoromethyl) phenyl)ethyl)-6-azaspiro[2.5]octan-1-yl) benzamide

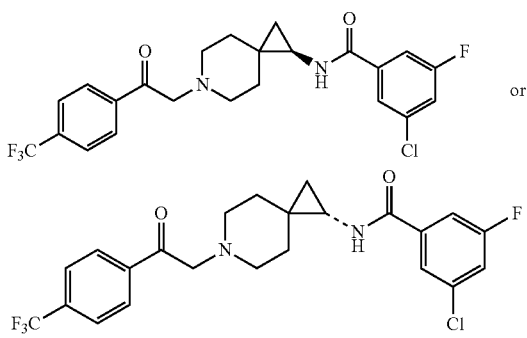

To a solution of (R)-3-chloro-5-fluoro-N-(6-azaspiro[2.5]octan-1-yl)benzamide or (S)-3-chloro-5-fluoro-N-(6-azaspiro[2.5]octan-1-yl)benzamide (Example 128, Step H; 100 mg, 0.35 mmol) and K₂CO₃ (70 mg, 0.53 mmol) in CH₃CN (10 mL) was added 2-bromo-1-(4-(trifluoromethyl)phenyl)ethan-1-one (75 mg, 0.28 mmol) at rt, the resulting mixture was stirred at rt for 2 h. The resulting solution was concentrated and the residue was diluted with ethyl acetate (50 mL) and washed with water (30 mL). The combined organic layers were dried over anhydrous sodium sulfate, filtered and concentrated to give the crude product. It was purified by prep-TLC with DCM/MeOH (20/1) to get the desired product as a white solid (60 mg, 37% yield). Mass Spectrum (ESI) m/z=469 (M+H). ¹H NMR (400 MHz, MeOD) δ 8.22 (d, J=8.1 Hz, 2H), 7.85 (d, J=8.3 Hz, 2H), 7.71 (d, J=1.4 Hz, 1H), 7.55 (m, 1H), 7.43 (dt, J=8.4, 2.1 Hz, 1H), 3.02-2.48 (m, 5H), 1.67 (m, 4H), 0.91 (dd, J=8.0, 5.8 Hz, 1H), 0.77 (t, J=5.1 Hz, 1H).

Example 137

3-Chloro-5-fluoro-N-((1R)-6-(2-hydroxy-2-(4-(trifluoromethyl)phenyl)ethyl)-6-azaspiro[2.5]octan-1-yl)benzamide or 3-Chloro-5-fluoro-N-((1S)-6-(2-hydroxy-2-(4-(trifluoromethyl)phenyl)ethyl)-6-azaspiro[2.5]octan-1-yl)benzamide

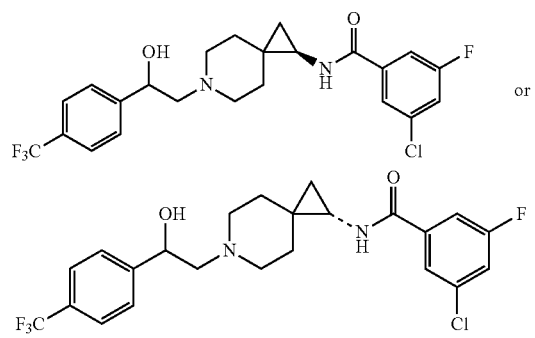

To a solution of Example 136 (40 mg, 0.09 mmol) in MeOH (5 mL) was added NaBH₄ (10 mg, 0.26 mmol) at 0° C. and the resulting mixture was stirred at rt for 1 h. The solution was concentrated and the residue was diluted with ethyl acetate (30 mL) and washed with water (30 mL). The combined organic layers were dried over anhydrous sodium sulfate, filtered and concentrated to give the crude product which was purified by prep-TLC with DCM/MeOH (10/1) to get the desired product as a white solid (17 mg, 43% yield). Mass Spectrum (ESI) m/z=471 (M+H). ¹H NMR (400 MHz, MeOD) δ 7.80-7.48 (m, 6H), 7.43 (dd, J=6.3, 2.1 Hz, 1H), 5.06 (s, 1H), 3.26-2.49 (m, 6H), 2.0-1.5 (m, 5H), 0.93 (m, 1H), 0.78 (m, 1H).

Example 138

(R)-3-Chloro-5-fluoro-N-(6-(2-(4-fluorophenyl)-2-oxoethyl)-6-azaspiro[2.5]octan-1-yl)benzamide or (S)-3-Chloro-5-fluoro-N-(6-(2-(4-fluorophenyl)-2-oxoethyl)-6-azaspiro[2.5]octan-1-yl)benzamide

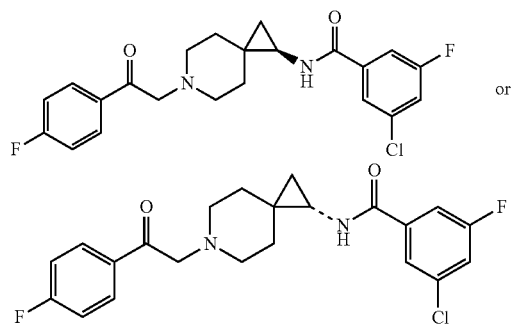

To a solution of (R)-3-chloro-5-fluoro-N-(6-azaspiro[2.5]octan-1-yl)benzamide or (S)-3-chloro-5-fluoro-N-(6-azaspiro[2.5]octan-1-yl)benzamide (Example 128, Step H;

150 mg, 0.53 mmol) and K$_2$CO$_3$ (74 mg, 1.06 mmol) in CH$_3$CN (10 mL) was added 2-bromo-1-(4-fluorophenyl) ethan-1-one (114 mg, 0.53 mmol) at rt, the resulting mixture was stirred at rt for 2 h. The resulting solution was concentrated and the residue was diluted with ethyl acetate (50 mL) and washed with water (30 mL). The combined organic layers were dried over anhydrous sodium sulfate, filtered and concentrated to give the crude product. It was purified by prep-HPLC to get the desired product as a white solid (120 mg, 55% yield). Mass Spectrum (ESI) m/z=419 (M+H). $^1$H NMR (400 MHz, MeOD) δ 8.27-7.95 (m, 2H), 7.70 (t, J=1.4 Hz, 1H), 7.54 (ddd, J=9.1, 2.4, 1.4 Hz, 1H), 7.47-7.35 (m, 1H), 7.30-7.09 (m, 2H), 4.02-3.83 (m, 1H), 2.71-2.45 (m, 5H), 1.74-1.44 (m, 4H), 0.87 (dd, J=8.0, 5.7 Hz, 1H), 0.81-0.66 (m, 1H).

Example 139

3-Chloro-5-fluoro-N-((1R)-6-(2-(4-fluorophenyl)-2-hydroxyethyl)-6-azaspiro[2.5]octan-1-yl)benzamide or 3-Chloro-5-fluoro-N-((1S)-6-(2-(4-fluorophenyl)-2-hydroxyethyl)-6-azaspiro[2.5]octan-1-yl)benzamide

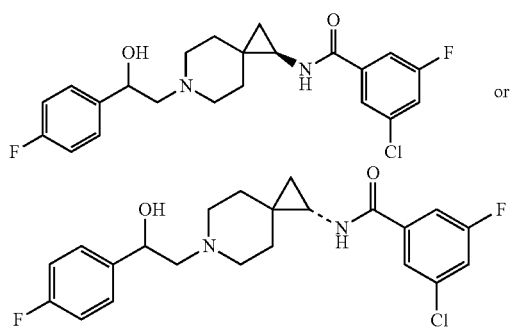

To a solution of Example 138 (90 mg, 0.22 mmol) in MeOH (5 mL) was added NaBH$_4$ (25 mg, 0.65 mmol) at 0° C., the resulting mixture was stirred at rt for 1 h. The resulting solution was concentrated and the residue was diluted with ethyl acetate (30 mL) and washed with water (30 mL). The combined organic layers were dried over anhydrous sodium sulfate, filtered and concentrated to give the crude product. It was purified by prep-TLC with DCM/MeOH (10/1) to get the desired product as a white solid (40 mg, 43% yield). Mass Spectrum (ESI) m/z=421 (M+H). $^1$H NMR (400 MHz, DMSO) δ 8.54 (s, 1H), 7.76 (s, 1H), 7.71-7.55 (m, 2H), 7.46-7.27 (m, 2H), 7.13 (t, J=8.8 Hz, 2H), 5.16 (s, 1H), 4.74 (s, 1H), 2.71-2.51 (m, 7H), 1.34 (s, 4H), 0.77-0.57 (m, 2H).

Example 140

(R)-3-Chloro-5-fluoro-N-(6-(2-(isopropylamino)-2-oxoethyl)-6-azaspiro[2.5]octan-1-yl)benzamide or (S)-3-Chloro-5-fluoro-N-(6-(2-(isopropylamino)-2-oxoethyl)-6-azaspiro[2.5]octan-1-yl)benzamide

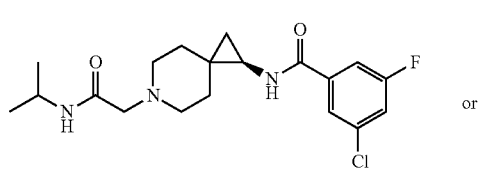

or

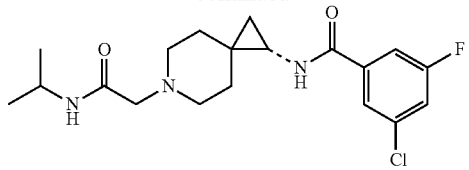

To a solution of (R)-3-chloro-5-fluoro-N-(6-azaspiro[2.5]octan-1-yl)benzamide or (S)-3-chloro-5-fluoro-N-(6-azaspiro[2.5]octan-1-yl)benzamide (Example 128, Step H; 80 mg, 0.28 mmol), KI (50 mg, 0.28 mmol) and K$_2$CO$_3$ (80 mg, 0.56 mmol) in ACN/DMF (5 mL/5 mL) was added 2-bromo-N-isopropylacetamide (45 mg, 0.26 mmol) at rt, the resulting mixture was stirred at 60° C. for 16 h. The resulting solution was concentrated and the residue was diluted with ethyl acetate (50 mL) and washed with water (30 mL). The combined organic layers were dried over anhydrous sodium sulfate, filtered and concentrated to give the crude product. It was purified by prep-HPLC to get the desired product as a white solid (15 mg, 14% yield). Mass Spectrum (ESI) m/z=382 (M+H). $^1$H NMR (400 MHz, MeOD) δ 7.71 (s, 1H), 7.55 (d, J=9.1 Hz, 1H), 7.43 (dt, J=8.4, 2.2 Hz, 1H), 4.03 (dt, J=13.2, 6.6 Hz, 1H), 3.20-2.21 (m, 6H), 1.63-1.50 (m, 5H), 1.18 (dd, J=6.6, 2.0 Hz, 6H), 0.92 (t, J=6.9 Hz, 1H), 0.77 (m, 1H).

Example 141

6-(2-(tert-Butylamino)-2-oxoethyl)-N-(3-fluoro-5-(trifluoromethyl)phenyl)-6-azaspiro[2.5]octane-1-carboxamide

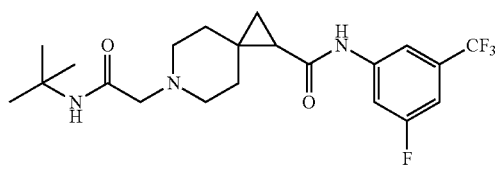 [SMILES: CC(C)(C)NC(=O)CN1CCC2(CC1)CC2C(=O)Nc1cc(F)cc(C(F)(F)F)c1]

The compound can be prepared by a procedure similar to the one described in Example 90, replacing 3,5-dichlorobenzenamine in step A with 3-fluoro-5-(trifluoromethyl)aniline.

$^1$H NMR (400 MHz, MeOD) δ 7.82-7.76 (m, 1H), 7.64 (d, J=8.9 Hz, 1H), 7.03 (d, J=8.3 Hz, 1H), 3.80-3.72 (m, 2H), 3.50-3.41 (m, 2H), 3.31-3.22 (m, 0.5H), 3.12 (t, J=10.6 Hz, 1H), 2.72-2.63 (m, 0.5H), 2.30-2.22 (m, 1H), 2.19-2.08 (m, 1H), 2.06-1.96 (m, 1H), 1.82-1.81 (m, 1H), 1.43-1.20 (m, 11H), 1.11-1.00 (m, 1H). Mass Spectrum (ESI) m/z=430 (M+1).

Example 142

2-Chloro-N-(6-(3,3-dimethylbutyl)-6-azaspiro[2.5]octan-1-yl)-5-(trifluoromethyl)benzamide

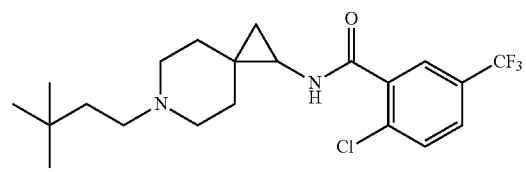 [SMILES: CC(C)(C)CCN1CCC2(CC1)CC2NC(=O)c1cc(C(F)(F)F)ccc1Cl]

The compound can be prepared by a procedure similar to the one described in Example 01, replacing benzoyl chloride in step F with 2-chloro-5-(trifluoromethyl)benzoyl chloride.

¹H NMR (400 MHz, MeOD) δ 7.80 (d, J=8.4 Hz, 2H), 7.74 (d, J=8.2 Hz, 1H), 3.53 (m, 3H), 3.21-3.01 (m, 3H), 2.87 (dd, J=7.9, 4.5 Hz, 1H), 2.20 (m, 2H), 1.70 (m, 2H), 1.31 (s, 2H), 1.07 (m, 1H), 1.02 (s, 9H), 0.80 (m, 1H). Mass Spectrum (ESI) m/z=417 (M+1).

Example 143

N-(6-(2-(tert-Butylamino)-2-oxoethyl)-6-azaspiro[2.5]octan-1-yl)adamantane-1-carboxamide

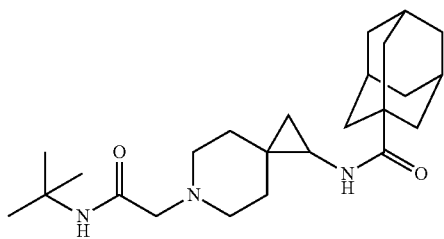 [SMILES: CC(C)(C)NC(=O)CN1CCC2(CC1)CC2NC(=O)C12CC3CC(CC(C3)C1)C2]

The compound can be prepared by a procedure similar to the one described in Example 01, replacing benzoyl chloride in step F with 2-chloro-5-(trifluoromethyl)benzoyl chloride.

¹H NMR (400 MHz, MeOD) δ 2.92 (d, J=0.7 Hz, 2H), 2.69-2.67 (m, 1H), 2.54-2.45 (m, 4H), 2.03 (s, 3H), 1.87 (m, 5H), 1.79-1.74 (m, 5H), 1.48 (m, 4H), 1.42-1.47 (m, 11H), 0.73 (dd, J=8.0, 5.6 Hz, 1H), 0.62-0.60 (m, 1H). Mass Spectrum (ESI) m/z=402 (M+1).

Example 144

((R)—N-(6-(2-(tert-butylamino)-2-oxoethyl)-6-azaspiro[2.5]octan-1-yl)-3,5-bis(trifluoromethyl)benzamide or (S)—N-(6-(2-(tert-butylamino)-2-oxoethyl)-6-azaspiro[2.5]octan-1-yl)-3,5-bis(trifluoromethyl)benzamide

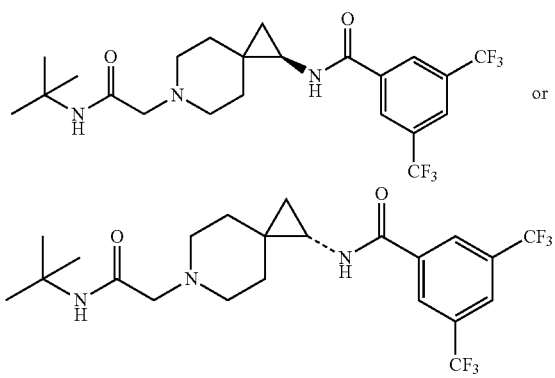

Example 143 can be prepared as described in Example 128, replacing 3-chloro-5-fluorobenzoic acid in Step G with 3,5-bis (trifluoromethyl)benzoic acid. ¹H NMR (400 MHz, MeOD) δ ppm 8.50 (s, 2H), 8.22 (s, 1H), 3.84 (s, 2H), 3.54 (d, J=49.4 Hz, 3H), 3.02 (s, 1H), 2.88 (s, 1H), 2.24 (s, 2H), 1.54-1.42 (m, 2H), 1.40 (d, J=14.4 Hz, 9H), 1.17-1.03 (m, 1H), 0.94 (s, 1H). Mass Spectrum (ESI) m/z=480 (M+1).

Example 145

N—((R)-6-(2-(tert-butylamino)-2-oxoethyl)-6-azaspiro[2.5]octan-1-yl)adamantane-1-carboxamide or N—((S)-6-(2-(tert-butylamino)-2-oxoethyl)-6-azaspiro[2.5]octan-1-yl)adamantane-1-carboxamide

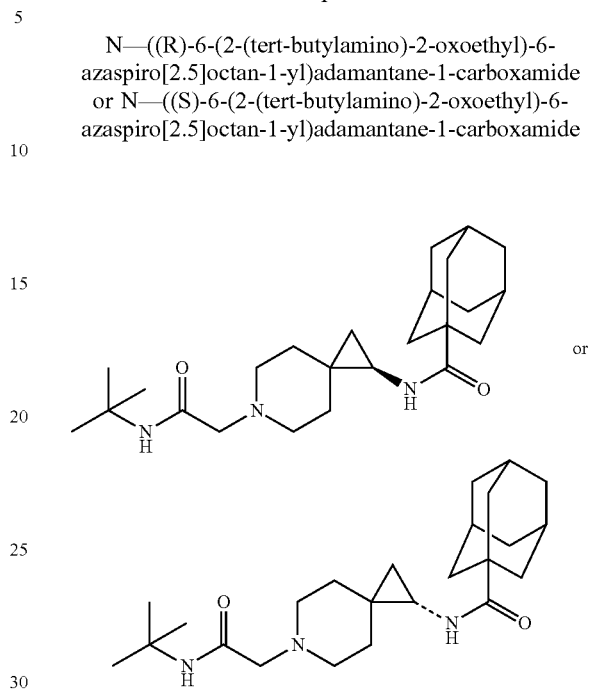

Example 145 can be prepared as described in Example 128, replacing 3-chloro-5-fluorobenzoic acid in Step G with 3 adamantane-1-carboxylic acid. Mass Spectrum (ESI) m/z=402 (M+1).

Example 146

(R)—N-(6-(3,3-dimethylbutyl)-6-azaspiro[2.5]octan-1-yl)-3,5-bis(trifluoromethyl)benzamide or (S)—N-(6-(3,3-dimethylbutyl)-6-azaspiro[2.5]octan-1-yl)-3,5-bis(trifluoromethyl)benzamide

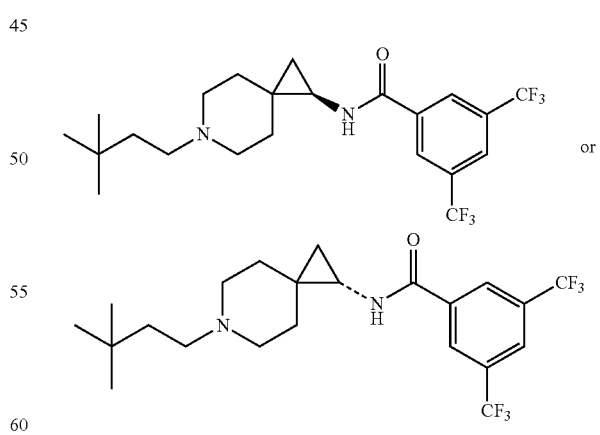

Example 146 can also be prepared as described in Example 128, replacing 3-chloro-5-fluorobenzoic acid in Step G with 3,5-bis (trifluoromethyl)benzoic acid and 2-bromo-N-tert-butylacetamide in Step I with 1-iodo-3,3-dimethylbutane. ¹H NMR (400 MHz, MeOD) δ ppm 8.52 (s, 2H), 8.23 (s, 1H), 3.63 (s, 1H), 3.45 (s, 2H), 3.19 (d, J=5.5

Hz, 3H), 2.92 (d, J=28.2 Hz, 2H), 2.22 (d, J=36.4 Hz, 2H), 1.79-1.61 (m, 1H), 1.47 (dd, J=45.5, 14.6 Hz, 2H), 1.09 (dd, J=7.9, 6.3 Hz, 1H), 1.02 (s, 9H), 0.94 (s, 1H). Mass Spectrum (ESI) m/z=451 (M+1).

Example 147

(R)-2-Chloro-N-(6-(3,3-dimethylbutyl)-6-azaspiro[2.5]octan-1-yl)-5-(trifluoromethyl)benzamide or (S)-2-Chloro-N-(6-(3,3-dimethylbutyl)-6-azaspiro[2.5]octan-1-yl)-5-(trifluoromethyl)benzamide

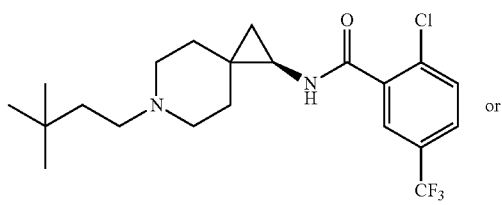

or

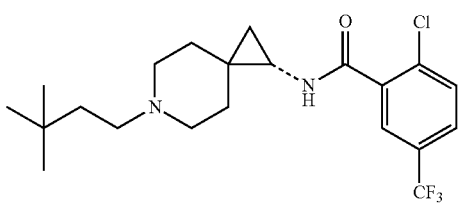

Example 147 can also be prepared as described in Example 128, replacing 3-chloro-5-fluorobenzoic acid in Step G with 2-chloro-5-(trifluoromethyl)benzoic acid and 2-bromo-N-tert-butylacetamide in Step I with 1-iodo-3,3-dimethylbutane. Mass Spectrum (ESI) m/z=417 (M+H).

Examples 148 to 158 can also prepared by procedures similar to the one described in EXAMPLE-1, replacing benzyl 4-oxopiperidine-1-carboxylate in Step A with the appropriate reagent.

| Example | | Reagent used in step A |
|---|---|---|
| 148 | *(structure)* | Benzyl 2-methyl-4-oxopiperidine-1-carboxylate |
| 149 | *(structure)* | Benzyl 2-methyl-4-oxopiperidine-1-carboxylate |
| 150 | *(structure)* | Benzyl 2,6-dimethyl-4-oxopiperidine-1-carboxylate |
| 151 | *(structure)* | Benzyl 2,6-dimethyl-4-oxopiperidine-1-carboxylate |
| 152 | *(structure)* | Benzyl 2,2,6,6-tetramethyl-4-oxopiperidine-1-carboxylate |

-continued

| Example | | Reagent used in step A |
|---|---|---|
| 153 | (structure) | Benzyl 2,2,6,6-tetramethyl-4-oxopiperidine-1-carboxylate |
| 154 | (structure) | Benzyl 3-fluoro-4-oxopiperidine-1-carboxylate |
| 155 | (structure) | Benzyl 3-fluoro-4-oxopiperidine-1-carboxylate |
| 156 | (structure) | Benzyl 3,3-difluoro-4-oxopiperidine-1-carboxylate |
| 157 | (structure) | Benzyl 3,3-difluoro-4-oxopiperidine-1-carboxylate |
| 158 | (structure) | 4-Oxopiperidine-1-carboxylate |

Clinical and Screening Examples

Example A

Preparation of HEK293 Cell Expressing $Ca_{v3.1}$, $Ca_{v3.2}$ or $Ca_{v3.3}$ Channels $Ca_{v3.1}$, $Ca_{v3.2}$ or $Ca_{v3.3}$ channels were expressed in human embryonic kidney (HEK)-293 cells using a tetracycline inducible expression system (Invitrogen). Cells were maintained in 25 cm² tissue culture flasks at 37° C., 5% $CO_2$, and 100% relative humidity in D-MEM/F12 (Dulbecco's Modified Eagle Medium/Nutrient Mixture F-12; Gibco) supplemented with fetal bovine serum (FBS, 10% v/v), sodium pyruvate (0.5 mM, Gibco), penicillin-streptomycin (100 U/mL, 100 µg/mL) and Geneticin® Selective antibiotic (G418; 0.5 mg/mL). Cells were detached from the flask base using a non-enzymatic cell dissociation solution (Cellstripper, Corning), removed and re-seeded on to poly-D-lysine coated glass coverslips in 35 mm dishes. Cells in dishes were further supplemented with G418 at a final concentration of 1 mg/mL and after 24 hours, expression of $Ca_{v3.2}$ was induced with 1 µg/mL tetracycline. The medium for the HEK-293 cells was composed of D-MEM/F-12 (Dulbecco's Modified Eagle Medium/Nutrient Mixture F-12; Gibco, #11330-032) and 15 mM HEPES buffer, with L-glutamine and pyridoxine hydrochloride. It was supplemented with FBS (Fetal Bovine Serum), P/S (Penicillin/Streptomycin) (Gibco, #15140-122), and sodium pyruvate 100 mM (Gibco, #11360-070). At least 24 hours before the assay, expression of the alpha-2-delta-1 and beta2a subunits of the calcium channel were induced with 1 ug/mL tetracycline.

Preparation of DRG Neurons

Mouse dorsal root ganglion (DRG) neurons were prepared from 1-2 months old C57/BC6 mice. All the procedures related to animal handling were in strict accordance with NIH guidelines and IACUC approved protocols. Briefly, the spine was taken out and split into two halves from the middle line after sacrificing the mice by decapitation. Lumbar DRG neurons were collected into a modified Krebs solution (130 mM NaCl, 10 mM HEPES-Na, 5 mM KCl, 1 mM $CaCl_2$, 10 mM glucose, 2 mM $MgCl_2$, pH adjusted to 7.35 with 1 N HCl) in a 1.5 mL tube. For digestion, the DRG neurons were removed into 0.5 mL of Hank's balanced salt solution (HBSS) with 1 mg/mL Collagenase and 0.5 mg/mL Trypsin added. The DRG neurons were minced with fine scissors and incubated at 35° C. for 50 min. After removing the HBSS solution, the DRG neurons were dispersed into modified Krebs solution and triturated with fire polished glass pipettes until no clumps were visible. Finally the cells were dispersed onto poly-1-ornithine-coated cover slips and maintained in a modified Krebs solution with streptomycin sulfate (0.2 mM), Penicillin G Sodium (0.3 mM), and Gentamycin (0.1 mM) at 21° C.

Patch Clamp Recordings

Whole-cell voltage clamp recordings were performed on rat or mouse DRG neurons within 2 days after acutely dissociation or cultured HEK293 cells expressing T-type channels (encoded by $Ca_{v3.1}$, $Ca_{v3.2}$ or $Ca_{v3.3}$ channels). All experiments were performed at room temperature (around 21° C.). Whole-cell currents were recorded using a Multi-Clamp 700B amplifier and analyzed offline with pCLAMP10.4 software (Molecular Devices, LLC, Sunnyvale Calif., USA). To record calcium currents in DRG and HEK293 cells, the external solution was composed (in mM) of 115 choline-Cl, 30 TEA-Cl, 2 $CaCl_2$, 10 glucose and 10 HEPES (pH 7.3-7.4 adjusted with TEA-OH; osmolality verified as 295 mOsm/kg). The internal solution was composed (in mM) of 125 CsCl, 10 HEPES (acid), 10 EGTA (ethylene glycol tetraacetic acid), 1 $CaCl_2$, 1 $MgCl_2$, 4 MgATP and 0.3 MgGTP (pH 7.3-7.4 adjusted with CsOH; osmolality verified as 295 mOsm/kg). Since the sodium ions were absent in the external solution, tetrodoctoxin was not needed. Calcium currents were recorded at a holding potential of −100 mV and then depolarized to −30 mV for 100 ms to activate either $Ca_{v3.1}$, $Ca_{v3.2}$, or $Ca_{v3.3}$ expressed in HEK cells. An interpulse interval of 10 seconds allowed the channel recovery from inactivation, and achieved stable current recordings. To record sodium ($Na^+$) currents in DRG neurons, the external solution used the modified Krebs solution specified above. The internal solution was composed (in mM) of 120 CsF, 10 HEPES, 11 EGTA, 1 $CaCl_2$, 1 $MgCl_2$, 10 TEA-Cl, 4 MgATP and 0.3 MgGTP (pH 7.3-7.4 adjusted with CsOH). Under these recording conditions, no obvious calcium current components were observed in most cells. Occasionally, some L-type calcium channel current components were observed in DRG neurons but decayed quickly. To record potassium currents in DRG neurons, the external solution used the modified Kreb's solution specified above. The internal solution was composed (in mM) of 65 KCl, 80 KF, 5 KOH, 10 EGTA, 2 MgATP (pH 7.3-7.4 adjusted with KOH). Recording electrodes were fabricated using a P-87 puller (Sutter Instrument Co., Novato, Calif., USA). The tip of resistance was 3-4 MΩ in bath and the series resistance was less than 10 MΩ after whole cell configuration. All reagents were purchased from Sigma unless specified otherwise. Test compounds were usually applied via a rapid solution exchange system with 8 fine polyplastic tubings (100 µm, OD) glued in a holder in parallel and located closely to the recorded cells. The current responses were normalized to the control, percent inhibition was calculated and sigmoidal dose-response curves were generated using XLFit (IDBS, Surrey, UK) or Prism (Graph-Pad Software, La Jolla, Calif., US) to calculate $IC_{50}$ values and Hill slopes using the following equation Y=Bottom+(Top−Bottom)/(1+10^((Log EC50−X)−HillSlope)). Representative results for T-type $Ca_{v3.2}$ channel inhibition are provided in Table 1 below. $IC_{50}$ values are given in micromolar units or percentage (%) of inhibition tested at 1 µM.

TABLE 1

Primary screening of EXAMPLE-1 to -147 against the $Ca_{v3.2}$ channel at 1 or 3 (µM). For compounds tested at at least 4 concentrations only $IC_{50}$ (µM) values are given.

| Example | % inhibition at 1 µM* | $IC_{50}$ (µM) |
|---|---|---|
| 1 | 15.3 at 3 µM | |
| 2 | 55.3 at 3 µM | |
| 3 | 47.7 at 3 µM | |
| 4 | 24.7 at 3 µM | |
| 5 | 44 at 3 µM | |
| 6 | 29.1 at 3 µM | |
| 7 | | 0.12 |
| 8 | | 0.12 |
| 9 | | 0.08 |
| 10 | | 0.8 |
| 11 | | 0.42 |
| 12 | | 0.05 |
| 13 | | 0.03 |
| 14 | | 0.03 |
| 15 | | 0.08 |
| 16 | | 0.12 |
| 17 | | 0.24 |
| 18 | | 0.25 |
| 19 | | 0.03 |
| 20 | 37 | |
| 21 | 67 | |
| 22 | 50 | |
| 23 | 69 | |
| 24 | | 0.02 |
| 25 | | 0.06 |
| 26 | 64 | |
| 27 | | 0.55 |
| 28 | | 0.07 |
| 29 | 69 | |
| 30 | | 0.09 |
| 31 | | 0.08 |
| 32 | | 0.29 |
| 33 | 63 | |
| 34 | | 1.4 |
| 37 | | 0.05 |
| 38 | | 0.04 |
| 39 | | 0.06 |
| 40 | | 0.16 |
| 41 | | 0.16 |
| 43 | | 0.12 |
| 44 | | 0.10 |
| 45 | | 0.04 |
| 46 | | 0.15 |
| 47 | | 0.16 |

TABLE 1-continued

Primary screening of EXAMPLE-1 to -147 against the $Ca_{v3.2}$ channel at 1 or 3 (μM). For compounds tested at at least 4 concentrations only $IC_{50}$ (μM) values are given.

| Example | % inhibition at 1 μM* | $IC_{50}$ (μM) |
|---|---|---|
| 48 | | 0.26 |
| 49 | | 0.16 |
| 50 | | 0.08 |
| 51 | 47 | |
| 52 | 29 | |
| 53 | 25 | |
| 54 | | 0.23 |
| 55 | | 0.07 |
| 56 | | 0.19 |
| 57 | | 0.06 |
| 58 | | 0.22 |
| 59 | | 0.07 |
| 62 | 68 | |
| 69 | | 0.28 |
| 71 | | 0.20 |
| 87 | | 0.69 |
| 88 | | 0.09 |
| 89 | | 0.09 |
| 90 | | 0.13 |
| 91 | | 0.06 |
| 92 | 35 | |
| 93 | | 0.10 |
| 94 | | 0.13 |
| 95 | 67 | |
| 96 | 40 | |
| 97 | 33 | |
| 99 | 75 | |
| 100 | 26 | |
| 101 | 44 | |
| 102 | 47 | |
| 107 | 21 | |
| 108 | 53 | |
| 110 | 44 | |
| 111 | 30 | 1.5 |
| 112 | 24 | |
| 113 | | 0.64 |
| 114 | | 0.23 |
| 115 | | 0.93 |
| 116 | 10 | |
| 117 | 24 | |
| 118 | 20 | |
| 119(17) | 5 at 3 uM | |
| 120 | 9.2 | |
| 121 | 75 | |
| 122 | 14.9 | |
| 123 | | 5.1 |
| 124 | 7.1 | |
| 125 | 20 | |
| 126 | 5.9 | |
| 127 | 8.5 | |
| 128 | | 0.11 |
| 129 | | 0.87 |
| 130 | | 0.18 |
| 131 | | 0.62 |
| 132 | | 0.14 |
| 133 | | 0.20 |
| 134 | | 0.12 |
| 135 | | 0.21 |
| 136 | | 0.26 |
| 137 | | 0.07 |
| 138 | | 0.18 |
| 139 | | 0.09 |
| 140 | | 0.52 |
| 141 | | 0.18 |
| 142 | | 0.09 |
| 143 | | 0.29 |
| 144 | | 0.08 |
| 145 | | 0.14 |
| 146 | | 0.07 |
| 147 | | 0.13 |

*unless indicated otherwise

Selectivity among the three subtypes of the $Ca_{v3}$ T-type channel, and off-target effects on other key ion channels of the representative example compounds are presented in Table 2. Sodium and potassium channels in the rodent DRG neurons were recorded and tested as described above. The human ether-a-go-go-related gene (hERG) encodes the rapidly activating potassium channel ($I_{Kr}$) contributing to the repolarization of the cardiac action potential. The blockade of hERG can lead to a QT prolongation in the electrocardiogram known as long QT syndrome (Sanguinetti, et al., 1995). Therefore the representative example compounds in Table 2 were tested against the hERG channel.

The hERG-expressing CHO cell line grows rapidly in EX-CELL 302 Media (Sigma), supplemented with 10% fetal bovine serum, 4 mM L-Glutamine, 1% Penicillin-Streptomycin, and 250 μg/mL G-418 (Geneticin) as the selection agent. Whole-cell patch clamp electrophysiology is employed to test compounds and a positive control compound. Extracellular Ringer's solution contains (in mM): NaCl (130), KCl (5), $CaCl_2$ (1), Glucose (10), HEPES-Na (10) (pH 7.4 adjusted with HCl). Internal pipette solution contains (in mM): KF (120), $CaCl_2$ (1), $MgCl_2$ (1), KCl (10), EGTA (11), HEPES (10), KOH (11) (pH 7.2 adjusted with KOH). The hERG potassium currents are recorded under a holding potential of −80 mV and then depolarized to 40 mV for 2.5 seconds to activate the hERG channel. The peak tail currents are induced by a repolarizing pulse to −50 mV for 4 seconds. A 250 millisecond prepulse to −50 mV is applied for leak subtraction. This voltage-clamp pulse protocol is performed continuously during the experiment every 20 seconds allowing recovery from inactivation. For IC50 determination, each concentration is applied for 2 mins to reach a steady-state inhibitory level prior to the next higher concentrations tested. Each concentration is tested at 2-3 times (n=2-3).

Cardiac sodium channels play a critical role in heart contraction. Inhibition of these sodium channels could potentially cause severe unwanted side effects. Therefore the representative example compounds in Table 2 were tested in cardiac sodium channels. Cardiomyocytes derived from human induced pluripotent stem cells (iPSC-CM) were obtained from Axol Bioscience Ltd (Cambridge, UK). Cells were thawed and grown on matrigel coated glass coverslips in Cardiomyocyte Maintenance Medium (Axol Bioscience). For electrophysiological recordings of sodium currents, the external solution was composed (in mM) of 35NaCl, 72.5 ChCl, 5 KCl, 30 TEA-Cl, 1 $CaCl_2$, 10 glucose and 10 HEPES (pH 7.2 adjusted with NaOH). The internal solution was composed (in mM) of 120 KF, 10 HEPES, 11 EGTA, 1 $CaCl_2$, 1 $MgCl_2$, 10 TEA-Cl (pH 7.2 adjusted with KOH). Sodium currents were recorded at a holding potential of −100 mV and depolarized to −20 mV. Cells were incubated with example compounds until currents reached a steady-state level. To determine $IC_{50}$ values, example compounds were applied gradually from low to high concentrations. The current responses were normalized to the control, percent inhibition was calculated and a sigmoidal dose response curve was plotted to determine $IC_{50}$ values as described above.

The structure of ML218 is

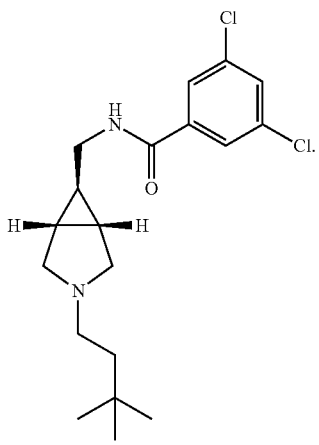 [SMILES: CC(C)(C)CCN1C[C@@H]2[C@@H](CNC(=O)c3cc(Cl)cc(Cl)c3)[C@@H]2C1]

The structure of Z944 is

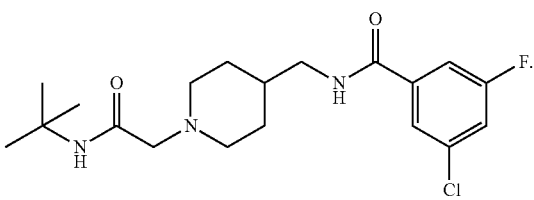 [SMILES: CC(C)(C)NC(=O)CN1CCC(CNC(=O)c2cc(F)cc(Cl)c2)CC1]

The results herein demonstrate the superiority of the compounds of the invention over Z944 and ML218.

rodents were created and effects of the representative EXAMPLE compounds were investigated on these pain models. T-channel specific inhibitors are not yet available for clinical treatment of neuropathic pain. The spared nerve injury (SNI) model, one of the reliable neuropathic pain models in mice and rats (Decosterd and Woolf, 2000), was used to assess the effects of the representative compounds.

Of the three branches of the sciatic nerve, the tibial and common peroneal nerves of the mice (C57BL/6, male, 25-30 g, Harlan) were cut and ligated, leaving the sural nerve intact. Pre-surgery baselines (100%) of the thermal and mechanical pain thresholds of the ipsilateral hind paws were measured using the Hargreaves thermal stimulator (Hargreaves et al., 1988) and von Frey hair monofilaments (up-down method, Chaplan et al., 1994), respectively. Mice underwent the SNI surgery on their left hind leg. Two weeks post-surgery, the thermal thresholds of each mouse were reassessed. The SNI mice displayed approximately 70% reduction in thermal pain thresholds and approximately 90% reduction in mechanical pain, confirming the presence of hyperalgesia and mechanical allodynia in the SNI mice.

Figure 1B:
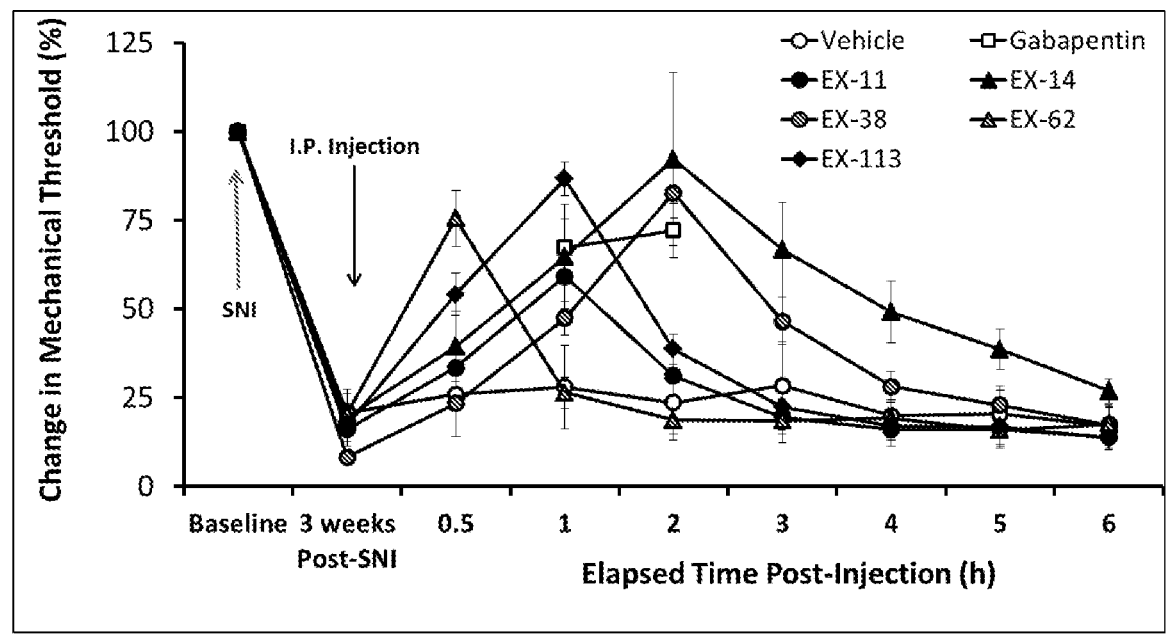
FIG. 1B. Mechanical pain threshold assessment (using von Frey monofilament test) of the same cohort of SNI mice's left hindpaws. Application of EXAMPLE-11, -14, -38, -62, or 113 (or gabapentin) reduced allodynia compared to the SNI-vehicle control group.
Figure 2A:
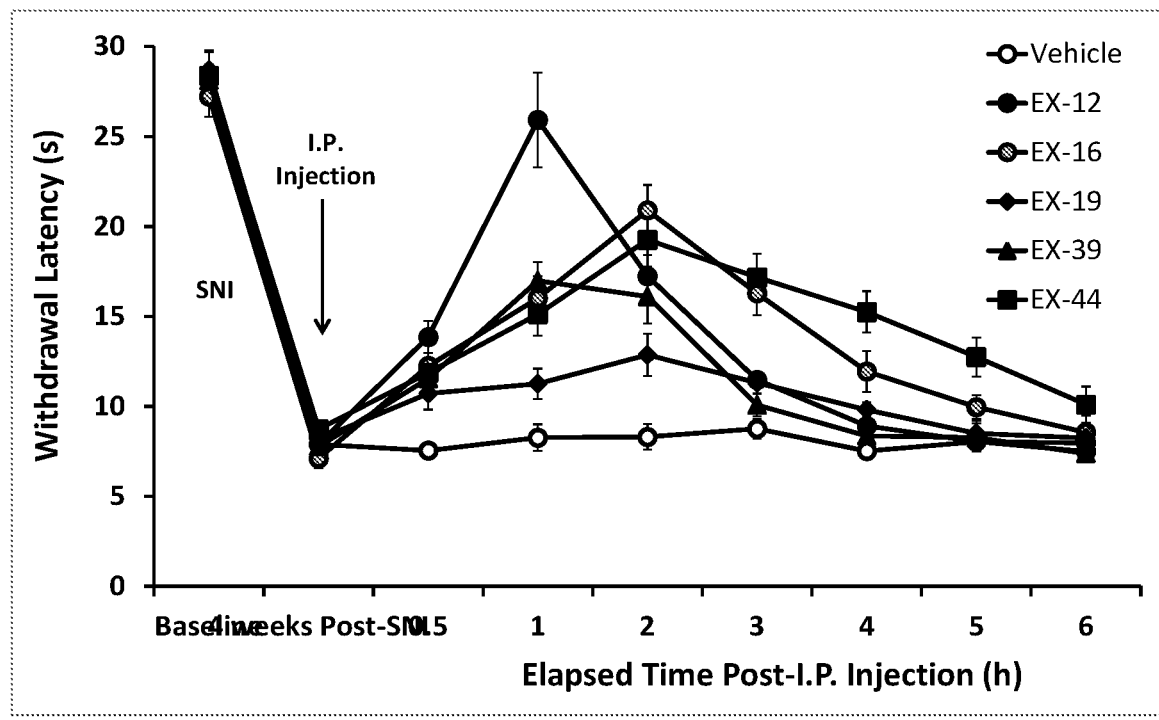
FIG. 2A. Other examples of compounds that alleviate neuropathic pain induced by SNI in another cohort of mice. The withdrawal latencies of the mice's left hindpaws (injured site) in response to thermal stimulation (Hargreaves test). Each SNI mouse received either EXAMPLE-12, -16, -19, -39, or -44 (each 30 mg/kg, 0.2 mL I.P.), or vehicle (0.2 mL I.P. 2% DMSO in 0.5% HPC). Application of EXAMPLE-12, -16, -19, -39, or -44 reduced hyperalgesia, while the SNI-vehicle group remained in a hyperalgesic state. 40 seconds were cutoff in order to prevent tissue damage (n=8 per treatment group).
Figure 2B:
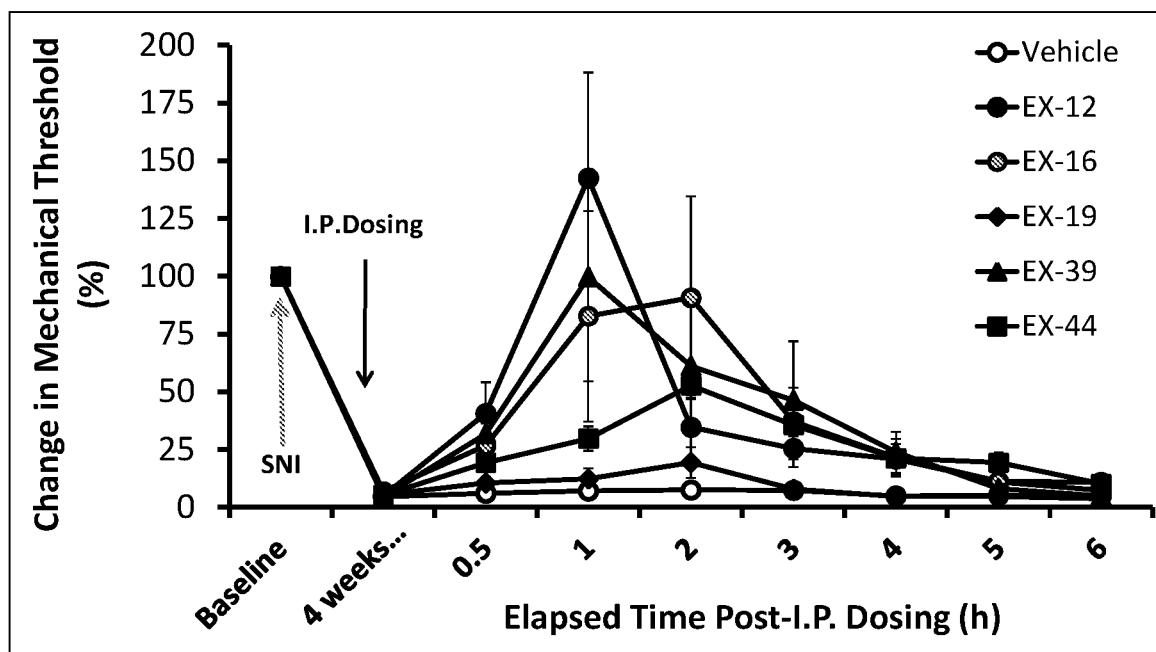
FIG. 2B. Mechanical pain threshold assessment (von Frey monofilament test) of the same cohort of SNI mice's left hindpaws. Application of EXAMPLE-12, -16, -19, -39, or -44 reduced allodynia compared to the SNI-vehicle control group.

EXAMPLE-11, 14, 38, 62, or 113 (FIGS. 1A and B) and EXAMPLE-12, 16, 19, 39, or 44 (FIGS. 2A and B) were administered at 30 mg/kg (0.2 mL I.P.) in a vehicle (pure DMSO to dissolve the powder first and then add 0.5% Hydroxyl Propyl Cellulose, HPC, to contain 2% DMSO in injection solution). All drug solutions used the same vehicle, unless specified otherwise. These tested compounds produced analgesic effects on both thermal and mechanical pain thresholds (FIGS. 1 and 2).

In additional examples shown here, the analgesic effects were further evaluated in another rat species. Baseline thermal and mechanical thresholds of male rats (Sprague-Dawley rats, 275 g-325 g, Harlan) were taken prior to surgery; baseline thresholds were measured on the rats' left hindpaws. Thirty-two rats underwent the SNI surgery on their left hind leg; 8 rats underwent surgery without injury of the nerves as a sham group. Two weeks post-surgery, the thermal thresholds of each rat were reassessed. The SNI rats

TABLE 2

Potency on three subtypes of $Ca_{v}3$ T-type Ca channels and selectivity over other key ion channels of example compounds

| Compound | $Ca_{v3.1}$ $IC_{50}$ (μM) | $Ca_{v3.2}$ $IC_{50}$ (μM) | $Ca_{v3.3}$ $IC_{50}$ (μM) | $Ca_{v2.2}$ $IC_{50}$ (μM) | DRG ion channels $Na^+$ $IC_{50}$ (μM) | $K^+$ $IC_{50}$ (μM) | hERG $IC_{50}$ (μM) or (%) inh. at 1 μM | Cardiac $Na^+$ $IC_{50}$ (μM) or (%) inh. at 3 μM |
|---|---|---|---|---|---|---|---|---|
| ML218 | 0.14 | 0.31 | 0.27 | 20.7 | 55.6 | 79.7 | 2.1 | 39.8 |
| Z944 | 0.11 | 0.19 | 0.57 | >30 | >30 | >30 | 9.5 | 21.4 |
| EX-128 | 0.06 | 0.09 | 0.75 | >10 | >100 | >100 | 7 | 83.5 |
| EX-130 | 0.11 | 0.18 | 0.28 | >30 | >100 | >100 | 8 | 31.4 |
| EX-132 | 0.12 | 0.14 | 7.61 | 3.1 | 14.3 | >100 | (9%) | 51.6 |
| EX-57 | 0.13 | 0.06 | 0.098 | >30 | 37.2 | >100 | (22%) | 50.9 |
| EX-28 | 0.28 | 0.07 | 0.21 | 9.4 | 23.4 | ~100 | 3.6 | 37.2 |
| EX-141 | 0.34 | 0.18 | 0.23 | 5.1 | >30 | >30 | 17.4 | (28%) |
| EX-146 | 0.12 | 0.07 | 0.11 | 2.5 | 8.7 | >100 | 1.2 | 27.8 |
| EX-144 | 0.04 | 0.08 | 0.25 | 12.3 | 34.4 | >30 | 4.6 | 19.2 |
| EX-145 | 0.07 | 0.14 | 0.31 | 15.6 | >30 | >30 | >30 | (0%) |
| EX-147 | 2.41 | 0.13 | 1.58 | 5.6 | 14.3 | >100 | 1.8 | 43.0 |
| EX-17 | 0.29 | 0.24 | 0.29 | >30 | >100 | >100 | 10.7 | NT |
| EX-129 | 1.04 | 0.87 | 1.63 | >30 | >100 | >100 | 16 | NT |

$Ca_{v3.1}$, $Ca_{v3.2}$, and $Ca_{v3.3}$ are human cDNA encoding three subtypes of the T-type Ca channel; $Ca_{v2.2}$ is human cDNA encoding the N-type Ca channel; Cardiac $Na^+$ channels were recorded from human iPSC. Abbreviation: Use-dep = Use-dependent; inh. = inhibition; NT = not tested.

Example B

In Vivo Analgesic Effects in Representative Pain Models

Figure 3A:
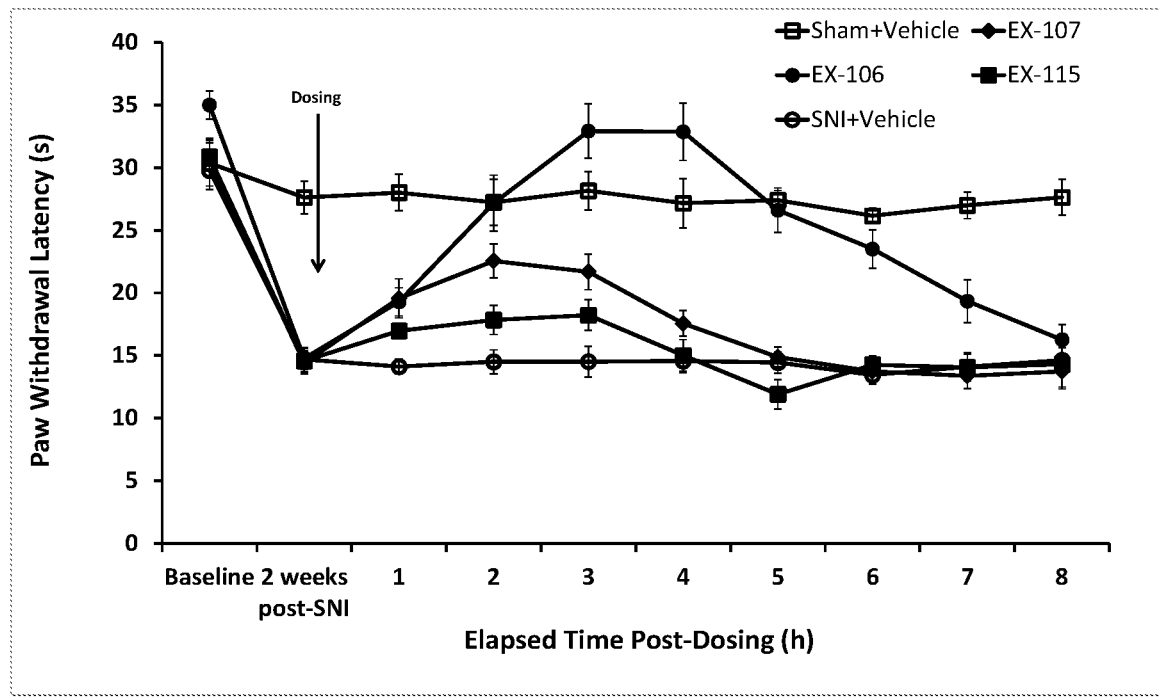
FIG. 3A. Spared Nerve Injury (SNI) rats' left hindpaw withdrawal latencies in response to thermal stimulation (Hargreaves test). Each SNI rat received either EXAMPLE-106, 107, or 115, (each 30 mg/kg, 1 mL I.P.), or vehicle (2% DMSO in 0.5% HPC). Sham rats also received vehicle I.P. injections. Application of EXAMPLE-106, -107, or -115 reduced hyperalgesia, while the SNI-vehicle group remained in a hyperalgesic state. 40 seconds were cutoff in order to prevent tissue damage. The sham-vehicle serves as a positive control (n=8 per treatment group).
Figure 3B:
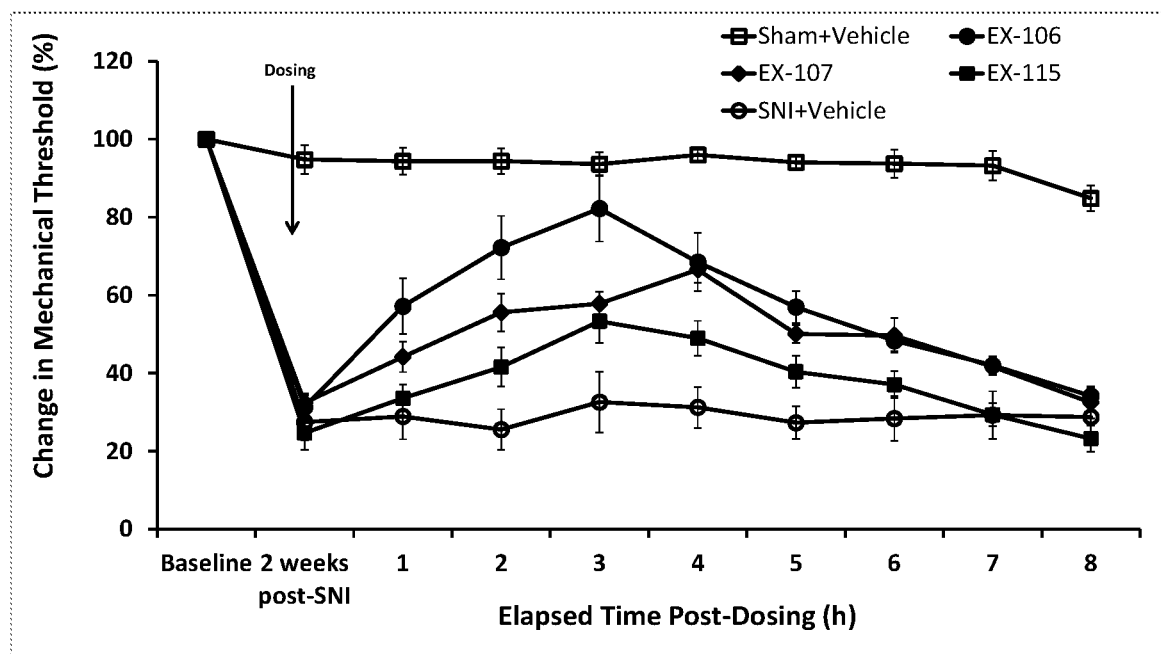
FIG. 3B. Mechanical pain threshold assessment (von Frey monofilament test) of SNI rats' left hindpaws. Each SNI rat received either EXAMPLE-106, -107, and -115 (each 30 mg/kg, 1 mL I.P.), or vehicle (1 mL I.P. 2% DMSO in 0.5% HPC). Sham rats also received vehicle I.P. injections. Application of EXAMPLE-106, -107 or -115 reduced allodynia compared to the SNI-vehicle group. The sham-vehicle serves as a positive control. Thermal and mechanical pain responses were measured once every hour for 8 consecutive hours after I.P. treatment (n=8 rats per treatment group).

To evaluate the therapeutic effects and safety of highly active compounds, a variety of chronic pain models in displayed approximately 55% reduction in thermal pain thresholds and approximately 75-80% reduction in mechanical pain thresholds, confirming the presence of hyperalgesia and mechanical allodynia in the SNI rats. Each rat received either EXAMPLE-106, -107, -115 (each 30 mg/kg, 1 mL I.P.), or vehicle (2% DMSO in 0.5% HPC). Thermal and mechanical thresholds were measured at 1, 2, 3, 4, 5, 6, 7, and 8 hours post-treatment/dosing. The tested compounds elevated both thermal and mechanical thresholds compared to vehicle. The drug actions started around 1 hour post-injection and peaked between 2 and 3 hours, and the drug effects gradually declined to pre-treatment levels over 6-7 hours (FIGS. 3A and B).

Figure 4:
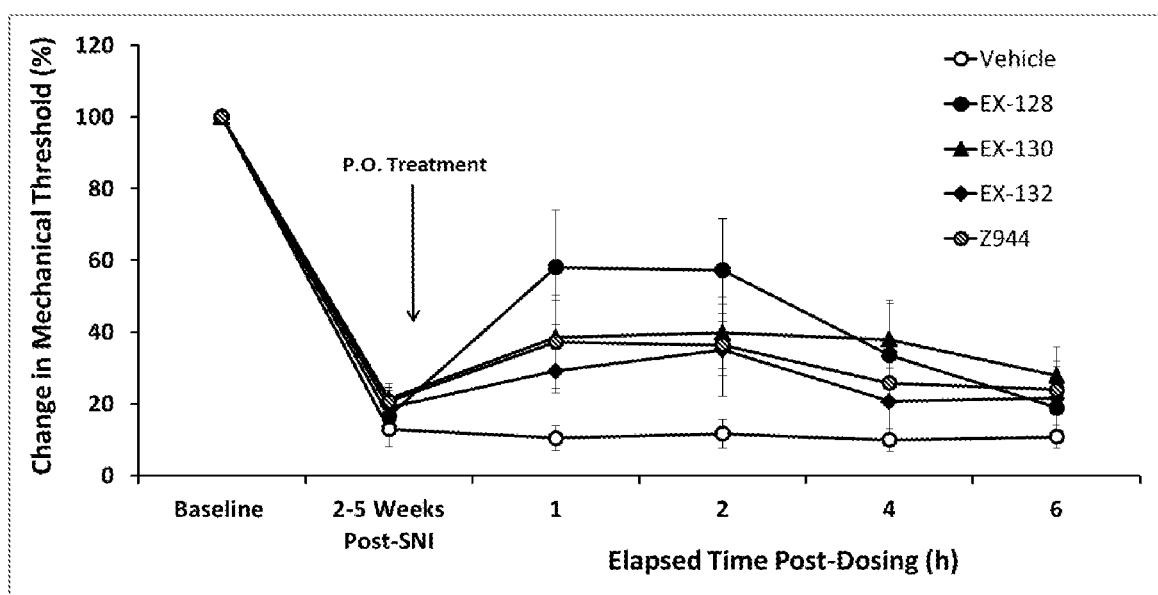
FIG. 4. Mechanical pain threshold assessment (von Frey monofilament test) of left hindpaws in another cohort of SNI rats. Each SNI rat received either EXAMPLE-128, -130, -132, or Z944 (as a reference compound, each 10 mg/kg, 2 mL oral gavage, P.O.). Application of EXAMPLE-128, -130, -132, or Z944 reduced allodynia compared to the SNI-vehicle group. Mechanical pain responses were measured at pre-dosing, 1, 2, 4, and 6 hours post-treatment using von Frey monofilament test (n=8 rats per group).

In another cohort of SNI rats ((n=8 per group)), mechanical thresholds were measured at pre-dosing, 1, 2, 4, and 6 hours post-treatment using von Frey monofilament test. The tested compounds EXAMPLE-128, -130, -132 and Z944 (each 10 mg/kg, 3 mL oral gavage, P.O.) elevated mechanical thresholds compared to vehicle (2% DMSO in 0.5% HPC; 3 mL P.O.) up to approximately 4 hours (FIG. 4).

Figure 5A:
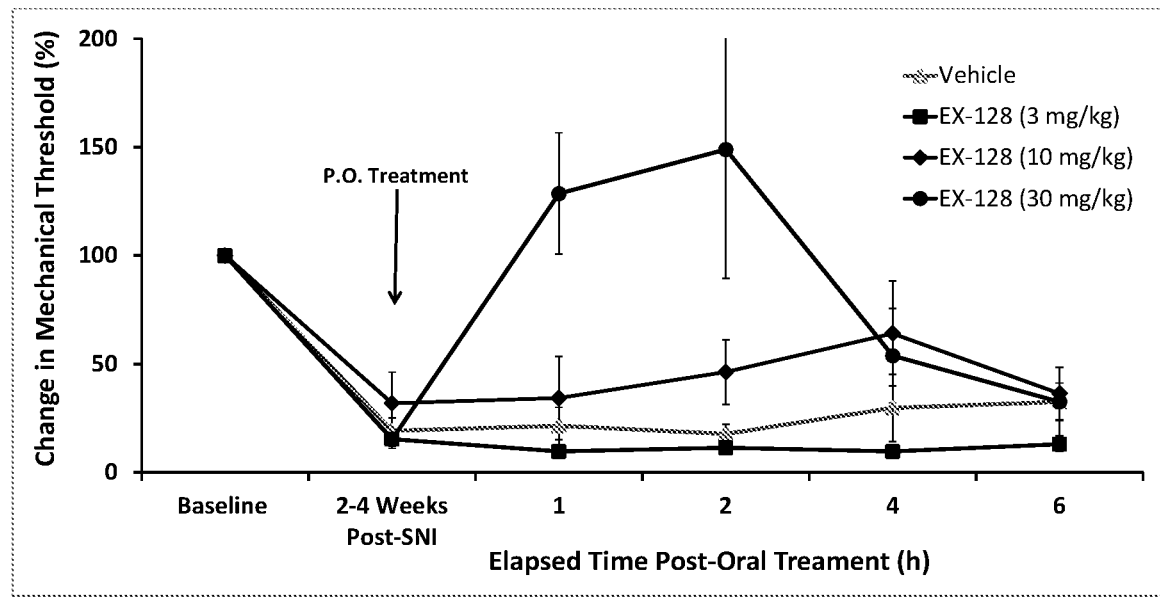
FIG. 5A. Mechanical pain threshold assessment (von Frey monofilament test) of spinal nerve ligation (SNL) rats' left hindpaws. Each SNL rat received either EXAMPLE-128, at 3, 10 or 30 mg/kg (2 mL oral gavage, P.O.), or vehicle (2 mL 2% DMSO in 0.5% HPC, P.O.). Application of EXAMPLE-128 reduced allodynia compared to the SNI-vehicle group in a dose-related manner. Mechanical pain responses were measured at 1, 2, 4 and 6 hours after treatment (n=8 rats per treatment group).
Figure 5B:
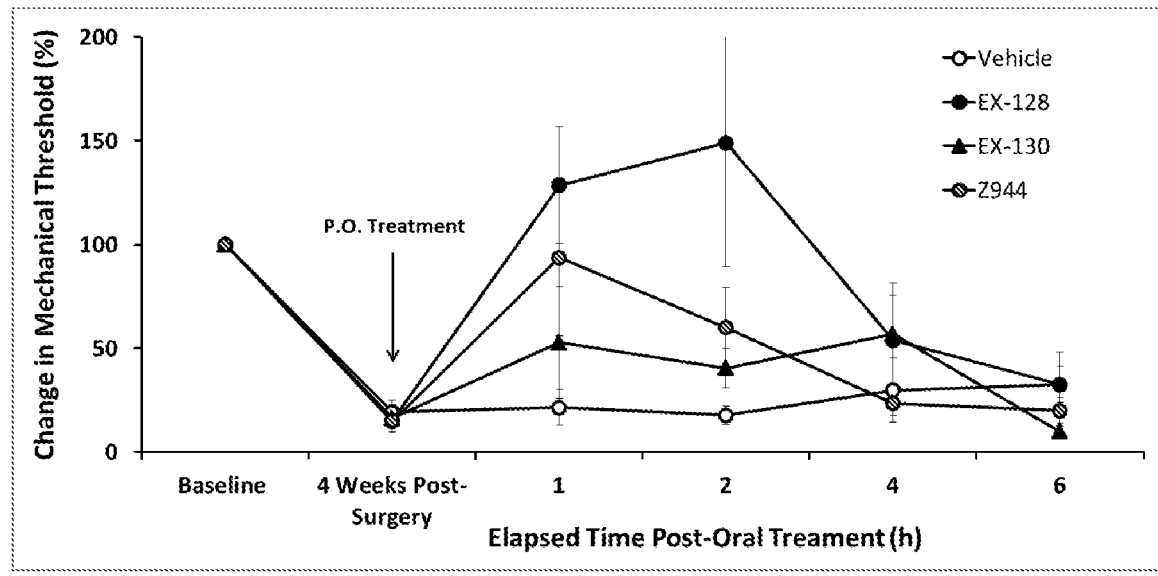
FIG. 5B. Mechanical pain threshold assessment (von Frey monofilament test) of SNL rats' left hindpaws. In the same cohort of animals, each SNL rat received either EXAMPLE-128, -130, Z944 (as a reference compound, each at 30 mg/kg, 2 mL oral gavage, P.O.), or vehicle (2 mL 2% DMSO in 0.5% HPC, P.O.). The degree of analgesia against allodynia in the order of EXAMPLE-128>Z944>EXAMPLE-130 compared to the SNI-vehicle group. Mechanical pain responses were measured at 1, 2, 4 and 6 hours after treatment (n=8 rats per treatment group).

The spinal nerve ligation (SNL) in rats is another commonly used neuropathic pain model (Kim & Chung, 1992). The analgesic effect of the selected EXAMPLE-128 was tested in this model. Baseline mechanical thresholds on the rats' left hindpaws of male rats (Sprague-Dawley rats, 300 g-350 g, Harlan) were taken using von Frey hair monofilaments prior to surgery. Ligation of the L5 peripheral nerve was made on the left side under anesthesia. Total 32 rats underwent surgery (n=8 rats per treatment group). Ten days post-surgery, approximately 75-85(%) reduction in mechanical pain was observed, confirming the presence of mechanical allodynia in the SNL rats. Each rat received either EXAMPLE-128 (at 3, 10 and 30 mg/kg, each dose in 3 mL, P.O.), or vehicle (2% DMSO in 0.5% HPC, 3 mL, P.O.). Mechanical thresholds were measured at 1, 2, 4, and 6 hours post-treatment/dosing. The EXAMPLE-128 elevated mechanical thresholds in a dose-related manner. The drug actions started around 1 hour post-injection and peaked between 1 and 2 hours, and the drug effects gradually declined to pre-treatment levels in 6 hours (FIG. 5A). After the drug had been eliminated, and the thresholds had returned to initial mechanical allodynia, a comparative test of EXAMPLE-128 and -130 vs Z944 (each at 30 mg/kg, P.O.) was conducted in the same cohort of SNL rats. The analgesic efficacy is in the order of EXAMPLE-128>Z944>EXAMPLE-130 (FIG. 5B).

Figure 6A:
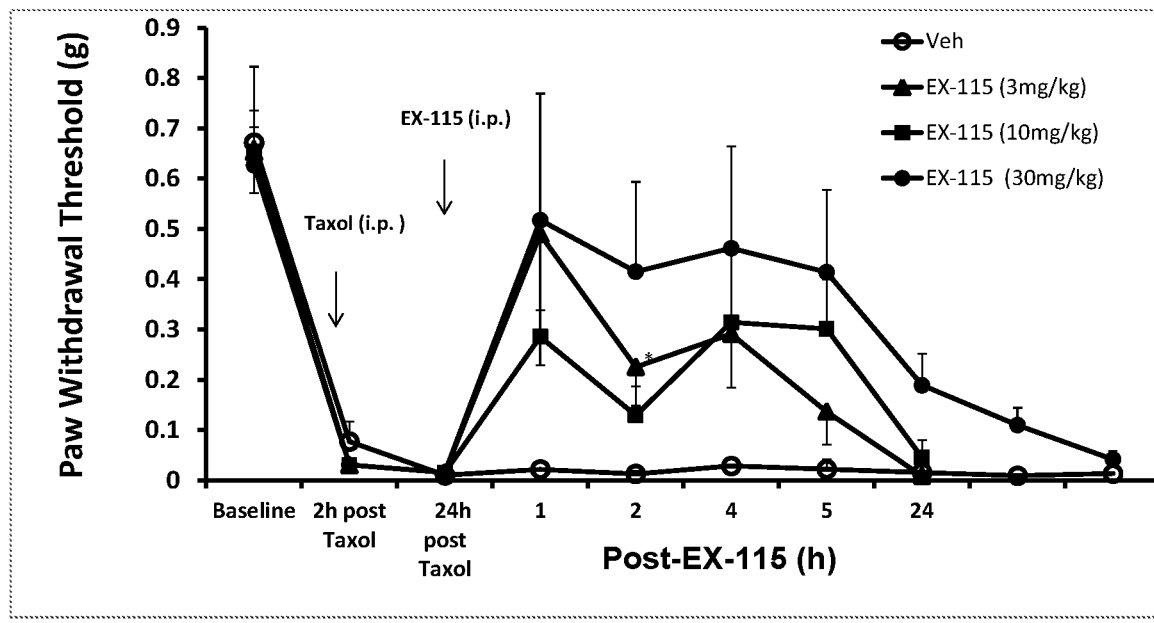
FIG. 6A. Effects of EXAMPLE-115 on taxol (4 mg/kg, I.P.)-induced neuropathic pain model in mice. Mechanical pain thresholds of left hindpaws were assessed using von Frey monofilament test. Each mouse received either EXAMPLE-115 (3, 10 or 30 mg/kg, I.P.) or vehicle (2% DMSO in 0.5% HPC, I.P.; n=8 per group). Injection of taxol lowered mechanical pain thresholds. Application of EXAMPLE-115 reversed the taxol-induced neuropathic pain in a dose-dependent manner.
Figure 6B:
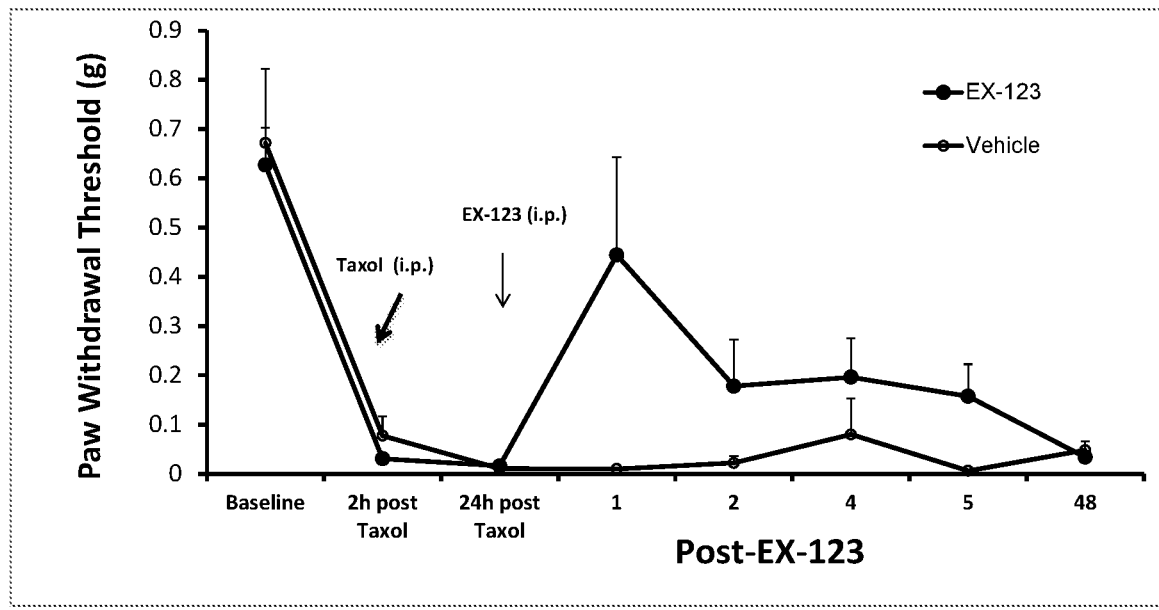
FIG. 6B. Effects of EXAMPLE-123 on taxol (4 mg/kg, I.P.)-induced neuropathic pain model in a separate cohort of mice. Mechanical pain thresholds of left hindpaws were assessed using von Frey monofilament test. Each mouse received either EXAMPLE-123 (30 mg/kg, I.P., n=8) or vehicle (2% DMSO in 0.5% HPC, I.P.). Application of EXAMPLE-123 reduced the taxol-induced neuropathic pain lasting for at least 5 hours in comparison with the control group (n=8 for each group).

Chemotherapy-induced painful neuropathy is a common side effect associated with chronic treatment with Taxol (paclitaxel) or other anticancer drugs based on cytotoxicity. Taxol or paclitaxel is one of the most popular drugs used for the treatment of various cancers (Chaudhry et al., 1994). The chemotherapy-induced peripheral neuropathy manifests as chronic hyperalgesia and other sensory abnormalities. Taxol (Sigma, 4.0 mg/kg, I.P.) was dissolved in saline containing 5% DMSO (vehicle) and injected to mice (freshly prepared before injection). EXAMPLE-115 (3, 10 and 30 mg/kg, I.P.) produced significant effects on Taxol-induced pain compared to vehicle in a dose-dependent manner (FIG. 6A). Another EXAMPLE-123 also caused significant effects on Taxol-induced pain compared to vehicle, indicating the representative EXAMPLE compounds can reduce allodynia (FIG. 6B).

Figure 7:
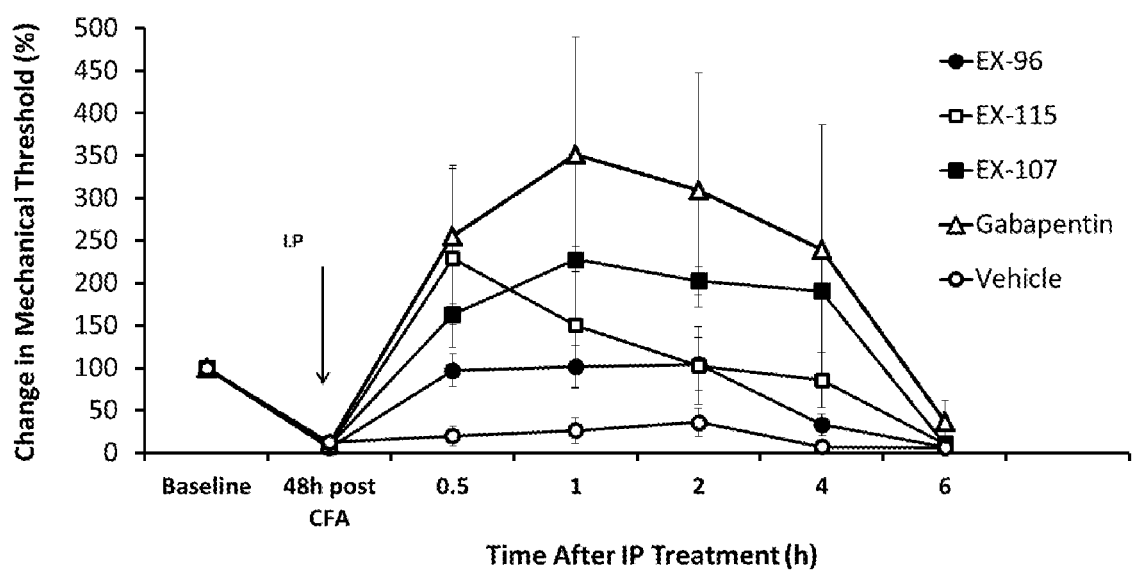
FIG. 7. Effects of EXAMPLE-96, 107 or 115 (each 30 mg/kg, I.P.) or gabapentin (as a benchmark, 100 mg/kg, I.P) on Complete Freund's Adjuvant (CFA)-induced inflammation in male, mice (C57BL/6, ~2 months old; n=8 mice per group). Mechanical pain threshold assessment of CFA mice's left hindpaws were measured using von Frey monofilament test at 0.5, 1, 2, 4, and 6 hours after treatment.

Because knockout or antisense knockdown of the Cav3.2 isoform produces analgesic effects in neuropathic pain as well as in inflammatory pain in mice (Choi et al., 2007), we used the Complete Freund adjuvant (CFA)-inflammatory pain in mice to investigate the drug effects. EXAMPLE-96, -115, and -107 (each at 30 mg/kg, I.P.) and a reference gabapentin (100 mg/kg, I.P.) was individually administered to mice that had CFA-induced inflammation on their left hindpaws. All drug treatment groups showed an analgesic effect in mechanical pain compared to the vehicle-treated group (FIG. 7).

Figure 8:
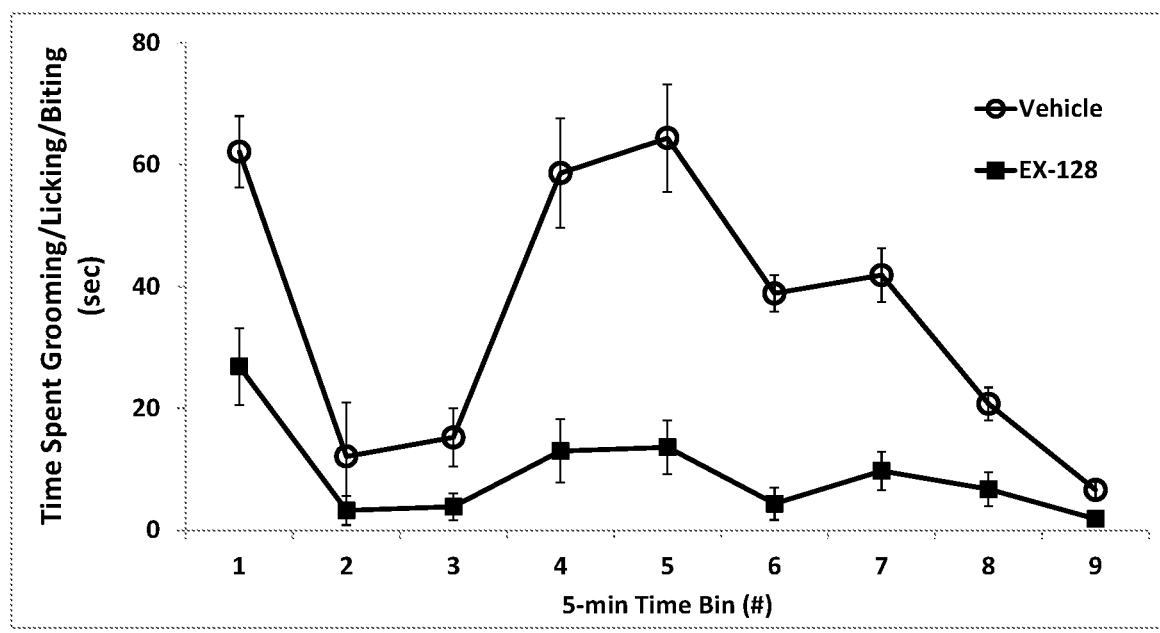
FIG. 8. Effects of EXAMPLE-128 (30 mg/kg, I.P.) or vehicle on formalin-induced inflammation in male mice (C57BL/6, ~3 months old; n=8 mice per group). The test compound was I.P. administered 30 min prior to local injection of 10% formalin into the left hindpaw (10 μl). Time spent in grooming, licking or biting the injury paw was manually scored immediately following formalin injection in 5-min time bin for 45 min.

Formalin-induced biphasic response, nociception followed by inflammatory pain in a mouse hindpaw, is an acute pain and chemical-induced inflammatory pain model. The EXAMPLE-128 was tested in this model. Mice (C57BL/6, male, ~2 months old; n=8 mice per treatment group) received a 10 µl intraplantar injection of 10% formalin in saline into the left hindpaw. Pain response scoring includes counts per episode of time of reactions to the pain stimulus as indicated by licks, twitches, raising or shaking of the injected paw. FIG. 8 shows that the EXAMPLE-128 (30 mg/kg, I.P.) produced inhibition of both phases, particularly on the second phase inflammatory pain compared to vehicle (2% DMSO in 0.5% HPC, I.P.).

Figure 9:
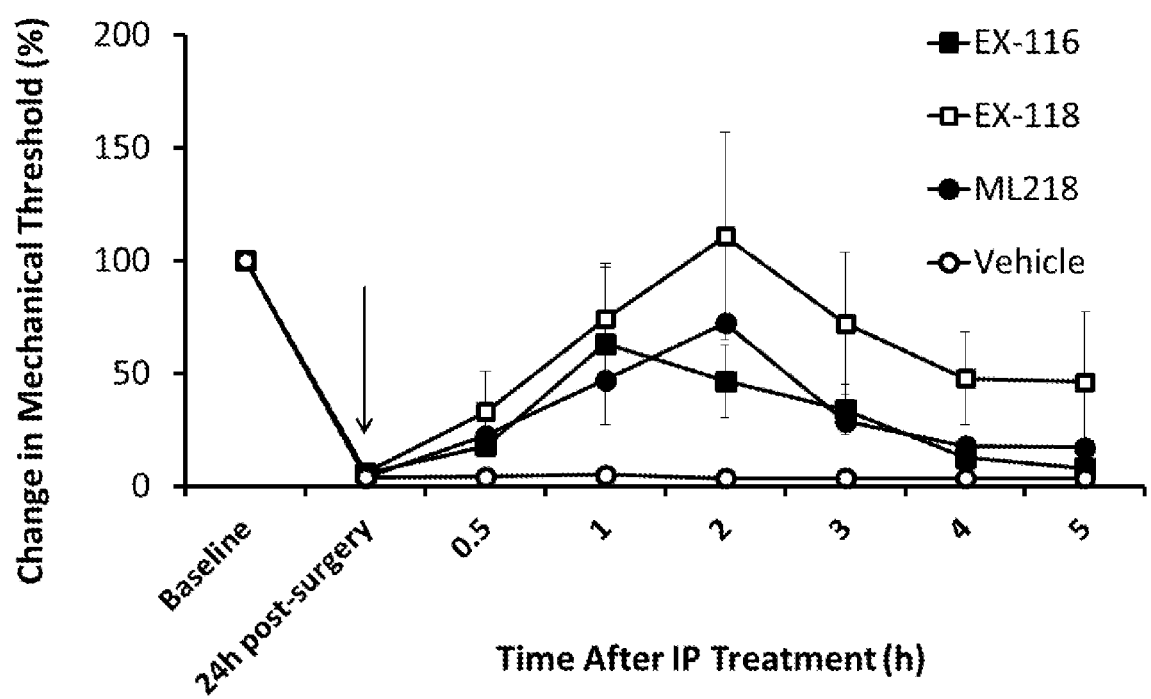
FIG. 9. Effects of EXAMPLE-116, -118 or ML218 (a reference compound) on incision-induced acute pain in mice (C57BL/6, male, ~2 months old; n=8 mice per treatment group). Mechanical pain threshold assessment (von Frey monofilament test) of the mice's incision left hindpaws. Each mouse received either EXAMPLE-116, -118, or ML218 (as a reference compound, each 30 mg/kg, I.P.) or vehicle (2% DMSO in 0.5% HPC, I.P.). Mechanical pain responses were measured at 0.5, 1, 2, 4, and 5 hours after treatment.

To further confirm the $Ca_{v3}$ modulator effects on acute pain and neurogenic inflammatory pain, an incision-pain mode in mice was used. Postoperative pain model induced by a deep incision in the hindpaw produces robust mechanical allodynia (Pogatzki et al., 2003). Mechanical pain thresholds were assessed using von Frey monofilament test of the incised left hindpaws. Each mouse received either EXAMPLE-116, -118, ML218 (as a reference compound, each 30 mg/kg, I.P.) or vehicle (2% DMSO in 0.5% HPC, I.P., n=8 mice per treatment group). Mechanical pain responses were measured at 0.5, 1, 2, 4, and 5 hours after treatment. FIG. 9 shows that EXAMPLE-116, -118 and ML218 inhibited incision-induced inflammatory pain compared to vehicle treatment.

Figure 10:
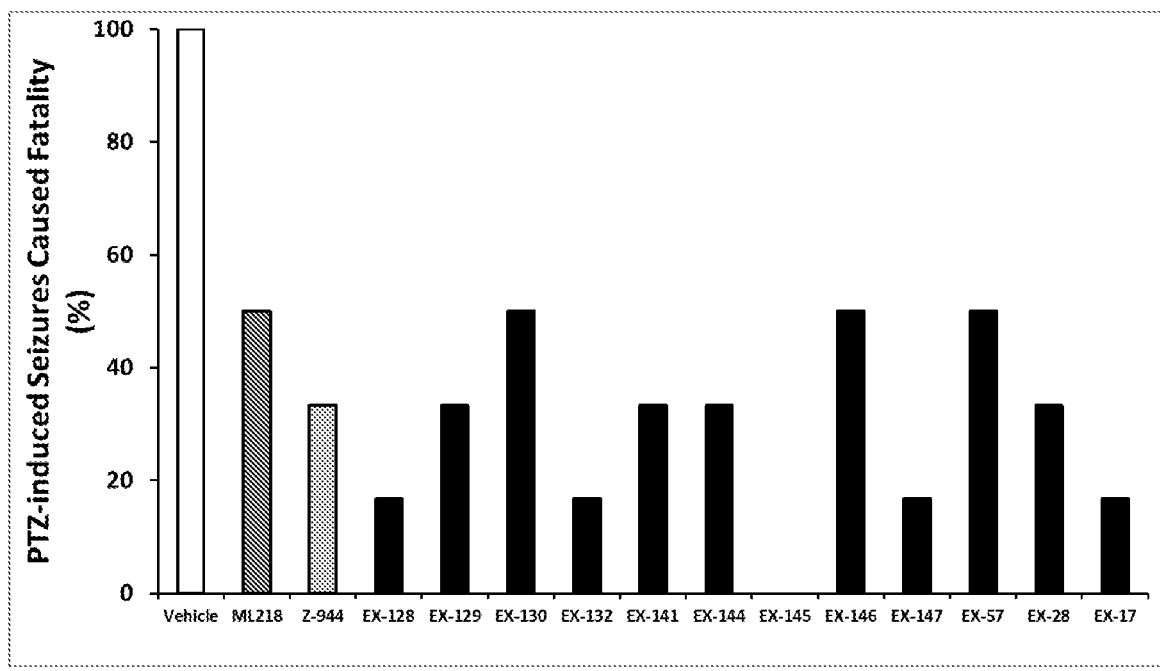
FIG. 10. Effects of Representative compounds EXAMPLE-17, -28, -57, -128, -129, -130, -132, -141, -144, -145, -146, -147 (12 examples), and ML218 and Z944 (as reference compounds, each 30 mg/kg, I.P.) on fatality caused by pentylenetetrazol (PTZ)-induced seizures in mice (C57BL/6, both sexes, 3-5 months, n=6-8 per group). Sixty minutes (min) prior to receiving PTZ (40 mg/kg, I.P.), each mouse was pretreated with either an Example compound, ML218, Z944 or vehicle (2% DMSO in 0.5% HPC). Fatality rate (%) of mice in each group that dies within the 20 minutes observation period—was calculated. Both fatality rate and latency (data not shown) to death were used to evaluate the Example compound's ability to prevent death resulting from PTZ-induced seizures. A cutoff of 20 minutes was set for observational and statistical analysis purposes.

It is well known that antiepileptics, e.g. carbamazepine, lamotrigine and gabapentin are used for the treatment of neuropathic pain (Xie et al., 1995, Caviedes and Herranz, 2001). T-channel overactivation is involved in the generation of seizure activity (Huguenard, 1998, Cribbs et al., 2000, Perez-Reyes et al., 2009, Perez-Reyes, 2010). Representative compounds EXAMPLE-17, -28, -57, -128, -129, -130, -132, -141, -144, -145, -146, -147 (12 examples), and ML218 or Z944 (as reference compounds, each 30 mg/kg, I.P. n=6-8 per group) significantly prolonged latencies to seizures and decreased the fatality rate (i.e., increased the survival rate) in the pentylenetetrazol (PTZ)-induced seizure model in mice compared to vehicle (2% DMSO in 0.5% HPC). Fatality latency and rate—the percentage (%) of mice in each treatment group that died within a 20 minute cutoff of the observational period, were recorded and calculated. Averaged fatality latency and rate of each treatment group was used to evaluate the Example compound's ability to either prevent or delay the onset of PTZ-induced seizures and death. FIG. 10 shows the representative compounds EXAMPLE-17, -28, -57, -128, -129, -130, -132, -141, -144, -145, -146, -147, and ML218 and Z944 differentially reduced fatality and prolonged fatality latencies (plot not shown, as it correlated well with the fatality rate).

Figure 11:
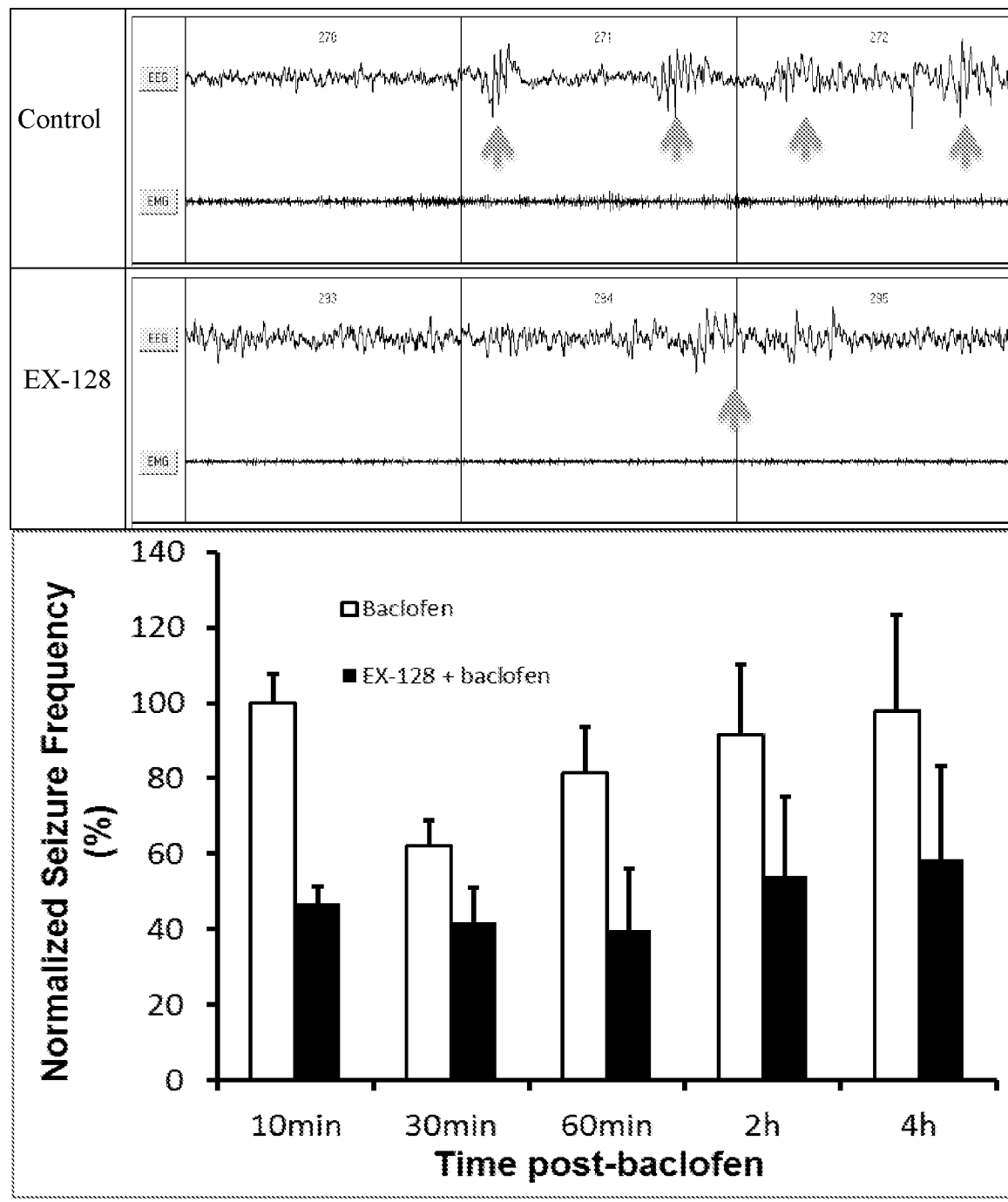
FIG. 11. Effects of EXAMPLE-128 on baclofen-induced absence seizures in mice. R-baclofen (5 mg/kg, I.P.) was administered to mice (C57BL/6, male, 2 months) caused abnormal brain seizure activity so-called "spike wave discharges" (SWD) revealed by the electroencephalogram (EEG, indicated by an arrow), mimicking absence seizures. EXAMPLE-128 (30 mg/kg, I.P.) was administered 30 min prior to baclofen injection significantly reduced the SWD occurring frequency compared to vehicle control (n=6 per group).

Absence seizures, especially childhood absence epilepsy, is characterized by a brief loss of consciousness and muscle tone as the primary manifestations. Ethosuximide, a weak and non-selective T-type calcium channel inhibitor, is effective in treating only absence seizures (Huguenard J R, 2002); while the $GABA_B$ baclofen exacerbates transgenic absence seizure models and alone induces absence seizures in wild-type animals (Han et al., 2012). Baclofen (5-10 mg/kg, I.P.) administered to mice (C57BL/6, male, 6 months) caused abnormal brain waves, i.e., so-called "spike wave discharges" (SWD) and "electrodecremental responses", which were revealed by the electroencephalogram (EEG). The baclofen-induced brain seizure activity mimics absence seizures. EXAMPLE-128 (30 mg/kg, I.P.) administrated 30 min prior to baclofen injection significantly reduced the SWD occurring frequence compared to vehicle control (n=6 per group, FIG. 11).

Figure 12:
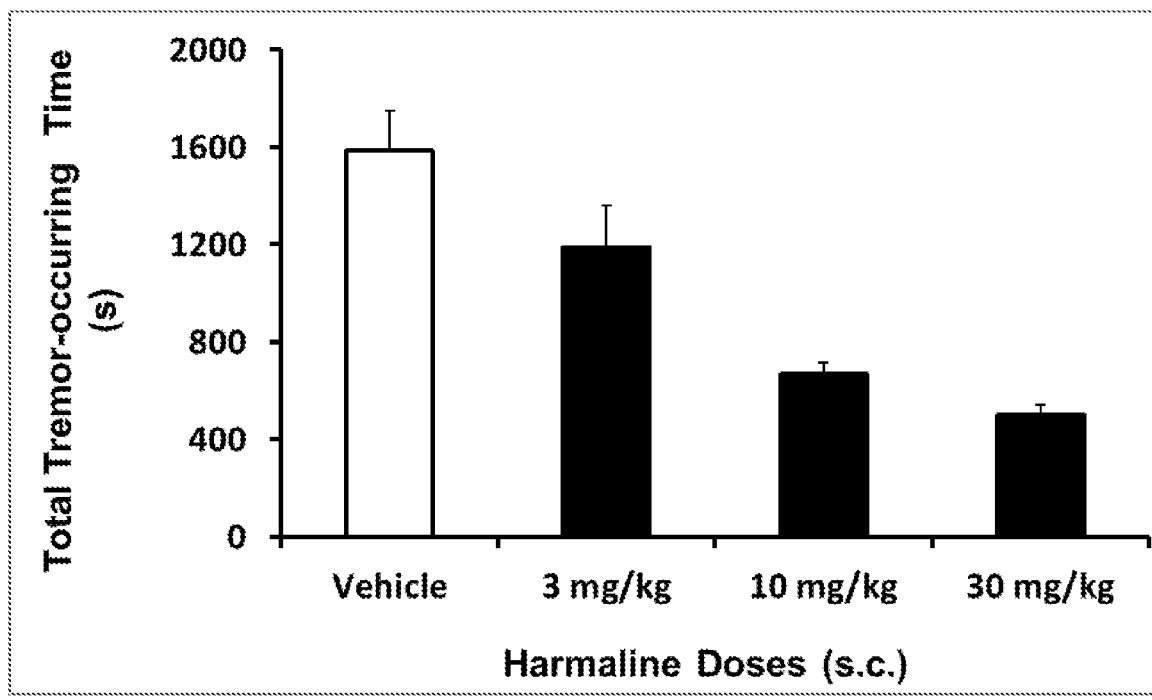
FIG. 12. Effects of EXAMPLE-128 on harmaline-induced essential tremor model in mice. Harmaline was dissolved in saline and administrated at 10 mg/kg (S.C.) mice (C57BL/6, male, 3-5 months). Ten minutes after tremors occurred, mice were treated with either EXAMPLE-128 (30 mg/kg, I.P.) or vehicle (2% DMSO in 0.5% HPC). Tremor episodes numbers and each episode duration were offline human scored; EXAMPLE-128 significantly reduced the total tremor occurring time in a period of 60 minutes following the I.P. drug treatment.

Harmaline can induce tremors modeling human essential tremor manifested as postural and kinetic tremors (Nahab et al., 2012). Harmaline was dissolved in saline and administrated at 10 mg/kg (s.c.) to mice (C57BL/6, male, 3 months) and the mice were immediately returned to homecage monitor with an piezoelectric sensor operated by the Smart-Cage™ for continual recordings for 60 min. Harmaline rapidly induced tremors modeling human essential tremor manifested as postural and kinetic tremors. Mice were randomly assigned to be treated with EXAMPLE-128 (3, 10 or 30 mg/kg, I.P.) or vehicle (2% DMSO in 0.5% HPC), starting ten min after tremors began, Tremor episode numbers and each episode's duration were offline human scored. EXAMPLE-128 significantly reduced the total time spent in tremors in a dose-dependent manner (FIG. 12).

Moreover, compounds useful in therapeutic formulations may be further screened for undesired side effect activities by utilizing large ancillary pharmacology panel screens, for example, SafetyScreen 44 and the Ames microsomemutagenicity assay (Eurofins-Cerep, US and France). Such further tests were performed to verify that there are no significant off-target activities present and that there is lack of mutagenicity for preferred compounds, for example EXAMPLE-128.

Example C

Pharmacokinetic Data

In vitro data of metabolic stability and protein binding as well as in vivo pharmacokinetic data for compounds of the invention can be generated using the techniques disclosed in, e.g., Obach, R. S. et al., *J. Pharmacol. Exp. Ther.* 283(1): 46-58 (1997), which is hereby incorporated by reference in its entirety. Various biological, pharmacokinetic and other properties of the compounds, including hepatic microsomal stability, determination of metabolites, binding to proteins such as plasma protein binding, and in vivo studies, including single-dose and multi-dose pharmacokinetic studies, can be determined using the protocols described in that publication and the publications cited therein. Other aspects and advantages of the present invention will become apparent from the above detailed description, as illustrated by way of example of the principles of the invention. The scope of the invention is to be defined by the claims appended hereto and their equivalents. Selected pharmacokinetic studies in vitro and in vivo in rats were performed for preferred compounds, for example EXAMPLE-128 and compared with two reference compounds ML218 and Z944 by a contract research organization (BioDuro, Inc., San Diego, US). Tables 3A and 3B summarize some of the in vitro and vivo pharmacodynamic and pharmacokinetic parameters, respectively. Tables 2 and 3 show that representative EXAMPLE compounds, particularly EXAMPLE-128, are not only structurally different from, but also superior in target potency, selectivity, and pharmacological actions to, T-type calcium channel inhibitors/antagonists, especially ML218 and Z944.

TABLE 3A

Comparative study of ML218 and Z944 and EX128 in in vitro and in vivo pharmacodynamics.

| | $Ca_{v3.2}$ | | PTZ- | Pain in rats (30 mg/kg, P.O.) | |
| --- | --- | --- | --- | --- | --- |
| | | | | SNI-Model Mechanical | SNL Model Mechanical |
| Compound | $IC_{50}$ (μM) | % Use-Dep | induced Fatality (%) | % of baseline | % of baseline |
| Vehicle | 0 | 0 | 100 | 10-20% (among different groups) | 25% |
| ML218 | 0.31 | 19.2 | 50 | 45 ± 11 | ND |
| Z944 | 0.20 | 17.6 | 33.3 | 28 ± 18 | 94 ± 38 |
| EX-128 | 0.089 | 21.3 | 16.7 | 45 ± 15 | 129 ± 28 |

$Ca_{v3.2}$ is human cDNA encoding T-type Ca channels;
Use-Dep. = Use-dependent drug action;
PTZ = pentylenetetrazole,
SNI = spared nerve injury neuropathic pain model in rats,
SNL = spinal nerve ligation neuropathic pain model in rats;
ND = not determined.

TABLE 3B

Comparative study of ML218 and Z944 and EX128 in in vitro and in vivo pharmacokinetic parameters

| | Human Liver Microsomes | | Rat Liver Microsomes | | Plasma | | | Rat PK | Plasma |
| --- | --- | --- | --- | --- | --- | --- | --- | --- | --- |
| Comp. | $t_{1/2}$ (min) | Clint (μL/min/ mg protein) | $t_{1/2}$ (min) | Clint (μL/min/ mg protein) | PPB % (Human/ Rat) | Stability @ 5 h % (Human/ Rat) | Recovery % (Human/ Rat) | $AUC_{total}$/ $AUC_{free}$ (μM*h) F (%) | $t_{1/2}$ (h) iv/ po |
| ML218 | 630 | 1.1 | 126 | 5.5 | 95.4/ 89.2 | 97.9/ 99.2 | 97.1/ 94.9 | 0.071/ 0.007 F = 28 | 236/ ND |
| Z944 | 126 | 5.5 | 52.5 | 13.2 | 93.6/ 71.3 | 100/ 100 | 93.6/ 91.1 | 0.51/ 0.14 F = 55 | 1.50/ 2.26 |

TABLE 3B-continued

Comparative study of ML218 and Z944 and EX128 in in vitro and in vivo pharmacokinetic parameters

| Comp. | Human Liver Microsomes | | Rat Liver Microsomes | | Plasma | | | Rat PK | Plasma |
|---|---|---|---|---|---|---|---|---|---|
| | $t_{1/2}$ (min) | Clint (μL/min/ mg protein) | $t_{1/2}$ (min) | Clint (μL/min/ mg protein) | PPB % (Human/ Rat) | Stability @ 5 h % (Human/ Rat) | Recovery % (Human/ Rat) | $AUC_{total}/$ $AUC_{free}$ (μM*h) F (%) | $t_{1/2}$ (h) iv/ po |
| EX-128 | 365 | 1.9 | 315 | 2.2 | 95.7/ 75.8 | 95.7/ 98.3 | 98.3/ 90.4 | 4.1/ 1.0 F = 62 | 3.34/ 3.66 |

Comp. = Compound,
Clint = Clearance infinitive,
PPB = plasma protein binding,
AUC = area under the curve,
F = bioavailability,
ND = not determined

TABLE 4

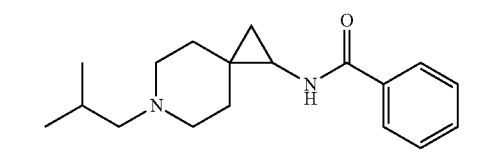 [SMILES: CC(C)CN1CCC2(CC1)CC2NC(=O)c1ccccc1]

1

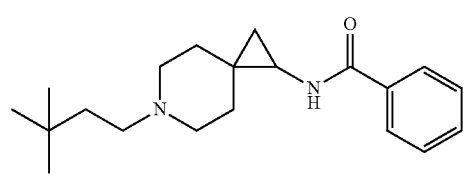 [SMILES: CC(C)(C)CCN1CCC2(CC1)CC2NC(=O)c1ccccc1]

2

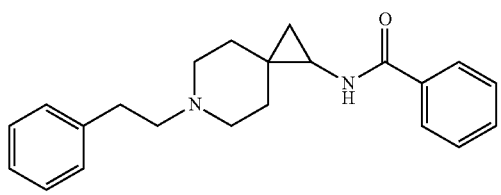 [SMILES: O=C(NC1CC12CCN(CCc1ccccc1)CC2)c1ccccc1]

3

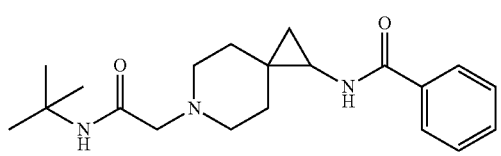 [SMILES: CC(C)(C)NC(=O)CN1CCC2(CC1)CC2NC(=O)c1ccccc1]

4

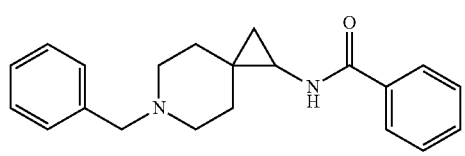 [SMILES: O=C(NC1CC12CCN(Cc1ccccc1)CC2)c1ccccc1]

5

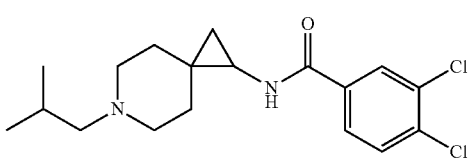 [SMILES: CC(C)CN1CCC2(CC1)CC2NC(=O)c1ccc(Cl)c(Cl)c1]

6

TABLE 4-continued

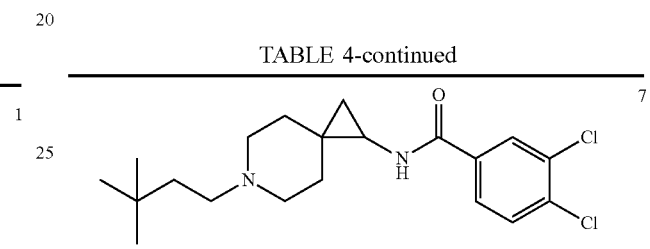

7

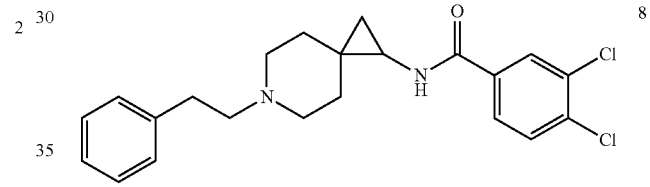

8

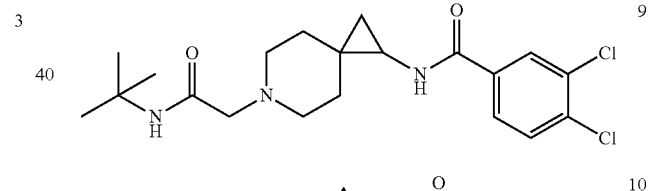

9

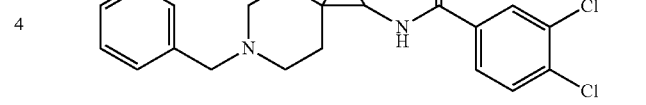

10

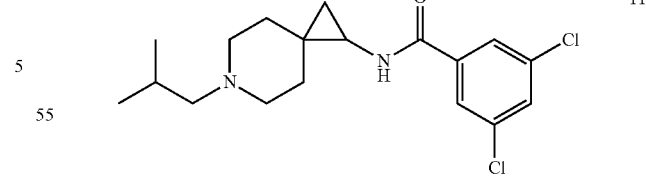

11

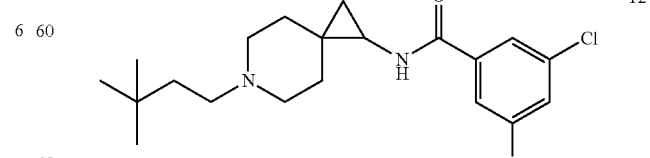

12

TABLE 4-continued
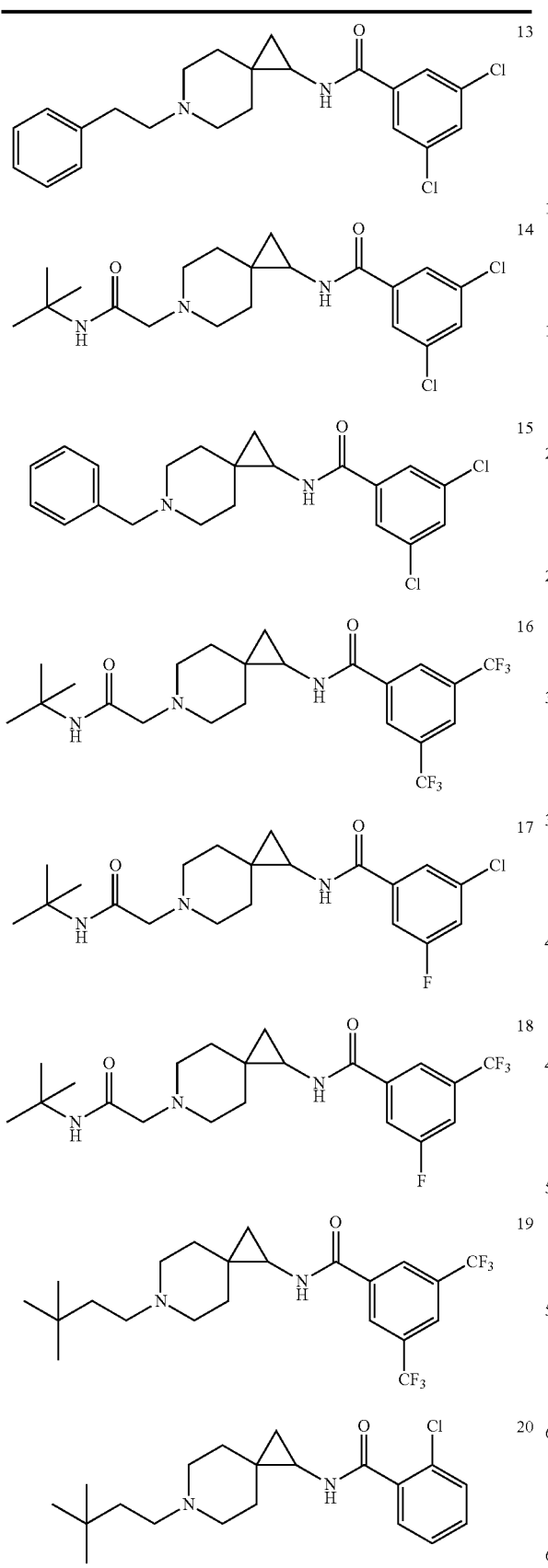
TABLE 4-continued
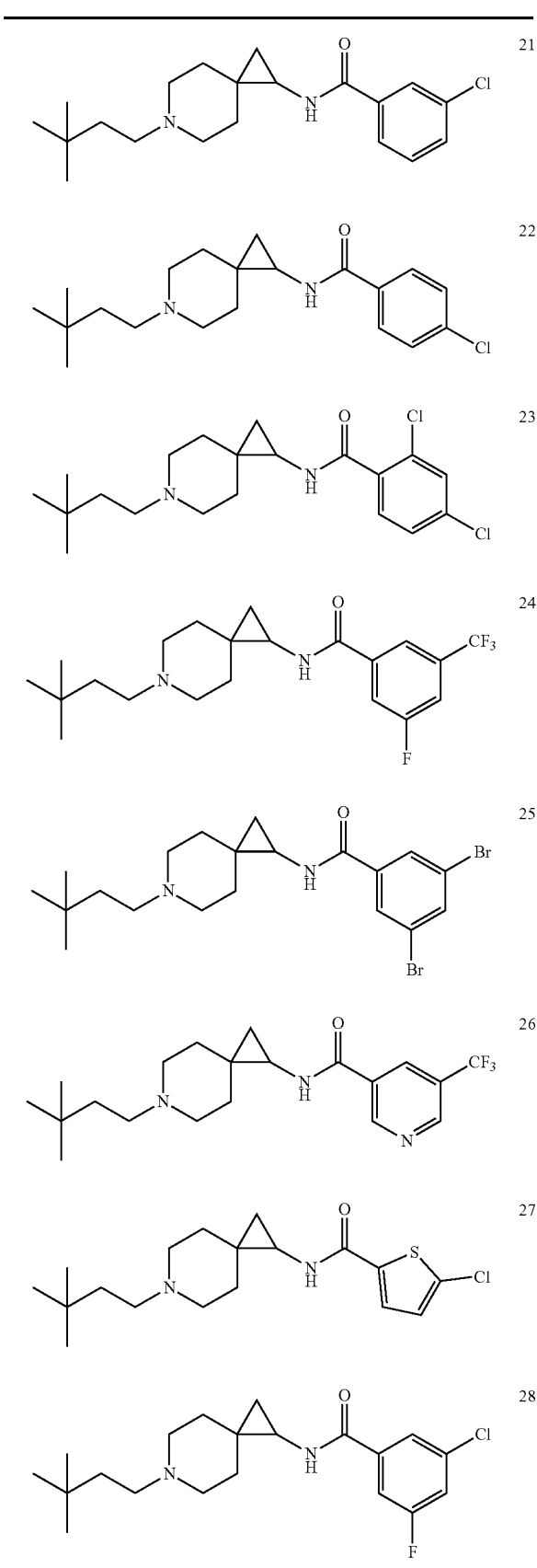

TABLE 4-continued
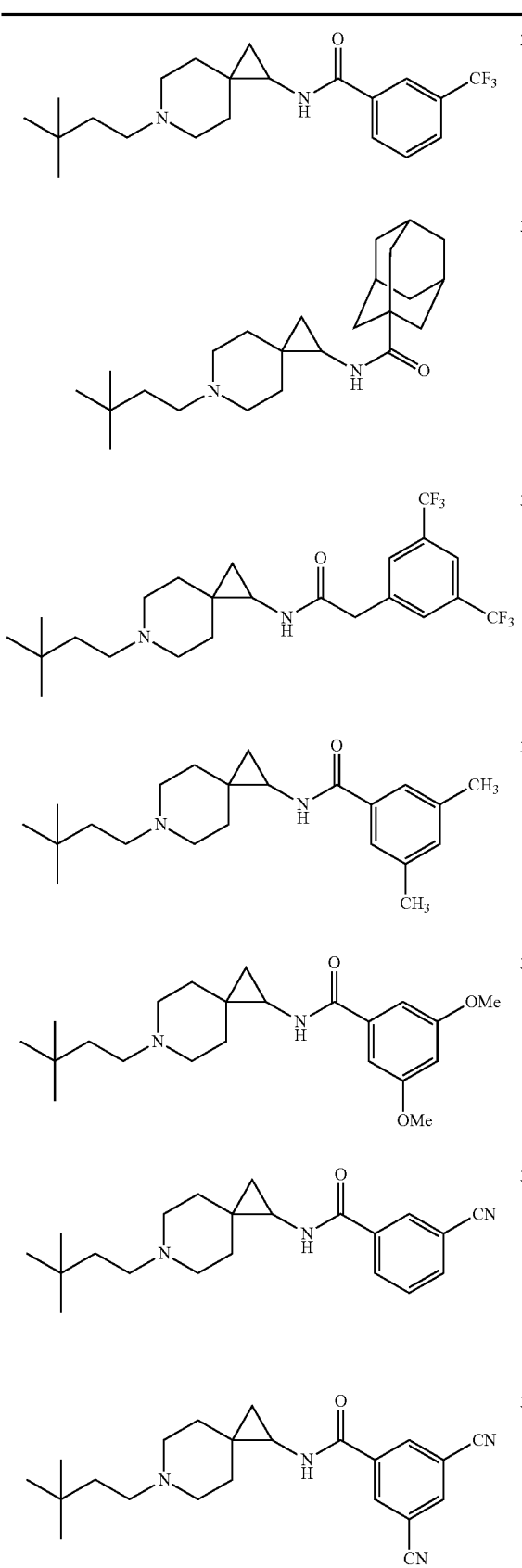
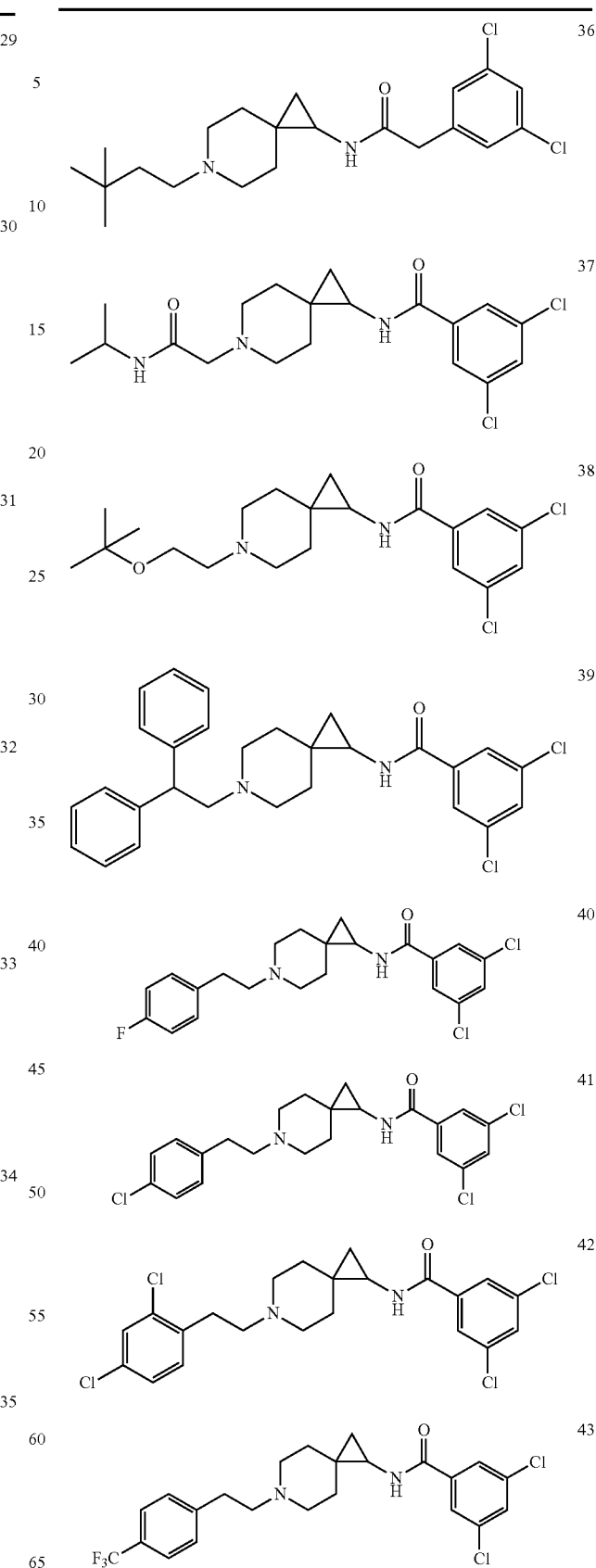

TABLE 4-continued
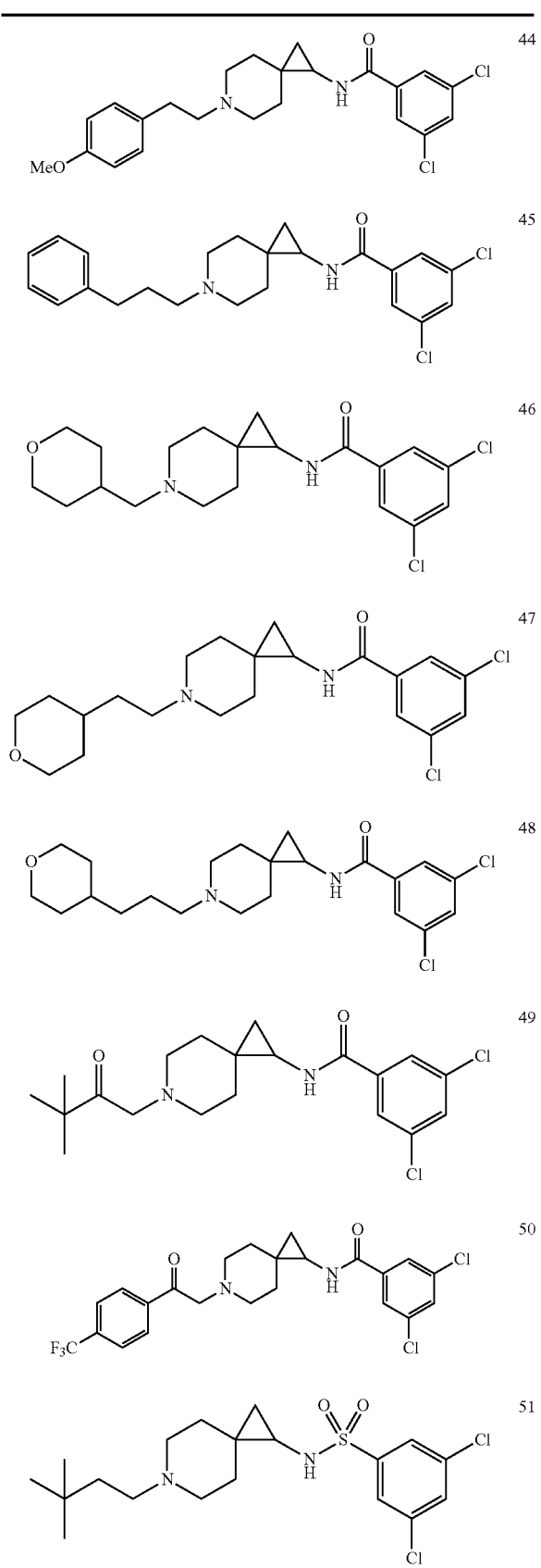
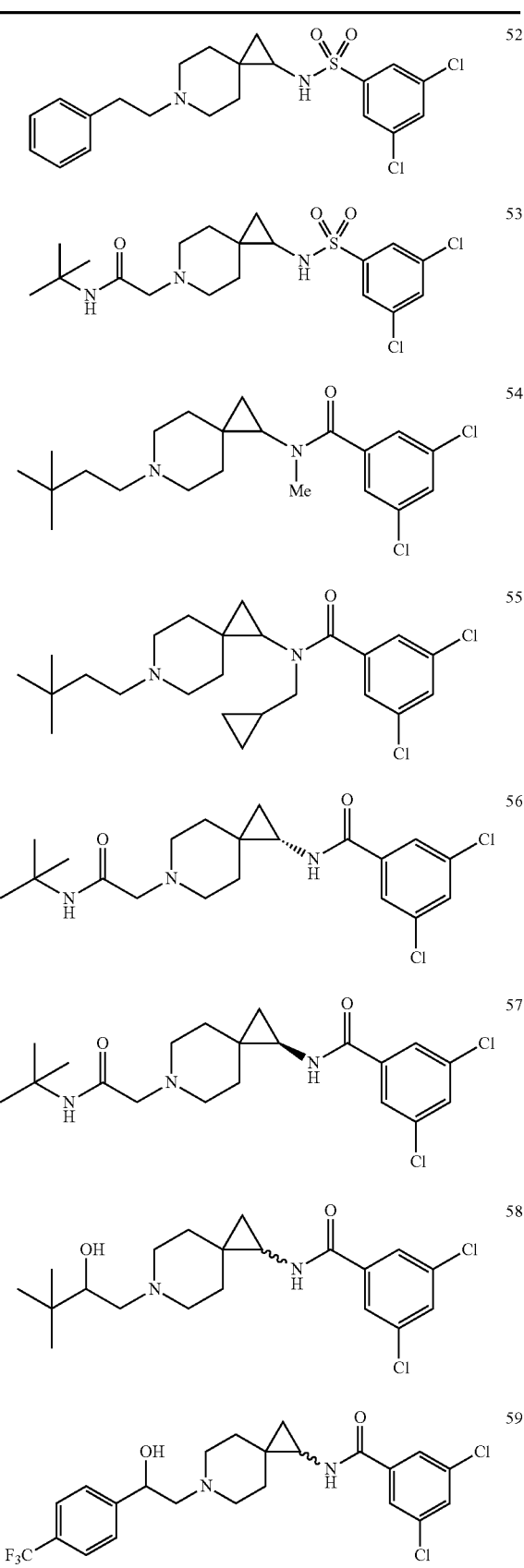

TABLE 4-continued
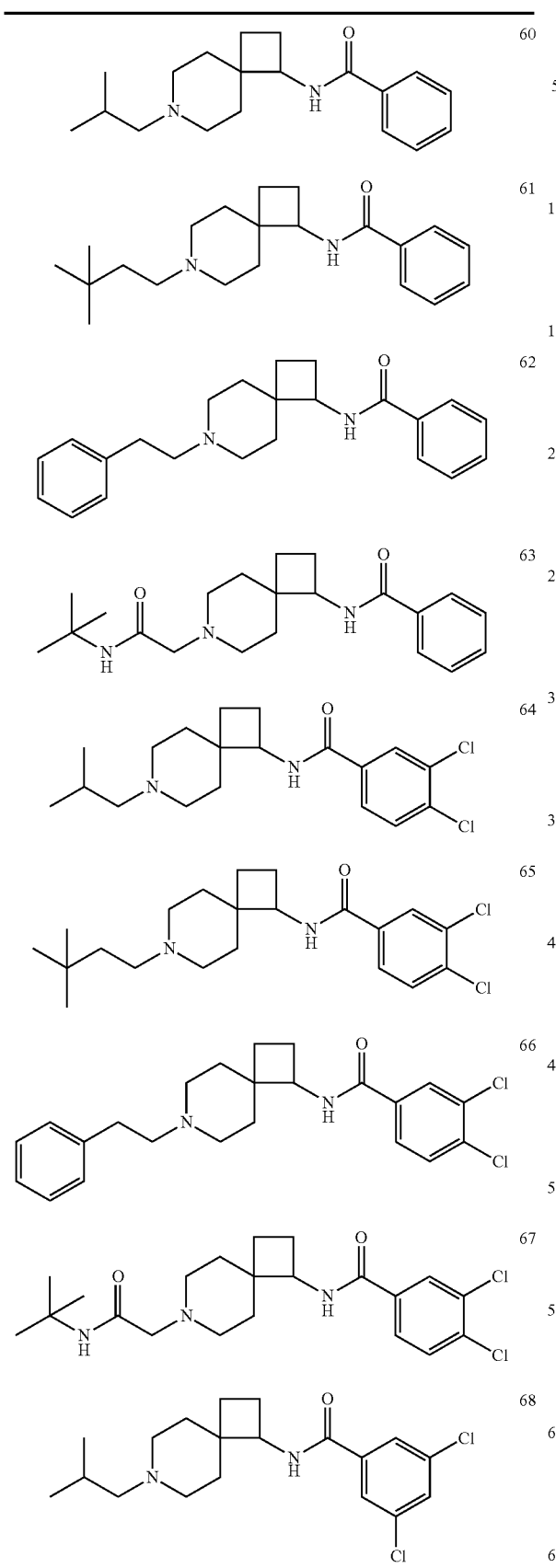
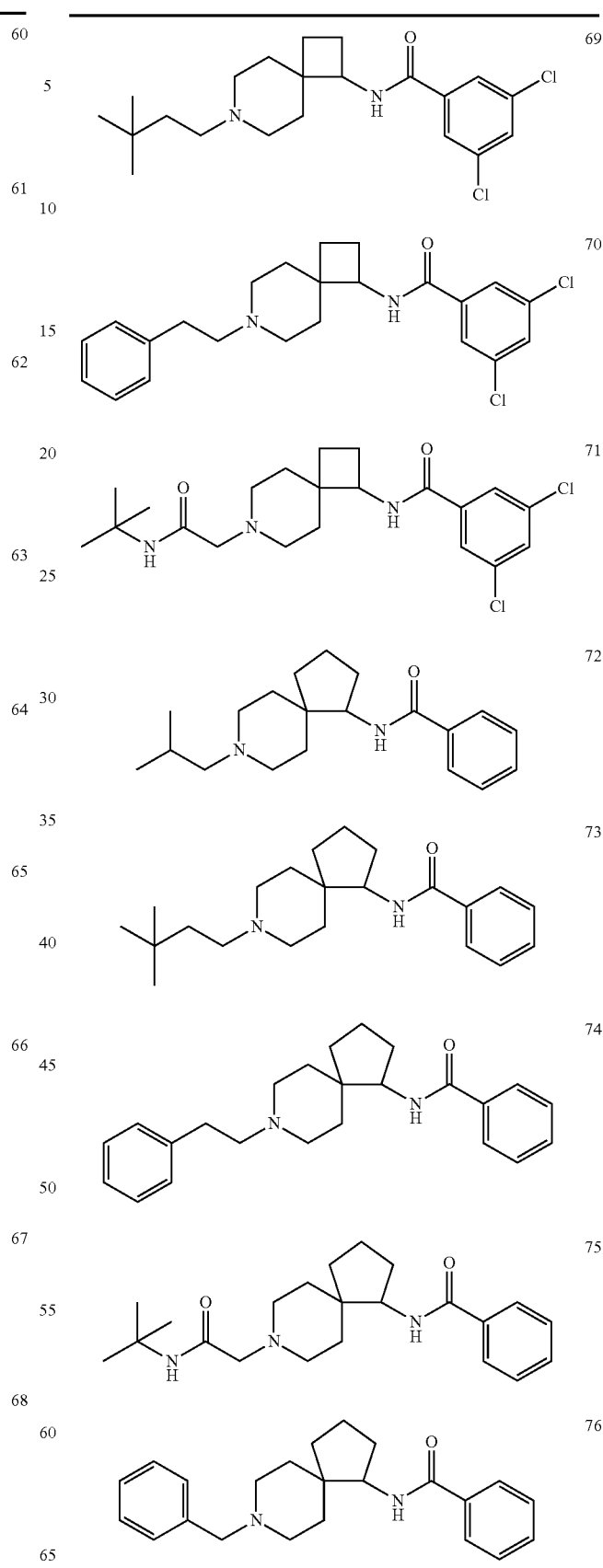

TABLE 4-continued
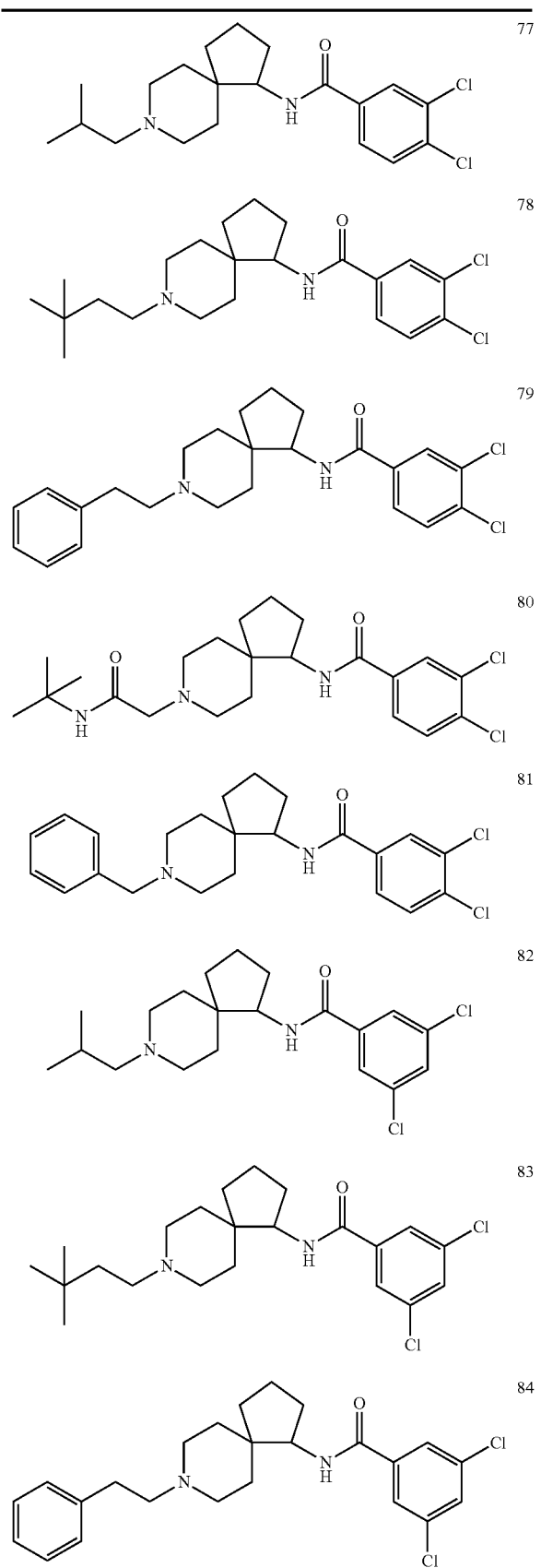
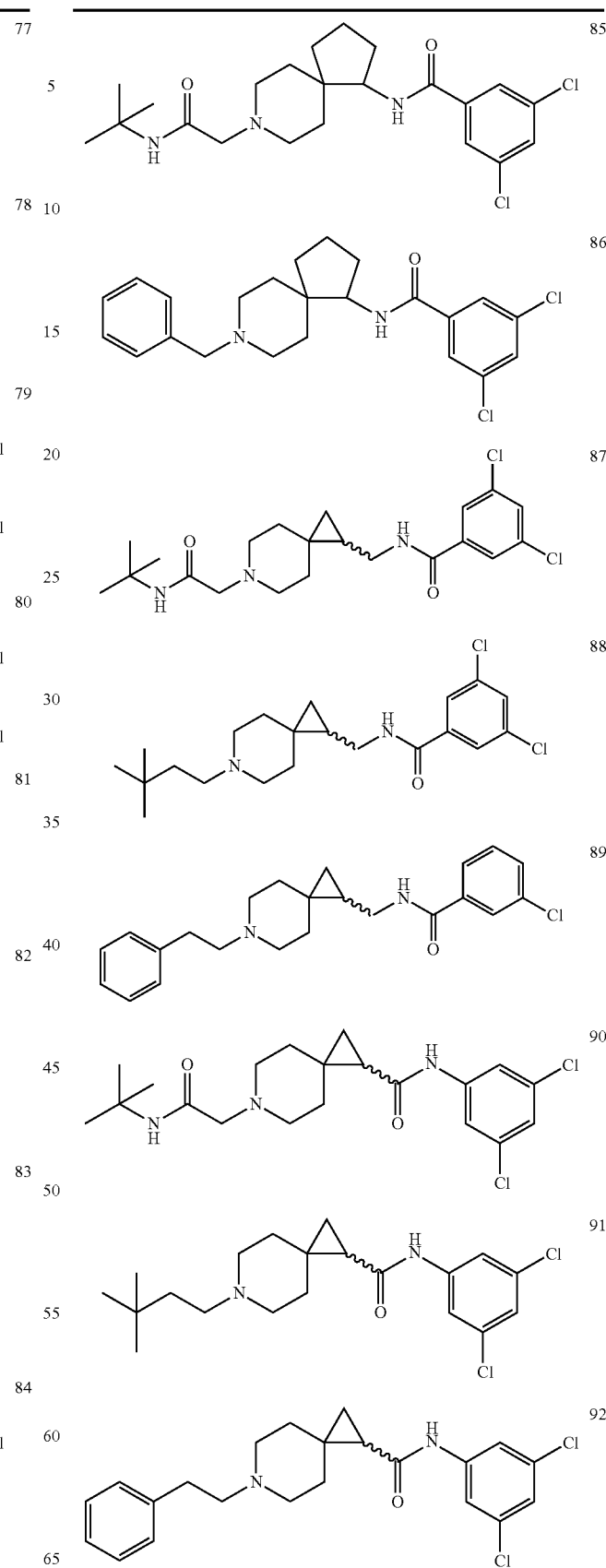

TABLE 4-continued
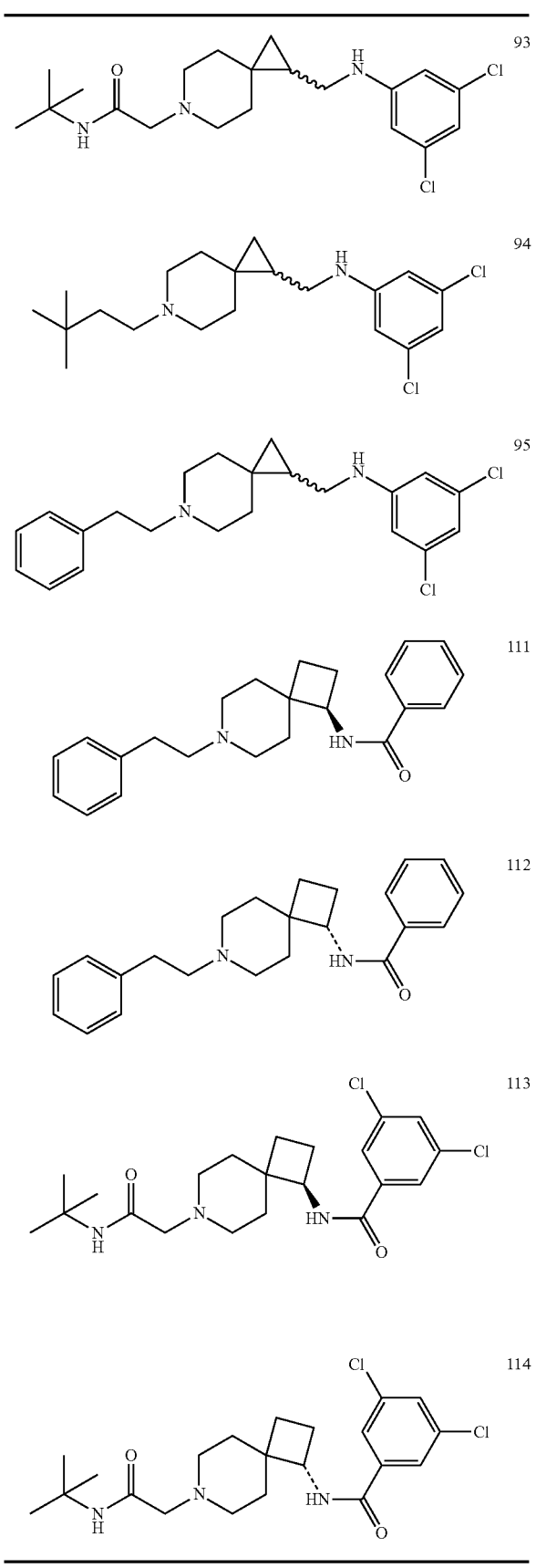
TABLE 5
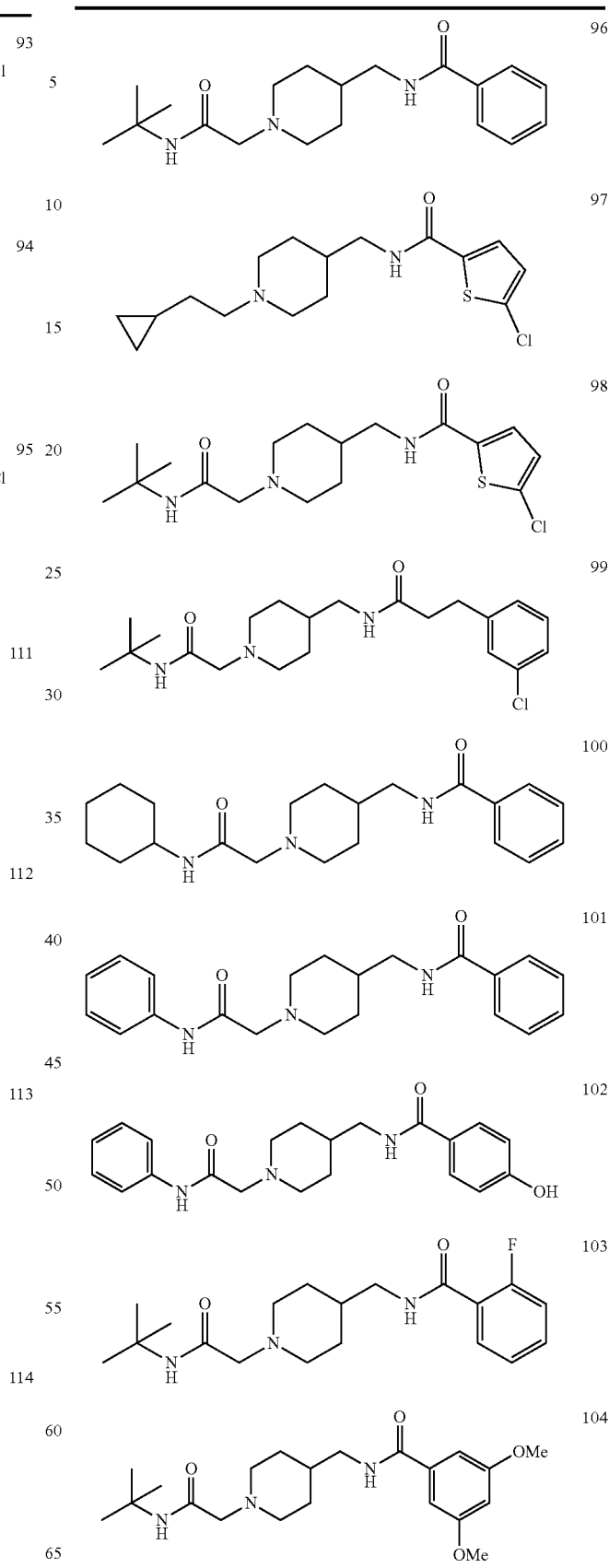

TABLE 5-continued
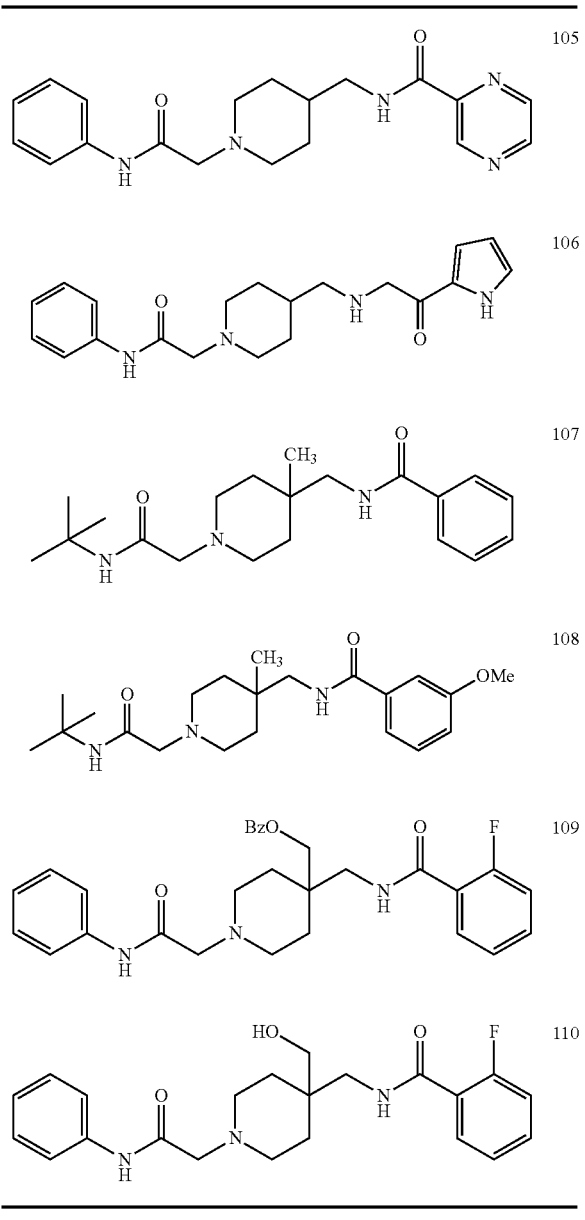
TABLE 6
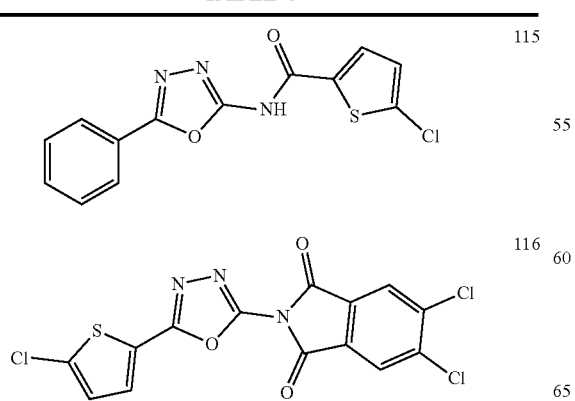

TABLE 6-continued

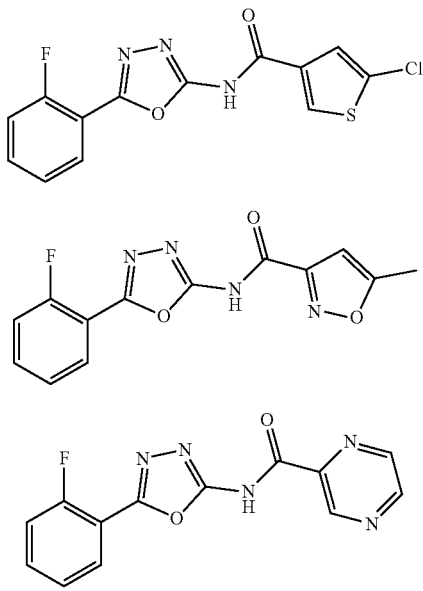

125, 126, 127

REFERENCES

Avdonin P V, Buhler F R, Tkachuk V A (2000) Ca2+-agonistic effect of a T-type Ca-channel blocker mibefradil (Ro 40-5967). Membr Cell Biol 13:645-655.

Caviedes B E, Herranz J L (2001) [Use of antiepileptic drugs in non epileptic disorders]. Rev Neurol 33:241-249.

Chaplan S R, Bach F W, Pogrel J W, Chung J M, Yaksh T L (1994) Quantitative assessment of tactile allodynia in the rat paw. Journal of neuroscience methods 53:55-63.

Chaudhry V, Rowinsky E K, Sartorius S E, Donehower R C, Cornblath D R (1994) Peripheral neuropathy from taxol and cisplatin combination chemotherapy: clinical and electrophysiological studies. Annals of neurology 35:304-311.

Choi S, Na H S, Kim J, et al. (2007) Attenuated pain responses in mice lacking Ca(V)3.2 T-type channels. Genes Brain Behav 6:425-431.

Cribbs L L, Gomora J C, Daud A N, Lee J H, Perez-Reyes E (2000) Molecular cloning and functional expression of Ca(v)3.1c, a T-type calcium channel from human brain. FEBS Lett 466:54-58.

Decosterd I, Woolf C J (2000) Spared nerve injury: an animal model of persistent peripheral neuropathic pain. Pain 87:149-158.

Gomora J C, Daud A N, Weiergraber M, Perez-Reyes E (2001) Block of cloned human T-type calcium channels by succinimide antiepileptic drugs. Mol Pharmacol 60:1121-1132.

Han H A, Cortez M A, Snead O C III. (2012) $GABA_B$ Receptor and Absence Epilepsy. In: Noebels J L, Avoli M, Rogawski M A, Olsen R W, Delgado-Escueta A V, editors. Jasper's Basic Mechanisms of the Epilepsies [Internet]. 4th edition. Bethesda (Md.): National Center for Biotechnology Information (US)

Huguenard J R (1998) Low-voltage-activated (T-type) calcium-channel genes identified. Trends Neurosci 21:451-452.

Huguenard J R (2002) Block of T-Type Ca(2+) Channels Is an Important Action of Succinimide Antiabsence Drugs. Epilepsy Curr 2:49-52.

Jagodic M M, Pathirathna S, Joksovic P M, Lee W, Nelson M T, Naik A K, Su P, Jevtovic-Todorovic V, Todorovic S M (2008) Upregulation of the T-type calcium current in small rat sensory neurons after chronic constrictive injury of the sciatic nerve. J Neurophysiol 99:3151-3156.

Jagodic M M, Pathirathna S, Nelson M T, Mancuso S, Joksovic P M, Rosenberg E R, Bayliss D A, Jevtovic-Todorovic V, Todorovic S M (2007) Cell-specific alterations of T-type calcium current in painful diabetic neuropathy enhance excitability of sensory neurons. J Neurosci 27:3305-3316.

Jarvis M F, Scott V E, McGaraughty S, Chu K L, Xu J, Niforatos W, Milicic I, Joshi S, Zhang Q, Xia Z (2014) A peripherally acting, selective T-type calcium channel blocker, ABT-639, effectively reduces nociceptive and neuropathic pain in rats. Biochemical pharmacology 89:536-544.

Jenkins I D, Lacrampe F, Ripper J, Alcaraz L, Le P V, Nikolakopoulos G, de Almeida Leone P, White R H, Quinn R J (2009) Synthesis of four novel natural product inspired scaffolds for drug discovery. The Journal of organic chemistry 74:1304-1313.

Kim S H, Chung J M (1992) An experimental model for peripheral neuropathy produced by segmental spinal nerve ligation in the rat. Pain. 50(3):355-63.

Kraus R L, Li Y, Gregan Y, Gotter A L, Uebele V N, Fox S V, Doran S M, Barrow J C, Yang Z Q, Reger T S, Koblan K S, Renger J J (2010) In vitro characterization of T-type calcium channel antagonist TTA-A2 and in vivo effects on arousal in mice. J Pharmacol Exp Ther 335:409-417.

Latham J R, Pathirathna S, Jagodic M M, Choe W J, Levin M E, Nelson M T, Lee W Y, Krishnan K, Covey D F, Todorovic S M, Jevtovic-Todorovic V (2009) Selective T-type calcium channel blockade alleviates hyperalgesia in ob/ob mice. Diabetes 58:2656-2665.

Lee M (2014) Z944: a first in class T-type calcium channel modulator for the treatment of pain. Journal of the peripheral nervous system: JPNS 19 Suppl 2:S11-12.

Messinger R B, Naik A K, Jagodic M M, Nelson M T, Lee W Y, Choe W J, Orestes P, Latham J R, Todorovic S M, Jevtovic-Todorovic V (2009) In vivo silencing of the Ca(V)3.2 T-type calcium channels in sensory neurons alleviates hyperalgesia in rats with streptozocin-induced diabetic neuropathy. Pain 145:184-195.

Nahab F B, Handforth A, Brown T, et al., (2012) Octanoic acid suppresses harmaline-induced tremor in mouse model of essential tremor. Neurotherapeutics, 9:635-638

Nelson S C, Friedman H S, Oakes W J, Halperin E C, Tien R, Fuller G N, Hockenberger B, Scroggs M W, Moncino M, Kurtzberg J, et al. (1992) Successful therapy for trilateral retinoblastoma. Am J Ophthalmol 114:23-29.

Perez-Reyes E (2003) Molecular physiology of low-voltage-activated t-type calcium channels. Physiol Rev 83:117-161.

Perez-Reyes E (2010) G protein-mediated inhibition of Cav3.2 T-type channels revisited. Molecular pharmacology 77:136-138.

Perez-Reyes E, Van Deusen A L, Vitko I (2009) Molecular Pharmacology of Human $Ca_{v3.2}$ T-Type Ca2+ Channels: Block by Antihypertensives, Antiarrhythmics, and Their Analogs. Journal of Pharmacology and Experimental Therapeutics 328:621-627.

Pexton T, Moeller-Bertram T, Schilling J M, Wallace M S (2011) Targeting voltage-gated calcium channels for the treatment of neuropathic pain: a review of drug development. Expert opinion on investigational drugs 20:1277-1284.

Pogatzki-Zahn E M, Wagner C, Meinhardt-Renner A (2003) Spinal glutamate receptor antagonists differentiate primary and secondary mechanical hyperalgesia caused by incision. Pain 105(1-2):97-107.

Sanguinetti, M C, Jiang C, Curran M E, Keating M T (1995) A mechanistic link between an inherited and an acquired cardiac arrhythmia: hERG encodes the IKr potassium channel. Cell, 81:299-307.

Talley E M, Cribbs L L, Lee J H, Daud A, Perez-Reyes E, Bayliss D A (1999) Differential distribution of three members of a gene family encoding low voltage-activated (T-type) calcium channels. J Neurosci 19:1895-1911.

Todorovic S M, Jevtovic-Todorovic V (2011) T-type voltage-gated calcium channels as targets for the development of novel pain therapies. British journal of pharmacology 163:484-495.

Tringham E, Powell K L, Cain S M, Kuplast K, Mezeyova J, Weerapura M, Eduljee C, Jiang X, Smith P, Morrison J L, Jones N C, Braine E, Rind G, Fee-Maki M, Parker D, Pajouhesh H, Parmar M, O'Brien T J, Snutch T P (2012) T-type calcium channel blockers that attenuate thalamic burst firing and suppress absence seizures. Science translational medicine 4:121ra119.

Uebele V N, Gotter A L, Nuss C E, Kraus R L, Doran S M, Garson S L, Reiss D R, Li Y, Barrow J C, Reger T S, Yang Z Q, Ballard J E, Tang C, Metzger J M, Wang S P, Koblan K S, Renger J J (2009) Antagonism of T-type calcium channels inhibits high-fat diet-induced weight gain in mice. J Clin Invest 119:1659-1667.

Wang Y, Liu J J, Dransfield P J, Zhu L, Wang Z, Du X, Jiao X, Su Y, Li A R, Brown S P, Kasparian A, Vimolratana M, Yu M, Pattaropong V, Houze J B, Swaminath G, Tran T, Nguyen K, Guo Q, Zhang J, Zhuang R, Li F, Miao L, Bartberger M D, Correll T L, Chow D, Wong S, Luo J, Lin D C, Medina J C (2013) Discovery and Optimization of Potent GPR40 Full Agonists Containing Tricyclic Spirocycles. ACS medicinal chemistry letters 4:551-555.

Xiang Z, Thompson A D, Brogan J T, Schulte M L, Melancon B J, Mi D, Lewis L M, Zou B, Yang L, Morrison R, Santomango T, Byers F, Brewer K, Aldrich J S, Yu H, Dawson E S, Li M, McManus O, Jones C K, Daniels J S, Hopkins C R, Xie X S, Conn P J, Weaver C D, Lindsley C W (2011) The Discovery and Characterization of ML218: A Novel, Centrally Active T-Type Calcium Channel Inhibitor with Robust Effects in STN Neurons and in a Rodent Model of Parkinson's Disease. ACS chemical neuroscience 2:730-742.

Xie X, Brogan J T, Schulte M L, Mi D, Yu H, Dawson E S, Li M, McManus O, Engers J, Lewis L M, Thompson A, Jones C K, Weaver C D, Lindsley C W (2010) Scaffold Hopping Affords a Highly Selective in vitro and in vivo T-Type Calcium Inhibitor Probe Free From I P Issues. In: Probe Reports from the NIH Molecular Libraries Program Bethesda (Md.).

Xie X, Lancaster B, Peakman T, Garthwaite J (1995) Interaction of the antiepileptic drug lamotrigine with recombinant rat brain type IIA Na+ channels and with native Na+ channels in rat hippocampal neurones. Pflugers Archiv: European journal of physiology 430:437-446.

Xie X, Van Deusen A L, Vitko I, Babu D A, Davies L A, Huynh N, Cheng H, Yang N, Barrett P Q, Perez-Reyes E (2007) Validation of high throughput screening assays against three subtypes of Ca(v)3 T-type channels using molecular and pharmacologic approaches. Assay and drug development technologies 5:191-203.

Yang Z Q, Barrow J C, Shipe W D, Schlegel K A, Shu Y, Yang F V, Lindsley C W, Rittle K E, Bock M G, Hartman G D, Uebele V N, Nuss C E, Fox S V, Kraus R L, Doran S M, Connolly T M, Tang C, Ballard J E, Kuo Y, Adarayan E D, Prueksaritanont T, Zrada M M, Marino M J, Graufelds V K, DiLella A G, Reynolds I J, Vargas H M, Bunting P B, Woltmann R F, Magee M M, Koblan K S, Renger J J (2008) Discovery of 1,4-substituted piperidines as potent and selective inhibitors of T-type calcium channels. J Med Chem 51:6471-6477.

Yue J, Liu L, Liu Z, Shu B, Zhang Y (2013) Upregulation of T-type Ca2+ channels in primary sensory neurons in spinal nerve injury. Spine 38:463-470.

Zhang Y F, Gibbs J W, 3rd, Coulter D A (1996) Anticonvulsant drug effects on spontaneous thalamocortical rhythms in vitro: ethosuximide, trimethadione, and dimethadione. Epilepsy Res 23:15-36.

What is claimed:

1. A compound of Formula I, or a pharmaceutically acceptable salt thereof, having a structure according to the following formula:

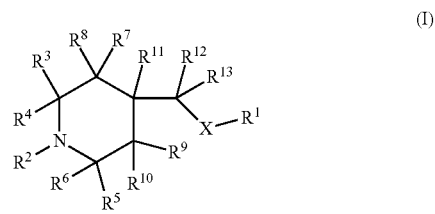

wherein
- $R^1$ is an unsubstituted aryl, an aryl substituted with 1 to 4 substituents selected from the group consisting of halo, cyano, substituted or unsubstituted $C_1$-$C_6$ alkyl, and substituted or unsubstituted $C_1$-$C_6$ haloalkyl, a substituted or unsubstituted benzyl, or a substituted or unsubstituted adamant-1-yl;
- X is selected from —N($R^{14}$)—C(=O)—, or —N($R^{14}$)—S(=O)$_k$—, or —CH$_2$—N($R^{14}$)—C(=O)—, or —CH$_2$—N($R^{14}$)—S(=O)$_k$—, or —C(=O)—N($R^{14}$), and —CH$_2$—C(=O)—N($R^{14}$);
- k is selected from 1 and 2; and
- $R^{14}$ is H or substituted or unsubstituted $C_1$-$C_6$ alkyl;
- $R^2$ is a monosubstituted methyl or ethyl group;
- $R^3$, $R^4$, $R^5$, $R^6$, $R^7$, $R^8$, $R^9$ and $R^{10}$ are each independently hydrogen, substituted or unsubstituted —$C_{1-6}$ alkyl, or substituted or unsubstituted —$C_{1-6}$ haloalkyl;
- $R^{12}$ and $R^{13}$ are each independently hydrogen, fluorine, substituted or unsubstituted-$C_{1-6}$ alkyl, substituted or unsubstituted-$C_{1-6}$ haloalkyl; and
- $R^{11}$ and either $R^{12}$ or $R^{13}$, together with the carbons to which they are attached form a 3-, 4-, 5-, 6- or 7-membered substituted or unsubstituted cycloalkyl group.

2. The compound according to claim 1, or a pharmaceutically acceptable salt thereof, wherein $R^1$ is an aryl substituted by 1, 2, 3 or 4 substituents selected from halo, substituted or unsubstituted $C_1$-$C_6$ haloalkyl, substituted or unsubstituted $C_1$-$C_6$ alkyl, and cyano.

3. The compound according to claim 1, or a pharmaceutically acceptable salt thereof, wherein the aryl in $R^1$ is phenyl.

4. The compound according to claim 1, or a pharmaceutically acceptable salt thereof, having a structure according to the following formula:

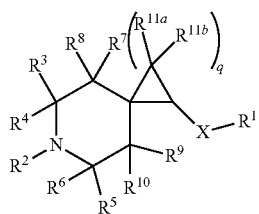

wherein $R^{11a}$ and $R^{11b}$ are members each independently selected from H, unsubstituted $C_1$-$C_3$ alkyl, and halogen;

q is an integer selected from 1, 2, 3, 4 and 5.

5. The compound according to claim 4, or a pharmaceutically acceptable salt thereof, wherein $R^{11a}$ and $R^{11b}$ are members each independently selected from H, methyl, and fluorine.

6. The compound according to claim 4, or a pharmaceutically acceptable salt thereof, having a structure according to the following formula:

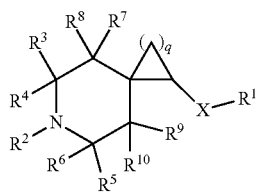

wherein q is an integer selected from 1, 2, 3, 4 and 5.

7. The compound according to claim 4, or a pharmaceutically acceptable salt thereof, wherein $R^1$ is substituted or unsubstituted benzyl or substituted or unsubstituted adamantyl.

8. The compound according to claim 4, or a pharmaceutically acceptable salt thereof, having a structure according to the following formula:

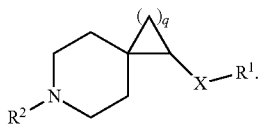

9. The compound according to claim 8, or a pharmaceutically acceptable salt thereof, wherein q is 1 or 2.

10. The compound according to claim 9 which is

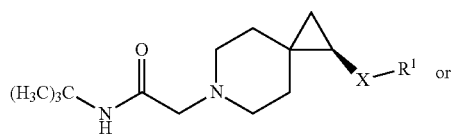

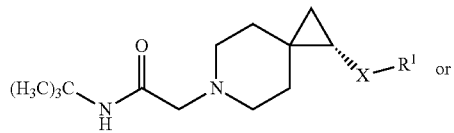

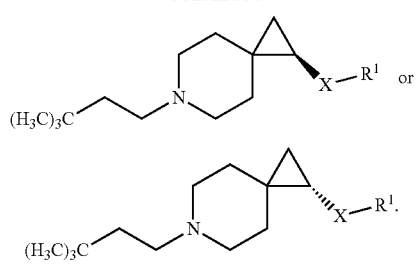

11. The compound according to claim 8 which is

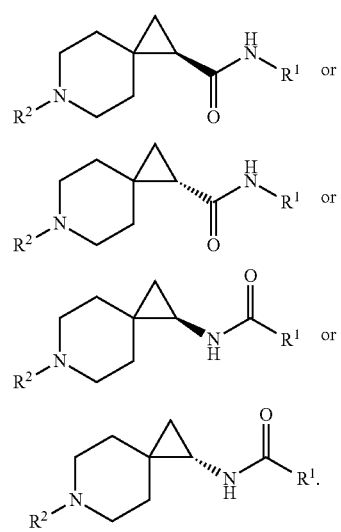

12. The compound according to claim 8 which is:

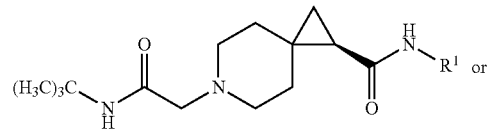

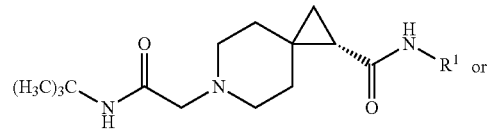

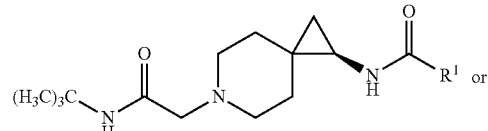

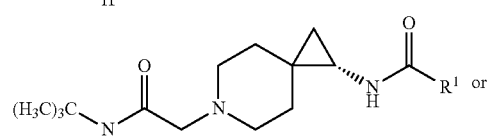

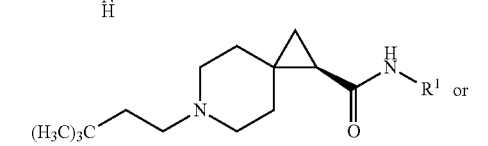

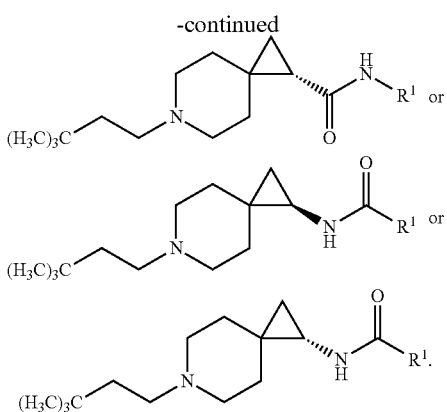

13. The compound according to claim 4, or a pharmaceutically acceptable salt thereof, wherein $R^1$ is phenyl substituted with one to three substituents, each of which is a member selected from the group consisting of F, Cl, and $CF_3$.

14. The compound according to claim 4, or a pharmaceutically acceptable salt thereof, which is:

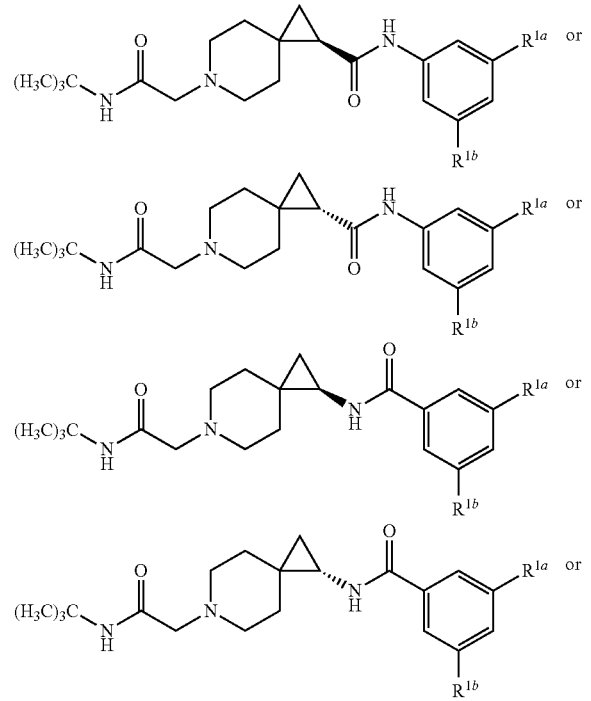

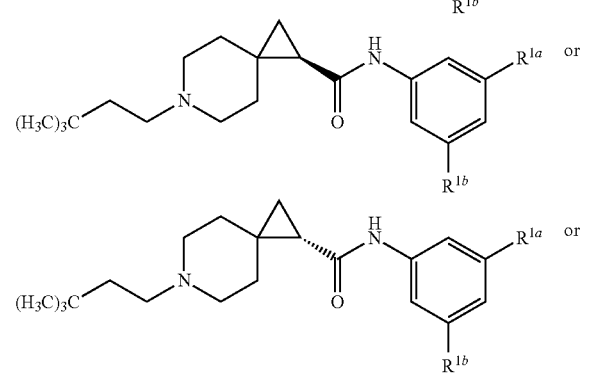

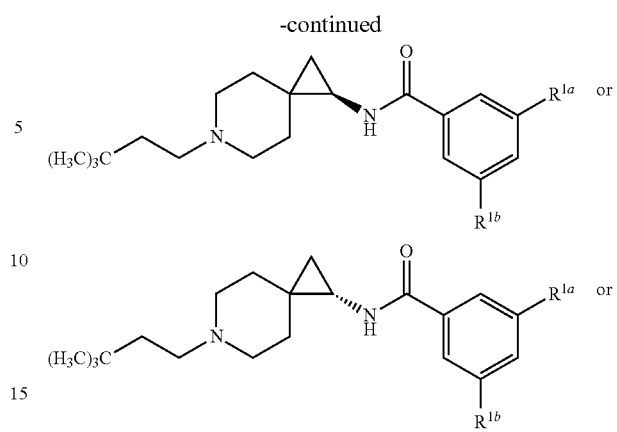

wherein $R^{1a}$ and $R^{1b}$ are members each independently selected from the group consisting of F, Cl, and $CF_3$.

15. The compound according to claim 1, or a pharmaceutically acceptable salt thereof, which is:

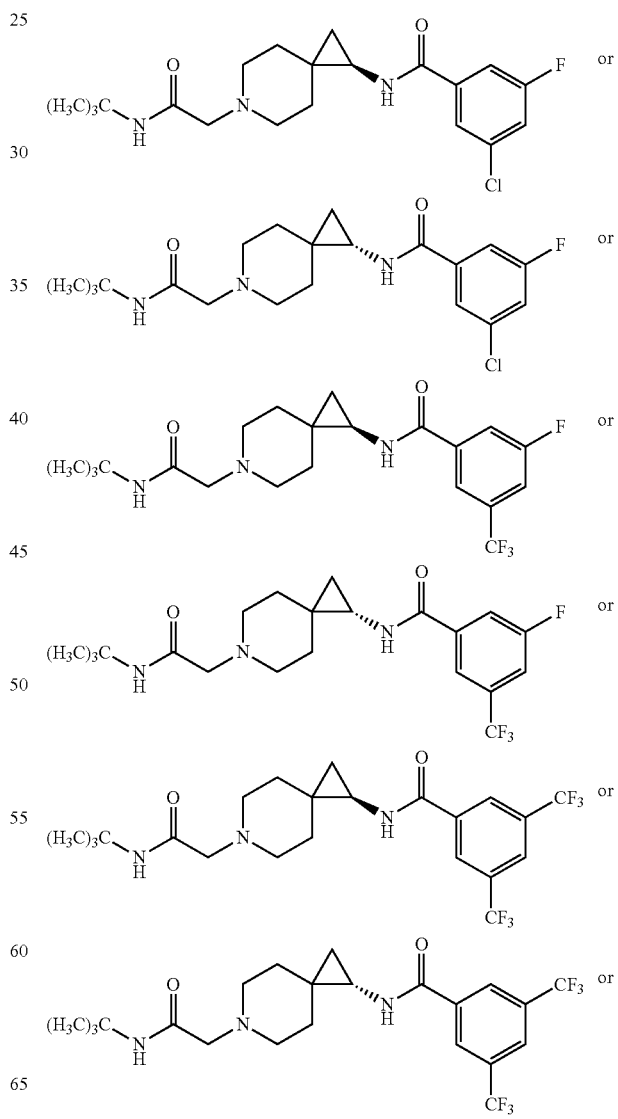

-continued

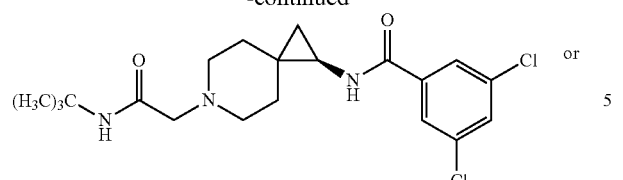 or

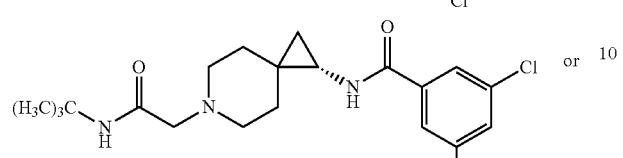 or

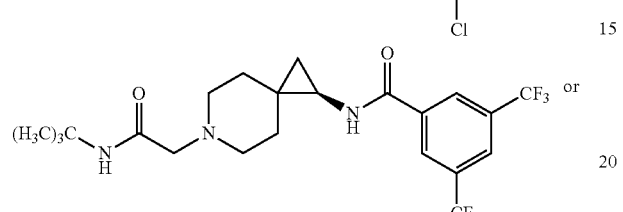 or

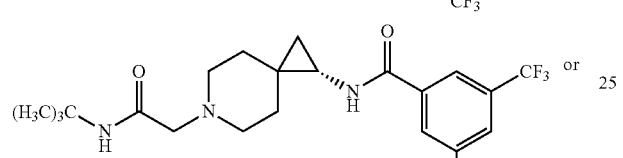 or

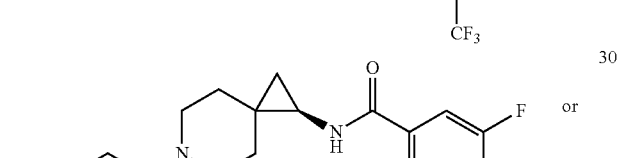 or

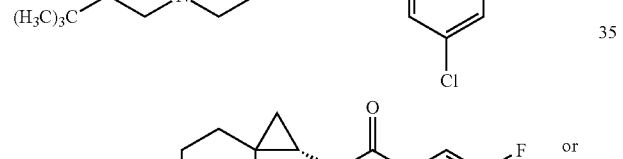 or

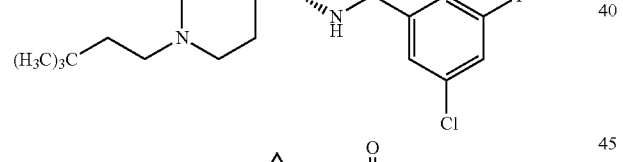 or

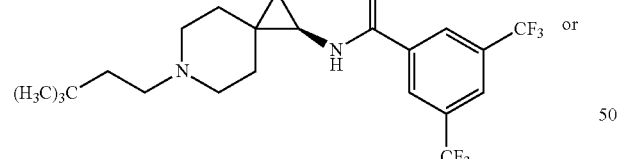 or

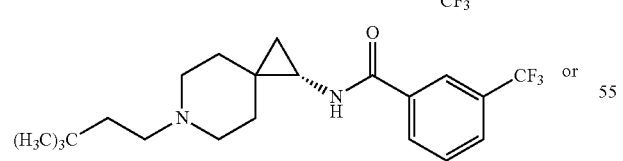 or

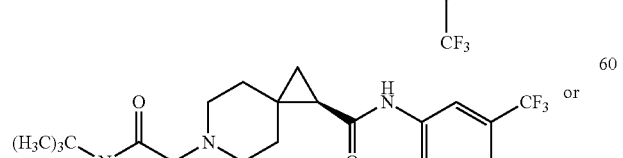 or

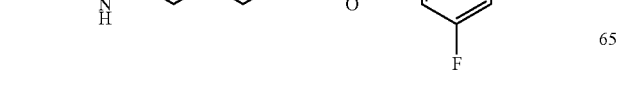 or

-continued

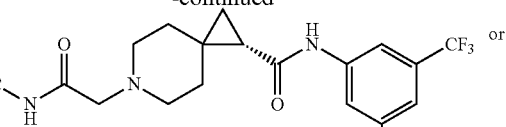 or

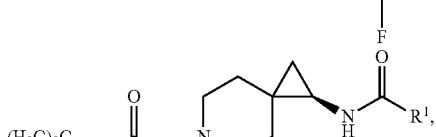, wherein R¹ is unsubstituted adamant-1-yl, or

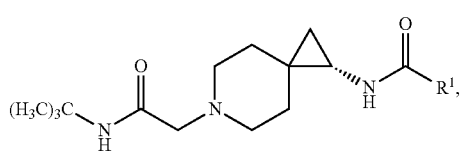, wherein R¹ is unsubstituted adamant-1-yl, or

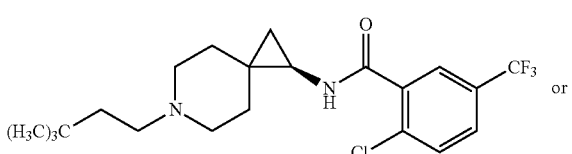 or

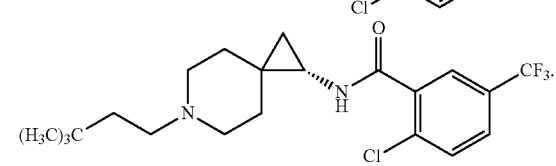.

16. A compound, or a pharmaceutically acceptable salt thereof, which is

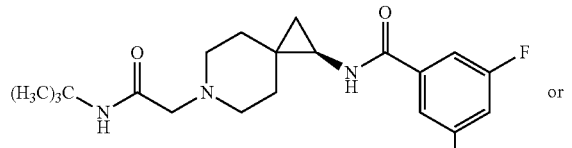 or

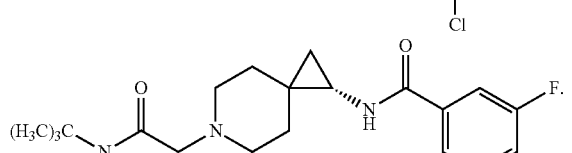 or

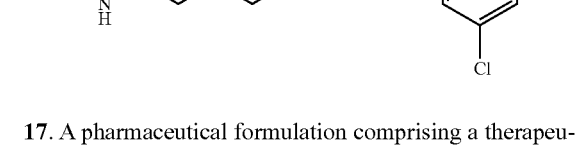.

17. A pharmaceutical formulation comprising a therapeutically effective amount of a compound according to claim 1, or a pharmaceutically acceptable salt thereof, and a pharmaceutically acceptable carrier.

18. The pharmaceutical formulation according to claim 1, wherein said formulation is in a unit dosage format.

19. A method of treating pain, epilepsy or essential tremor in a human, comprising administering the compound according to claim 1, or a pharmaceutically acceptable salt thereof, to the human, wherein the human is in need of treatment thereof, thereby treating the pain, epilepsy or essential tremor in the human.

20. The method of claim 19, wherein the compound selectively inhibits the T Channel known as the $Ca_{v3.2}$ channel.

21. The method of claim 19, wherein the pain is neuropathic or inflammatory pain.

22. The compound according to claim 1, or a pharmaceutically acceptable salt thereof, wherein $R^2$ is a monosubstituted methyl or ethyl group substituted with a substituent selected from the group consisting of fluoro, chloro, bromo, iodo, —($C_1$-$C_4$) alkyl, —($C_1$-$C_4$) haloalkyl, —C(═O)NH (straight or branched $C_1$-$C_4$ alkyl), and —NHC(═O) (straight or branched $C_1$-$C_4$ alkyl).

23. The compound according to claim 1, or a pharmaceutically acceptable salt thereof, wherein $R^2$ is t-butyl carboxamide-substituted methyl.

\* \* \* \* \*